US008993586B2

(12) United States Patent
Griffith et al.

(10) Patent No.: US 8,993,586 B2
(45) Date of Patent: Mar. 31, 2015

(54) N1/N2-LACTAM ACETYL-COA CARBOXYLASE INHIBITORS

(71) Applicant: Pfizer Inc., New York, NY (US)

(72) Inventors: David A. Griffith, Sudbury, MA (US); Robert L. Dow, Groton, CT (US); Scott W. Bagley, Mystic, CT (US); Aaron Smith, North Providence, RI (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/497,396

(22) Filed: Sep. 26, 2014

(65) Prior Publication Data

US 2015/0025098 A1 Jan. 22, 2015

Related U.S. Application Data

(63) Continuation of application No. 13/282,964, filed on Oct. 27, 2011, now Pat. No. 8,859,773.

(60) Provisional application No. 61/531,744, filed on Sep. 7, 2011, provisional application No. 61/408,127, filed on Oct. 29, 2010.

(51) Int. Cl.
*C07D 471/20* (2006.01)
*A61K 31/438* (2006.01)

(52) U.S. Cl.
CPC ............................ *C07D 471/20* (2013.01)
USPC ............................................ 514/278; 546/17

(58) Field of Classification Search
CPC ......................................................... C07D 471/20
USPC ............................................ 514/278; 546/17
See application file for complete search history.

(56) References Cited

U.S. PATENT DOCUMENTS

| | | | |
|---|---|---|---|
| 8,288,405 B2 | 10/2012 | Bagley et al. | |
| 8,318,762 B2 | 11/2012 | Corbett et al. | |
| 8,507,681 B2 | 8/2013 | Bagley et al. | |
| 2008/0171761 A1 | 7/2008 | Iino et al. | |
| 2009/0253725 A1 | 10/2009 | Chang et al. | |
| 2009/0270435 A1 | 10/2009 | Corbett et al. | |
| 2010/0009982 A1 | 1/2010 | Anderson et al. | |

(Continued)

FOREIGN PATENT DOCUMENTS

| EP | 1911753 | 11/2009 |
|---|---|---|
| EP | 2123652 | 11/2009 |

(Continued)

OTHER PUBLICATIONS

Database WPI Week 200537; Derwent Publications Ltd. No. 2005-359210 (XP002471702) (2005).

Abu-Elheiga, et al., "Acetyl-CoA carboxylase 2 mutant mice are protected against obesity and diabetes induced by high-fat/high-carbohydrate diets", PNAS, vol. 100(18), pp. 10207-10212 (2003).

(Continued)

*Primary Examiner* — Rita Desai
(74) *Attorney, Agent, or Firm* — James T. Wasicak

(57) ABSTRACT

The invention provides a compound of Formula (I)

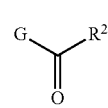

Formula (I)

or a pharmaceutically acceptable salt thereof; wherein G is

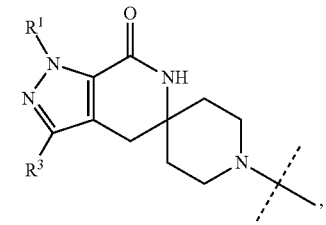

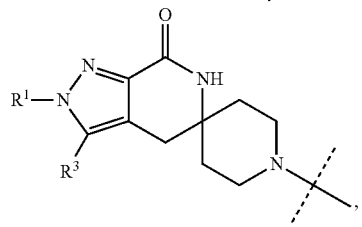

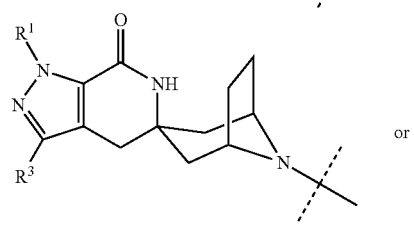

or

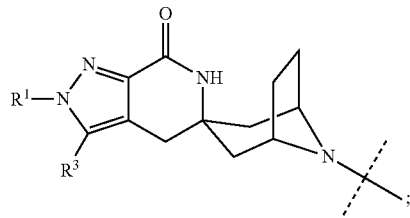

$R^1$, $R^2$ and $R^3$ are as described herein; pharmaceutical compositions thereof; and the use thereof in treating diseases, conditions or disorders modulated by the inhibition of an acetyl-CoA carboxylase enzyme(s) in an animal.

3 Claims, 4 Drawing Sheets

(56) References Cited

U.S. PATENT DOCUMENTS

| | | |
|---|---|---|
| 2011/0028390 A1 | 2/2011 | Corbett et al. |
| 2011/0111046 A1 | 5/2011 | Bagley et al. |

FOREIGN PATENT DOCUMENTS

| | | |
|---|---|---|
| JP | 2005119987 | 5/2005 |
| WO | 03072197 | 9/2003 |
| WO | 2004002986 | 1/2004 |
| WO | 2004092179 | 10/2004 |
| WO | 2005113069 | 12/2005 |
| WO | 2007011809 | 1/2007 |
| WO | 2007011811 | 1/2007 |
| WO | 2007061676 | 5/2007 |
| WO | 2007095603 | 8/2007 |
| WO | 2008065508 | 6/2008 |
| WO | 2008088689 | 7/2008 |
| WO | 2008102749 | 8/2008 |
| WO | 2008125945 | 10/2008 |
| WO | 2009144554 | 12/2009 |
| WO | 2009144555 | 12/2009 |
| WO | 2010002010 | 1/2010 |
| WO | 2011058473 | 5/2011 |
| WO | 2011058474 | 5/2011 |
| WO | 2012042433 | 4/2012 |

OTHER PUBLICATIONS

Choi, et al., "Continuous fat oxidation in acetyl-CoA carboxylase 2 knockout mice increases total energy expenditure, reduces fat mass, and improves insulin sensitivity", PNAS, vol. 104(42), pp. 16480-16485 (2007).

Oh, et al., "Glucose and fat metabolism in adipose tissue of acetyl-CoA carboxylase 2 knockout mice", PNAS, vol. 102 (5), pp. 1384-1389 (2005).

Savage, et al. "Reversal of diet-induced hepatic steatosis and hepatic insulin resistance by antisense oligonucleotide inhibitors of acetyl-CoA carboxylases 1 and 2", J. Clin. Invest., vol. 116(3), pp. 817-824 (2006).

Bagley, et al., "Synthesis of 7-oxo-dihydrospiro[indazole-5,4'-piperidine] Acetyl-CoA Carboxylase Inhibitors", The Journal of Organic Chemistry, vol. 77(3), pp. 1497-1506 (2012).

FIGURE 1

SEQ. ID NO. 1:

MAHHHHHHDEVDDEPSPLAQPLELNQHSRFIIGSVSEDNSEDEISNLVKLDLLEKEGSLS
PASVGSDTLSDLGISSLQDGLALHIRSSMSGLHLVKQGRDRKKIDSQRDFTVASPAEFVT
RFGGNKVIEKVLIANNGIAAVKCMRSIRRWSYEMFRNERAIRFVVMVTPEDLKANAEYIK
MADHYVPVPGGPNNNNYANVELILDIAKRIPVQAVWAGWGHASENPKLPELLLKNGIAF
MGPPSQAMWALGDKIASSIVAQTAGIPTLPWSGSGLRVDWQENDFSKRILNVPQELYEK
GYVKDVDDGLQAAEEVGYPVMIKASEGGGGKGIRKVNNADDFPNLFRQVQAEVPGSPI
FVMRLAKQSRHLEVQILADQYGNAISLFGRDCSVQRRHQKIIEEAPATIATPAVFEHMEQ
CAVKLAKMVGYVSAGTVEYLYSQDGSFYFLELNPRLQVEHPCTEMVADVNLPAAQLQIA
MGIPLYRIKDIRMMYGVSPWGDSPIDFEDSAHVPCPRGHVIAARITSENPDEGFKPSSGT
VQELNFRSNKNVWGYFSVAAAGGLHEFADSQFGHCFSWGENREEAISNMVVALKELSI
RGDFRTTVEYLIKLLETESFQMNRIDTGWLDRLIAEKVQAERPDTMLGVVCGALHVADV
SLRNSVSNFLHSLERGQVLPAHTLLNTVDVELIYEGVKYVLKVTRQSPNSYVVIMNGSCV
EVDVHRLSDGGLLLSYDGSSYTTYMKEEVDRYRITIGNKTCVFEKENDPSVMRSPSAGK
LIQYIVEDGGHVFAGQCYAEIEVMKMVMTLTAVESGCIHYVKRPGAALDPGCVLAKMQL
DNPSKVQQAELHTGSLPRIQSTALRGEKLHRVFHYVLDNLVNVMNGYCLPDPFFSSKVK
DWVERLMKTLRDPSLPLLELQDIMTSVSGRIPPNVEKSIKKEMAQYASNITSVLCQFPSQ
QIANILDSHAATLNRKSEREVFFMNTQSIVQLVQRYRSGIRGHMKAVVMDLLRQYLRVET
QFQNGHYDKCVFALREENKSDMNTVLNYIFSHAQVTKKNLLVTMLIDQLCGRDPTLTDE
LLNILTELTQLSKTTNAKVALRARQVLIASHLPSYELRHNQVESIFLSAIDMYGHQFCIENL
QKLILSETSIFDVLPNFFYHSNQVVRMAALEVYVRRAYIAYELNSVQHRQLKDNTCVVEF
QFMLPTSHPNRGNIPTLNRMSFSSNLNHYGMTHVASVSDVLLDNSFTPPCQRMGGMV
SFRTFEDFVRIFDEVMGCFSDSPPQSPTFPEAGHTSLYDEDKVPRDEPIHILNVAIKTDC
DIEDDRLAAMFREFTQQNKATLVDHGIRRLTFLVAQKDFRKQVNYEVDRRFHREFPKFF
TFRARDKFEEDRIYRHLEPALAFQLELNRMRNFDLTAIPCANHKMHLYLGAAKVEVGTEV
TDYRFFVRAIIRHSDLVTKEASFEYLQNEGERLLLEAMDELEVAFNNTNVRTDCNHIFLNF
VPTVIMDPSKIEESVRSMVMRYGSRLWKLRVLQAELKINIRLTPTGKAIPIRLFLTNESGY
YLDISLYKEVTDSRTAQIMFQAYGDKQGPLHGMLINTPYVTKDLLQSKRFQAQSLGTTYI
YDIPEMFRQSLIKLWESMSTQAFLPSPPLPSDMLTYTELVLDDQGQLVHMNRLPGGNEI
GMVAWKMTFKSPEYPEGRDIIVIGNDITYRIGSFGPQEDLLFLRASELARAEGIPRIYVSA
NSGARIGLAEEIRHMFHVAWVDPEDPYKGYRYLYLTPQDYKRVSALNSVHCEHVEDEG
ESRYKITDIIGKEEGIGPENLRGSGMIAGESSLAYNEIITISLVTCRAIGIGAYLVRLGQRTIQ

FIGURE 1 (continued)

VENSHLILTGAGALNKVLGREVYTSNNQLGGIQIMHNNGVTHCTVCDDFEGVFTVLHWL
SYMPKSVHSSVPLLNSKDPIDRIIEFVPTKTPYDPRWMLAGRPHPTQKGQWLSGFFDYG
SFSEIMQPWAQTVVVGRARLGGIPVGVVAVETRTVELSIPADPANLDSEAKIIQQAGQVW
FPDSAFKTYQAIKDFNREGLPLMVFANWRGFSGGMKDMYDQVLKFGAYIVDGLRECCQ
PVLVYIPPQAELRGGSWVVIDSSINPRHMEMYADRESRGSVLEPEGTVEIKFRRKDLVKT
MRRVDPVYIHLAERLGTPELSTAERKELENKLKEREEFLIPIYHQVAVQFADLHDTPGRM
QEKGVISDILDWKTSRTFFYWRLRRLLLEDLVKKKIHNANPELTDGQIQAMLRRWFVEVE
GTVKAYVWDNNKDLAEWLEKQLTEEDGVHSVIEENIKCISRDYVLKQIRSLVQANPEVA
MDSIIHMTQHISPTQRAEVIRILSTMDSPST

FIGURE 2

SEQ. ID NO. 2:

MVLLLCLSCLIFSCLTFSWLKIWGKMTDSKPITKSKSEANLIPSQEPFPASDNSGETP
QRNGEGHTLPKTPSQAEPASHKGPKDAGRRRNSLPPSHQKPPRNPLSSSDAAPS
PELQANGTGTQGLEATDTNGLSSSARPQGQQAGSPSKEDKKQANIKRQLMTNFIL
GSFDDYSSDEDSVAGSSRESTRKGSRASLGALSLEAYLTTGEAETRVPTMRPSMS
GLHLVKRGREHKKLDLHRDFTVASPAEFVTRFGGDRVIEKVLIANNGIAAVKCMRSI
RRWAYEMFRNERAIRFVVMVTPEDLKANAEYIKMADHYVPVPGGPNNNNYANVEL
IVDIAKRIPVQAVWAGWGHASENPKLPELLCKNGVAFLGPPSEAMWALGDKIASTV
VAQTLQVPTLPWSGSGLTVEWTEDDLQQGKRISVPEDVYDKGCVKDVDEGLEAA
ERIGFPLMIKASEGGGGKGIRKAESAEDFPILFRQVQSEIPGSPIFLMKLAQHARHLE
VQILADQYGNAVSLFGRDCSIQRRHQKIVEEAPATIAPLAIFEFMEQCAIRLAKTVGY
VSAGTVEYLYSQDGSFHFLELNPRLQVEHPCTEMIADVNLPAAQLQIAMGVPLHRL
KDIRLLYGESPWGVTPISFETPSNPPLARGHVIAARITSENPDEGFKPSSGTVQELN
FRSSKNVWGYFSVAATGGLHEFADSQFGHCFSWGENREEAISNMVVALKELSIRG
DFRTTVEYLINLLETESFQNNDIDTGWLDYLIAEKVQAEKPDIMLGVVCGALNVADA
MFRTCMTDFLHSLERGQVLPADSLLNLVDVELIYGGVKYILKVARQSLTMFVLIMNG
CHIEIDAHRLNDGGLLLSYNGNSYTTYMKEEVDSYRITIGNKTCVFEKENDPTVLRS
PSAGKLTQYTVEDGGHVEAGSSYAEMEVMKMIMTLNVQERGRVKYIKRPGAVLEA
GCVVARLELDDPSKVHPAEPFTGELPAQQTLPILGEKLHQVFHSVLENLTNVMSGF
CLPEPVFSIKLKEWVQKLMMTLRHPSLPLLELQEIMTSVAGRIPAPVEKSVRRVMA
QYASNITSVLCQFPSQQIATILDCHAATLQRKADREVFFINTQSIVQLVQRYRSGIRG
YMKTVVLDLLRRYLRVEHHFQQAHYDKCVINLREQFKPDMSQVLDCIFSHAQVAKK
NQLVIMLIDELCGPDPSLSDELISILNELTQLSKSEHCKVALRARQILIASHLPSYELR
HNQVESIFLSAIDMYGHQFCPENLKKLILSETTIFDVLPTFFYHANKVVCMASLEVYV
RRGYIAYELNSLQHRQLPDGTCVVEFQFMLPSSHPNRMTVPISITNPDLLRHSTELF
MDSGFSPLCQRMGAMVAFRRFEDFTRNFDEVISCFANVPKDTPLFSEARTSLYSE
DDCKSLREEPIHILNVSIQCADHLEDEALVPILRTFVQSKKNILVDYGLRRITFLIAQEK
EFPKFFTFRARDEFAEDRIYRHLEPALAFQLELNRMRNFDLTAVPCANHKMHLYLG
AAKVKEGVEVTDHRFFIRAIIRHSDLITKEASFEYLQNEGERLLLEAMDELEVAFNNT

FIGURE 2 (continued)

SVRTDCNHIFLNFVPTVIMDPFKIEESVRYMVMRYGSRLWKLRVLQAEVKINIRQTT
TGSAVPIRLFITNESGYYLDISLYKEVTDSRSGNIMFHSFGNKQGPQHGMLINTPYV
TKDLLQAKRFQAQTLGTTYIYDFPEMFRQALFKLWGSPDKYPKDILTYTELVLDSQ
GQLVEMNRLPGGNEVGMVAFKMRFKTQEYPEGRDVIVIGNDITFRIGSFGPGEDLL
YLRASEMARAEGIPKIYVAANSGARIGMAEEIKHMFHVAWVDPEDPHKGFKYLYLT
PQDYTRISSLNSVHCKHIEEGGESRYMITDIIGKDDGLGVENLRGSGMIAGESSLAY
EEIVTISLVTCRAIGIGAYLVRLGQRVIQVENSHIILTGASALNKVLGREVYTSNNQLG
GVQIMHYNGVSHITVPDDFEGVYTILEWLSYMPKDNHSPVPIITPTDPIDREIEFLPS
RAPYDPRWMLAGRPHPTLKGTWQSGFFDHGSFKEIMAPWAQTVVTGRARLGGIP
VGVIAVETRTVEVAVPADPANLDSEAKIIQQAGQVWFPDSAYKTAQAIKDFNREKLP
LMIFANWRGFSGGMKDMYDQVLKFGAYIVDGLRQYKQPILIYIPPYAELRGGSWVV
IDATINPLCIEMYADKESRGGVLEPEGTVEIKFRKKDLIKSMRRIDPAYKKLMEQLGE
PDLSDKDRKDLEGRLKAREDLLLPIYHQVAVQFADFHDTPGRMLEKGVISDILEWK
TARTFLYWRLRRLLLEDQVKQEILQASGELSHVHIQSMLRRWFVETEGAVKAYLW
DNNQVVVQWLEQHWQAGDGPRSTIRENITYLKHDSVLKTIRGLVEENPEVAVDCVI
YLSQHISPAERAQVVHLLSTMDSPAST

SEQUENCE LISTING

```
<160> NUMBER OF SEQ ID NOS: 2

<210> SEQ ID NO 1
<211> LENGTH: 2356
<212> TYPE: PRT
<213> ORGANISM: Homo sapiens

<400> SEQUENCE: 1

Met Ala His His His His His His Asp Glu Val Asp Asp Glu Pro Ser
1               5                   10                  15

Pro Leu Ala Gln Pro Leu Glu Leu Asn Gln His Ser Arg Phe Ile Ile
            20                  25                  30

Gly Ser Val Ser Glu Asp Asn Ser Glu Asp Glu Ile Ser Asn Leu Val
        35                  40                  45

Lys Leu Asp Leu Leu Glu Lys Glu Gly Ser Leu Ser Pro Ala Ser Val
    50                  55                  60

Gly Ser Asp Thr Leu Ser Asp Leu Gly Ile Ser Ser Leu Gln Asp Gly
65                  70                  75                  80

Leu Ala Leu His Ile Arg Ser Ser Met Ser Gly Leu His Leu Val Lys
                85                  90                  95

Gln Gly Arg Asp Arg Lys Lys Ile Asp Ser Gln Arg Asp Phe Thr Val
            100                 105                 110

Ala Ser Pro Ala Glu Phe Val Thr Arg Phe Gly Gly Asn Lys Val Ile
            115                 120                 125
```

-continued

```
Glu Lys Val Leu Ile Ala Asn Asn Gly Ile Ala Ala Val Lys Cys Met
    130                 135                 140
Arg Ser Ile Arg Arg Trp Ser Tyr Glu Met Phe Arg Asn Glu Arg Ala
145                 150                 155                 160
Ile Arg Phe Val Val Met Val Thr Pro Glu Asp Leu Lys Ala Asn Ala
                165                 170                 175
Glu Tyr Ile Lys Met Ala Asp His Tyr Val Pro Val Pro Gly Gly Pro
                180                 185                 190
Asn Asn Asn Asn Tyr Ala Asn Val Glu Leu Ile Leu Asp Ile Ala Lys
            195                 200                 205
Arg Ile Pro Val Gln Ala Val Trp Ala Gly Trp Gly His Ala Ser Glu
210                 215                 220
Asn Pro Lys Leu Pro Glu Leu Leu Lys Asn Gly Ile Ala Phe Met
225                 230                 235                 240
Gly Pro Pro Ser Gln Ala Met Trp Ala Leu Gly Asp Lys Ile Ala Ser
                245                 250                 255
Ser Ile Val Ala Gln Thr Ala Gly Ile Pro Thr Leu Pro Trp Ser Gly
                260                 265                 270
Ser Gly Leu Arg Val Asp Trp Gln Glu Asn Asp Phe Ser Lys Arg Ile
            275                 280                 285
Leu Asn Val Pro Gln Glu Leu Tyr Glu Lys Gly Tyr Val Lys Asp Val
290                 295                 300
Asp Asp Gly Leu Gln Ala Ala Glu Glu Val Gly Tyr Pro Val Met Ile
305                 310                 315                 320
Lys Ala Ser Glu Gly Gly Gly Lys Gly Ile Arg Lys Val Asn Asn
                325                 330                 335
Ala Asp Asp Phe Pro Asn Leu Phe Arg Gln Val Gln Ala Glu Val Pro
                340                 345                 350
Gly Ser Pro Ile Phe Val Met Arg Leu Ala Lys Gln Ser Arg His Leu
            355                 360                 365
Glu Val Gln Ile Leu Ala Asp Gln Tyr Gly Asn Ala Ile Ser Leu Phe
370                 375                 380
Gly Arg Asp Cys Ser Val Gln Arg Arg His Gln Lys Ile Ile Glu Glu
385                 390                 395                 400
Ala Pro Ala Thr Ile Ala Thr Pro Ala Val Phe Glu His Met Glu Gln
                405                 410                 415
Cys Ala Val Lys Leu Ala Lys Met Val Gly Tyr Val Ser Ala Gly Thr
                420                 425                 430
Val Glu Tyr Leu Tyr Ser Gln Asp Gly Ser Phe Tyr Phe Leu Glu Leu
            435                 440                 445
Asn Pro Arg Leu Gln Val Glu His Pro Cys Thr Glu Met Val Ala Asp
450                 455                 460
Val Asn Leu Pro Ala Ala Gln Leu Gln Ile Ala Met Gly Ile Pro Leu
465                 470                 475                 480
Tyr Arg Ile Lys Asp Ile Arg Met Met Tyr Gly Val Ser Pro Trp Gly
                485                 490                 495
Asp Ser Pro Ile Asp Phe Glu Asp Ser Ala His Val Pro Cys Pro Arg
                500                 505                 510
Gly His Val Ile Ala Ala Arg Ile Thr Ser Glu Asn Pro Asp Glu Gly
            515                 520                 525
Phe Lys Pro Ser Ser Gly Thr Val Gln Glu Leu Asn Phe Arg Ser Asn
530                 535                 540
```

-continued

```
Lys Asn Val Trp Gly Tyr Phe Ser Val Ala Ala Gly Gly Leu His
545                 550                 555                 560

Glu Phe Ala Asp Ser Gln Phe Gly His Cys Phe Ser Trp Gly Glu Asn
            565                 570                 575

Arg Glu Glu Ala Ile Ser Asn Met Val Val Ala Leu Lys Glu Leu Ser
        580                 585                 590

Ile Arg Gly Asp Phe Arg Thr Thr Val Glu Tyr Leu Ile Lys Leu Leu
    595                 600                 605

Glu Thr Glu Ser Phe Gln Met Asn Arg Ile Asp Thr Gly Trp Leu Asp
610                 615                 620

Arg Leu Ile Ala Glu Lys Val Gln Ala Glu Arg Pro Asp Thr Met Leu
625                 630                 635                 640

Gly Val Val Cys Gly Ala Leu His Val Ala Asp Val Ser Leu Arg Asn
                645                 650                 655

Ser Val Ser Asn Phe Leu His Ser Leu Glu Arg Gly Gln Val Leu Pro
            660                 665                 670

Ala His Thr Leu Leu Asn Thr Val Asp Val Glu Leu Ile Tyr Glu Gly
        675                 680                 685

Val Lys Tyr Val Leu Lys Val Thr Arg Gln Ser Pro Asn Ser Tyr Val
    690                 695                 700

Val Ile Met Asn Gly Ser Cys Val Glu Val Asp Val His Arg Leu Ser
705                 710                 715                 720

Asp Gly Gly Leu Leu Ser Tyr Asp Gly Ser Ser Tyr Thr Thr Tyr
                725                 730                 735

Met Lys Glu Glu Val Asp Arg Tyr Arg Ile Thr Ile Gly Asn Lys Thr
            740                 745                 750

Cys Val Phe Glu Lys Glu Asn Asp Pro Ser Val Met Arg Ser Pro Ser
        755                 760                 765

Ala Gly Lys Leu Ile Gln Tyr Ile Val Glu Asp Gly Gly His Val Phe
    770                 775                 780

Ala Gly Gln Cys Tyr Ala Glu Ile Glu Val Met Lys Met Val Met Thr
785                 790                 795                 800

Leu Thr Ala Val Glu Ser Gly Cys Ile His Tyr Val Lys Arg Pro Gly
                805                 810                 815

Ala Ala Leu Asp Pro Gly Cys Val Leu Ala Lys Met Gln Leu Asp Asn
            820                 825                 830

Pro Ser Lys Val Gln Gln Ala Glu Leu His Thr Gly Ser Leu Pro Arg
        835                 840                 845

Ile Gln Ser Thr Ala Leu Arg Gly Glu Lys Leu His Arg Val Phe His
    850                 855                 860

Tyr Val Leu Asp Asn Leu Val Asn Val Met Asn Gly Tyr Cys Leu Pro
865                 870                 875                 880

Asp Pro Phe Phe Ser Ser Lys Val Lys Asp Trp Val Glu Arg Leu Met
                885                 890                 895

Lys Thr Leu Arg Asp Pro Ser Leu Pro Leu Leu Glu Leu Gln Asp Ile
            900                 905                 910

Met Thr Ser Val Ser Gly Arg Ile Pro Pro Asn Val Glu Lys Ser Ile
        915                 920                 925

Lys Lys Glu Met Ala Gln Tyr Ala Ser Asn Ile Thr Ser Val Leu Cys
    930                 935                 940

Gln Phe Pro Ser Gln Gln Ile Ala Asn Ile Leu Asp Ser His Ala Ala
945                 950                 955                 960

Thr Leu Asn Arg Lys Ser Glu Arg Glu Val Phe Phe Met Asn Thr Gln
```

-continued

```
                 965                 970                 975
Ser Ile Val Gln Leu Val Gln Arg Tyr Arg Ser Gly Ile Arg Gly His
                     980                 985                 990
Met Lys Ala Val Val Met Asp Leu Leu Arg Gln Tyr Leu Arg Val Glu
                 995                1000                1005
Thr Gln Phe Gln Asn Gly His Tyr Asp Lys Cys Val Phe Ala Leu
            1010                1015                1020
Arg Glu Glu Asn Lys Ser Asp Met Asn Thr Val Leu Asn Tyr Ile
            1025                1030                1035
Phe Ser His Ala Gln Val Thr Lys Lys Asn Leu Leu Val Thr Met
            1040                1045                1050
Leu Ile Asp Gln Leu Cys Gly Arg Asp Pro Thr Leu Thr Asp Glu
            1055                1060                1065
Leu Leu Asn Ile Leu Thr Glu Leu Thr Gln Leu Ser Lys Thr Thr
            1070                1075                1080
Asn Ala Lys Val Ala Leu Arg Ala Arg Gln Val Leu Ile Ala Ser
            1085                1090                1095
His Leu Pro Ser Tyr Glu Leu Arg His Asn Gln Val Glu Ser Ile
            1100                1105                1110
Phe Leu Ser Ala Ile Asp Met Tyr Gly His Gln Phe Cys Ile Glu
            1115                1120                1125
Asn Leu Gln Lys Leu Ile Leu Ser Glu Thr Ser Ile Phe Asp Val
            1130                1135                1140
Leu Pro Asn Phe Phe Tyr His Ser Asn Gln Val Val Arg Met Ala
            1145                1150                1155
Ala Leu Glu Val Tyr Val Arg Arg Ala Tyr Ile Ala Tyr Glu Leu
            1160                1165                1170
Asn Ser Val Gln His Arg Gln Leu Lys Asp Asn Thr Cys Val Val
            1175                1180                1185
Glu Phe Gln Phe Met Leu Pro Thr Ser His Pro Asn Arg Gly Asn
            1190                1195                1200
Ile Pro Thr Leu Asn Arg Met Ser Phe Ser Ser Asn Leu Asn His
            1205                1210                1215
Tyr Gly Met Thr His Val Ala Ser Val Ser Asp Val Leu Leu Asp
            1220                1225                1230
Asn Ser Phe Thr Pro Pro Cys Gln Arg Met Gly Gly Met Val Ser
            1235                1240                1245
Phe Arg Thr Phe Glu Asp Phe Val Arg Ile Phe Asp Glu Val Met
            1250                1255                1260
Gly Cys Phe Ser Asp Ser Pro Pro Gln Ser Pro Thr Phe Pro Glu
            1265                1270                1275
Ala Gly His Thr Ser Leu Tyr Asp Glu Asp Lys Val Pro Arg Asp
            1280                1285                1290
Glu Pro Ile His Ile Leu Asn Val Ala Ile Lys Thr Asp Cys Asp
            1295                1300                1305
Ile Glu Asp Asp Arg Leu Ala Ala Met Phe Arg Glu Phe Thr Gln
            1310                1315                1320
Gln Asn Lys Ala Thr Leu Val Asp His Gly Ile Arg Arg Leu Thr
            1325                1330                1335
Phe Leu Val Ala Gln Lys Asp Phe Arg Lys Gln Val Asn Tyr Glu
            1340                1345                1350
Val Asp Arg Arg Phe His Arg Glu Phe Pro Lys Phe Phe Thr Phe
            1355                1360                1365
```

```
Arg Ala Arg Asp Lys Phe Glu Glu Asp Arg Ile Tyr Arg His Leu
1370            1375                1380

Glu Pro Ala Leu Ala Phe Gln Leu Glu Leu Asn Arg Met Arg Asn
1385            1390                1395

Phe Asp Leu Thr Ala Ile Pro Cys Ala Asn His Lys Met His Leu
1400            1405                1410

Tyr Leu Gly Ala Ala Lys Val Glu Val Gly Thr Glu Val Thr Asp
1415            1420                1425

Tyr Arg Phe Phe Val Arg Ala Ile Ile Arg His Ser Asp Leu Val
1430            1435                1440

Thr Lys Glu Ala Ser Phe Glu Tyr Leu Gln Asn Glu Gly Glu Arg
1445            1450                1455

Leu Leu Leu Glu Ala Met Asp Glu Leu Glu Val Ala Phe Asn Asn
1460            1465                1470

Thr Asn Val Arg Thr Asp Cys Asn His Ile Phe Leu Asn Phe Val
1475            1480                1485

Pro Thr Val Ile Met Asp Pro Ser Lys Ile Glu Glu Ser Val Arg
1490            1495                1500

Ser Met Val Met Arg Tyr Gly Ser Arg Leu Trp Lys Leu Arg Val
1505            1510                1515

Leu Gln Ala Glu Leu Lys Ile Asn Ile Arg Leu Thr Pro Thr Gly
1520            1525                1530

Lys Ala Ile Pro Ile Arg Leu Phe Leu Thr Asn Glu Ser Gly Tyr
1535            1540                1545

Tyr Leu Asp Ile Ser Leu Tyr Lys Glu Val Thr Asp Ser Arg Thr
1550            1555                1560

Ala Gln Ile Met Phe Gln Ala Tyr Gly Asp Lys Gln Gly Pro Leu
1565            1570                1575

His Gly Met Leu Ile Asn Thr Pro Tyr Val Thr Lys Asp Leu Leu
1580            1585                1590

Gln Ser Lys Arg Phe Gln Ala Gln Ser Leu Gly Thr Thr Tyr Ile
1595            1600                1605

Tyr Asp Ile Pro Glu Met Phe Arg Gln Ser Leu Ile Lys Leu Trp
1610            1615                1620

Glu Ser Met Ser Thr Gln Ala Phe Leu Pro Ser Pro Pro Leu Pro
1625            1630                1635

Ser Asp Met Leu Thr Tyr Thr Glu Leu Val Leu Asp Asp Gln Gly
1640            1645                1650

Gln Leu Val His Met Asn Arg Leu Pro Gly Gly Asn Glu Ile Gly
1655            1660                1665

Met Val Ala Trp Lys Met Thr Phe Lys Ser Pro Glu Tyr Pro Glu
1670            1675                1680

Gly Arg Asp Ile Ile Val Ile Gly Asn Asp Ile Thr Tyr Arg Ile
1685            1690                1695

Gly Ser Phe Gly Pro Gln Glu Asp Leu Leu Phe Leu Arg Ala Ser
1700            1705                1710

Glu Leu Ala Arg Ala Glu Gly Ile Pro Arg Ile Tyr Val Ser Ala
1715            1720                1725

Asn Ser Gly Ala Arg Ile Gly Leu Ala Glu Glu Ile Arg His Met
1730            1735                1740

Phe His Val Ala Trp Val Asp Pro Glu Asp Pro Tyr Lys Gly Tyr
1745            1750                1755
```

```
Arg Tyr Leu Tyr Leu Thr Pro Gln Asp Tyr Lys Arg Val Ser Ala
1760                1765                1770

Leu Asn Ser Val His Cys Glu His Val Glu Asp Glu Gly Glu Ser
1775                1780                1785

Arg Tyr Lys Ile Thr Asp Ile Ile Gly Lys Glu Glu Gly Ile Gly
1790                1795                1800

Pro Glu Asn Leu Arg Gly Ser Gly Met Ile Ala Gly Ser Ser
1805                1810                1815

Leu Ala Tyr Asn Glu Ile Ile Thr Ile Ser Leu Val Thr Cys Arg
1820                1825                1830

Ala Ile Gly Ile Gly Ala Tyr Leu Val Arg Leu Gly Gln Arg Thr
1835                1840                1845

Ile Gln Val Glu Asn Ser His Leu Ile Leu Thr Gly Ala Gly Ala
1850                1855                1860

Leu Asn Lys Val Leu Gly Arg Glu Val Tyr Thr Ser Asn Asn Gln
1865                1870                1875

Leu Gly Gly Ile Gln Ile Met His Asn Asn Gly Val Thr His Cys
1880                1885                1890

Thr Val Cys Asp Asp Phe Glu Gly Val Phe Thr Val Leu His Trp
1895                1900                1905

Leu Ser Tyr Met Pro Lys Ser Val His Ser Ser Val Pro Leu Leu
1910                1915                1920

Asn Ser Lys Asp Pro Ile Asp Arg Ile Ile Glu Phe Val Pro Thr
1925                1930                1935

Lys Thr Pro Tyr Asp Pro Arg Trp Met Leu Ala Gly Arg Pro His
1940                1945                1950

Pro Thr Gln Lys Gly Gln Trp Leu Ser Gly Phe Phe Asp Tyr Gly
1955                1960                1965

Ser Phe Ser Glu Ile Met Gln Pro Trp Ala Gln Thr Val Val Val
1970                1975                1980

Gly Arg Ala Arg Leu Gly Gly Ile Pro Val Gly Val Val Ala Val
1985                1990                1995

Glu Thr Arg Thr Val Glu Leu Ser Ile Pro Ala Asp Pro Ala Asn
2000                2005                2010

Leu Asp Ser Glu Ala Lys Ile Ile Gln Gln Ala Gly Gln Val Trp
2015                2020                2025

Phe Pro Asp Ser Ala Phe Lys Thr Tyr Gln Ala Ile Lys Asp Phe
2030                2035                2040

Asn Arg Glu Gly Leu Pro Leu Met Val Phe Ala Asn Trp Arg Gly
2045                2050                2055

Phe Ser Gly Gly Met Lys Asp Met Tyr Asp Gln Val Leu Lys Phe
2060                2065                2070

Gly Ala Tyr Ile Val Asp Gly Leu Arg Glu Cys Cys Gln Pro Val
2075                2080                2085

Leu Val Tyr Ile Pro Pro Gln Ala Glu Leu Arg Gly Gly Ser Trp
2090                2095                2100

Val Val Ile Asp Ser Ser Ile Asn Pro Arg His Met Glu Met Tyr
2105                2110                2115

Ala Asp Arg Glu Ser Arg Gly Ser Val Leu Glu Pro Glu Gly Thr
2120                2125                2130

Val Glu Ile Lys Phe Arg Arg Lys Asp Leu Val Lys Thr Met Arg
2135                2140                2145

Arg Val Asp Pro Val Tyr Ile His Leu Ala Glu Arg Leu Gly Thr
```

```
                    2150                2155                2160

Pro Glu Leu Ser Thr Ala Glu Arg Lys Glu Leu Glu Asn Lys Leu
        2165                2170                2175

Lys Glu Arg Glu Glu Phe Leu Ile Pro Ile Tyr His Gln Val Ala
2180                2185                2190

Val Gln Phe Ala Asp Leu His Asp Thr Pro Gly Arg Met Gln Glu
        2195                2200                2205

Lys Gly Val Ile Ser Asp Ile Leu Asp Trp Lys Thr Ser Arg Thr
2210                2215                2220

Phe Phe Tyr Trp Arg Leu Arg Leu Leu Glu Asp Leu Val
        2225                2230                2235

Lys Lys Lys Ile His Asn Ala Asn Pro Glu Leu Thr Asp Gly Gln
2240                2245                2250

Ile Gln Ala Met Leu Arg Arg Trp Phe Val Glu Val Glu Gly Thr
        2255                2260                2265

Val Lys Ala Tyr Val Trp Asp Asn Asn Lys Asp Leu Ala Glu Trp
2270                2275                2280

Leu Glu Lys Gln Leu Thr Glu Glu Asp Gly Val His Ser Val Ile
        2285                2290                2295

Glu Glu Asn Ile Lys Cys Ile Ser Arg Asp Tyr Val Leu Lys Gln
2300                2305                2310

Ile Arg Ser Leu Val Gln Ala Asn Pro Glu Val Ala Met Asp Ser
        2315                2320                2325

Ile Ile His Met Thr Gln His Ile Ser Pro Thr Gln Arg Ala Glu
2330                2335                2340

Val Ile Arg Ile Leu Ser Thr Met Asp Ser Pro Ser Thr
        2345                2350                2355

<210> SEQ ID NO 2
<211> LENGTH: 2458
<212> TYPE: PRT
<213> ORGANISM: Homo sapiens

<400> SEQUENCE: 2

Met Val Leu Leu Leu Cys Leu Ser Cys Leu Ile Phe Ser Cys Leu Thr
1               5                   10                  15

Phe Ser Trp Leu Lys Ile Trp Gly Lys Met Thr Asp Ser Lys Pro Ile
                20                  25                  30

Thr Lys Ser Lys Ser Glu Ala Asn Leu Ile Pro Ser Gln Glu Pro Phe
            35                  40                  45

Pro Ala Ser Asp Asn Ser Gly Glu Thr Pro Gln Arg Asn Gly Glu Gly
        50                  55                  60

His Thr Leu Pro Lys Thr Pro Ser Gln Ala Glu Pro Ala Ser His Lys
65                  70                  75                  80

Gly Pro Lys Asp Ala Gly Arg Arg Asn Ser Leu Pro Pro Ser His
                85                  90                  95

Gln Lys Pro Pro Arg Asn Pro Leu Ser Ser Asp Ala Ala Pro Ser
            100                 105                 110

Pro Glu Leu Gln Ala Asn Gly Thr Gly Thr Gln Gly Leu Glu Ala Thr
        115                 120                 125

Asp Thr Asn Gly Leu Ser Ser Ser Ala Arg Pro Gln Gly Gln Gln Ala
    130                 135                 140

Gly Ser Pro Ser Lys Glu Asp Lys Lys Gln Ala Asn Ile Lys Arg Gln
145                 150                 155                 160
```

```
Leu Met Thr Asn Phe Ile Leu Gly Ser Phe Asp Asp Tyr Ser Ser Asp
                165                 170                 175

Glu Asp Ser Val Ala Gly Ser Ser Arg Glu Ser Thr Arg Lys Gly Ser
            180                 185                 190

Arg Ala Ser Leu Gly Ala Leu Ser Leu Glu Ala Tyr Leu Thr Thr Gly
        195                 200                 205

Glu Ala Glu Thr Arg Val Pro Thr Met Arg Pro Ser Met Ser Gly Leu
    210                 215                 220

His Leu Val Lys Arg Gly Arg Glu His Lys Lys Leu Asp Leu His Arg
225                 230                 235                 240

Asp Phe Thr Val Ala Ser Pro Ala Glu Phe Val Thr Arg Phe Gly Gly
                245                 250                 255

Asp Arg Val Ile Glu Lys Val Leu Ile Ala Asn Asn Gly Ile Ala Ala
            260                 265                 270

Val Lys Cys Met Arg Ser Ile Arg Arg Trp Ala Tyr Glu Met Phe Arg
        275                 280                 285

Asn Glu Arg Ala Ile Arg Phe Val Val Met Val Thr Pro Glu Asp Leu
    290                 295                 300

Lys Ala Asn Ala Glu Tyr Ile Lys Met Ala Asp His Tyr Val Pro Val
305                 310                 315                 320

Pro Gly Gly Pro Asn Asn Asn Tyr Ala Asn Val Glu Leu Ile Val
                325                 330                 335

Asp Ile Ala Lys Arg Ile Pro Val Gln Ala Val Trp Ala Gly Trp Gly
            340                 345                 350

His Ala Ser Glu Asn Pro Lys Leu Pro Glu Leu Leu Cys Lys Asn Gly
        355                 360                 365

Val Ala Phe Leu Gly Pro Pro Ser Glu Ala Met Trp Ala Leu Gly Asp
    370                 375                 380

Lys Ile Ala Ser Thr Val Ala Gln Thr Leu Gln Val Pro Thr Leu
385                 390                 395                 400

Pro Trp Ser Gly Ser Gly Leu Thr Val Glu Trp Thr Glu Asp Asp Leu
                405                 410                 415

Gln Gln Gly Lys Arg Ile Ser Val Pro Glu Asp Val Tyr Asp Lys Gly
            420                 425                 430

Cys Val Lys Asp Val Asp Glu Gly Leu Glu Ala Ala Glu Arg Ile Gly
        435                 440                 445

Phe Pro Leu Met Ile Lys Ala Ser Glu Gly Gly Gly Lys Gly Ile
    450                 455                 460

Arg Lys Ala Glu Ser Ala Glu Asp Phe Pro Ile Leu Phe Arg Gln Val
465                 470                 475                 480

Gln Ser Glu Ile Pro Gly Ser Pro Ile Phe Leu Met Lys Leu Ala Gln
                485                 490                 495

His Ala Arg His Leu Glu Val Gln Ile Leu Ala Asp Gln Tyr Gly Asn
            500                 505                 510

Ala Val Ser Leu Phe Gly Arg Asp Cys Ser Ile Gln Arg Arg His Gln
        515                 520                 525

Lys Ile Val Glu Glu Ala Pro Ala Thr Ile Ala Pro Leu Ala Ile Phe
    530                 535                 540

Glu Phe Met Glu Gln Cys Ala Ile Arg Leu Ala Lys Thr Val Gly Tyr
545                 550                 555                 560

Val Ser Ala Gly Thr Val Glu Tyr Leu Tyr Ser Gln Asp Gly Ser Phe
                565                 570                 575

His Phe Leu Glu Leu Asn Pro Arg Leu Gln Val Glu His Pro Cys Thr
```

```
                580              585              590
Glu Met Ile Ala Asp Val Asn Leu Pro Ala Gln Leu Gln Ile Ala
            595              600              605

Met Gly Val Pro Leu His Arg Leu Lys Asp Ile Arg Leu Leu Tyr Gly
610              615              620

Glu Ser Pro Trp Gly Val Thr Pro Ile Ser Phe Glu Thr Pro Ser Asn
625              630              635              640

Pro Pro Leu Ala Arg Gly His Val Ile Ala Ala Arg Ile Thr Ser Glu
                645              650              655

Asn Pro Asp Glu Gly Phe Lys Pro Ser Ser Gly Thr Val Gln Glu Leu
            660              665              670

Asn Phe Arg Ser Ser Lys Asn Val Trp Gly Tyr Phe Ser Val Ala Ala
        675              680              685

Thr Gly Gly Leu His Glu Phe Ala Asp Ser Gln Phe Gly His Cys Phe
    690              695              700

Ser Trp Gly Glu Asn Arg Glu Glu Ala Ile Ser Asn Met Val Val Ala
705              710              715              720

Leu Lys Glu Leu Ser Ile Arg Gly Asp Phe Arg Thr Thr Val Glu Tyr
                725              730              735

Leu Ile Asn Leu Leu Glu Thr Glu Ser Phe Gln Asn Asn Asp Ile Asp
            740              745              750

Thr Gly Trp Leu Asp Tyr Leu Ile Ala Glu Lys Val Gln Ala Glu Lys
        755              760              765

Pro Asp Ile Met Leu Gly Val Val Cys Gly Ala Leu Asn Val Ala Asp
    770              775              780

Ala Met Phe Arg Thr Cys Met Thr Asp Phe Leu His Ser Leu Glu Arg
785              790              795              800

Gly Gln Val Leu Pro Ala Asp Ser Leu Leu Asn Leu Val Asp Val Glu
                805              810              815

Leu Ile Tyr Gly Gly Val Lys Tyr Ile Leu Lys Val Ala Arg Gln Ser
            820              825              830

Leu Thr Met Phe Val Leu Ile Met Asn Gly Cys His Ile Glu Ile Asp
        835              840              845

Ala His Arg Leu Asn Asp Gly Gly Leu Leu Leu Ser Tyr Asn Gly Asn
    850              855              860

Ser Tyr Thr Thr Tyr Met Lys Glu Glu Val Asp Ser Tyr Arg Ile Thr
865              870              875              880

Ile Gly Asn Lys Thr Cys Val Phe Glu Lys Glu Asn Asp Pro Thr Val
                885              890              895

Leu Arg Ser Pro Ser Ala Gly Lys Leu Thr Gln Tyr Thr Val Glu Asp
            900              905              910

Gly Gly His Val Glu Ala Gly Ser Ser Tyr Ala Glu Met Glu Val Met
        915              920              925

Lys Met Ile Met Thr Leu Asn Val Gln Glu Arg Gly Arg Val Lys Tyr
    930              935              940

Ile Lys Arg Pro Gly Ala Val Leu Glu Ala Gly Cys Val Val Ala Arg
945              950              955              960

Leu Glu Leu Asp Asp Pro Ser Lys Val His Pro Ala Glu Pro Phe Thr
                965              970              975

Gly Glu Leu Pro Ala Gln Gln Thr Leu Pro Ile Leu Gly Glu Lys Leu
            980              985              990

His Gln Val Phe His Ser Val Leu  Glu Asn Leu Thr Asn  Val Met Ser
        995              1000              1005
```

-continued

```
Gly Phe Cys Leu Pro Glu Pro Val Phe Ser Ile Lys Leu Lys Glu
1010                1015                1020

Trp Val Gln Lys Leu Met Met Thr Leu Arg His Pro Ser Leu Pro
1025                1030                1035

Leu Leu Glu Leu Gln Glu Ile Met Thr Ser Val Ala Gly Arg Ile
1040                1045                1050

Pro Ala Pro Val Glu Lys Ser Val Arg Arg Val Met Ala Gln Tyr
1055                1060                1065

Ala Ser Asn Ile Thr Ser Val Leu Cys Gln Phe Pro Ser Gln Gln
1070                1075                1080

Ile Ala Thr Ile Leu Asp Cys His Ala Ala Thr Leu Gln Arg Lys
1085                1090                1095

Ala Asp Arg Glu Val Phe Phe Ile Asn Thr Gln Ser Ile Val Gln
1100                1105                1110

Leu Val Gln Arg Tyr Arg Ser Gly Ile Arg Gly Tyr Met Lys Thr
1115                1120                1125

Val Val Leu Asp Leu Leu Arg Arg Tyr Leu Arg Val Glu His His
1130                1135                1140

Phe Gln Gln Ala His Tyr Asp Lys Cys Val Ile Asn Leu Arg Glu
1145                1150                1155

Gln Phe Lys Pro Asp Met Ser Gln Val Leu Asp Cys Ile Phe Ser
1160                1165                1170

His Ala Gln Val Ala Lys Lys Asn Gln Leu Val Ile Met Leu Ile
1175                1180                1185

Asp Glu Leu Cys Gly Pro Asp Pro Ser Leu Ser Asp Glu Leu Ile
1190                1195                1200

Ser Ile Leu Asn Glu Leu Thr Gln Leu Ser Lys Ser Glu His Cys
1205                1210                1215

Lys Val Ala Leu Arg Ala Arg Gln Ile Leu Ile Ala Ser His Leu
1220                1225                1230

Pro Ser Tyr Glu Leu Arg His Asn Gln Val Glu Ser Ile Phe Leu
1235                1240                1245

Ser Ala Ile Asp Met Tyr Gly His Gln Phe Cys Pro Glu Asn Leu
1250                1255                1260

Lys Lys Leu Ile Leu Ser Glu Thr Thr Ile Phe Asp Val Leu Pro
1265                1270                1275

Thr Phe Phe Tyr His Ala Asn Lys Val Val Cys Met Ala Ser Leu
1280                1285                1290

Glu Val Tyr Val Arg Arg Gly Tyr Ile Ala Tyr Glu Leu Asn Ser
1295                1300                1305

Leu Gln His Arg Gln Leu Pro Asp Gly Thr Cys Val Val Glu Phe
1310                1315                1320

Gln Phe Met Leu Pro Ser Ser His Pro Asn Arg Met Thr Val Pro
1325                1330                1335

Ile Ser Ile Thr Asn Pro Asp Leu Leu Arg His Ser Thr Glu Leu
1340                1345                1350

Phe Met Asp Ser Gly Phe Ser Pro Leu Cys Gln Arg Met Gly Ala
1355                1360                1365

Met Val Ala Phe Arg Arg Phe Glu Asp Phe Thr Arg Asn Phe Asp
1370                1375                1380

Glu Val Ile Ser Cys Phe Ala Asn Val Pro Lys Asp Thr Pro Leu
1385                1390                1395
```

```
Phe Ser Glu Ala Arg Thr Ser Leu Tyr Ser Glu Asp Asp Cys Lys
    1400            1405            1410

Ser Leu Arg Glu Glu Pro Ile His Ile Leu Asn Val Ser Ile Gln
1415                1420            1425

Cys Ala Asp His Leu Glu Asp Glu Ala Leu Val Pro Ile Leu Arg
    1430            1435            1440

Thr Phe Val Gln Ser Lys Lys Asn Ile Leu Val Asp Tyr Gly Leu
    1445            1450            1455

Arg Arg Ile Thr Phe Leu Ile Ala Gln Glu Lys Glu Phe Pro Lys
1460                1465            1470

Phe Phe Thr Phe Arg Ala Arg Asp Glu Phe Ala Glu Asp Arg Ile
    1475            1480            1485

Tyr Arg His Leu Glu Pro Ala Leu Ala Phe Gln Leu Glu Leu Asn
    1490            1495            1500

Arg Met Arg Asn Phe Asp Leu Thr Ala Val Pro Cys Ala Asn His
1505                1510            1515

Lys Met His Leu Tyr Leu Gly Ala Ala Lys Val Lys Glu Gly Val
    1520            1525            1530

Glu Val Thr Asp His Arg Phe Phe Ile Arg Ala Ile Ile Arg His
1535                1540            1545

Ser Asp Leu Ile Thr Lys Glu Ala Ser Phe Glu Tyr Leu Gln Asn
1550                1555            1560

Glu Gly Glu Arg Leu Leu Leu Glu Ala Met Asp Glu Leu Glu Val
1565                1570            1575

Ala Phe Asn Asn Thr Ser Val Arg Thr Asp Cys Asn His Ile Phe
    1580            1585            1590

Leu Asn Phe Val Pro Thr Val Ile Met Asp Pro Phe Lys Ile Glu
    1595            1600            1605

Glu Ser Val Arg Tyr Met Val Met Arg Tyr Gly Ser Arg Leu Trp
    1610            1615            1620

Lys Leu Arg Val Leu Gln Ala Glu Val Lys Ile Asn Ile Arg Gln
    1625            1630            1635

Thr Thr Thr Gly Ser Ala Val Pro Ile Arg Leu Phe Ile Thr Asn
    1640            1645            1650

Glu Ser Gly Tyr Tyr Leu Asp Ile Ser Leu Tyr Lys Glu Val Thr
    1655            1660            1665

Asp Ser Arg Ser Gly Asn Ile Met Phe His Ser Phe Gly Asn Lys
    1670            1675            1680

Gln Gly Pro Gln His Gly Met Leu Ile Asn Thr Pro Tyr Val Thr
    1685            1690            1695

Lys Asp Leu Leu Gln Ala Lys Arg Phe Gln Ala Gln Thr Leu Gly
    1700            1705            1710

Thr Thr Tyr Ile Tyr Asp Phe Pro Glu Met Phe Arg Gln Ala Leu
    1715            1720            1725

Phe Lys Leu Trp Gly Ser Pro Asp Lys Tyr Pro Lys Asp Ile Leu
    1730            1735            1740

Thr Tyr Thr Glu Leu Val Leu Asp Ser Gln Gly Gln Leu Val Glu
    1745            1750            1755

Met Asn Arg Leu Pro Gly Gly Asn Glu Val Gly Met Val Ala Phe
    1760            1765            1770

Lys Met Arg Phe Lys Thr Gln Glu Tyr Pro Glu Gly Arg Asp Val
    1775            1780            1785

Ile Val Ile Gly Asn Asp Ile Thr Phe Arg Ile Gly Ser Phe Gly
```

```
                    1790              1795                1800
Pro Gly Glu Asp Leu Leu Tyr Leu Arg Ala Ser Glu Met Ala Arg
    1805                1810                1815
Ala Glu Gly Ile Pro Lys Ile Tyr Val Ala Ala Asn Ser Gly Ala
    1820                1825                1830
Arg Ile Gly Met Ala Glu Glu Ile Lys His Met Phe His Val Ala
    1835                1840                1845
Trp Val Asp Pro Glu Asp Pro His Lys Gly Phe Lys Tyr Leu Tyr
    1850                1855                1860
Leu Thr Pro Gln Asp Tyr Thr Arg Ile Ser Ser Leu Asn Ser Val
    1865                1870                1875
His Cys Lys His Ile Glu Glu Gly Gly Glu Ser Arg Tyr Met Ile
    1880                1885                1890
Thr Asp Ile Ile Gly Lys Asp Asp Gly Leu Gly Val Glu Asn Leu
    1895                1900                1905
Arg Gly Ser Gly Met Ile Ala Gly Glu Ser Ser Leu Ala Tyr Glu
    1910                1915                1920
Glu Ile Val Thr Ile Ser Leu Val Thr Cys Arg Ala Ile Gly Ile
    1925                1930                1935
Gly Ala Tyr Leu Val Arg Leu Gly Gln Arg Val Ile Gln Val Glu
    1940                1945                1950
Asn Ser His Ile Ile Leu Thr Gly Ala Ser Ala Leu Asn Lys Val
    1955                1960                1965
Leu Gly Arg Glu Val Tyr Thr Ser Asn Asn Gln Leu Gly Gly Val
    1970                1975                1980
Gln Ile Met His Tyr Asn Gly Val Ser His Ile Thr Val Pro Asp
    1985                1990                1995
Asp Phe Glu Gly Val Tyr Thr Ile Leu Glu Trp Leu Ser Tyr Met
    2000                2005                2010
Pro Lys Asp Asn His Ser Pro Val Pro Ile Ile Thr Pro Thr Asp
    2015                2020                2025
Pro Ile Asp Arg Glu Ile Glu Phe Leu Pro Ser Arg Ala Pro Tyr
    2030                2035                2040
Asp Pro Arg Trp Met Leu Ala Gly Arg Pro His Pro Thr Leu Lys
    2045                2050                2055
Gly Thr Trp Gln Ser Gly Phe Phe Asp His Gly Ser Phe Lys Glu
    2060                2065                2070
Ile Met Ala Pro Trp Ala Gln Thr Val Val Thr Gly Arg Ala Arg
    2075                2080                2085
Leu Gly Gly Ile Pro Val Gly Val Ile Ala Val Glu Thr Arg Thr
    2090                2095                2100
Val Glu Val Ala Val Pro Ala Asp Pro Ala Asn Leu Asp Ser Glu
    2105                2110                2115
Ala Lys Ile Ile Gln Gln Ala Gly Gln Val Trp Phe Pro Asp Ser
    2120                2125                2130
Ala Tyr Lys Thr Ala Gln Ala Ile Lys Asp Phe Asn Arg Glu Lys
    2135                2140                2145
Leu Pro Leu Met Ile Phe Ala Asn Trp Arg Gly Phe Ser Gly Gly
    2150                2155                2160
Met Lys Asp Met Tyr Asp Gln Val Leu Lys Phe Gly Ala Tyr Ile
    2165                2170                2175
Val Asp Gly Leu Arg Gln Tyr Lys Gln Pro Ile Leu Ile Tyr Ile
    2180                2185                2190
```

-continued

```
Pro Pro Tyr Ala Glu Leu Arg Gly Gly Ser Trp Val Val Ile Asp
    2195            2200            2205
Ala Thr Ile Asn Pro Leu Cys Ile Glu Met Tyr Ala Asp Lys Glu
    2210            2215            2220
Ser Arg Gly Gly Val Leu Glu Pro Glu Gly Thr Val Glu Ile Lys
    2225            2230            2235
Phe Arg Lys Lys Asp Leu Ile Lys Ser Met Arg Arg Ile Asp Pro
    2240            2245            2250
Ala Tyr Lys Lys Leu Met Glu Gln Leu Gly Glu Pro Asp Leu Ser
    2255            2260            2265
Asp Lys Asp Arg Lys Asp Leu Glu Gly Arg Leu Lys Ala Arg Glu
    2270            2275            2280
Asp Leu Leu Leu Pro Ile Tyr His Gln Val Ala Val Gln Phe Ala
    2285            2290            2295
Asp Phe His Asp Thr Pro Gly Arg Met Leu Glu Lys Gly Val Ile
    2300            2305            2310
Ser Asp Ile Leu Glu Trp Lys Thr Ala Arg Thr Phe Leu Tyr Trp
    2315            2320            2325
Arg Leu Arg Arg Leu Leu Leu Glu Asp Gln Val Lys Gln Glu Ile
    2330            2335            2340
Leu Gln Ala Ser Gly Glu Leu Ser His Val His Ile Gln Ser Met
    2345            2350            2355
Leu Arg Arg Trp Phe Val Glu Thr Glu Gly Ala Val Lys Ala Tyr
    2360            2365            2370
Leu Trp Asp Asn Asn Gln Val Val Val Gln Trp Leu Glu Gln His
    2375            2380            2385
Trp Gln Ala Gly Asp Gly Pro Arg Ser Thr Ile Arg Glu Asn Ile
    2390            2395            2400
Thr Tyr Leu Lys His Asp Ser Val Leu Lys Thr Ile Arg Gly Leu
    2405            2410            2415
Val Glu Glu Asn Pro Glu Val Ala Val Asp Cys Val Ile Tyr Leu
    2420            2425            2430
Ser Gln His Ile Ser Pro Ala Glu Arg Ala Gln Val Val His Leu
    2435            2440            2445
Leu Ser Thr Met Asp Ser Pro Ala Ser Thr
    2450            2455
```

N1/N2-LACTAM ACETYL-COA CARBOXYLASE INHIBITORS

FIELD OF THE INVENTION

This invention relates to substituted pyrazolospiroketone compounds that act as inhibitors of an acetyl-CoA carboxylase(s) and their use in treating diseases, conditions or disorders modulated by the inhibition of acetyl-CoA carboxylase enzyme(s).

BACKGROUND OF THE INVENTION

Acetyl-CoA carboxylases (ACC) are a family of enzymes found in most species and are associated with fatty acid synthesis and metabolism through catalyzing the production of malonyl-CoA from acetyl-CoA. In mammals, two isoforms of the ACC enzyme have been identified. ACC1, which is expressed at high levels in lipogenic tissues, such as fat and the liver, controls the first committed step in the biosynthesis of long-chain fatty acids. If acetyl-CoA is not carboxylated to form malonyl-CoA, it is metabolized through the Krebs cycle. ACC2, a minor component of hepatic ACC but the predominant isoform in heart and skeletal muscle, catalyzes the production of malonyl-CoA at the cytosolic surface of mitochondria, and regulates how much fatty acid is utilized in β-oxidation by inhibiting carnitine palm itoyl transferase. Thus, by increasing fatty acid utilization and by preventing increases in de novo fatty acid synthesis, chronic administration of an ACC inhibitor (ACC-I) may also deplete liver and adipose tissue triglyceride (TG) stores in obese subjects consuming a high or low-fat diet, leading to selective loss of body fat.

Studies conducted by Abu-Etheiga, et al., suggest that ACC2 plays an essential role in controlling fatty acid oxidation and, as such it would provide a target in therapy against obesity and obesity-related diseases, such as type-2 diabetes. See, Abu-Etheiga, L., et al., "Acetyl-CoA carboxylase 2 mutant mice are protected against obesity and diabetes induced by high-fat/high-carbohydrate diets" *PNAS*, 100(18) 10207-10212 (2003). See also, Choi, C. S., et al., "Continuous fat oxidation in acetyl-CoA carboxylase 2 knockout mice increases total energy expenditure, reduces fat mass, and improves insulin sensitivity" *PNAS*, 104(42) 16480-16485 (2007).

It is becoming increasingly clear that hepatic lipid accumulation causes hepatic insulin resistance and contributes to the pathogenesis of type 2 diabetes. Salvage, et al., demonstrated that ACC1 and ACC2 are both involved in regulating fat oxidation in hepatocytes while ACC1, the dominant isoform in rat liver, is the sole regulator of fatty acid synthesis. Furthermore, in their model, combined reduction of both isoforms is required to significantly lower hepatic malonyl-CoA levels, increase fat oxidation in the fed state, reduce lipid accumulation, and improve insulin action in vivo. Thus, showing that hepatic ACC1 and ACC2 inhibitors may be useful in the treatment of nonalcoholic fatty liver disease (NAFLD) and hepatic insulin resistance. See, Savage, D. B., et al., "Reversal of diet-induced hepatic steatosis and hepatic insulin resistance by antisense oligonucleotide inhibitors of acetyl-CoA carboxylases 1 and 2" *J Clin Invest* doi: 10.1172/JCI27300. See also, Oh, W., et al., "Glucose and fat metabolism in adipose tissue of acetyl-CoA carboxylase 2 knockout mice" *PNAS*, 102(5) 1384-1389 (2005).

Consequently, there is a need for medicaments containing ACC1 and/or ACC2 inhibitors to treat obesity and obesity-related diseases (such as, NAFLD and type-2 diabetes) by inhibiting fatty acid synthesis and by increasing fatty acid oxidation.

SUMMARY OF THE INVENTION

The present invention relates to compounds having the structure of Formula (I)

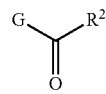

Formula (I)

wherein G is

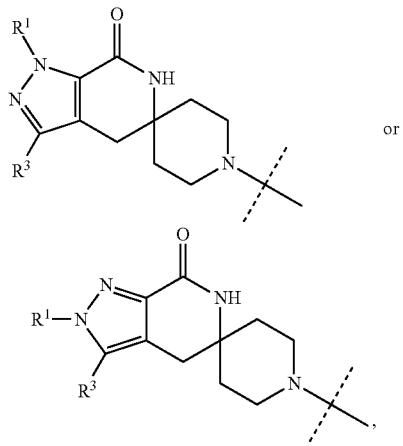

$R^1$ is a $(C_1-C_6)$alkyl or $(C_3-C_5)$ cycloalkyl; $R^2$ is phenyl, naphthyl, a 5 to 12 membered heteroaryl or a 8 to 12 membered fused heterocyclicaryl; wherein each $R^2$ group is optionally substituted with one to three substituents independently selected from $(C_1-C_3)$alkyl, $(C_1-C_3)$alkoxy halo and $CONH_2$; and $R^3$ is hydrogen or $(C_1-C_3)$alkyl; or a pharmaceutically acceptable salt thereof.

A preferred embodiment of the present invention are compounds of Formula (I) wherein $R^1$ is isopropyl or t-butyl; or a pharmaceutically acceptable salt thereof.

Another preferred embodiment of the present invention are compounds of Formula (I) wherein $R^2$ is benzoimidazolyl, pyrrolopyridinyl, pyrazolopyridinyl, indazolyl, quinolinyl or isoquinolinyl, said $R^2$ is optionally mono- or di-substituted independently with one to two substituents independently selected from a $(C_1-C_3)$alkyl, $(C_1-C_3)$alkoxy and halo; or a pharmaceutically acceptable salt thereof. Yet another preferred embodiment of the present invention are compounds of Formula (I) wherein $R^2$ is indazolyl, benzoimidazolyl, or 1H-pyrrolo[3,2-b]pyridinyl, said $R^2$ isoptionally substituted with one to two methyl, methoxy or chloro; or a pharmaceutically acceptable salt thereof.

Another preferred embodiment of the present invention is a compound selected from 1'-isopropyl-1-(2-methyl-1H-benzo[d]imidazole-5-carbonyl)-4',6'-dihydrospiro[piperidine-4,5'-pyrazolo[3,4-c]pyridin]-7'(1'H)-one; 1'-isopropyl-1-(2-methyl-2H-indazole-5-carbonyl)-4',6'-dihydrospiro[piperidine-4,5'-pyrazolo[3,4-c]pyridin]-7'(1'H)-one; 1'-isopropyl-1-(1H-pyrrolo[2,3-b]pyridine-5-carbonyl)-4', 6'-dihydrospiro[piperidine-4,5'-pyrazolo[3,4-c]pyridin]-7'

(1'H)-one; and 1'-isopropyl-1-(1H-pyrrolo[3,2-b]pyridine-6-carbonyl)-4',6'-dihydrospiro[piperidine-4,5'-pyrazolo[3,4-c]pyridin]-7'(1'H)-one; or a pharmaceutically acceptable salt thereof.

Another preferred embodiment of the present invention is a compound selected from 1'-isopropyl-1-(1-methyl-1H-indazole-5-carbonyl)-4',6'-dihydrospiro[piperidine-4,5'-pyrazolo[3,4-c]pyridin]-7'(1'H)-one; 1-(4,8-dimethoxyquinoline-2-carbonyl)-1'-isopropyl-4',6'-dihydrospiro[piperidine-4,5'-pyrazolo[3,4-c]pyridin]-7'(1'H)-one; 1'-isopropyl-1-(1H-pyrrolo[3,2-b]pyridine-2-carbonyl)-4',6'-dihydrospiro[piperidine-4,5'-pyrazolo[3,4-c]pyridin]-7'(1'H)-one; and 1'-isopropyl-1-(1H-pyrazolo[4,3-b]pyridine-6-carbonyl)-4',6'-dihydrospiro[piperidine-4,5'-pyrazolo[3,4-c]pyridin]-7'(1'H)-one; or a pharmaceutically acceptable salt thereof.

Another preferred embodiment of the present invention is a compound selected from 1-(3,7-dimethyl-1H-indazole-5-carbonyl)-1'-isopropyl-4',6'-dihydrospiro[piperidine-4,5'-pyrazolo[3,4-c]pyridin]-7'(1'H)-one; 1'-isopropyl-1-(7-methyl-1H-indazole-5-carbonyl)-4',6'-dihydrospiro[piperidine-4,5'-pyrazolo[3,4-c]pyridin]-7'(1'H)-one; 1-(1H-indazole-5-carbonyl)-1'-isopropyl-4',6'-dihydrospiro[piperidine-4,5'-pyrazolo[3,4-c]pyridin]-7'(1'H)-one; 1'-tert-butyl-1-(1H-indazole-5-carbonyl)-4',6'-dihydrospiro[piperidine-4,5'-pyrazolo[3,4-c]pyridin]-7'(1'H)-one; 1'-tert-butyl-1-(7-methyl-1H-indazole-5-carbonyl)-4',6'-dihydrospiro[piperidine-4,5'-pyrazolo[3,4-c]pyridin]-7'(1'H)-one; and 1'-tert-butyl-1-(3,7-dimethyl-1H-indazole-5-carbonyl)-4',6'-dihydrospiro[piperidine-4,5'-pyrazolo[3,4-c]pyridin]-7'(1'H)-one; or a pharmaceutically acceptable salt thereof.

Another preferred embodiment of the present invention is a compound selected from 1-(7-chloro-1H-indazole-5-carbonyl)-1'-isopropyl-4',6'-dihydrospiro[piperidine-4,5'-pyrazolo[3,4-c]pyridin]-7'(1'H)-one; 1'-isopropyl-1-(4-methoxy-1H-indazole-6-carbonyl)-4',6'-dihydrospiro[piperidine-4,5'-pyrazolo[3,4-c]pyridin]-7'(1'H)-one; 1-(7-ethyl-1H-indazole-5-carbonyl)-1'-isopropyl-4',6'-dihydrospiro[piperidine-4,5'-pyrazolo[3,4-c]pyridin]-7'(1'H)-one; 1-(3-ethyl-1H-indazole-5-carbonyl)-1'-isopropyl-4',6'-dihydrospiro[piperidine-4,5'-pyrazolo[3,4-c]pyridin]-7'(1'H)-one; and 1'-isopropyl-1-(3-methyl-1H-indazole-5-carbonyl)-4',6'-dihydrospiro[piperidine-4,5'-pyrazolo[3,4-c]pyridin]-7'(1'H)-one; or a pharmaceutically acceptable salt thereof.

Another preferred embodiment of the present invention is a compound selected from 1-(1H-indazole-5-carbonyl)-2'-isopropyl-4',6'-dihydrospiro[piperidine-4,5'-pyrazolo[3,4-c]pyridin]-7'(2'H)-one; 2'-tert-butyl-1-(1H-indazole-5-carbonyl)-4',6'-dihydrospiro[piperidine-4,5'-pyrazolo[3,4-c]pyridin]-7'(2'H)-one; 2'-isopropyl-1-(7-methyl-1H-indazole-5-carbonyl)-4',6'-dihydrospiro[piperidine-4,5'-pyrazolo[3,4-c]pyridin]-7'(2'H)-one; 1-(3,7-dimethyl-1H-indazole-5-carbonyl)-2'-isopropyl-4',6'-dihydrospiro[piperidine-4,5'-pyrazolo[3,4-c]pyridin]-7'(2'H)-one; 2'-tert-butyl-1-(7-methyl-1H-indazole-5-carbonyl)-4',6'-dihydrospiro[piperidine-4,5'-pyrazolo[3,4-c]pyridin]-7'(2'H)-one; 2'-tert-butyl-1-(3,7-dimethyl-1H-indazole-5-carbonyl)-4',6'-dihydrospiro[piperidine-4,5'-pyrazolo[3,4-c]pyridin]-7'(2'H)-one; and 2'-isopropyl-1-(2-methyl-1H-benzo[d]imidazole-5-carbonyl)-4',6'-dihydrospiro[piperidine-4,5'-pyrazolo[3,4-c]pyridin]-7'(2'H)-one; or a pharmaceutically acceptable salt thereof.

Another preferred embodiment of the present invention is a compound selected from 1'-isopropyl-1-(quinoline-3-carbonyl)-4',6'-dihydrospiro[piperidine-4,5'-pyrazolo[3,4-c]pyridin]-7'(1'H)-one; 1'-isopropyl-1-(quinoline-6-carbonyl)-4',6'-dihydrospiro[piperidine-4,5'-pyrazolo[3,4-c]pyridin]-7'(1'H)-one; 1'-isopropyl-1-(isoquinoline-6-carbonyl)-4',6'-dihydrospiro[piperidine-4,5'-pyrazolo[3,4-c]pyridin]-7'(1'H)-one; 1'-isopropyl-1-(isoquinoline-7-carbonyl)-4',6'-dihydrospiro[piperidine-4,5'-pyrazolo[3,4-c]pyridin]-7'(1'H)-one; and 1'-isopropyl-1-(quinoline-7-carbonyl)-4',6'-dihydrospiro[piperidine-4,5'-pyrazolo[3,4-c]pyridin]-7'(1'H)-one; or a pharmaceutically acceptable salt thereof.

Another embodiment of the present invention is the compound of Formula (I)

or a pharmaceutically acceptable salt thereof; wherein G is

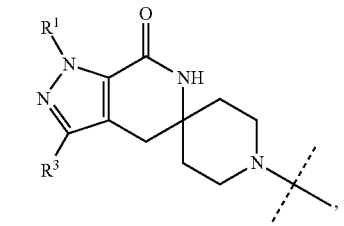

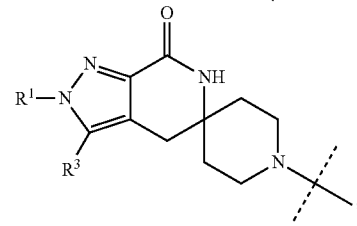

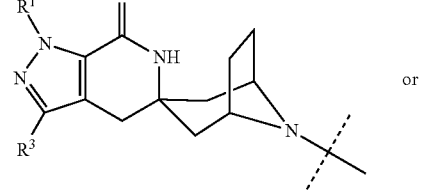

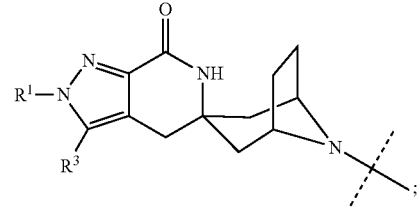

$R^1$ is a $(C_1-C_6)$alkyl or $(C_3-C_5)$ cycloalkyl; $R^2$ is phenyl; naphthyl; a 5 to 12 membered heteroaryl or a 8 to 12 membered fused heterocyclicaryl; wherein each $R^2$ group is optionally substituted with one to three substituents independently selected from $(C_1-C_6)$alkyl, $(C_3-C_7)$cycloalkyl, $(C_1-C_6)$alkoxy, halo, cyano, $CONR^4R^5$, $NR^4R^5$, or a 3 to 7 membered heterocyclyl, wherein said $(C_1-C_6)$alkyl, $(C_3-C_7)$cycloalkyl or $(C_1-C_6)$alkoxy are optionally substituted with 1 to 5 fluoro; $R^3$ is hydrogen or $(C_1-C_3)$alkyl; and $R^4$ and $R^5$ at each occurrence are independently selected from hydrogen, $(C_1-C_6)$alkyl, $(C_3-C_7)$cycloalkyl, $(C_1-C_3)$alkoxy-$(C_1-C_6)$alkyl or a 3 to 7 membered heterocyclyl; wherein said $(C_1$-

$C_6$)alkyl, ($C_3$-$C_7$)cycloalkyl or ($C_1$-$C_3$)alkoxy-($C_1$-$C_6$)alkyl are optionally substituted with 1 to 5 fluoro.

Yet another embodiment of the present invention is the compound of Formula (I) wherein G is

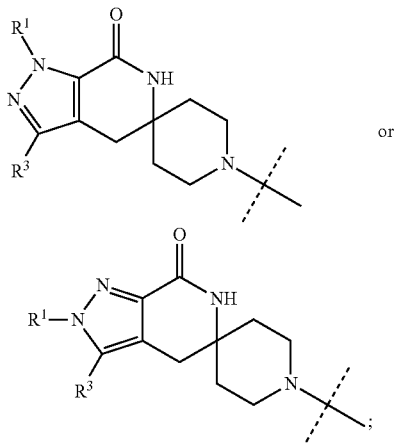

or and $R^1$ is isopropyl or t-butyl; or a pharmaceutically acceptable salt thereof.

Another embodiment of the present invention is the compound of Formula (I) wherein $R^2$ is benzoimidazolyl, benzotriazolyl, pyrrolopyridinyl, pyrazolopyridinyl, indolyl, indazolyl, quinolinyl or isoquinolinyl, said $R^2$ is optionally substituted with one to two substituents independently selected from ($C_1$-$C_6$)alkyl, ($C_1$-$C_6$)alkoxy, halo or $NR^4R^5$, wherein said ($C_1$-$C_6$)alkyl or ($C_1$-$C_6$)alkoxy are optionally substituted with 1 to 5 fluoro; or a pharmaceutically acceptable salt thereof.

Another embodiment of the present invention is the compound of Formula (I) wherein $R^2$ is indazolyl, indolyl, benzoimidazolyl, or 1H-pyrrolo[3,2-b]pyridinyl, said $R^2$ optionally substituted independently with one to two methyl, methoxy, $NH_2$, $NHCH_3$ or chloro; or a pharmaceutically acceptable salt thereof.

Yet another embodiment of the present invention is the compound of Formula (I) wherein $R^2$ is quinolinyl or isoquinolinyl, said $R^2$ optionally substituted independently with one to two methyl, methoxy, $NH_2$, $NHCH_3$, $NHCH_2CH_3$, $NHCH_2CF_3$ or chloro; or a pharmaceutically acceptable salt thereof.

A preferred embodiment of the present invention is a compound selected from the group consisting of 1-(3,7-dimethyl-1H-indazole-5-carbonyl)-1'-isopropyl-4',6'-dihydrospiro[piperidine-4,5'-pyrazolo[3,4-c]pyridin]-7'(1'H)-one; 1-(3,7-dimethyl-1H-indazole-5-carbonyl)-1'-tert-butyl-4',6'-dihydrospiro[piperidine-4,5'-pyrazolo[3,4-c]pyridin]-7'(1'H)-one; 1-(3,7-dimethyl-1H-indazole-5-carbonyl)-2'-isopropyl-4',6'-dihydrospiro[piperidine-4,5'-pyrazolo[3,4-c]pyridin]-7'(1'H)-one; 1-(6-methoxyquinoline-3-carbonyl)-2'-tert-butyl-4',6'-dihydrospiro[piperidine-4,5'-pyrazolo[3,4-c]pyridin]-7'(1'H)-one; 1-(1-methoxyisoquinoline-7-carbonyl)-2'-tert-butyl-4',6'-dihydrospiro[piperidine-4,5'-pyrazolo[3,4-c]pyridin]-7'(1'H)-one; 1-(3-chloro-7-methyl-1H-indazole-5-carbonyl)-2'-tert-butyl-4',6'-dihydrospiro[piperidine-4,5'-pyrazolo[3,4-c]pyridin]-7'(1'H)-one; 1-(2-methoxyquinoline-7-carbonyl)-2'-tert-butyl-4',6'-dihydrospiro[piperidine-4,5'-pyrazolo[3,4-c]pyridin]-7'(1'H)-one; 1-(2-aminoquinoline-7-carbonyl)-2'-tert-butyl-4',6'-dihydrospiro[piperidine-4,5'-pyrazolo[3,4-c]pyridin]-7'(1'H)-one; 1-(5-methoxyquinoline-3-carbonyl)-2'-tert-butyl-4',6'-dihydrospiro[piperidine-4,5'-pyrazolo[3,4-c]pyridin]-7'(1'H)-one; 1-(2-amino-1H-benzo[d]imidazole-5-carbonyl)-2'-tert-butyl-4',6'-dihydrospiro[piperidine-4,5'-pyrazolo[3,4-c]pyridin]-7'(1'H)-one; 1-(2-(methylamino)quinoline-7-carbonyl)-2'-tert-butyl-4',6'-dihydrospiro[piperidine-4,5'-pyrazolo[3,4-c]pyridin]-7'(1'H)-one; 1-(1-(methylamino)isoquinoline-7-carbonyl)-2'-tert-butyl-4',6'-dihydrospiro[piperidine-4,5'-pyrazolo[3,4-c]pyridin]-7'(1'H)-one; 1-(3-chloro-1H-indole-6-carbonyl)-2'-tert-butyl-4',6'-dihydrospiro[piperidine-4,5'-pyrazolo[3,4-c]pyridin]-7'(1'H)-one; 1-(3-chloro-1H-pyrrolo[3,2-b]pyridine-6-carbonyl)-2'-tert-butyl-4',6'-dihydrospiro[piperidine-4,5'-pyrazolo[3,4-c]pyridin]-7'(1'H)-one; 1-(2-(methylamino)quinoline-7-carbonyl)-1'-isopropyl-4',6'-dihydrospiro[piperidine-4,5'-pyrazolo[3,4-c]pyridin]-7'(1'H)-one; 1-(1-(2,2,2-trifluoroethylamino)quinoline-7-carbonyl)-2'-tert-butyl-4',6'-dihydrospiro[piperidine-4,5'-pyrazolo[3,4-c]pyridin]-7'(1'H)-one; and 1-(1-(ethylamino)isoquinoline-7-carbonyl)-2'-tert-butyl-4',6'-dihydrospiro[piperidine-4,5'-pyrazolo[3,4-c]pyridin]-7'(1'H)-one; or a pharmaceutically acceptable salt thereof.

Another aspect of the present invention is a pharmaceutical composition comprising an amount of a compound of Formula (I) as described in any of the embodiments; or a pharmaceutically acceptable salt thereof and a pharmaceutically acceptable excipient, diluent, or carrier. Preferably, the composition comprises a therapeutically effective amount of a compound of the present invention. The composition may also contain at least one additional pharmaceutical agent. Preferred agents include anti-diabetic agents and/or anti-obesity agents.

In yet another aspect of the present invention is a method for treating a disease, condition, or disorder mediated by the inhibition of acetyl-CoA carboxylase enzyme(s) in a mammal that includes the step of administering to a mammal, preferably a human, in need of such treatment a therapeutically effective amount of a compound of the present invention, or a pharmaceutically acceptable salt thereof or a pharmaceutical composition thereof.

Diseases, disorders, or conditions mediated by inhibitors of acetyl-CoA carboxylases include Type II diabetes and diabetes-related diseases, such as nonalcoholic fatty liver disease (NAFLD), hepatic insulin resistance, hyperglycemia, metabolic syndrome, impaired glucose tolerance, diabetic neuropathy, diabetic nephropathy, diabetic retinopathy, obesity, dyslipidemia, hypertension, hyperinsulinemia, and insulin resistance syndrome. Preferred diseases, disorders, or conditions include Type II diabetes, nonalcoholic fatty liver disease (NAFLD), hepatic insulin resistance, hyperglycemia, impaired glucose tolerance, obesity, and insulin resistance syndrome. More preferred are Type II diabetes, nonalcoholic fatty liver disease (NAFLD), hepatic insulin resistance, hyperglycemia, and obesity. Most preferred is Type II diabetes.

A preferred embodiment is a method for treating (e.g. delaying the progression or onset of) Type 2 diabetes and diabetes-related disorders in animals comprising the step of administering to an animal in need of such treatment a therapeutically effective amount of a compound of the present invention or a pharmaceutically acceptable salt thereof or a composition thereof.

Another preferred embodiment is a method for treating obesity and obesity-related disorders in animals comprising the step of administering to an animal in need of such treatment a therapeutically effective amount of a compound of the present invention or a pharmaceutically acceptable salt thereof or a composition thereof.

Yet another preferred embodiment is a method for treating nonalcoholic fatty liver disease (NAFLD) or hepatic insulin resistance in animals comprising the step of administering to an animal in need of such treatment a therapeutically effective amount of a compound of the present invention or a pharmaceutically acceptable salt thereof or a composition thereof.

Compounds of the present invention may be administered in combination with other pharmaceutical agents (in particular, anti-obesity and anti-diabetic agents described herein below). The combination therapy may be administered as (a) a single pharmaceutical composition which comprises a compound of the present invention, at least one additional pharmaceutical agent described herein and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

BRIEF DESCRIPTION OF THE DRAWINGS

FIG. 1 SEQ. ID NO. 1 provides a sequence of recombinant human ACC1 (SEQ. ID NO. 1) that can be employed in the Transcreener in vitro assay.

FIG. 2 SEQ. ID NO. 2 provides a sequence of recombinant human ACC2 (SEQ. ID NO. 2) that can be employed in the Transcreener in vitro assay.

DETAILED DESCRIPTION OF THE INVENTION

Definitions

The phrase "therapeutically effective amount" means an amount of a compound of the present invention or a pharmaceutically acceptable salt thereof that: (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulated" or "modulating", or "modulate(s)", as used herein, unless otherwise indicated, refers to the inhibition of the Acetyl-CoA carboxylases (ACC) enzyme(s) with compounds of the present invention.

The terms "mediated" or "mediating" or "mediate(s)", as used herein, unless otherwise indicated, refers to the (i) treatment or prevention the particular disease, condition, or disorder, (ii) attenuation, amelioration, or elimination of one or more symptoms of the particular disease, condition, or disorder, or (iii) prevention or delay of the onset of one or more symptoms of the particular disease, condition, or disorder described herein, by inhibiting the Acetyl-CoA carboxylases (ACC) enzyme(s). The term "compounds of the present invention" (unless specifically identified otherwise) refer to compounds of Formula (I) and any pharmaceutically acceptable salts of the compounds, as well as, all stereoisomers (including diastereoisomers and enantiomers), tautomers, conformational isomers, and isotopically labeled compounds. Hydrates and solvates of the compounds of the present invention are considered compositions of the present invention, wherein the compound is in association with water or solvent, respectively.

The terms "$(C_1-C_6)$alkyl" and "$(C_1-C_3)$alkyl" are alkyl groups of the specified number of carbons, from one to six or one to three carbons, respectively, which can be either straight chain or branched. For example, the term "$(C_1-C_3)$alkyl" has from one to three carbons and consists of methyl, ethyl, n-propyl and isopropyl.

The term "$(C_3-C_7)$cycloalkyl" means a cycloalkyl group with three to seven carbon atoms and consists of cyclopropyl, cyclobutyl, cyclopentyl, cyclohexyl and cycloheptyl. The term "halo" means fluoro, chloro, bromo or iodo. The term "$(C_6-C_{10})$aryl" means an aromatic carbocyclic group consisting of six to ten carbon atoms such as phenyl or naphthyl.

The term "5 to 12 membered heteroaryl" means a five to twelve membered aromatic group which contains at least one heteroatom selected from nitrogen, oxygen and sulfur. As used herein the point of attachment of the "5 to 12 membered heteroaryl" group is on a carbon atom of that group. The "5 to 12 membered heteroaryl" group can be bicyclic. Preferred embodiments of bicyclic heteroaryls include, but are not limited to, radicals of the following ring systems:

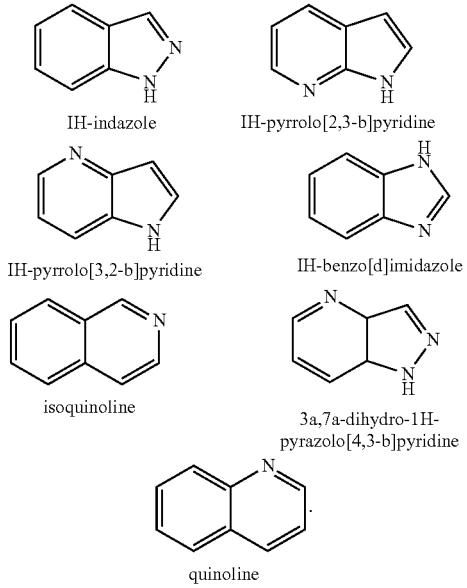

The term "8 to 12 membered fused heterocyclicaryl" means an 8 to 12 membered ring system in which a non-aromatic heterocyclic ring is fused to an aryl ring. As used herein the point of attachment of the "8 to 12 membered fused heterocyclicaryl" group is on a carbon atom of that group. The term "3 to 7 membered heterocyclyl" means a three to seven membered saturated ring wherein one to three of the atoms are heteroatoms selected independently from nitrogen, oxygen and sulfur. Examples of "3 to 7 membered heterocyclyl"

groups include but are not limited to groups such as aziridinyl, azetidinyl, pyrrolidinyl, piperidinyl, oxiranyl, oxetanyl, tetrahydrofuranyl, tetrahydro-2H-pyranyl, tetrahydro-2H-thiopyranyl, piperazinyl, morpholinyl and thiomorpholinyl. The point of attachment for the "3 to 7 membered heterocyclyl" can be on a carbon or nitrogen atom, as appropriate for the particular group.

In one embodiment, the compound of Formula I is a N1 lactam ACC inhibitor compound having the following structure:

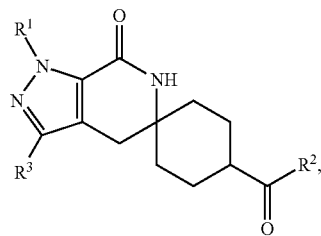

wherein $R^1$ is a $(C_1-C_6)$alkyl or $(C_3-C_5)$cycloalkyl; $R^2$ is phenyl, naphthyl, a 5 to 12 membered heteroaryl, or a 8 to 12 membered fused heterocyclicaryl; wherein each $R^2$ group is optionally substituted with one to three substituents independently selected from $(C_1-C_3)$alkyl, $(C_1-C_3)$alkoxy, halo and CON $H_2$; and $R^3$ is hydrogen or $(C_1-C_3)$alkyl; or a pharmaceutically acceptable salt thereof.

In one embodiment, the compound of Formula I is a N2 lactam ACC inhibitor compound having the following structure:

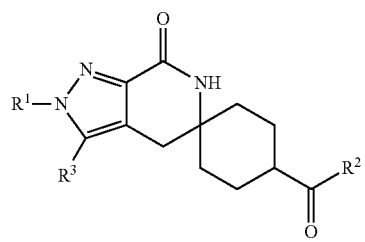

wherein $R^1$ is a $(C_1-C_6)$alkyl or $(C_3-C_5)$cycloalkyl; $R^2$ is phenyl; naphthyl; a 5 to 12 membered heteroaryl or a 8 to 12 membered fused heterocyclicaryl; wherein each $R^2$ group is optionally substituted with one to three substituents independently selected from $(C_1-C_3)$alkyl, $(C_1-C_3)$alkoxy, halo and CON $H_2$; and $R^3$ is hydrogen or $(C_1-C_3)$alkyl; or a pharmaceutically acceptable salt thereof.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie*, 4, Aufl. ed. Springer-Verlag, Berlin, including supplements (also available via the *Beilstein* online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). Similarly, a "hydroxy-protecting group" refers to a substituent of a hydroxy group that blocks or protects the hydroxy functionality. Suitable hydroxyl-protecting groups (O-Pg) include for example, allyl, acetyl, silyl, benzyl, para-methoxybenzyl, trityl, and the like. The need for such protection is readily determined by one skilled in the art. For a general description of protecting groups and their use, see T. W. Greene, *Protective Groups in Organic Synthesis*, John Wiley & Sons, New York, 1991.

The following reaction schemes, Reaction Schemes I through Reaction Scheme V, provide representative procedures that are used to prepare the compounds of Formula (I). It is to be understood that these reaction schemes are to be construed in a non-limiting manner and that reasonable variations of the depicted methods can be used to prepare the compounds of Formula (I).

Reaction Scheme I outlines the general procedures one could use to provide N1 lactam ACC inhibitor compounds of the present invention having Formula Ia, in which $R^1$ is a $(C_1-C_6)$alkyl or $(C_3-C_5)$cycloalkyl and $R^2$ is phenyl, naphthyl, a 5 to 12 membered heteroaryl or a 8 to 12 membered fused heterocyclicaryl; wherein each $R^2$ group is optionally substituted with one to three substituents independently selected from $(C_1-C_3)$alkyl, $(C_1-C_3)$alkoxy, halo and $CONH_2$.

REACTION SCHEME I

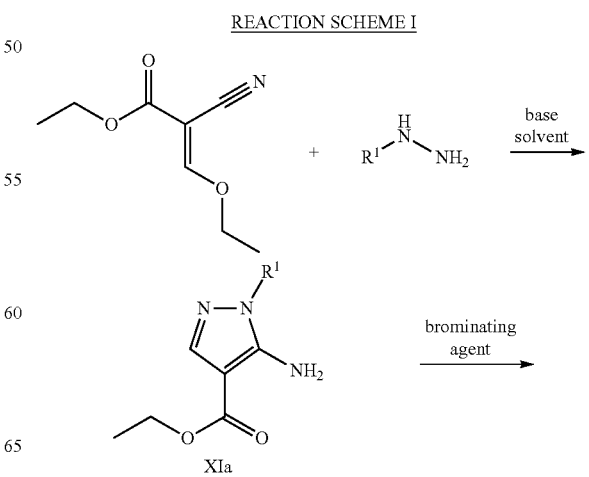

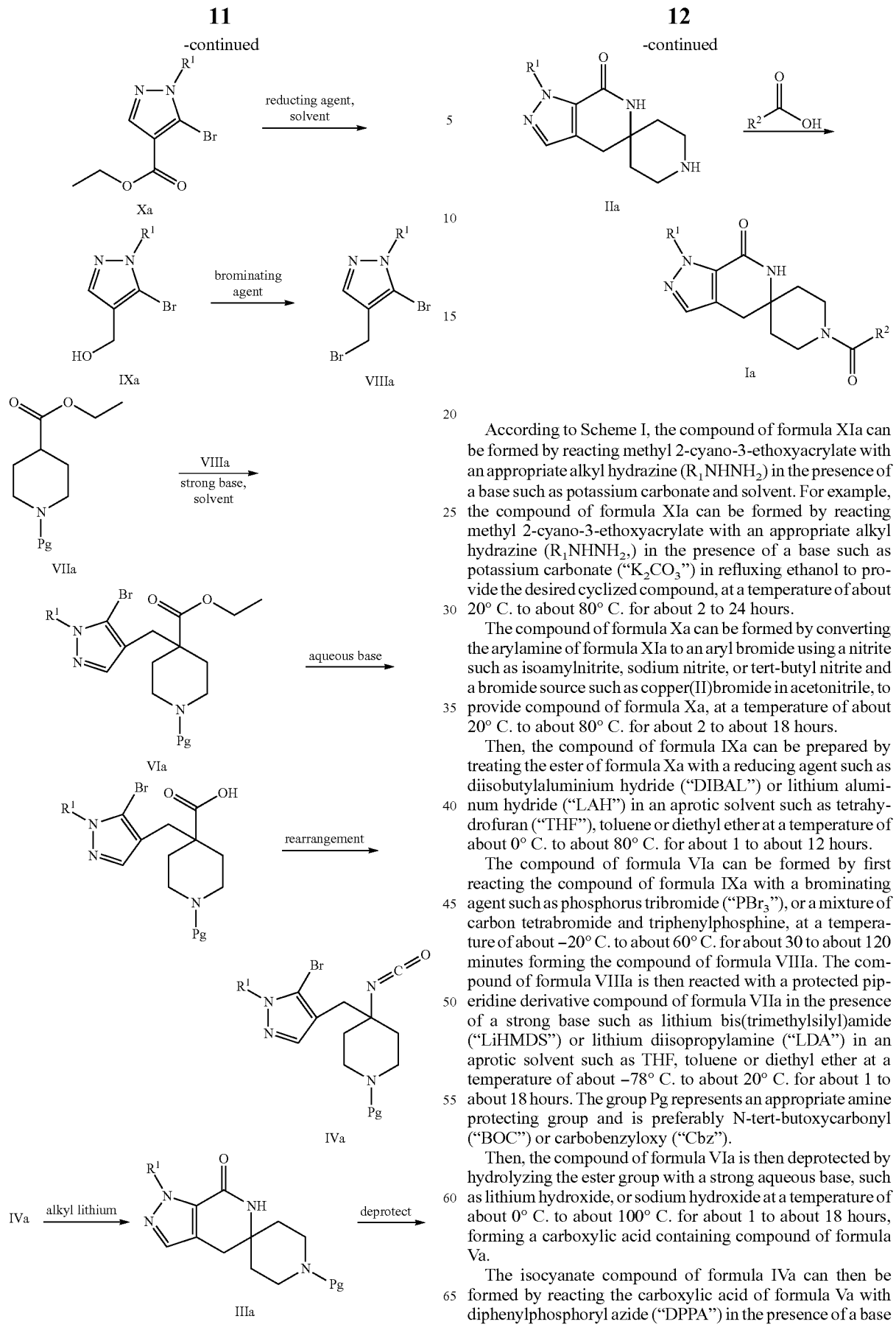

According to Scheme I, the compound of formula XIa can be formed by reacting methyl 2-cyano-3-ethoxyacrylate with an appropriate alkyl hydrazine ($R_1NHNH_2$) in the presence of a base such as potassium carbonate and solvent. For example, the compound of formula XIa can be formed by reacting methyl 2-cyano-3-ethoxyacrylate with an appropriate alkyl hydrazine ($R_1NHNH_2$,) in the presence of a base such as potassium carbonate ("$K_2CO_3$") in refluxing ethanol to provide the desired cyclized compound, at a temperature of about 20° C. to about 80° C. for about 2 to 24 hours.

The compound of formula Xa can be formed by converting the arylamine of formula XIa to an aryl bromide using a nitrite such as isoamylnitrite, sodium nitrite, or tert-butyl nitrite and a bromide source such as copper(II)bromide in acetonitrile, to provide compound of formula Xa, at a temperature of about 20° C. to about 80° C. for about 2 to about 18 hours.

Then, the compound of formula IXa can be prepared by treating the ester of formula Xa with a reducing agent such as diisobutylaluminium hydride ("DIBAL") or lithium aluminum hydride ("LAH") in an aprotic solvent such as tetrahydrofuran ("THF"), toluene or diethyl ether at a temperature of about 0° C. to about 80° C. for about 1 to about 12 hours.

The compound of formula VIa can be formed by first reacting the compound of formula IXa with a brominating agent such as phosphorus tribromide ("$PBr_3$"), or a mixture of carbon tetrabromide and triphenylphosphine, at a temperature of about −20° C. to about 60° C. for about 30 to about 120 minutes forming the compound of formula VIIIa. The compound of formula VIIIa is then reacted with a protected piperidine derivative compound of formula VIIa in the presence of a strong base such as lithium bis(trimethylsilyl)amide ("LiHMDS") or lithium diisopropylamine ("LDA") in an aprotic solvent such as THF, toluene or diethyl ether at a temperature of about −78° C. to about 20° C. for about 1 to about 18 hours. The group Pg represents an appropriate amine protecting group and is preferably N-tert-butoxycarbonyl ("BOC") or carbobenzyloxy ("Cbz").

Then, the compound of formula VIa is then deprotected by hydrolyzing the ester group with a strong aqueous base, such as lithium hydroxide, or sodium hydroxide at a temperature of about 0° C. to about 100° C. for about 1 to about 18 hours, forming a carboxylic acid containing compound of formula Va.

The isocyanate compound of formula IVa can then be formed by reacting the carboxylic acid of formula Va with diphenylphosphoryl azide ("DPPA") in the presence of a base such as triethylamine ("$Et_3N$") or diisopropylethylamine at a temperature of about 60° C. to about 120° C. for about 1 to about 12 hours. The lactam compound of formula IIIa can then be formed by cyclization of the isocyanate (formula IVa) using an alkyl lithium, such as n-butyllithium ("n-BuLi") or t-butyllithium ("t-BuLi") at a temperature of about −78° C. to about 0° C. for about 5 to about 120 minutes.

The lactam compound of formula (IIIa) can then be deprotected to provide the free spiropiperidine derivative of formula (IIa) using standard methods which depend on which protecting group Pg has been employed. For example, when Pg represents BOC, standard strong acid deprotection conditions, such as 4N hydrochloric acid in dioxane or trifluoroacetic acid in an appropriate solvent such as dichloromethane, can be used to remove the BOC group. When Pg represents Cbz, hydrogenation over palladium on carbon in ethanol or treatment with a hydrogen source such as ammonium formate or 1-methyl-1,4-cyclohexadiene in the presence of palladium on carbon in ethanol or ethyl acetate can be employed to carry out the deprotection.

The spiropiperidine derivative of Formula (IIa) can then be acylated by employing standard methods to provide the compound of Formula (Ia). For example, the compound (Ia) may then be formed using a standard peptide coupling reaction with the desired carboxylic acid ($R^2CO_2H$). For example, the spiropiperidine intermediate (IIa) and carboxylic acid ($R^2CO_2H$) may be coupled by forming an activated carboxylic acid ester, such as by contacting the carboxylic acid ($R^2CO_2H$) with a peptide coupling reagent, such as O-(7-azabenzotriazol-1-yl)-N,N,N',N'-tetramethyluronium hexafluorophosphate ("HATU") or 1-ethyl-3-(3-dimethyilaminopropyl)carbodiimide hydrocloride ("EDC.HCl"), in the presence or absence of an activating agent, such as hydroxybenzotriazole ("HOBt") and in the presence of a suitable base, such as N,N-diisopropylethylamine ("DIEA"), triethylamine or N-methylmorpholine ("NMM"), in a suitable solvent such as THF and/or DMF, dimethylacetamide ("DMA") or dichloromethane and then contacting the activated carboxylic acid ester with the spiropiperidine derivative (IIa) to form a compound of Formula (Ia).

Reaction Scheme II outlines the general procedures one could use to provide N2 lactam ACC inhibitor compounds of the present invention having Formula Ib, in which $R^1$ is a ($C_1$-$C_6$)alkyl or ($C_3$-$C_5$)cycloalkyl and $R^2$ is phenyl, naphthyl, a 5 to 12 membered heteroaryl or a 8 to 12 membered fused heterocyclicaryl; wherein each $R^2$ group is optionally substituted with one to three substituents independently selected from ($C_1$-$C_3$)alkyl, ($C_1$-$C_3$)alkoxy, halo and CONH$_2$.

REACTION SCHEME II

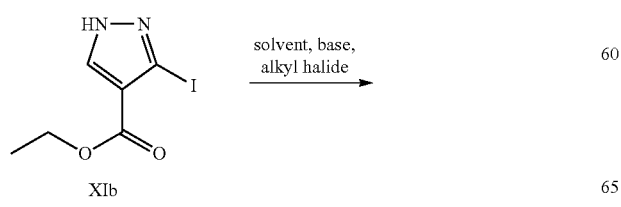

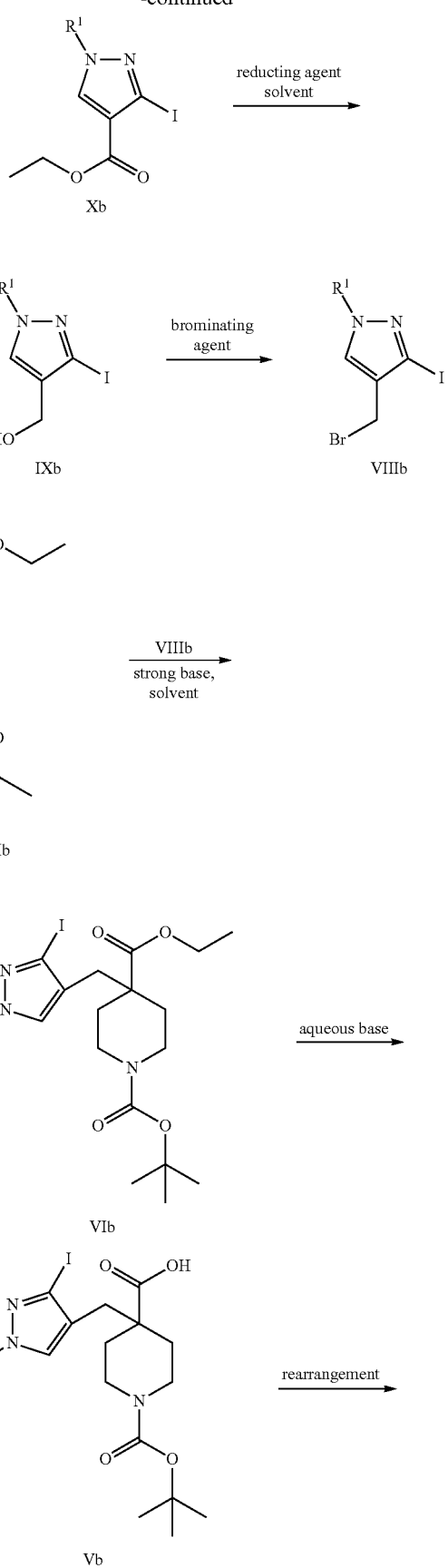

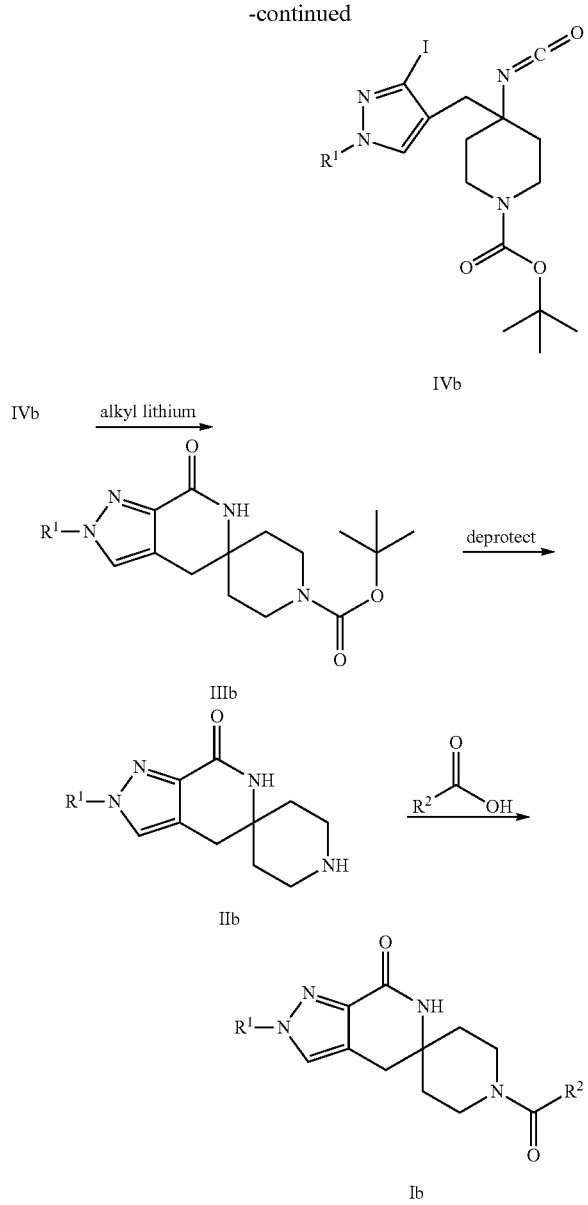

According to Scheme II, alkylation of the pyrazole compound of formula XIb to the compound of formula X using a primary or secondary alkyl halide, such as methyl iodide, ethyl iodide, 1-bromopropane, 1-iodopropane, 2-bromopropane, 2 iodopropane 1-iodobutane, 2-iodobutane, 1-iodo-2-methylpropane, or 1-(bromomethyl)cyclopropane, can be carried out in the presence of a base such as cesium carbonate ("$Cs_2CO_3$") or potassium carbonate ("$K_2CO_3$") and a solvent such as dimethylformamide ("DMF"), at a temperature of about 20° C. to about 100° C. for about 1 to about 12 hours.

Then, the compound of formula IXb can be prepared by treating formula Xb with a reducing agent such as DIBAL or LAH in an aprotic solvent such as THF, toluene, or diethyl ether, at a temperature of about −78° C. to about 60° C. for about 1 to about 12 hours.

The compound of formula VIb can be formed by first reacting the compound of formula IXb with a brominating agent such as $PBr_3$ or a mixture of carbon tetrabromide and triphenylphosphine, at a temperature of about −20° C. to about 60° C. for about 30 to about 120 minutes forming the compound of formula VIIIb. The compound of formula VIIIb is then reacted with a protected piperidine derivative compound of formula VIIb using a strong base such as lithium bis(trimethylsilyl)amide ("LiHMDS") or lithium diisopropylamine ("LDA") in an aprotic solvent such as THF, toluene or diethyl ether at a temperature of about −78° C. to about 20° C. for about 1 to about 18 hours. The group Pg represents an appropriate amine protecting group and is preferably BOC or Cbz.

Then, the compound formula VIb is then deprotected by hydrolyzing the ester group with a strong aqueous base, such as lithium hydroxide, or sodium hydroxide at a temperature of about 0° C. to about 100° C. for about 1 to about 18 hours, forming a carboxylic acid containing compound of formula Vb. The isocyanate compound of formula IVb can then be formed by reacting the carboxylic acid of formula Vb with DPPA in the presence of a base such as $Et_3N$ or diisopropylethylamine at a temperature of about 60° C. to about 120° C. for about 1 to about 12 hours.

The lactam compound of formula IIIb can then be formed by cyclization of the isocyanate (formula IVb) using an alkyl lithium, such as n-BuLi or t-BuLi at a temperature of about −78° C. to about 0° C. for about 5 to about 120 minutes.

The lactam compound of formula (IIIb) can then be deprotected to provide the free spiropiperidine derivative of formula (IIb) using standard methods which depend on which protecting group Pg has been employed. For example, when Pg represents BOC, standard strong acid deprotection conditions, such as 4N hydrochloric acid in dioxane or trifluoroacetic acid in an appropriate solvent such as dichloromethane, can be used to remove the BOC group. When Pg represents Cbz, hydrogenation over palladium on carbon in ethanol or treatment with a hydrogen source such as ammonium formate or 1-methyl-1,4-cyclohexadiene in the presence of palladium on carbon in ethanol or ethyl acetate can be employed to carry out the deprotection.

The spiropiperidine derivative of Formula (IIb) can then be acylated by employing standard methods to provide the compound of Formula (Ib). For example, the compound (Ib) may then be formed using a standard peptide coupling reaction with the desired carboxylic acid ($R^2CO_2H$). For example, the spiropiperidine intermediate (IIb) and carboxylic acid ($R^2CO_2H$) may be coupled by forming an activated carboxylic acid ester, such as by contacting the carboxylic acid ($R^2CO_2H$) with a peptide coupling reagent, such as HATU or EDC.HCl, in the presence or absence of an activating agent, such as HOBt and in the presence of a suitable base, such as DIEA, NMM, in a suitable solvent such as THF and/or DMF, DMA or dichloromethane and then contacting the activated carboxylic acid ester with the spiropiperidine derivative (IIb) to form a compound of Formula (Ib).

Reaction Scheme III outlines the general procedures one could use to provide N2 lactam ACC inhibitor compounds of the present invention having Formula Ic, in which $R^1$ is a ($C_1$-$C_6$)alkyl or ($C_3$-$C_5$)cycloalkyl and $R^2$ is phenyl, naphthyl, a 5 to 12 membered heteroaryl or a 8 to 12 membered fused heterocyclicaryl; wherein each $R^2$ group is optionally substituted with one to three substituents independently selected from ($C_1$-$C_3$)alkyl, ($C_1$-$C_3$)alkoxy, halo and $CONH_2$.

REACTION SCHEME III

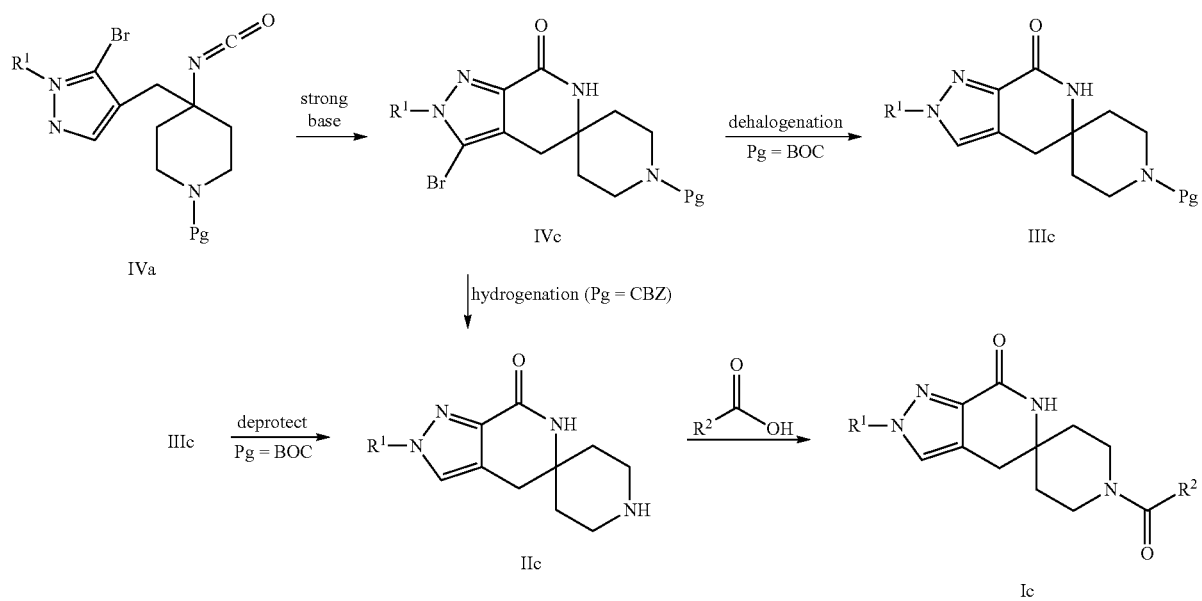

The lactam compound of formula IVc may be formed by cyclization of the isocyanate (formula IVa) using a strong base such as lithium 2,2,6,6-tetramethylpiperidide ("LTMP") or magnesium 2,2,6,6-tetramethylpiperidide at a temperature of about −78° C. to about 0° C. for about 30 minutes to about 6 hours.

The lactam compound of formula (IVc), when Pg represents BOC, may then be dehalogenated to provide the lactam compound of formula (IIIc) by hydrogenation in the presence of a base such as $Et_3N$ over palladium on carbon in ethanol or treatment with a hydrogen source such as ammonium formate or 1-methyl-1,4-cyclohexadiene in the presence of a base such as $Et_3N$ and palladium on carbon in ethanol or ethyl acetate at a temperature of about 20° C. to about 100° C. for about 30 minutes to about 6 hours.

The lactam compound of formula (IIIc), when Pg represents BOC, may then be deprotected to provide the free spiropiperidine derivative of formula (IIc) using standard strong acid deprotection conditions, such as 4N hydrochloric acid in dioxane or trifluoroacetic acid in an appropriate solvent such as dichloromethane, to remove the BOC group.

The lactam compound of formula (IVc), when Pg represents Cbz, may be dehalogenated and deprotected simultaneously by hydrogenation over palladium on carbon in ethanol or treatment with a hydrogen source such as ammonium formate or 1-methyl-1,4-cyclohexadiene in the presence of palladium on carbon in ethanol or ethyl acetate.

The spiropiperidine derivative of Formula (IIc) may then be acylated by employing standard methods to provide the compound of Formula (Ic). For example, the compound (Ic) may then be formed using a standard peptide coupling reaction with the desired carboxylic acid ($R^2CO_2H$). For example, the spiropiperidine intermediate (IIc) and carboxylic acid ($R^2CO_2H$) may be coupled by forming an activated carboxylic acid ester, such as by contacting the carboxylic acid ($R^2CO_2H$) with a peptide coupling reagent, such as HATU or EDC.HCl, in the presence or absence of an activating agent, such as HOBt and in the presence of a suitable base, such as DIEA, triethylamine or NMM, in a suitable solvent such as THF and/or DMF, DMA or dichloromethane and then contacting the activated carboxylic acid ester with the spiropiperidine derivative (IIc) to form a compound of Formula (Ic).

Reaction Scheme IV outlines the general procedures one could use to provide N2 lactam ACC inhibitor compounds of the present invention having Formula Id, in which $R^1$ is a $(C_1-C_6)$alkyl or $(C_3-C_5)$cycloalkyl and $R^2$ is phenyl, naphthyl, a 5 to 12 membered heteroaryl or a 8 to 12 membered fused heterocyclicaryl; wherein each $R^2$ group is optionally substituted with one to three substituents independently selected from $(C_1-C_3)$alkyl, $(C_1-C_3)$alkoxy, halo and $CONH_2$.

REACTION SCHEME IV

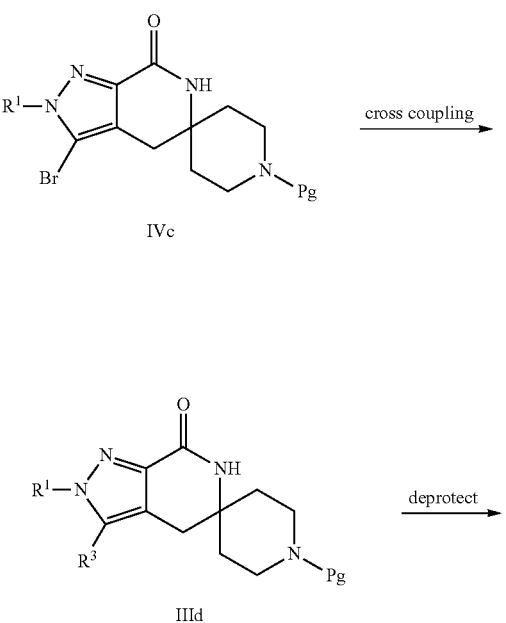

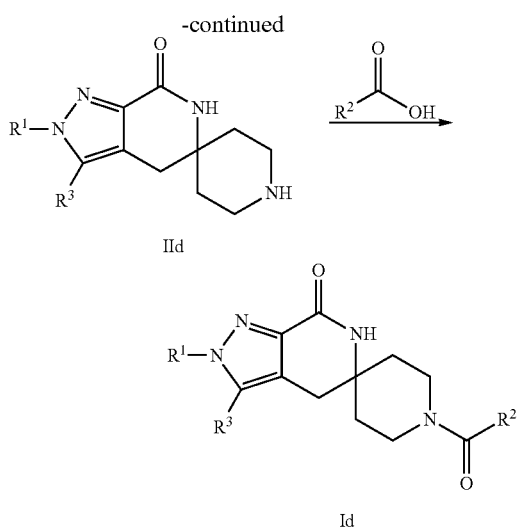

The lactam compound of formula IIId may be formed by palladium catalyzed cross-coupling of the bromide of formula IVc with an alkyl or alkenyl tributylstannane such as methyl tri-nbutylstannane or vinyl tri-nbutylstannane or allyl tri-nbutylstannane or a trialkyl boroxine such as trimethyl boroxine or trivinyl boroxine in the presence of a palladium catalyst such as tetrakis(triphenylphosphine)palladium(0) or a precatalyst and ligand combination such as palladium(II) acetate and 2-dicyclohexylphosphino-2',6'-dimethoxybiphenyl ("SPhos") and in the presence or absence of a base such as potassium carbonate in a protic solvent such as ethanol or t-amyl alcohol or an aprotic solvent such as tetrahydrofuran or dimethylformamide at a temperature of about 20° C. to about 100° C. for about 2 hours to about 18 hours or at a temperature of about 100° C. to about 150° C. for about 5 minutes to about 60 minutes under microwave heating. If a alkenyl trialkylstannane or alkenyl boroxine is utilized to install the $R^3$ group, reduction of the resulting olefin may be affected by hydrogenation over palladium on carbon in ethanol or treatment with a hydrogen source such as ammonium formate or 1-methyl-1,4-cyclohexadiene in the presence of palladium on carbon in ethanol or ethyl acetate.

The lactam compound of formula (IIId) may then be deprotected to provide the free spiropiperidine derivative of formula (IId) using standard methods which depend on which protecting group Pg has been employed. For example, when Pg represents BOC, standard strong acid deprotection conditions. such as 4N hydrochloric acid in dioxane or trifluoroacetic acid in an appropriate solvent such as dichloromethane, can be used to remove the BOC group. When Pg represents Cbz, hydrogenation over palladium on carbon in ethanol or treatment with a hydrogen source such as ammonium formate or 1-methyl-1,4-cyclohexadiene in the presence of palladium on carbon in ethanol or ethyl acetate may be employed to carry out the deprotection.

The spiropiperidine derivative of Formula (IId) may then be acylated by employing standard methods to provide the compound of Formula (Id). For example, the compound (Id) may then be formed using a standard peptide coupling reaction with the desired carboxylic acid ($R^2CO_2H$). For example, the spiropiperidine intermediate (IId) and carboxylic acid ($R^2CO_2H$) may be coupled by forming an activated carboxylic acid ester, such as by contacting the carboxylic acid ($R^2CO_2H$) with a peptide coupling reagent, such as HATU or EDC.HCl, in the presence or absence of an activating agent, such as HOBt and in the presence of a suitable base, such as DIEA, triethylamine or NMM, in a suitable solvent such as THF and/or DMF, DMA or dichloromethane and then contacting the activated carboxylic acid ester with the spiropiperidine derivative (IId) to form a compound of Formula (Id).

Reaction Scheme V outlines the general procedures one could use to provide N2 lactam ACC inhibitor compounds of the present invention having Formula Id, in which $R^1$ is a $(C_1-C_6)$alkyl or $(C_3-C_5)$cycloalkyl and $R^2$ is phenyl, naphthyl, a 5 to 12 membered heteroaryl or a 8 to 12 membered fused heterocyclicaryl; wherein each $R^2$ group is optionally substituted with one to three substituents independently selected from $(C_1-C_3)$alkyl, $(C_1-C_3)$alkoxy, halo and $CONH_2$.

REACTION SCHEME V

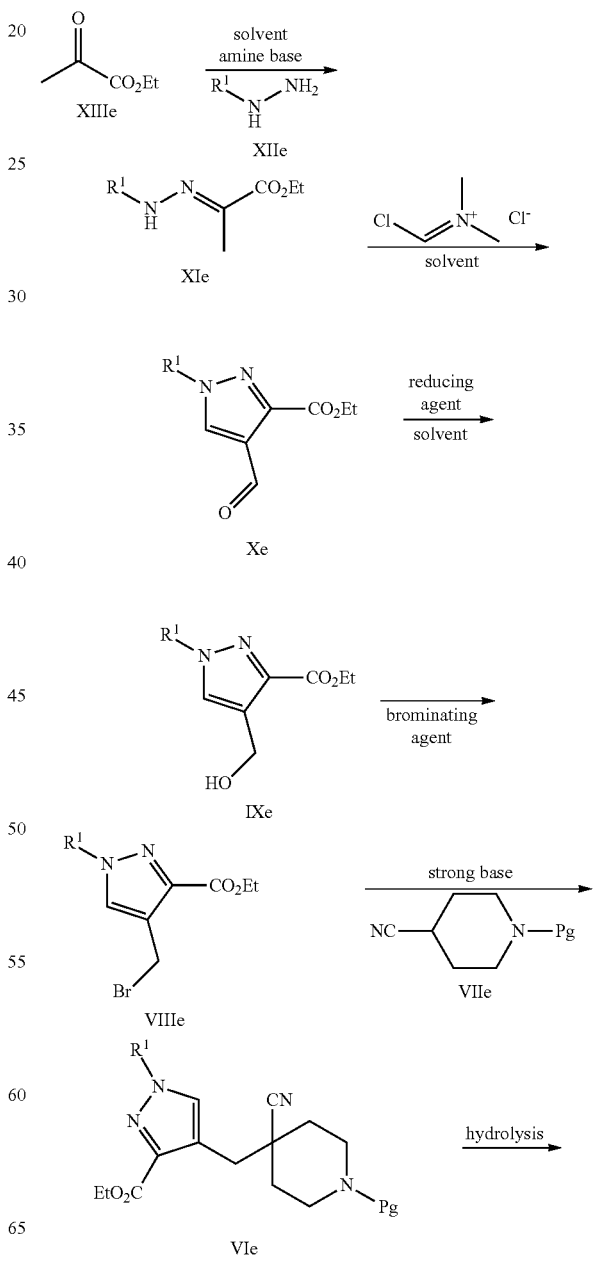

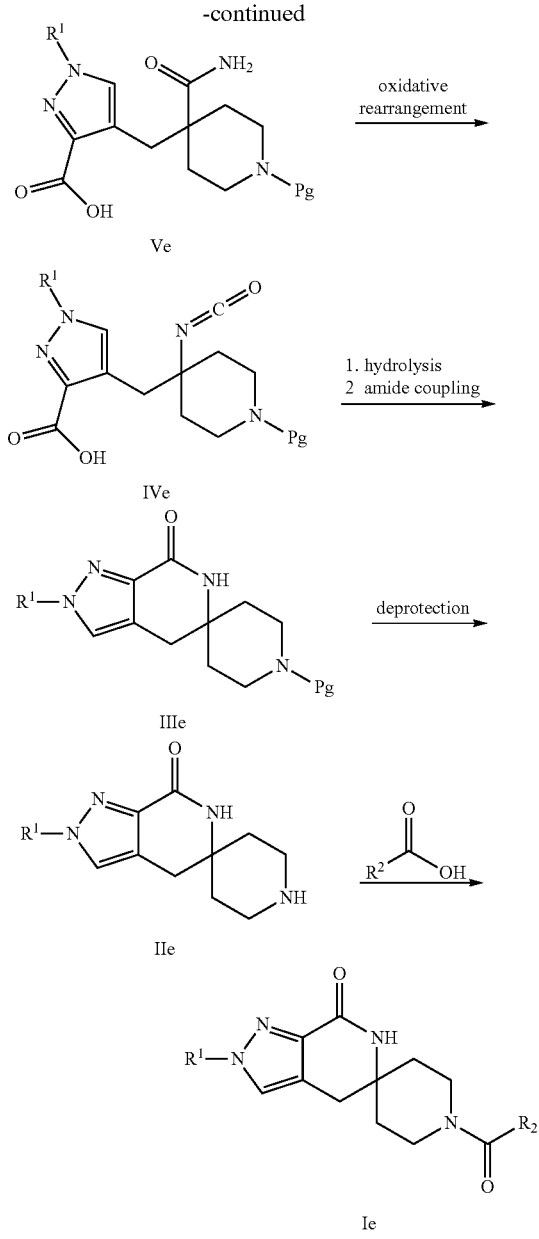

According to Scheme V, the compound of formula XIe can be prepared by condensation of a keto ester compound of formula XIIIe with an appropriate an alkyl hydrazine hydrochloride of formula XIIe such as t-butylhydrazine hydrochloride in the presence of a tertiary amine base such as triethylamine or N,N-diisopropylethylamine in a polar protic solvent such as ethanol at a temperature of about 20° C. to about 100° C. for about 1 to about 12 hours.

The compound of formula Xe can be prepared by treating the compound of formula XIe with (chloromethylene)dimethylammonium chloride (Vilsmeier Salt, Sigma-Aldrich, cat #280909) in a non-protic solvent such as dimethylformamide or toluene or 1,2-dichloroethane at a temperature of about 0° C. to about 120° C. for about 1 to 12 hours.

The compound of formula IXe can be prepared by treating the aldehyde of formula Xe with a reducing agent such as sodium borohydride in a protic solvent such as methanol or ethanol at a temperature of about 0° C. to about 60° C. for about 1 to about 6 hours.

The compound of formula VIe can be formed by first reacting the compound of formula IXe with a brominating agent such as phosphorus tribromide ("PBr$_3$"), or a mixture of carbon tetrabromide and triphenylphosphine, at a temperature of about −20° C. to about 60° C. for about 30 to about 120 minutes forming the compound of formula VIIIe. The compound of formula VIIIe is then reacted with a protected 4-cyanopiperidine derivative compound of formula VIIa in the presence of a strong base such as lithium bis(trimethylsilyl)amide ("LiHMDS") or lithium diisopropylamine ("LDA") in an aprotic solvent such as tetrahydrofuran ("THF"), toluene or diethyl ether at a temperature of about −78° C. to about 20° C. for about 1 to about 18 hours. The group Pg represents an appropriate amine protecting group and is preferably N-tert-butoxycarbonyl ("BOC") or carbobenzyloxy ("Cbz").

The amide compound of formula Ve can be prepared by subjecting the nitrile compound of formula VIe to hydrolysis conditions such as an aqueous hydroxide base such as lithium hydroxide or sodium hydroxide and a solvent such as methanol or ethanol or tetrahydrofuran at a temperature of about 20° C. to about 100° C. for about 1 to 12 hours. Alternatively a peroxide complex can be used such as urea-hydrogen peroxide in combination with an aqueous hydroxide base such as sodium hydroxide in a solvent such as methanol or ethanol at a temperature of about 0° C. to about 60° C. for about 1 to 12 hours.

Rearrangement of the amide compound of formula Ve to the isocyanate compound of formula IVe can be carried out by treatment with a reagent such as (bis(trifluoroacetoxy)iodo)benzene in the presence of an inorganic base such as sodium bicarbonate in a solvent such as acetonitrile at a temperature of about 20° C. to about 60° C. for about 1 to 6 hours.

Conversion of the isocyante compound of formula IVe to the lactam compound of formula IIIe can proceed by first hydrolyzing the isocyanate in aqueous hydroxide base such as sodium hydroxide or lithium hydroxide in a solvent such as methanol or tetrahydrofuran. The resulting amine can then be treated with an amide coupling reagent such as 1-ethyl-3-(3-dimethylaminopropyl)carbodiimide or 2-(7-aza-1H-benzotriazole-1-yl)-1,1,3,3-tetramethyluronium hexafluorophosphate with a alkyl amine base such as triethylamine or N,N-diisopropylethylamine in a solvent such as dichloromethane or dimethylformamide at a temperature of about 0° C. to about 60° C. for about 1 to 24 hours to give the lactam compound of formula IIIe.

The lactam compound of formula (IIIe) can then be deprotected to provide the free spiropiperidine derivative of formula (IIe) using standard methods which depend on which protecting group Pg has been employed. For example, when Pg represents tert-butyloxycarbonyl ("BOC") standard strong acid deprotection conditions such as 4N hydrochloric acid in dioxane or trifluoroacetic acid in an appropriate solvent such as dichloromethane can be used to remove the BOC group. When Pg represents carbobenzyloxy ("Cbz"), hydrogenation over palladium on carbon in ethanol or treatment with a hydrogen source such as ammonium formate or 1-methyl-1,4-cyclohexadiene in the presence of palladium on carbon in ethanol or ethyl acetate can be employed to carry out the deprotection.

The spiropiperidine derivative of Formula (IIe) can then be acylated by employing standard methods to provide the compound of Formula (Ie). For example, the compound (Ie) can then be formed using a standard peptide coupling reaction with the desired carboxylic acid (R$^2$CO$_2$H). For example, the spiropiperidine intermediate (IIe) and carboxylic acid (R$^2$CO$_2$H) can be coupled by forming an activated carboxylic acid ester, such as by contacting the carboxylic acid ($R^2CO_2H$) with a peptide coupling reagent, such as HATU or EDC.HCl, in the presence or absence of an activating agent, such as hydroxybenzotriazole ("HOBt") and in the presence of a suitable base, such as DIEA, NMM, in a suitable solvent such as THF and/or DMF, DMA or dichloromethane and then contacting the activated carboxylic acid ester with the spiropiperidine derivative (Ile) to form a compound of Formula (Ie).

The compounds of the present invention may be isolated and used per se or in the form of their pharmaceutically acceptable salts. In accordance with the present invention, compounds with multiple basic nitrogen atoms can form salts with varying number of equivalents ("eq.") of acid. It will be understood by practitioners that all such salts are within the scope of the present invention.

Pharmaceutically acceptable salts, as used herein in relation to compounds of the present invention, include pharmaceutically acceptable inorganic and organic salts of the compound. These salts can be prepared in situ during the final isolation and purification of a compound, or by separately reacting the compound thereof, with a suitable organic or inorganic acid and isolating the salt thus formed. Representative salts include, but are not limited to, the hydrobromide, hydrochloride, hydroiodide, sulfate, bisulfate, nitrate, acetate, trifluoroacetate, oxalate, besylate, palmitate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate and laurylsulphonate salts, and the like. These may also include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylammonium, dimethylammonium, trimethylammonium, triethylammonium, ethylammonium, and the like. For additional examples see, for example, Berge, et al., J. Pharm. Sci., 66, 1-19 (1977).

Compounds of the present invention may exist in more than one crystal form. Polymorphs of compounds of Formula (I) and salts thereof (including solvates and hydrates) form part of this invention and may be prepared by crystallization of a compound of the present invention under different conditions. For example, using different solvents or different solvent mixtures for recrystallization; crystallization at different temperatures; various modes of cooling, ranging from very fast to very slow cooling during crystallization. Polymorphs may also be obtained by heating or melting a compound of the present invention followed by gradual or fast cooling. The presence of polymorphs may be determined by solid probe nuclear magnetic resonance (NMR) spectroscopy, infrared (IR) spectroscopy, differential scanning calorimetry, powder X-ray diffraction or such other techniques.

This invention also includes isotopically-labeled compounds, which are identical to those described by Formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, sulfur and fluorine, such as $^2H$, $^3H$, $^{13}C$, $^{14}C$, $^{15}N$, $^{18}O$ $^{17}O$, $^{35}S$, $^{36}Cl$, $^{125}I$, $^{129}I$, and $^{18}F$ respectively. Certain isotopically-labeled compounds of the present invention, for example those into which radioactive isotopes such as $^3H$ and $^{14}C$ are incorporated, are useful in drug and/or substrate tissue distribution assays. Tritiated (i.e., $^3H$), and carbon-14 (i.e., $^{14}C$), isotopes are particularly preferred for their ease of preparation and detectability. Further, substitution with heavier isotopes such as deuterium (i.e., $^2H$), can afford certain therapeutic advantages resulting from greater metabolic stability, for example increased in vivo half-life or reduced dosage requirements and, hence, may be preferred in some circumstances. Isotopically labeled compounds of the present invention can generally be prepared by carrying out the procedures disclosed in the schemes and/or in the Examples below, by substituting a readily available isotopically labeled reagent for a non-isotopically labeled reagent.

The compounds of the present invention may contain stereogenic centers. These compounds may exist as mixtures of enantiomers or as pure enantiomers. Wherein a compound includes a stereogenic center, the compounds may be resolved into the pure enantiomers by methods known to those skilled in the art, for example by formation of diastereoisomeric salts which may be separated, for example, by crystallization; formation of stereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, the specific stereoisomers may be synthesized by using an optically active starting material, by asymmetric synthesis using optically active reagents, substrates, catalysts or solvents, or by converting one stereoisomer into the other by asymmetric transformation.

Compounds of the present invention may exist in different stable conformational forms which may be separable. Torsional asymmetry due to restricted rotation about an asymmetric single bond, for example because of steric hindrance or ring strain, may permit separation of different conformers. The compounds of the present invention further include each conformational isomer of compounds of Formula (I) and mixtures thereof.

Compounds of the present invention are useful for treating diseases, conditions and/or disorders modulated by the inhibition of the acetyl-CoA carboxylases enzyme(s) (in particular, ACC1 and ACC2). Another embodiment of the present invention is a pharmaceutical composition comprising a therapeutically effective amount of a compound of the present invention and a pharmaceutically acceptable excipient, diluent or carrier. The compounds of the present invention (including the compositions and processes used therein) may also be used in the manufacture of a medicament for the therapeutic applications described herein.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., for use in the preparing a medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The dissolution rate of poorly water-soluble compounds may be enhanced by the use of a spray-dried dispersion, such as those described by Takeuchi, H., et al. in "Enhancement of the dissolution rate of a poorly water-soluble drug (tolbutamide) by a spray-drying solvent deposition method and disintegrants" *J. Pharm. Pharmacol.*, 39, 769-773 (1987); and EP0901786B1 (US2002/009494), incorporated herein by reference. The compound of the present invention is typically formulated into pharmaceutical dosage forms to provide an easily controllable dosage of the drug and to give the patient an elegant and easily handleable product.

The pharmaceutical compositions also include solvates and hydrates of the compounds of the present invention. The term "solvate" refers to a molecular complex of a compound represented by Formula (I) (including pharmaceutically acceptable salts thereof) with one or more solvent molecules. Such solvent molecules are those commonly used in the pharmaceutical art, which are known to be innocuous to the recipient, e.g., water, ethanol, ethylene glycol, and the like, The term "hydrate" refers to the complex where the solvent molecule is water. The solvates and/or hydrates preferably exist in crystalline form. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders modulated by the inhibition of the acetyl-CoA carboxylases enzyme(s) in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders that benefit from the inhibition of acetyl-CoA carboxylases enzyme(s).

One aspect of the present invention is the treatment of obesity, and obesity-related disorders (e.g., overweight, weight gain, or weight maintenance).

Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Washington, DC: U.S. Department of Health and Human Services, NIH publication no. 98-4083 (1998).

Another aspect of the present invention is for the treatment (e.g., delaying the progression or onset) of diabetes or diabetes-related disorders including Type 1 (insulin-dependent diabetes mellitus, also referred to as "IDDM") and Type 2 (noninsulin-dependent diabetes mellitus, also referred to as "NIDDM") diabetes, impaired glucose tolerance, insulin resistance, hyperglycemia, and diabetic complications (such as atherosclerosis, coronary heart disease, stroke, peripheral vascular disease, nephropathy, hypertension, neuropathy, and retinopathy).

In yet another aspect of the present invention is the treatment of obesity co-morbidities, such as metabolic syndrome. Metabolic syndrome includes diseases, conditions or disorders such as dyslipidemia, hypertension, insulin resistance, diabetes (e.g., Type 2 diabetes), coronary artery disease and heart failure. For more detailed information on Metabolic Syndrome, see, e.g., Zimmet, P. Z., et al., "The Metabolic Syndrome: Perhaps an Etiologic Mystery but Far From a Myth—Where Does the International Diabetes Federation Stand'?," *Diabetes & Endocrinology*, 7(2), (2005); and Alberti, K. G., et al., "The Metabolic Syndrome—A New Worldwide Definition," *Lancet*, 366, 1059-62 (2005). Preferably, administration of the compounds of the present invention provides a statistically significant ($p<0.05$) reduction in at least one cardiovascular disease risk factor, such as lowering of plasma leptin, C-reactive protein (CRP) and/or cholesterol, as compared to a vehicle control containing no drug. The administration of compounds of the present invention may also provide a statistically significant ($p<0.05$) reduction in glucose serum levels.

In yet another aspect of the invention is the treatment of nonalcoholic fatty liver disease (NAFLD) and hepatic insulin resistance.

For a normal adult human having a body weight of about 100 kg, a dosage in the range of from about 0.001 mg to about 10 mg per kilogram body weight is typically sufficient, preferably from about 0.01 mg/kg to about 5.0 mg/kg, more preferably from about 0.01 mg/kg to about 1 mg/kg. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents (including appetite suppressants), anti-diabetic agents, anti-hyperglycemic agents, lipid lowering agents, and anti-hypertensive agents.

Suitable lipid lowering agents that can be combined with the compounds of the present invention include, for example, those described at page 30, line 20 through page 31, line 30 of WO 2011005611. The lipid lowering agents include bile acid sequestrants, HMG-CoA reductase inhibitors, HMG-CoA synthase inhibitors, cholesterol absorption inhibitors, acyl coenzyme A-cholesterol acyl transferase (ACAT) inhibitors, CETP inhibitors, squalene synthetase inhibitors, PPAR α agonists, FXR receptor modulators, LXR receptor modulators, lipoprotein synthesis inhibitors, rennin angiotensisn system inhibitors, PPAR δ partial agonists, bile acid reabsorption inhibitors, PPAR α agonists, triglyceride synthesis inhibitors, microsomal triglyceride transport inhibitors, transcription modulators, squalene epoxidase inhibitors, low density lipoprotein receptor inducers, platelet aggregation inhibitors, 5-LO or FLAP inhibitors, niacin bound chromium and other agents that affect lipid composition.

Suitable anti-hypertensive agents that can be combined with the compounds of the present invention include, for example, those described at page 31, line 31 through page 32, line 18 of WO 2011005611. The anti-hypertensive agents include diuretics, beta-adrenergic blockers, calcium channel blockers, angiotensin converting enzyme (ACE) inhibitors, neutral endopeptidase inhibitors, endothelin antagonists, vasodilators, angiotensin II receptor antagonists, α/β adrenergic blockers, alpha 1 blockers, alpha 2 agonists, aldosterone inhibitors, mineraocorticoid receptor inhibitors, renin inhibitors and angiopoietin-2-binding agents.

Suitable anti-diabetic agents include an acetyl-CoA carboxylase-(ACC) inhibitor such as those described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, diacylglycerol O-acyltransferase 2 (DGAT-2) inhibitor, monoacylglycerol O-acyltransferase inhibitors, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone, rosiglitazone and troglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, taspoglutide, lixisenatide, dulaglutide, semaglutide, NN-9924,TTP-054, a protein tyrosine phosphatase-1B (PTP-1B) inhibitor (e.g., trodusquemine, hyrtiosal extract, and compounds disclosed by Zhang, S., et al., *Drug Discovery Today*, 12(9/10), 373-381 (2007)), SIRT-1 inhibitor (e.g., resveratrol, GSK2245840 or GSK184072), a dipeptidyl peptideasae IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (July 2010) including dapagliflozin, canagliflozin, BI-10733, tofogliflozin (CSG452), ASP-1941, THR1474, TS-071, ISIS388626 and LX4211 as well as those in WO2010023594, a glucagon receptor modulator such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4)359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKC), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1 beta, modulators of RXRalpha. In addition suitable anti-diabetic agents include mechanisms listed by Carpino, P. A., Goodwin, B. Expert Opin. Ther. Pat, 2010, 20(12), 1627-51.

Suitable anti-obesity agents (some of which may also act as anti-diabetic agents as well) include 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, $β_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists such as velneperit), $PYY_{3-36}$ (including analogs thereof), BRS3 modulator, mixed antagonists of opiod receptor subtypes, thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, histamine 3 antagonists or inverse agonists, neuromedin U agonists, MTP/ApoB inhibitors (e.g., gut-selective MTP inhibitors, such as dirlotapide, JTT130, Usistapide, SLx4090), opioid antagonist, mu opioid receptor modulators, including but not limited to GSK1521498, MetAp2 inhibitors, including but not limited to ZGN-433, agents with mixed modulatory activity at 2 or more of glucagon, GIP and GLP1 receptors, such as MAR-701 or ZP2929, norepinephrine transporter inhibitors, cannabinoid-1-receptor antagonist/inverse agonists, ghrelin agonists/antagonists, oxyntomodulin and analogs, monoamine uptake inhibitors, such as but not limited to tesofensine, an orexin antagonist, combination agents (such as bupropion plus zonisamide, pramlintide plus metreleptin, bupropion plus naltrexone, phentermine plus topiramate), and the like.

Preferred anti-obesity agents for use in the combination aspects of the present invention include gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), $PYY_{3-36}$ (as used herein "$PYY_{3-36}$" includes analogs, such as peglated $PYY_{3-36}$ e.g., those described in US Publication 2006/0178501), opioid antagonists (e.g., naltrexone), oleoyl-estrone (CAS No. 180003-17-2), obinepitide (TM30338), pramlintide (Symlin®), tesofensine (NS2330), leptin, bromocriptine, orlistat, AOD-9604 (CAS No. 221231-10-3) and sibutramine. Preferably, compounds of the present invention and combination therapies are administered in conjunction with exercise and a sensible diet.

All of the recited U.S. patents and publications (including all technical bulletins referenced in the Examples) are incorporated herein by reference in their entireties.

The Examples set forth herein below are for illustrative purposes only. The compositions, methods, and various parameters reflected herein are intended only to exemplify various aspects and embodiments of the invention, and are not intended to limit the scope of the claimed invention in any way.

The preparations described below were used in the synthesis of compounds exemplified in the following examples.

The following commercially available starting materials were used to prepare compounds described in the Examples below: methyl 3-iodo-1H-indazole-5-carboxylate (Anichem LLC, North Brunswick, N.J.), (1R,5S)-8-(tert-butoxycarbonyl)-8-azabicyclo[3.2.1]octane-3-carboxylic acid (AstaTech, Inc., Bristol, Pa.), 6-bromoisoquinolin-3-amine (Ark Pharm, Inc., Libertyville, Ill.), 3-hydroxy-1H-indazole-5-carboxylic acid (Aces Pharma, Inc., Branford, Conn.), ethyl quinoline-7-carboxylate (ASW MedChem, Inc., New Brunswick, N.J.), 7-bromoisoquinolin-1(2H)-one (Alfa Aesar, Ward Hill, Mass.), 3-oxo-2,3-dihydro-1H-indazole-6-carboxylic acid (ASW MedChem, Inc., New Brunswick, N.J.), 5-bromo-3-(trifluoromethyl)-1H-indazole (J&W Pharm Lab LLC., Levittown, Pa.), 6-bromoisoquinolin-1(2H)-one (Anichem LLC, North Brunswick, N.J.), methyl 1H-pyrrolo[3,2-b]pyridine-6-carboxylate (ACS Scientific Inc., Metuchen, N.J.), 4-bromo-2-fluoro-N-methylbenzamide (Oakwood Products, Inc., West Columbia, S.C.), 7-bromo-3-chloroisoquinoline (Allichem LLC, Baltimore, Md.), 7-bromoisoquinolin-3-amine (Allichem LLC, Baltimore, Md.), 6-bromoisoquinolin-3-ol (Ark Pharm, Inc., Libertyville, Ill.), 1H-pyrrolo[2,3-b]pyridine-5-carboxylic acid (ASDI Inc., Newark, Del.), 1-chloroisoquinoline-7-carboxylic acid (American Custom Chemicals Corp., San Diego, Calif.), 3,7-dimethyl-1H-indazole-5-carboxylic acid (Annker Organics Co. Ltd., Wuhan, China), 7-methyl-1H-indazole-5-carboxylic acid (J & W PharmLab LLC, Levittown, Pa.), 2-methyl-2H-indazole-5-carboxylic acid (Bepharm Ltd., Shanghai, China), 1H-pyrrolo[3,2-b]pyridine-6-carboxylic acid (Sinova Inc., Bethesda, Md.), 7-chloro-1H-indazole-5-carboxylic acid (Annker Organics Co. Ltd., Wuhan, China), 4-methoxy-1H-indazole-6-carboxylic acid (ASW MedChem Inc., New Brunswick, N.J.), 1-methyl-1H-indazole-5-carboxylic acid (J & W PharmLab LLC, Levittown, Pa.), 7-ethyl-1H-indazole-5-carboxylic acid (Annker Organics Co. Ltd., Wuhan, China), 3-ethyl-1H-indazole-5-carboxylic acid (Allichem LLC, Baltimore, Md.), 3-methyl-1H-indazole-5-carboxylic acid (Ark Pharm Inc., Libertyville, Ill.), 1H-pyrrolo[3,2-b]pyridine-2-carboxylic acid (Aces Pharma Inc., Branford, Conn.), quinoline-3-carboxylic acid (Beta Pharma Inc., Branford, Conn.), quinoline-7-carboxylic acid (Ark Pharm Inc., Libertyville, Ill.), isoquinoline-6-carboxylic acid (Ark Pharm Inc., Libertyville, Ill.), isoquinoline-7-carboxylic acid (Indofine Chemical Company Inc., Hillsborough, N.J.), 6-methoxyquinoline-3-carboxylic acid (Princeton Biomolecular Research Inc., Monmouth Junction, N.J.), 4-methoxy-7-methyl-1H-indole-2-carboxylic acid (Aurora Fine Chemicals LLC, San Diego, Calif.), 2-aminoquinoline-6-carboxylic acid (Princeton Biomolecular Research Inc., Monmouth Junction, N.J.), 8-methoxyquinoline-3-carboxylic acid (BioBlocks Inc., San Diego, Calif.), 2-aminoquinoline-7-carboxylic acid (Princeton Biomolecular Research Inc., Monmouth Junction, N.J.), 2-methyl-1H-benzo[d]imidazole-5-carboxylic acid (Acros Organics, Geel, Belgium), 1H-indazole-5-carboxylic acid (Sigma Aldrich, St. Louis, Mo.), quinoline-6-carboxylic acid (Acros Organics, Geel, Belgium), 6-methoxy-2-naphthoic acid (Sigma Aldrich, St. Louis, Mo.), 1H-indazole-6-carboxylic acid (Sigma Aldrich, St. Louis, Mo.), 1H-benzo[d][1,2,3]triazole-5-carboxylic acid (Sigma Aldrich, St. Louis, Mo.), 3,4-diamino-5-chlorobenzoic acid (Princeton BioMolecular Research, Inc., Monmouth Junction, N.J.), 7-bromo-1-chloroisoquinoline (Alfa Aesar, Ward Hill, Mass.) 7-bromoquinoline (Anichem LLC, North Brunswick, N.J.).

The following carboxylic acids (which were used to prepare compounds described in the Examples below) were prepared by previously published means: 3,7-dimethyl-1H-indazole-5-carboxylic acid (PCT Publication No. WO2009144554), 7-methyl-1H-indazole-5-carboxylic acid (PCT Publication No. WO2009144554), 7-methoxy-2-naphthoic acid (PCT Publication No. WO2003018586), 5-methoxy-2-naphthoic acid (PCT Publication No. WO2003072578), 4,8-dim ethoxyquinoline-2-carboxylic acid (PCT Publication No. WO2007011809), 3-chloro-7-methyl-1H-indazole-5-carboxylic acid (PCT Publication No. WO2009144554), 3-chloro-1H-indazole-5-carboxylic acid (PCT Publication No. WO2009144554), 8-methoxy-2-naphthoic acid (PCT Publication No. WO2003072578), 3-chloro-1H-indole-5-carboxylic acid (PCT Publication No. WO2008065508), 3-chloro-1H-indole-6-carboxylic acid (PCT Publication No. WO2008065508), 7-methoxy-3-methyl-1H-indazole-5-carboxylic acid (WO2009144554), 4,8-dimethoxyquinoline-2-carboxylic acid (PCT Publication No. WO2007011809).

EXAMPLES

The compounds and intermediates described below were named using the naming convention provided with Chemdraw Ultra, Version 11.0.1 (CambridgeSoft Corp., Cambridge Mass.). The naming convention provided with Chemdraw Ultra, Version 11.0.1 are well known by those skilled in the art and it is believed that the naming convention provided with Chemdraw Ultra, Version 11.0.1 generally comports with the IUPAC (International Union for Pure and Applied Chemistry) recommendations on Nomenclature of Organic Chemistry and the CAS Index rules. Unless noted otherwise, all reactants were obtained commercially. All of the references cited herein below are incorporated by reference.

Flash chromatography was performed according to the method described by Still et al., J. Org. Chem., 1978, 43, 2923.

All Biotage® purifications, discussed herein, were performed using Biotage® SNAP columns containing KP-SIL silica (40-63 μM, 60 Angstroms) (Biotage AB; Uppsala, Sweden).

All Combiflash® purifications, discussed herein, were performed using a CombiFlash® Companion system (Teledyne Isco; Lincoln, Nebr.) utilizing packed RediSep® silica columns Mass Spectra were recorded on a Waters (Waters Corp.; Milford, Mass.) Micromass Platform II spectrometer. Unless otherwise specified, mass spectra were recorded on a Waters (Milford, Mass.) Micromass Platform II spectrometer.

Proton NMR chemical shifts are given in parts per million downfield from tetramethylsilane and were recorded on a Varian Unity 300, 400 or 500 MHz (megaHertz) spectrometer (Varian Inc.; Palo Alto, Calif.). NMR chemical shifts are given in parts per million downfield from tetramethylsilane (for proton) or fluorotrichloromethane (for fluorine).

HPLC retention times were measured using the following methods: Method A: column: Waters Atlantis dC18 4.6×50 mm, 5 μm; mobile phase A: 0.05% TFA in water (v/v); mobile phase B: 0.05% TFA in acetonitrile (v/v); gradient: 95% N5% B linear to 5% A/95% B in 4.0 minutes, hold at 5% N95% B to 5.0 minutes; flow rate: 2.0 mL/minute. Method B: column: Waters XBridge C18 4.6×50 mm, 5 μm; mobile phase A: 0.03% NH$_4$OH in water (v/v); mobile phase B: 0.03% NH$_4$OH in acetonitrile (v/v); gradient: 95% N5% B linear to 5% A/95% B in 4.0 minutes, hold at 5% A/95% B to 5.0 minutes; flow rate: 2.0 mL/minute.

The preparations described below were used in the synthesis of compounds exemplified in the following examples.

Preparation of Intermediates and Starting Materials

Carboxylic acid intermediates were purchased commercially, prepared as described below, prepared as described in PCT Publication No. WO 2009/144554, prepared using preparations well-known to those skilled in the art, or prepared in a manner analogous to routes described above for other carboxylic acid intermediates.

Intermediate 1: 1'-tert-butyl-4',6'-dihydrospiro[piperidine-4,5'-pyrazolo[3,4-c]pyridin]-7'(1'H)-one hydrochloride salt

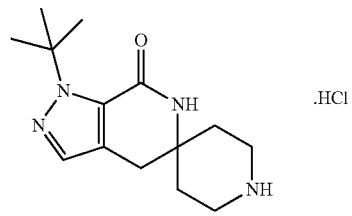 [SMILES: CC(C)(C)n1ncc2c1C(=O)NC1(CCNCC1)C2 ; ".HCl"]

Step 1. ethyl 5-bromo-1-tert-butyl-1H-pyrazole-4-carboxylate

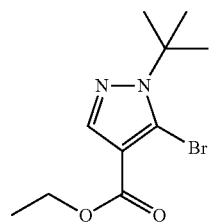

To a solution of ethyl 5-amino-1-tert-butyl-1H-pyrazole-4-carboxylate (674 mg, 3.19 mmol, Li et al. J. Heterocycl. Chem., 2007, 44, 749) in acetonitrile (20 mL) were added copper(II)bromide (720 mg, 3.19 mmol) and isoamylnitrite (0.56 mL, 4.15 mmol). The golden suspension was heated at 45° C. for 2 hours and then cooled to room temperature, diluted with ethyl acetate (100 mL) and washed with saturated aqueous sodium bicarbonate (50 mL), water (50 mL) and brine (50 mL). The organic phase was dried over sodium sulfate, filtered and concentrated under reduced pressure. The resultant residue was purified by flash chromatography (5-40% ethyl acetate/heptanes, 10 g silica gel) to yield 685 mg of ethyl 5-bromo-1-tert-butyl-1H-pyrazole-4-carboxylate as a clear oil. +APCI (M+H) 275.0; $^1$H NMR (400 MHz, CDCl$_3$, δ): 7.87 (s, 1H), 4.32 (q, J=7.0 Hz, 2H), 1.77 (s, 9H), 1.36 (t, J=7.1 Hz, 3H).

Step 2: (5-bromo-1-tert-butyl-1H-pyrazol-4-yl)methanol

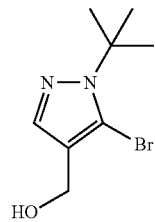

A solution of ethyl 5-bromo-1-tert-butyl-1H-pyrazole-4-carboxylate (685 mg, 2.49 mmol) in THF (20 mL) was cooled to −78° C. and treated with diisobutylaluminum hydride (7.47 mL, 7.47 mmol, 1 M THF), dropwise. The mixture was stirred at −78° C. for 30 minutes and then warmed to room temperature for 18 hours. The mixture was quenched with ethyl acetate 10 mL) and stirred 15 minutes. The mixture was then treated with saturated aqueous Rochelle's salt (25 mL) and stirred 1 hour at room temperature. The mixture was diluted with ethyl acetate (100 mL) and washed with water (100 mL). The organic layer was dried over sodium sulfate, filtered and concentrated. The residue was purified by flash chromatography (10-80% ethyl acetate/heptane gradient, 25 g silica gel) to yield 460 mg of (5-bromo-1-tert-butyl-1H-pyrazol-4-yl)methanol as a clear oil. +APCI (M+H) 233.1, (M+2+H) 235.1; $^1$H NMR (400 MHz, CDCl$_3$, δ): 7.51 (s, 1H), 4.53 (d, 2H), 1.74 (s, 9H), 1.55 (t, J=5.8 Hz, 1H).

Step 3:
5-bromo-4-(bromomethyl)-1-tert-butyl-1H-pyrazole

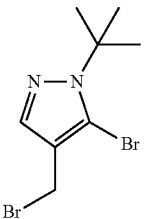

A solution of (5-bromo-1-tert-butyl-1H-pyrazol-4-yl)methanol (460 mg, 1.97 mmol) in dichloromethane (25 mL) was cooled to 0° C. and then treated with phosphorus(III) bromide (0.37 mL, 3.46 mmol), dropwise, over 5 minutes. The mixture was stirred 30 minutes at 0° C. and then 1 hour at room temp. The mixture was quenched slowly with water (50 mL), stirred 30 minutes, and then extracted with ethyl acetate (2×50 mL). The organic phase was washed with saturated aqueous sodium bicarbonate (50 mL), dried over sodium sulfate, filtered and concentrated to yield 362 mg of 5-bromo-4-(bromomethyl)-1-tert-butyl-1H-pyrazole as a clear oil. $^1$H NMR (400 MHz, CDCl$_3$, δ): 7.54 (s, 1H), 4.39 (s, 2H), 1.74 (s, 9H).

Step 4: 1-tert-butyl 4-ethyl 4-((5-bromo-1-tert-butyl-1H-pyrazol-4-yl)methyl)piperidine-1,4-dicarboxylate

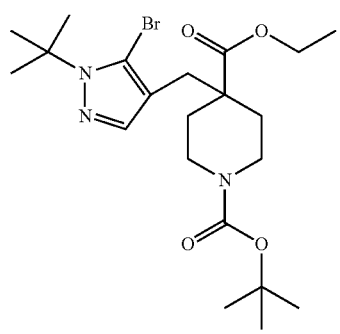 [SMILES: CCOC(=O)C1(Cc2cnn(C(C)(C)C)c2Br)CCN(C(=O)OC(C)(C)C)CC1]

A solution of 1-tert-butyl 4-ethyl piperidine-1,4-dicarboxylate (0.37 mL, 1.47 mmol) in THF (15 mL) was cooled to −78° C. and then treated with lithium bis(trimethylsilyl)amide (1.48 mL, 1.48 mmol, 1 M toluene), dropwise. The reaction was stirred 15 minutes at −78° C., warmed to 0° C. for 30 minutes and then cooled back to −78° C. A solution of 5-bromo-4-(bromomethyl)-1-tert-butyl-1H-pyrazole (335 mg, 1.13 mmol) in THF (10 mL) was added, the mixture was stirred 1 hour at −78° C., and then allowed to stir 18 hours at room temperature. The reaction was quenched with saturated aqueous ammonium chloride (20 mL), stirred 30 minutes at room temperature, diluted with water (50 mL) and extracted with ethyl acetate (2×50 mL). The organics were combined, dried over sodium sulfate, filtered and concentrated. The resultant residue was purified by flash chromatography (5-40% ethyl acetate/heptane, 25 g silica gel) to yield 256 mg of 1-tert-butyl 4-ethyl 4-((5-bromo-1-tert-butyl-1H-pyrazol-4-yl)methyl)piperidine-1,4-dicarboxylate as a clear oil. +ESI (M+H) 474.2, (M+2+H) 476.2; $^1$H NMR (400 MHz, CDCl$_3$, δ): 7.20 (s, 1H), 4.16 (q, J=7.2 Hz, 2H), 3.93 (br. s., 2H), 2.84 (m, 2H), 2.66 (s, 2H), 2.10 (d, J=12.5 Hz, 2H), 1.72 (s, 9H), 1.45 (m, 11H), 1.25 (t, J=7.1 Hz, 3H).

Step 5: 4-((5-bromo-1-tert-butyl-1H-pyrazol-4-yl)methyl)-1-(tert-butoxycarbonyl)piperidine-4-carboxylic acid

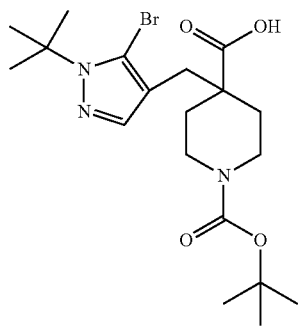 [SMILES: CC(C)(C)OC(=O)N1CCC(Cc2cnn(C(C)(C)C)c2Br)(C(=O)O)CC1]

To a solution of 1-tert-butyl 4-ethyl 4-((5-bromo-1-tert-butyl-1H-pyrazol-4-yl)methyl)piperidine-1,4-dicarboxylate (256 mg, 0.54 mmol) in methanol (15 mL) was added aqueous 2.5 M NaOH (5 mL), and the resultant mixture was heated at reflux for 18 hours. The mixture was cooled to room temperature and methanol was removed under reduced pressure. The resultant slurry was taken up in 25 mL water, acidified with aqueous 1 N HCl, and then extracted with ethyl acetate (2×50 mL). The combined organics were dried over sodium sulfate, filtered and concentrated to yield 241 mg of 4-((5-bromo-1-tert-butyl-1H-pyrazol-4-yl)methyl)-1-(tert-butoxycarbonyl)piperidine-4-carboxylic acid as a colorless solid. +APCI (M+H) 444.2, (M+2+H) 446.2; $^1$H NMR (400 MHz, CDCl₃, δ): 7.35 (s, 1H), 3.95 (br. s., 2H), 2.92 (br. s., 2H), 2.71 (s, 2H), 2.08 (d, J=12.9 Hz, 2H), 1.73 (s, 9H), 1.50 (m, 11H).

Step 6: tert-butyl 4-((5-bromo-1-tert-butyl-1H-pyrazol-4-yl)methyl)-4-isocyanatopiperidine-1-carboxylate

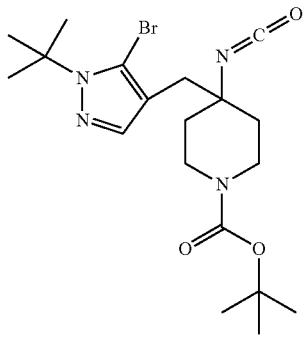 [SMILES: CC(C)(C)OC(=O)N1CCC(Cc2cnn(C(C)(C)C)c2Br)(N=C=O)CC1]

To a solution of 4-((5-bromo-1-tert-butyl-1H-pyrazol-4-yl)methyl)-1-(tert-butoxycarbonyl)piperidine-4-carboxylic acid (241 mg, 0.54 mmol) in toluene (10 mL) was added triethylamine (91 µL, 0.65 mmol) and diphenylphosphoryl azide (0.14 mL, 0.65 mmol). The mixture was heated at 120° C. for 3 hours, the reaction was cooled and the volatiles were removed under reduced pressure. The resultant oil was purified by flash chromatography (25 g silica, 7-60% ethyl acetate/heptane gradient) to yield 225 mg of tert-butyl 4-((5-bromo-1-tert-butyl-1H-pyrazol-4-yl)methyl)-4-isocyanatopiperidine-1-carboxylate as a clear oil. +APCI (M+H) 385.1; ¹H NMR (400 MHz, CDCl₃, δ): 7.40 (s, 1H), 4.03 (br. s., 2H), 2.97 (br. t, J=12.3, 12.3 Hz, 2H), 2.70 (s, 2H), 1.74 (s, 9H), 1.67 (m, 2H), 1.62 (m, 2H), 1.46 (s, 9H).

Step 7: tert-butyl 1'-tert-butyl-7'-oxo-1',4',6',7'-tetrahydrospiro[piperidine-4,5'-pyrazolo[3,4-c]pyridine]-1-carboxylate

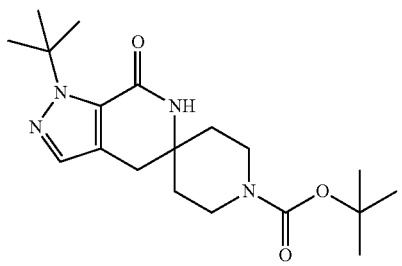 [SMILES: CC(C)(C)OC(=O)N1CCC2(CC1)Cc1cnn(C(C)(C)C)c1C(=O)N2]

A solution of tert-butyl 4-((5-bromo-1-tert-butyl-1H-pyrazol-4-yl)methyl)-4-isocyanatopiperidine-1-carboxylate (225 mg, 0.51 mmol) in THF (10 mL) was cooled to −78° C. and t-butyl lithium (0.6 mL, 1.7 M in pentane) was added, dropwise, over 2 minutes. The mixture was stirred 30 minutes at −78° C., warmed to 0° C., and then quenched with saturated aqueous NH₄Cl (20 mL). The mixture was stirred 30 minutes at room temperature, diluted with water (25 mL), and then extracted with ethyl acetate (2×50 mL). The combined organics were dried over sodium sulfate, filtered and concentrated. The residue was purified by flash chromatography (12-100% ethyl acetate/heptane, 10 g silica gel) to yield 137 mg of tert-butyl 1'-tert-butyl-7'-oxo-1',4',6',7'-tetrahydrospiro[piperidine-4,5'-pyrazolo[3,4-c]pyridine]-1-carboxylate as a colorless solid. +ESI (M-tBu) 307.2; ¹H NMR (400 MHz, DMSO-d₆, δ): 7.74 (s, 1H), 7.30 (s, 1H), 3.51 (m, 2H), 3.20 (m, 2H), 2.79 (s, 2H), 1.64 (s, 9H), 1.56 (t, J=5.8 Hz, 4H), 1.38 (s, 9H).

Step 8: 1'-tert-butyl-4',6'-dihydrospiro[piperidine-4,5'-pyrazolo[3,4-c]pyridin]-7'(1'H)-one hydrochloride salt To a solution of tert-butyl 1'-tert-butyl-7'-oxo-1',4',6',7'-tetrahydrospiro[piperidine-4,5'-pyrazolo[3,4-c]pyridine]-1-carboxylate (137 mg, 0.39 mmol) in ethyl acetate (4 mL) was added 4 N HCl in dioxane (2 mL). After stirring 1 hour at room temperature, the volatiles were removed under reduced pressure and the resultant colorless solid was triturated from heptane (10 mL) to yield 112 mg of the title compound as a colorless solid. +APCI (M+H) 263.3; ¹H NMR (400 MHz, DMSO-d₆, δ): 8.84 (m, 2H), 8.00 (s, 1H), 7.29 (s, 1H), 3.13 (d, J=6.1 Hz, 2H), 3.03 (br. s., 2H), 2.78 (s, 2H), 1.76 (m, 4H), 1.60 (s, 9H).

Intermediate 2: 1'-isopropyl-4',6'-dihydrospiro[piperidine-4,5'-pyrazolo[3,4-c]pyridin]-7'(1'H)-one shown below, was prepared as follows

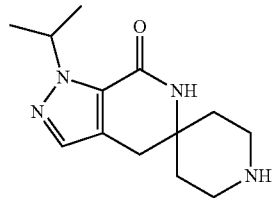 [SMILES: CC(C)n1ncc2c1C(=O)NC1(CCNCC1)C2]

Step 1:
5-amino-1-isopropyl-1H-pyrazole-4-carboxylate

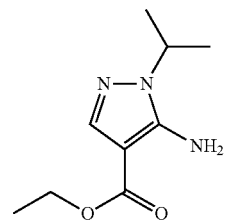

A mixture of ethyl 2-cyano-3-ethoxyacrylate (84.4 g, 0.50 mol), isopropyl hydrazine hydrochloride (55.2 g, 0.50 mol) and potassium carbonate (68.8 g, 0.50 mol) in 90% ethanol/methanol (1.5 L) was heated under reflux for 16 hours. The solvent was then removed in vacuo and water and ethyl acetate were added. The mixture was separated and the organic layer was dried over magnesium sulfate, filtered and the solvent was removed in vacuo to yield ethyl 5-amino-1-isopropyl-1H-pyrazole-4-carboxylate (92.4 g, 94%). +ESI (M+H) 198.1; ¹H NMR (400 MHz, CDCl₃, δ): 7.63 (s, 1H), 4.97 (br.s., 2H), 4.28 (q, 2H), 4.18 (m, 1H), 1.45 (d, 6H), 1.31 (t, 3H).

Step 2:
5-amino-1-isopropyl-1H-pyrazole-4-carboxylate

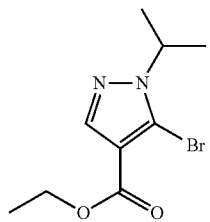

To a mixture of ethyl 5-amino-1-isopropyl-1H-pyrazole-4-carboxylate (107.5 g, 0.55 mol) in acetonitrile (1 L) was added copper (II) bromide (182.6 g, 0.82 mol) at room temperature, under argon. The mixture was heated to 50° C. and isoamyl nitrite (109.8 mL, 0.82 mol) was added dropwise (an exotherm was observed and the temperature increased to 65° C.). The reaction was stirred at 50° C. for 2 hours, the mixture was then cooled to room temperature and poured onto 2 M HCl, stirred for 15 minutes and then extracted twice with ethyl acetate. The organic layers were combined, washed with brine and then saturated aqueous sodium bicarbonate, dried over magnesium sulfate, filtered and the solvent removed in vacuo to give ethyl 5-bromo-1-isopropyl-1H-pyrazole-4-carboxylate (163 g, quantitative) which was used in the next step without further purification. ¹H NMR (400 MHz, CDCl₃, δ): 7.97 (s, 1H), 4.77 (m, 1H), 4.28 (q, 2H), 1.35 (t, 3H), 0.90 (d, 6H).

Step 3:
(5-bromo-1-isopropyl-1H-pyrazol-4-yl)methanol

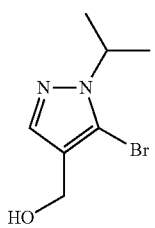

To a solution of ethyl 5-bromo-1-isopropyl-1H-pyrazole-4-carboxylate (163 g, 0.50 mol) in 2-methyl tetrahydrofuran (400 mL) was added borane-DMS (140 mL, 1.50 mol) at 0° C., under argon (effervescence ceased after 50 mL was added). The mixture was stirred at room temperature for 30 minutes and then heated to 70° C. for 2 hours, and then to reflux for 17 hours. Additional portion of borane DMS (40 mL) was added and the mixture was stirred at reflux for an additional 3 hours. The mixture was cooled to room temperature then added gradually to ice-cold methanol (500 mL) with stirring, over a period of 30 minutes. The mixture was stirred at room temperature for 30 minutes then 2 M aqueous sodium hydroxide (1.5 L) was added. The layers were separated and the aqueous layer was extracted with ethyl acetate (2×500 mL). The organic layers were combined, washed with brine (500 mL), dried over magnesium sulfate, filtered and the solvent removed in vacuo. The crude product was purified by dry flash chromatography (0-50% ethyl acetate in heptane) to give (5-bromo-1-isopropyl-1H-pyrazol-4-yl)methanol (70.8 g, 65% over two steps). +ESI (M+H) 220.9; ¹H NMR (400 MHz, CDCl₃, δ): 7.52 (s, 1H), 4.67 (m, 1H), 4.47 (s, 2H), 2.59 (br. s., 1H), 1.41 (s, 6H).

Step 4:
5-bromo-4-(bromomethyl)-1-isopropyl-1H-pyrazole

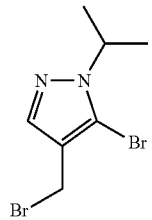

To a stirred solution of (5-bromo-1-isopropyl-1H-pyrazol-4-yl)methanol (10.0 g, 45.7 mmol) in dichloromethane (200 mL) was added PBr₃ (6.5 mL, 68.5 mmol) at 0° C. After the addition was complete the mixture was allowed to warm to room temperature and stirred for 3 hours. The mixture was poured into ice-cold water (300 mL), shaken, separated, and then washed twice with ice-cold water (2×100 mL) and then brine (100 mL), dried over sodium sulfate, filtered and the solvent removed in vacuo to give 5-bromo-4-(bromomethyl)-1-isopropyl-1H-pyrazole (12.2 g, 95%). ¹H NMR (300 MHz, CDCl₃, δ): 7.58 (s, 1H), 4.64 (m, 1H), 4.35 (s, 2H), 1.43 (d, 6H).

Step 5: 1-tert-butyl 4-ethyl 4-((5-bromo-1-isopropyl-1H-pyrazol-4-yl)methyl)piperidine-1,4-dicarboxylate

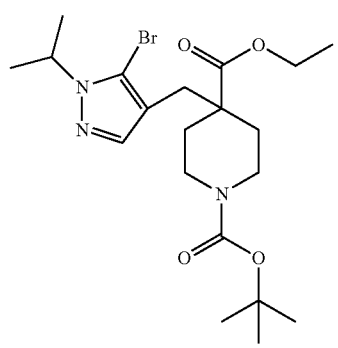 [SMILES: CCOC(=O)C1(Cc2cnn(C(C)C)c2Br)CCN(C(=O)OC(C)(C)C)CC1]

To a stirred solution of 1-tert-butyl 4-ethyl piperidine-1,4-dicarboxylate (14.5 g, 56.3 mmol) in 2-methyl tetrahydrofuran (120 mL) was added, dropwise, 1 M LiHMDS in tetrahydrofuran (57 mL, 56.3 mmol) at −78° C. under argon. After 20 min, 5-bromo-4-(bromomethyl)-1-isopropyl-1H-pyrazole (12.2 g, 43.3 mmol) in 2-methyltetrahydrofuran (10 mL) was added. The mixture was allowed to warm to room temperature and stirred for 18 hours. The mixture was diluted with water (200 mL) and the mixture was separated. The organic phase was washed with 10% citric acid solution (2×100 mL), then brine (100 mL), dried over sodium sulfate, filtered and the solvent removed in vacuo. The crude product was purified by flash column chromatography (10-30% ethyl acetate in heptane) to give 1-tert-butyl 4-ethyl 4-((5-bromo-1-isopropyl-1H-pyrazol-4-yl)methyl)piperidine-1,4-dicarboxylate (9.3 g). Also isolated from the column was a 7.1 g mixed fraction of starting ester and desired product. This was stirred with 1 equivalent of sodium hydroxide in 90% ethanol/methanol for 2 hours at room temperature. The solvent was removed in vacuo and ethyl acetate (100 mL) was added. The mixture was washed with 2 N sodium hydroxide (2×50 mL) and then brine (100 mL), dried over sodium sulfate, filtered and the solvent removed in vacuo to give a second crop of 1-tert-butyl 4-ethyl 4-((5-bromo-1-isopropyl-1H-pyrazol-4-yl)methyl)piperidine-1,4-dicarboxylate (5.1 g). The combined yield is 14.4 g (72%). +ESI (M+H) 404.0; $^1$H NMR (400 MHz, CDCl$_3$, δ): 4.62 (m, 1H), 4.12 (q, 2H), 3.90 (br. s., 2H), 2.82 (m, 2H), 2.63 (s, 2H), 2.08 (d, 2H), 1.66 (m, 2H), 1.42 (s, 9H), 1.21 (t, 3H).

Step 6: 4-((5-bromo-1-isopropyl-1H-pyrazol-4-yl)methyl)-1-(tert-butoxycarbonyl)piperidine-4-carboxylic acid

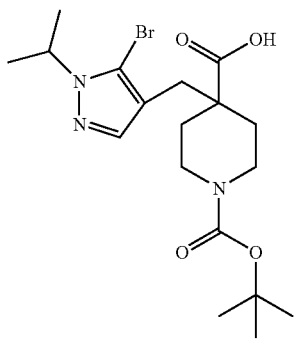 [SMILES: CC(C)n1ncc(CC2(C(=O)O)CCN(C(=O)OC(C)(C)C)CC2)c1Br]

To a solution of 1-tert-butyl 4-ethyl 4-((5-bromo-1-isopropyl-1H-pyrazol-4-yl)methyl)piperidine-1,4-dicarboxylate (14.5 g, 31.6 mmol) in methanol (50 mL) was added lithium hydroxide (1.52 g, 36.2 mmol) and the mixture was stirred at 80° C. for 18 hours. An additional portion of lithium hydroxide (2.55 g, 63.3 mmol) was added and the mixture was heated under vigorous reflux for 3 hours, cooled to room temperature, the solvent was removed in vacuo. The residue was washed with ethyl acetate, filtered, and the filtrate was saved. The solids were dissolved in 2 N aqueous sodium hydroxide (40 mL) and then acidified to pH 5 with 10% citric acid solution. The aqueous solution was extracted with ethyl acetate (3×40 mL), the organics were combined, dried over magnesium sulfate, filtered and then combined with the original filtrate. The solvent was removed from the filtrate under reduced pressure and the resulting residue was purified by flash column chromatography (ethyl acetate/heptanes) to afford 4-((5-bromo-1-isopropyl-1H-pyrazol-4-yl)methyl)-1-(tert-butoxycarbonyl)piperidine-4-carboxylic acid (10.1 g, 74%) as a colorless solid. +ESI (M+H) 429.9; $^1$H NMR (300 MHz, CDCl$_3$, δ): 7.41 (s, 1H), 4.64 (m, 1H), 3.94 (m, 2H), 2.95 (m, 2H), 2.68 (m, 2H), 2.09 (m, 2H), 1.47 (m, 17H).

Step 7: tert-butyl 4-((5-bromo-1-isopropyl-1H-pyrazol-4-yl)methyl)-4-isocyanatopiperidine-1-carboxylate

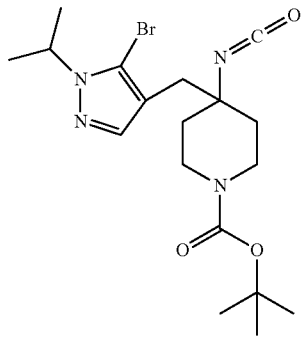 [SMILES: CC(C)n1ncc(CC2(N=C=O)CCN(C(=O)OC(C)(C)C)CC2)c1Br]

A mixture of 4-((5-bromo-1-isopropyl-1H-pyrazol-4-yl)methyl)-1-(tert-butoxycarbonyl)piperidine-4-carboxylic acid (2.54 g, 5.9 mmol), diphenylphosphoryl azide (1.79 g, 6.5 mmol) and triethylamine (0.91 mL, 6.5 mmol) in toluene (15 mL) was heated at reflux for 3 hours. The mixture was then cooled to room temperature and the solvent removed in vacuo. The crude product was purified by column chromatography to give tert-butyl 4-((5-bromo-1-isopropyl-1H-pyrazol-4-yl)methyl)-4-isocyanatopiperidine-1-carboxylate (2.8 g, 100%). $^1$H NMR (300 MHz, CDCl$_3$, δ): 7.47 (s, 1H), 4.68 (m, 1H), 3.99 (m, 2H), 2.95 (m, 2H), 2.67 (s, 2H), 1.62 (m, 4H), 1.45 (m, 15H).

Step 8: tert-butyl 1'-isopropyl-7'-oxo-1',4',6',7'-tetrahydrospiro[piperidine-4,5'-pyrazolo[3,4-c]pyridine]-1-carboxylate

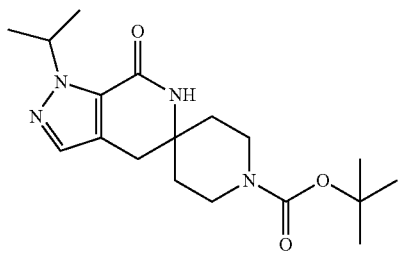 [SMILES: CC(C)n1ncc2c1C(=O)NC1(CCN(C(=O)OC(C)(C)C)CC1)C2]

To a mixture of tert-butyl 4-((5-bromo-1-isopropyl-1H-pyrazol-4-yl)methyl)-4-isocyanatopiperidine-1-carboxylate (1.4 g, 3.3 mmol) in 2-methyl tetrahydrofuran (10 mL) was added t-butyl lithium (1.7 M in hexane, 4.3 mL, 7.2 mmol) at −78° C., under argon. After the addition was complete the mixture was allowed to warm to room temperature and was stirred for 18 hours. The mixture was quenched with water (10 mL) and then diluted with ethyl acetate (20 mL). The layers were separated and the organic layer was washed with brine (10 mL), dried over sodium sulfate, filtered and the solvent removed in vacuo. The crude product was purified by flash column chromatography to give tert-butyl tetrahydrospiro[piperidine-4,5'-pyrazolo[3,4-c]pyridine]-1-carboxylate (0.77 g, 67%). +ESI (M+H) 374.1; $^1$H NMR (300

MHz, CDCl₃, δ): 7.34 (s, 1H), 6.35 (s, 1H), 5.45 (m, 1H), 3.57 (m, 2H), 3.42 (m, 2H), 2.79 (s, 2H), 1.70 (m, 4H), 1.45 (m, 15H).

Step 9: 1'-isopropyl-4',6'-dihydrospiro[piperidine-4, 5'-pyrazolo[3,4-c]pyridin]-7'(1'H)-one To a solution of tert-butyl 1'-isopropyl-7'-oxo-1',4',6',7'-tetrahydrospiro[piperidine-4,5'-pyrazolo[3,4-c]pyridine]-1-carboxylate (100 mg, 0.29 mmol) in 4 mL ethyl acetate was added 4 N HCl in dioxane (2 mL). After stirring 30 minutes at room temperature, methanol (1 mL) was added and the resultant solution was stirred for 5 hours at room temperature. The volatiles were removed under reduced pressure and the resultant colorless solid triturated with 1:1 acetonitrile/dichloromethane to yield 71 mg of the title compound as a colorless solid. ¹H NMR (400 MHz, DMSO-d₆, δ): 8.72 (br. s., 2H), 8.05 (s, 1H), 7.37 (s, 1H), 5.36 (m, 1H), 3.15 (m, 2H), 3.05 (m, 2H), 2.78 (s, 2H), 1.78 (m, 4H), 1.33 (d, J=6.6 Hz, 6H).

Intermediate 3: 2'-isopropyl-4',6'-dihydrospiro[piperidine-4,5'-pyrazolo[3,4-c]pyridin]-7'(2'H)-one hydrochloride salt, shown below, was prepared as follows

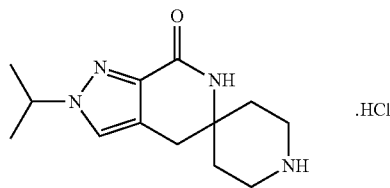 [SMILES: CC(C)n1cc2c(n1)C(=O)NC1(CCNCC1)C2 ; ".HCl"]

Step 1: ethyl 3-iodo-1-isopropyl-1H-pyrazole-4-carboxylate

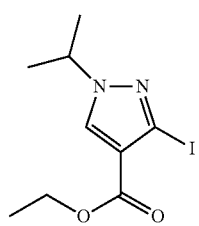

To a solution of ethyl 3-iodopyrazole-4-carboxylate (1.58 g, 5.94 mmol, Truong; et al. Bioorg. Med. Chem. Lett., 19, 4920 (2009)) in 20 mL N,N-dimethylformamide was added cesium carbonate (3.87 g, 11.9 mmol) and 2-iodopropane (0.89 mL, 8.90 mmol). The mixture was stirred 2 hours at 60° C. and then cooled to ambient temperature. The reaction mixture was diluted with 150 mL water and extracted with 2×100 mL diethyl ether. The combined organics were washed with 50 mL brine, dried over sodium sulfate, filtered and concentrated. The resultant oil was purified by flash chromatography (7-60% ethyl acetate/heptane gradient, 50 g silica) to yield 340 mg of ethyl 5-iodo-1-isopropyl-1H-pyrazole-4-carboxylate as a clear oil which crystallized on standing and 740 mg of ethyl 3-iodo-1-isopropyl-1H-pyrazole-4-carboxylate as a clear oil. Ethyl 5-iodo-1-isopropyl-1H-pyrazole-4-carboxylate: +APCI (M+H) 309.0; ¹H NMR (400 MHz, CDCl₃, δ): 8.05 (s, 1H) 4.82 (spt, J=6.6 Hz, 1H) 4.33 (q, J=7.2 Hz, 2H) 1.50 (d, J=6.6 Hz, 6H) 1.37 (t, J=7.1 Hz, 3H). Ethyl 3-iodo-1-isopropyl-1H-pyrazole-4-carboxylate: +APCI (M+H) 309.0; ¹H NMR (400 MHz, CDCl₃, δ): 7.84 (s, 1H) 4.52 (spt, J=6.7 Hz, 1H) 4.32 (q, J=7.1 Hz, 2H) 1.52 (d, J=6.6 Hz, 6H) 1.37 (t, J=7.1 Hz, 3H).

Step 2: (3-iodo-1-isopropyl-1H-pyrazol-4-yl)methanol

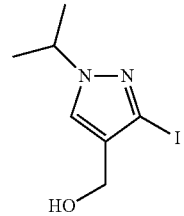

A solution of ethyl 3-iodo-1-isopropyl-1H-pyrazole-4-carboxylate (740 mg, 2.40 mmol) in tetrahydrofuran (20 mL) was cooled to −78° C. and treated with diisobutylaluminum hydride (1.5 M in toluene, 0.8 mL, 7.21 mmol), dropwise. The mixture was stirred at −78° C. for 1 hour and then warmed to room temperature for 2 hours. The mixture was quenched with 10 mL ethyl acetate, stirred 15 minutes, and then treated with 25 mL saturated aqueous Rochelle's salts. After stirring an additional 1 hour at room temperature, the mixture was diluted with 50 mL ethyl acetate and washed with 100 mL water. The aqueous layer was extracted with an additional 50 mL ethyl acetate. The combined organic layers were dried over sodium sulfate, filtered and concentrated. The residue was then purified by flash chromatography (12-100% ethyl acetate/heptanes, 25 g silica gel) to yield 630 mg of (3-iodo-1-isopropyl-1H-pyrazol-4-yl)methanol as a clear oil. +APCI (M+H) 266.8; ¹H NMR (400 MHz, CDCl₃, δ): 7.37 (s, 1H), 4.49 (m, 3H), 1.67 (t, J=5.9 Hz, 1H), 1.50 (s, 6H).

Step 3: 4-(bromomethyl)-3-iodo-1-isopropyl-1H-pyrazole

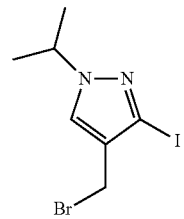

A solution of (3-iodo-1-isopropyl-1H-pyrazol-4-yl)methanol (0.63 g, 2.37 mmol) in 20 mL dichloromethane was cooled to 0° C. Phosphorus(III)bromide (0.67 mL, 7.10 mmol) was added to the solution and the mixture was stirred 30 minutes at 0° C., 1 hour at room temperature, and then quenched with 50 mL water and stirred 15 minutes at room temperature. The mixture was treated with saturated aqueous sodium bicarbonate and extracted with ethyl acetate (2×50 mL). The combined organic layers were washed with brine (50 mL), dried over sodium sulfate, filtered and concentrated. The residue was purified by flash chromatography (10-80% ethyl acetate/heptanes, 25 g silica gel) to yield 400 mg of 4-(bromomethyl)-3-iodo-1-isopropyl-1H-pyrazole as a colorless solid. +APCI (M+H) 329.0; $^1$H NMR (400 MHz, CDCl$_3$, δ): 7.42 (s, 1H), 4.47 (spt, J=6.7 Hz, 1H), 4.35 (s, 2H), 1.50 (d, J=6.6 Hz, 6H).

Step 4: 1-tert-butyl 4-ethyl 4-((3-iodo-1-isopropyl-1H-pyrazol-4-yl)methyl)piperidine-1,4-dicarboxylate

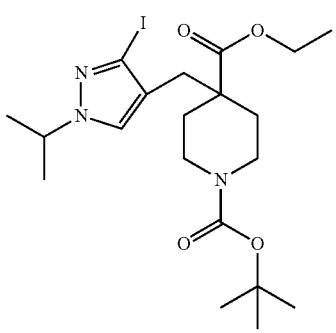 [SMILES: CCOC(=O)C1(Cc2cn(C(C)C)nc2I)CCN(C(=O)OC(C)(C)C)CC1]

A solution of 1-tert-butyl 4-ethyl piperidine-1,4-dicarboxylate (0.54 mL, 2.11 mmol) in tetrahydrofuran (15 mL) in a dry 100 mL round bottom flask under nitrogen was cooled to −78° C. and then treated with lithium bis(trimethylsilyl)amide (1 M toluene, 2.13 mL, 2.13 mmol). After stirring for 45 minutes at −78° C., 4-(bromomethyl)-3-iodo-1-isopropyl-1H-pyrazole (535 mg, 1.63 mmol) was added as a suspension in 10 mL tetrahydrofuran. The mixture was stirred 1 hour at −78° C. and then allowed to stir 18 hours at room temperature. The reaction mixture was quenched with 20 mL saturated aqueous ammonium chloride, stirred 30 minutes at room temperature, diluted with 50 mL water and then extracted with ethyl acetate (2×50 mL). The combined organics were dried over sodium sulfate, filtered and concentrated. The residue was purified by flash chromatography (10-80% ethyl acetate/heptanes, 25 g silica gel) to yield 1-tert-butyl 4-ethyl 4-((3-iodo-1-isopropyl-1H-pyrazol-4-yl)methyl)piperidine-1,4-dicarboxylate (645 mg) as a clear oil. +ESI (M-tBu) 450.1; $^1$H NMR (400 MHz, CDCl$_3$, δ): 7.02 (s, 3H), 4.44 (spt, J=6.6 Hz, 1H), 4.17 (m, 2H), 3.92 (m, 2H), 2.86 (m, 2H), 2.62 (s, 2H), 2.08 (m, 2H), 1.46 (m, 17H), 1.25 (t, J=7.1 Hz, 3H).

Step 5: 1-(tert-butoxycarbonyl)-4-((3-iodo-1-isopropyl-1H-pyrazol-4-yl)methyl)piperidine-4-carboxylic acid

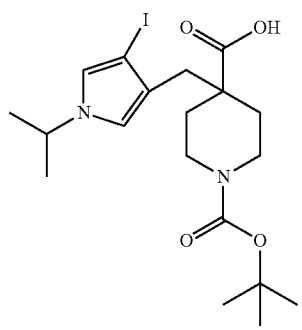 [SMILES: CC(C)n1cc(I)c(CC2(C(=O)O)CCN(C(=O)OC(C)(C)C)CC2)c1]

To a solution of 1-tert-butyl 4-ethyl 4-((3-iodo-1-isopropyl-1H-pyrazol-4-yl)methyl)piperidine-1,4-dicarboxylate (455 mg, 0.9 mmol) in methanol (20 mL) was added 2 N NaOH (5 mL). After stirring for 18 hours at room temperature, the methanol was removed under reduced pressure and the resultant slurry was taken up in 20 mL water, acidified with 2 N HCl and extracted with ethyl acetate (2×30 mL). The combined organic extracts were dried over sodium sulfate, filtered and concentrated to yield 1-(tert-butoxycarbonyl)-4-((3-iodo-1-isopropyl-1H-pyrazol-4-yl)methyl)piperidine-4-carboxylic acid (430 mg) as a colorless solid. −APCI (M−H) 476.1; $^1$H NMR (400 MHz, CDCl$_3$, δ): 7.11 (s, 1H), 4.45 (dquin, J=13.4, 6.7 Hz, 1H), 3.95 (br. s., 2H), 2.91 (m, 2H), 2.69 (s, 2H), 2.08 (m, 2H), 1.47 (m, 8H).

Step 6: tert-butyl 4-((3-iodo-1-isopropyl-1H-pyrazol-4-yl)methyl)-4-isocyanatopiperidine-1-carboxylate

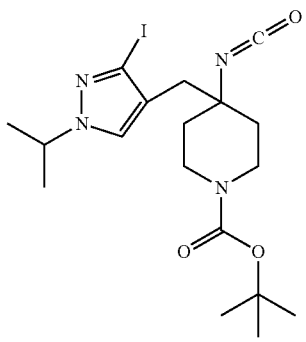 [SMILES: CC(C)n1cc(CC2(N=C=O)CCN(C(=O)OC(C)(C)C)CC2)c(I)n1]

To a solution of 1-(tert-butoxycarbonyl)-4-((3-iodo-1-isopropyl-1H-pyrazol-4-yl)methyl)piperidine-4-carboxylic acid (430 mg, 0.90 mmol) in toluene (10 mL) was added triethylamine (0.15 mL, 1.08 mmol) and diphenylphosphoryl azide (0.24 mL, 1.08 mmol). The mixture was heated at 120° C. for 3 hours, the volatiles were removed under reduced pressure and the resultant oil was purified by flash chromatography (7-60% ethyl acetate/heptanes, 25 g silica gel) to yield tert-butyl 4-((3-iodo-1-isopropyl-1H-pyrazol-4-yl)methyl)-4-isocyanatopiperidine-1-carboxylate (280 mg) as a clear oil. FT-IR (cm$^{-1}$): 2253; $^1$H NMR (400 MHz, CDCl$_3$, δ): 7.27 (s, 1H), 4.50 (m, 1H), 4.03 (br. s., 2H), 2.97 (br. s., 2H), 2.65 (s, 2H), 1.65 (m, 4H), 1.50 (s, 6H), 1.47 (s, 9H).

Step 7: tert-butyl 2'-isopropyl-7'-oxo-2',4',6',7'-tetrahydrospiro[piperidine-4,5'-pyrazolo[3,4-c]pyridine]-1-carboxylate

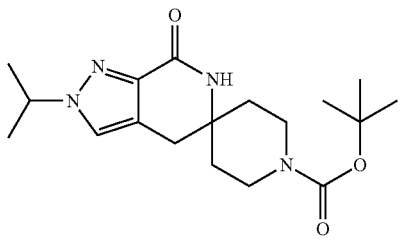 [SMILES: CC(C)n1cc2c(n1)C(=O)NC1(CCN(C(=O)OC(C)(C)C)CC1)C2]

To a −78° C. solution of tert-butyl 4-((3-iodo-1-isopropyl-1H-pyrazol-4-yl)methyl)-4-isocyanatopiperidine-1-carboxylate (280 mg, 0.59 mmol) in tetrahydrofuran (10 mL)

was added t-butyl lithium (0.7 mL, 1.7 M in pentane), dropwise. After stirring for 30 minutes at −78° C. the mixture was warmed to 0° C., quenched with 20 mL saturated aqueous ammonium chloride, and stirred an additional 30 minutes at room temperature. The reaction mixture was diluted with 25 mL water and extracted with ethyl acetate (2×50 mL). The combined organics were dried over sodium sulfate, filtered and concentrated. The residue was then purified by flash chromatography (12-100% ethyl acetate/heptanes, 10 g silica gel) to yield tert-butyl 2'-isopropyl-7'-oxo-2',4',6',7'-tetrahydrospiro[piperidine-4,5'-pyrazolo[3,4-c]pyridine]-1-carboxylate (130 mg) as a colorless solid. +ESI (M+H) 349.1; $^1$H NMR (500 MHz, CDCl$_3$, δ): 7.28 (s, 1H), 5.78 (s, 1H), 4.57 (spt, J=6.6 Hz, 1H), 3.59 (m, 2H), 3.37 (m, 2H), 2.82 (s, 2H), 1.74 (m, 4H), 1.55 (d, J=6.6 Hz, 6H), 1.47 (s, 9H).

Step 8: 2'-isopropyl-4',6'-dihydrospiro[piperidine-4,5'-pyrazolo[3,4-c]pyridin]-7'(2'H)-one hydrochloride To a solution of tert-butyl 2'-isopropyl-7'-oxo-2',4',6',7'-tetrahydrospiro[piperidine-4,5'-pyrazolo[3,4-c]pyridine]-1-carboxylate (130 mg, 0.37 mmol) in ethyl acetate (5 mL) was added 4 M hydrochloric acid (2 mL) in 1,4-dioxane. The reaction mixture was stirred 3 hours at room temperature, the volatiles were removed under reduced pressure and the resultant residue was triturated with 10 mL heptane. The solid was dried under reduced pressure to yield 2'-isopropyl-4',6'-dihydrospiro[piperidine-4,5'-pyrazolo[3,4-c]pyridin]-7'(2'H)-one hydrochloride (105 mg) as an off-white solid. +ESI (M+H) 249.1; $^1$H NMR (500 MHz, DMSO-d$_6$, δ): 7.91 (s, 1H) 7.69 (s, 1H) 4.48-4.62 (m, 1H) 3.02-3.28 (m, 4H) 2.78 (s, 2H) 1.74-1.89 (m, 4H) 1.41 (d, J=6.59 Hz, 6H).

Intermediate 4: 2'-tert-butyl-4',6'-dihydrospiro[piperidine-4,5'-pyrazolo[3,4-c]pyridin]-7'(2'H)-one hydrochloride salt, shown below, was prepared as follows

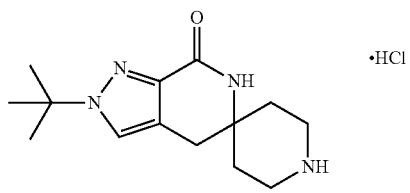 [SMILES: CC(C)(C)n1cc2c(n1)C(=O)NC1(CCNCC1)C2 ; Cl]

Step 1: (E)-ethyl 2-(2-tert-butylhydrazono)propanoate

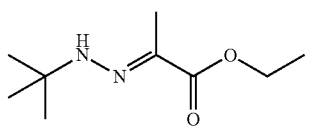

To a solution of ethyl pyruvate (20.22 g, 174.1 mmol) in ethanol (150 mL) was added t-butyl hydrazine hydrochloride (21.7 g, 174 mmol) and N,N-diisopropylethyl amine (33.4 mL, 192 mmol). After stirring at reflux for 18 hours, the reaction was cooled and the volatiles were removed under reduced pressure. The resultant golden oil was taken up in 300 mL ethyl acetate and washed with 200 mL water and 300 mL saturated aqueous sodium bicarbonate. The organic layer was dried over sodium sulfate, filtered and concentrated to yield (E)-ethyl 2-(2-tert-butylhydrazono)propanoate (23.1 g) as a clear pale yellow oil. +APCI (M+H) 187.3; $^1$H NMR (400 MHz, CDCl$_3$, δ): 5.51 (br. s., 1H), 4.25 (q, J=7.2 Hz, 2H), 1.89 (s, 3H), 1.32 (t, J=7.1 Hz, 3H), 1.28 (s, 9H).

Step 2: ethyl 1-tert-butyl-4-formyl-1H-pyrazole-3-carboxylate

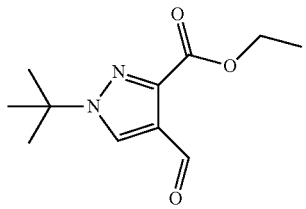 [SMILES: CCOC(=O)c1nn(C(C)(C)C)cc1C=O]

To a yellow orange solution of (E)-ethyl 2-(2-tert-butylhydrazono)propanoate (22.9 g, 123 mmol) in toluene (300 mL) was added (chloromethylene)dimethylammonium chloride (Vilsmeier salt, 34.0 g, 252 mmol) in a single portion. The suspension was stirred 3 hours at room temperature, slowly becoming a biphasic mixture of toluene over a thick orange oil. The reaction mixture was cooled to 0° C. and slowly neutralized with saturated aqueous sodium bicarbonate. The layers were separated and the aqueous layer extracted with additional ethyl acetate (2×200 mL). The organic layers were combined, washed with 200 mL brine, dried over sodium sulfate, filtered and concentrated to yield ethyl 1-tert-butyl-4-formyl-1H-pyrazole-3-carboxylate (18.6 g) as a tan-orange oil which solidified on standing. +APCI (M+H) 225.1; $^1$H NMR (400 MHz, CDCl$_3$, δ): 10.37 (s, 1H), 8.14 (s, 1H), 4.48 (q, J=7.0 Hz, 2H), 1.65 (s, 9H), 1.44 (t, 3H).

Step 3: ethyl 1-tert-butyl-4-(hydroxymethyl)-1H-pyrazole-3-carboxylate

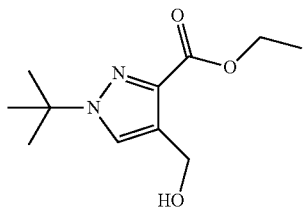 [SMILES: CCOC(=O)c1nn(C(C)(C)C)cc1CO]

To a solution of ethyl 1-tert-butyl-4-formyl-1H-pyrazole-3-carboxylate (2.87 g, 12.8 mmol) in ethanol (50 mL) was added sodium borohydride (0.97 g, 25.6 mmol) in one portion. After stirring for 30 minutes at room temperature the mixture was quenched with 1 N aqueous hydrochloric acid (100 mL), stirred for 15 minutes, and then neutralized with saturated aqueous sodium bicarbonate. The mixture was extracted with ethyl acetate (2×150 mL), the combined organics then dried over sodium sulfate, filtered and concentrated to yield ethyl 1-tert-butyl-4-(hydroxymethyl)-1H-pyrazole-3-carboxylate (2.57 g) as a clear oil. +APCI (M+Na) 249.2; $^1$H NMR (400 MHz, CDCl₃, δ): 7.49 (s, 1H), 4.65 (d, J=6.8 Hz, 2H), 4.43 (q, J=7.2 Hz, 2H), 3.62 (t, J=6.9 Hz, 1H), 1.59 (s, 9H), 1.41 (t, J=7.1 Hz, 3H).

Step 4: ethyl 4-(bromomethyl)-1-tert-butyl-1H-pyrazole-3-carboxylate

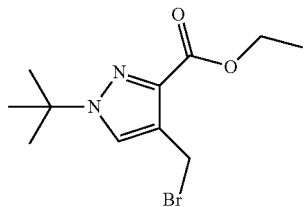 [SMILES: CCOC(=O)c1nn(C(C)(C)C)cc1CBr]

To a 0° C. solution of ethyl 1-tert-butyl-4-(hydroxymethyl)-1H-pyrazole-3-carboxylate (3.9 g, 17.24 mmol) in dichloromethane (120 mL) was added phosphorus tribromide (4.91 mL, 51.7 mmol), and the resultant mixture was stirred 30 minutes at 0° C. and then 1 hour at room temperature. The mixture was quenched with 50 mL water, neutralized with saturated aqueous sodium bicarbonate, stirred 30 minutes, and then extracted with dichloromethane (2×150 mL). The combined organic extracts were washed with 100 mL brine, dried over sodium sulfate, filtered and concentrated. The resulting residue was purified by flash chromatography (7-60% ethyl acetate/heptanes, 50 g silica gel) to yield ethyl 4-(bromomethyl)-1-tert-butyl-1H-pyrazole-3-carboxylate (4.12 g) as a clear oil. +APCI (M+H) 289.1; ¹H NMR (400 MHz, CDCl₃, δ): 7.61 (s, 1H), 4.70 (s, 2H), 4.41 (q, J=7.2 Hz, 2H), 1.60 (s, 9H), 1.40 (t, 3H).

Step 5: tert-butyl 4-((1-tert-butyl-3-(ethoxycarbonyl)-1H-pyrazol-4-yl)methyl)-4-cyanopiperidine-1-carboxylate

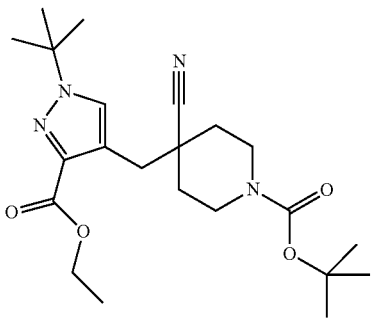 [SMILES: CCOC(=O)c1nn(C(C)(C)C)cc1CC1(C#N)CCN(C(=O)OC(C)(C)C)CC1]

To a −78° C. solution of tert-butyl 4-cyanopiperidine-1-carboxylatepiperidine (1.0 g, 4.76 mmol) in tetrahydrofuran (20 mL) was added lithium bis(trimethylsilyl)amide (4.76 mL, 1 M in tetrahydrofuran). The mixture was stirred 30 minutes at −78° C., warmed to 0° C. for 30 minutes and then cooled to −78° C. A solution of ethyl 4-(bromomethyl)-1-tert-butyl-1H-pyrazole-3-carboxylate (1.38 g, 4.76 mmol) in tetrahydrofuran was then added, dropwise. After stirring 30 minutes at −78° C. the mixture was allowed to warm to room temperature and stir an additional 18 hours. The reaction mixture was quenched with saturated aqueous ammonium chloride (50 mL), stirred for 30 minutes, diluted with water (50 mL) and then extracted with ethyl acetate (2×50 mL). The organics were combined, dried over sodium sulfate, filtered and concentrated. The residue was purified by flash chromatography (7-60% ethyl acetate/heptanes, 100 g silica gel) to yield tert-butyl 4-((1-tert-butyl-3-(ethoxycarbonyl)-1H-pyrazol-4-yl)methyl)-4-cyanopiperidine-1-carboxylate (455 mg) as a clear oil. +APCI (M+H) 419.3; ¹H NMR (500 MHz, CDCl₃, δ): 7.68 (s, 1H), 4.40 (q, J=7.2 Hz, 2H), 4.13 (br. s., 2H), 3.17 (s, 2H), 2.97 (br. s., 2H), 1.81 (d, J=13.2 Hz, 2H), 1.63 (s, 9H), 1.56 (m, 2H), 1.46 (s, 9H), 1.41 (t, J=7.2 Hz, 3H).

Step 6: 4-((1-(tert-butoxycarbonyl)-4-carbamoylpiperidin-4-yl)methyl)-1-tert-butyl-1H-pyrazole-3-carboxylic acid

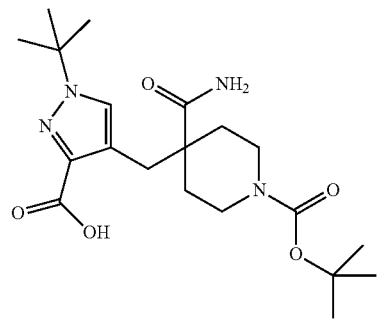 [SMILES: CC(C)(C)OC(=O)N1CCC(Cc2cn(C(C)(C)C)nc2C(=O)O)(C(N)=O)CC1]

To a 0° C. solution of tert-butyl 4-((1-tert-butyl-3-(ethoxycarbonyl)-1H-pyrazol-4-yl)methyl)-4-cyanopiperidine-1-carboxylate (455 mg, 1.09 mmol) in methanol (11 mL) was added a solution of urea-hydrogen peroxide (1.05 g, 10.9 mmol) in 1 M aqueous sodium hydroxide (10.9 mL), dropwise. After stirring for 18 hours at room temperature, volatiles were removed under reduced pressure and the resultant slurry was taken up in water (50 mL), acidified with 2 N aqueous hydrochloric acid and extracted with ethyl acetate (2×50 mL). The combined organic extracts were dried over sodium sulfate, filtered and concentrated to yield 4-((1-(tert-butoxycarbonyl)-4-carbamoylpiperidin-4-yl)methyl)-1-tert-butyl-1H-pyrazole-3-carboxylic acid (418 mg) as a colorless solid. −APCI (M−H) 407.3; ¹H NMR (400 MHz, DMSO-d₆, δ): 12.33 (br. s., 1H), 7.47 (s, 1H), 7.11 (br. s., 1H), 6.99 (s, 1H), 3.59 (d, J=13.3 Hz, 2H), 2.89 (s, 2H), 2.77 (m, 2H), 1.84 (m, 2H), 1.44 (s, 9H), 1.31 (s, 9H), 1.16 (m, 2H).

Step 7: 4-((1-(tert-butoxycarbonyl)-4-isocyanatopiperidin-4-yl)methyl)-1-tert-butyl-1H-pyrazole-3-carboxylic acid

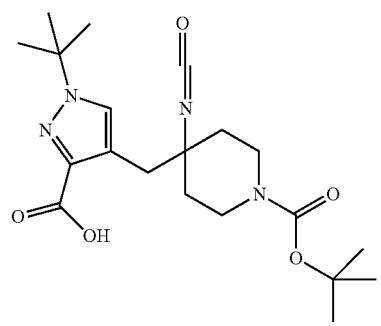 [SMILES: CC(C)(C)OC(=O)N1CCC(Cc2cn(C(C)(C)C)nc2C(=O)O)(N=C=O)CC1]

To a suspension of 4-((1-(tert-butoxycarbonyl)-4-carbamoylpiperidin-4-yl)methyl)-1-tert-butyl-1H-pyrazole-3-carboxylic acid (388 mg, 0.95 mmol) in acetonitrile (20 mL) was added sodium bicarbonate (319 mg, 3.80 mmol) and bis(trifluoroacetoxy) iodosobenzene (632 mg, 1.42 mmol). The mixture was stirred 90 minutes at room temperature, diluted with 50 mL water, acidified with 1 N aqueous hydrochloric acid, and then extracted with ethyl acetate (2×50 mL). The combined organic extracts were dried over sodium sulfate, filtered and concentrated. The resulting residue was purified by flash chromatography (1-10% methanol/dichloromethane, 25 g silica gel) to yield 4-((1-(tert-butoxycarbonyl)-4-isocyanatopiperidin-4-yl)methyl)-1-tert-butyl-1H-pyrazole-3-carboxylic acid (172 mg) as a colorless solid. –APCI (M–H) 405.4; $^1$H NMR (400 MHz, DMSO-$d_6$, δ): 12.52 (br. s., 1H), 7.82 (s, 1H), 3.83 (br. s., 2H), 3.03 (s, 2H), 2.82 (br. s., 2H), 1.49 (m, 13H), 1.36 (m, 9H).

Step 8: tert-butyl 2'-tert-butyl-7'-oxo-2',4',6',7'-tetrahydrospiro[piperidine-4,5'-pyrazolo[3,4-c]pyridine]-1-carboxylate

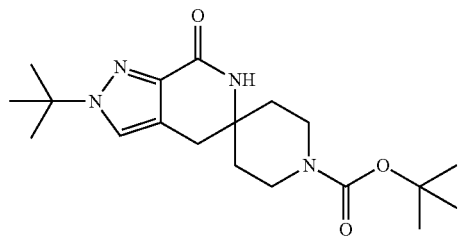 [SMILES: CC(C)(C)OC(=O)N1CCC2(CC1)Cc1cn(C(C)(C)C)nc1C(=O)N2]

A solution of 4-((1-(tert-butoxycarbonyl)-4-isocyanatopiperidin-4-yl)methyl)-1-tert-butyl-1H-pyrazole-3-carboxylic acid (180 mg, 0.44 mmol) in tetrahydrofuran (5 mL) was treated with 2 N aqueous sodium hydroxide (0.664 mL, 1.33 mmol). The mixture was stirred 3 hours at room temperature, tetrahydrofuran and water were removed on a rotary evaporator and the resultant colorless solid was slurried in acetonitrile (10 mL) and then concentrated to dryness. The trituration was repeated twice more from acetonitrile (10 mL). The resultant colorless solid was taken up in dichloromethane (10 mL) and treated with (3-(dimethylamino)propyl)ethyl carbodiimide hydrochloride (170 mg, 0.89 mmol). The mixture was stirred 18 hours at room temperature and then diluted with dichloromethane (50 mL) and washed with water (30 mL). The organic phase was dried over sodium sulfate, filtered and concentrated. The residue was then purified by flash chromatography (30-100% ethyl acetate/heptanes, 10 g silica gel) to yield tert-butyl 2'-tert-butyl-7'-oxo-2',4',6',7'-tetrahydrospiro[piperidine-4,5'-pyrazolo[3,4-c]pyridine]-1-carboxylate (70 mg) as a colorless solid. +ESI (M+H) 363.3; $^1$H NMR (400 MHz, DMSO-$d_6$, δ): 7.68 (s, 1H), 7.57 (s, 1H), 3.47 (m, 2H), 3.20 (m, 2H), 2.73 (s, 2H), 1.53 (t, J=5.7 Hz, 4H), 1.49 (s, 9H), 1.36 (s, 9H).

Step 9: The title compound, 2'-tert-butyl-4',6'-dihydrospiro[piperidine-4,5'-pyrazolo[3,4-c]pyridin]-7'(2'H)-one hydrochloride salt To a solution of tert-butyl 2'-tert-butyl-7'-oxo-2',4',6',7'-tetrahydrospiro[piperidine-4,5'-pyrazolo[3,4-c]pyridine]-1-carboxylate (70 mg, 0.19 mmol) in ethyl acetate (5 mL) was added 4 M hydrochloric acid in 1,4-dioxane (2 mL) and the mixture was stirred 3 hours at room temperature. The volatiles were removed under reduced pressure and the resultant colorless solid was triturated from heptanes (10 mL) and dried under reduced pressure to yield 2'-tert-butyl-4',6'-dihydrospiro[piperidine-4,5'-pyrazolo[3,4-c]pyridin]-7'(2'H)-one hydrochloride salt (56 mg) as an off-white solid. +ESI (M+H) 263.1; $^1$H NMR (500 MHz, DMSO-$d_6$, δ): 8.72 (m, 2H), 7.92 (s, 1H), 7.75 (s, 1H), 3.20 (br. s, 2H), 3.09 (br. s., 2H), 2.78 (s, 2H), 1.79 (m, 4H), 1.48 (s, 9H).

Intermediate 5: 2'-tert-pentyl-4',6'-dihydrospiro[piperidine-4,5'-pyrazolo[3,4-c]pyridin]-7'(2'H)-one, shown below, was prepared as follows

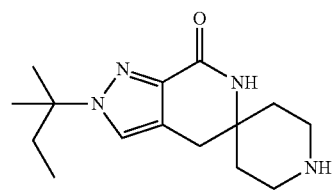 [SMILES: CCC(C)(C)n1cc2c(n1)C(=O)NC1(CCNCC1)C2]

Step 1: ethyl 3-bromo-1H-pyrazole-4-carboxylate

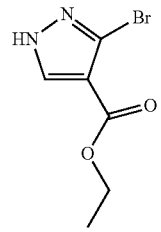

To a 0° C. solution of ethyl 3-amino-1H-pyrazole-4-carboxylate (5.0 g, 32 mmol) and copper (II) bromide (7.2 g, 32 mmol) in acetonitrile (65 mL) was slowly added isoamyl nitrite (12 mL, 86 mmol). The reaction was heated to 50° C. and stirred overnight. The reaction was cooled to room temperature and quenched with 1 N aqueous hydrochloric acid (150 mL). The mixture was extracted with ethyl acetate (3×100 mL). The combined organics were washed with water, dried over sodium sulfate, filtered, and concentrated to give the title compound as a brown oil that partially solidified under vacuum overnight (7.1 g, 100%). $^1$H NMR (400 MHz, CDCl$_3$, δ): 9.78 (br. s., 1H), 8.10 (br. s., 1H), 4.33 (q, J=7.22 Hz, 2H), 1.36 (m, 3H).

Step 2: (3-bromo-1-tert-pentyl-1H-pyrazol-4-yl)methanol

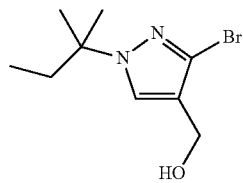

Concentrated sulfuric acid (0.45 mL, 4.8 mmol) was added to a mixture of ethyl 3-bromo-1H-pyrazole-4-carboxylate (1.0 g, 4.6 mmol) and tert-amyl alcohol (3.0 mL, 27 mmol). The reaction was heated to 100° C. for 2.5 hours. The reaction was then cooled to room temperature and left stirring overnight. The reaction was diluted with ethyl acetate and washed with water. The organic layer was dried over sodium sulfate, filtered, and concentrated to yield ethyl 3-bromo-1-tert-pentyl-1H-pyrazole-4-carboxylate (1.3 g) as a crude brown oil.

This crude product (1.3 g) was dissolved in tetrahydrofuran (24 mL) and cooled to −78° C. A solution of diisobutylaluminum hydride (1.5 M in toluene, 9.0 mL, 160 mmol) was slowly added, and the reaction was stirred at −78° C. for 1 hour. The reaction was then allowed to warm to room temperature and stir for another 2 hours. The reaction was diluted with ethyl acetate (20 mL) and saturated aqueous Rochelle's salt (20 mL).

The mixture was stirred at room temperature overnight. The layers were separated and the aqueous layer was extracted with ethyl acetate. The combined organics were washed with brine, dried over sodium sulfate, filtered, and concentrated. Purification by flash column chromatography (0-100% ethyl acetate/heptanes) gave the title compound (685 mg, 62%) as a pale yellow oil. $^1$H NMR (400 MHz, CDCl$_3$, δ): 7.45 (s, 1H), 4.51 (s, 2H), 1.86 (q, J=7.41 Hz, 2H), 1.66 (s, 1H), 1.51 (s, 6H), 0.69 (m, 3H).

Step 3:
3-bromo-4-(chloromethyl)-1-tert-pentyl-1H-pyrazole

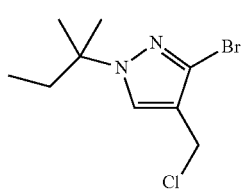

A solution of (3-bromo-1-tert-pentyl-1H-pyrazol-4-yl)methanol (675 mg, 2.73 mmol) in dichloromethane (10 mL) was cooled to 0° C. Triethylamine (0.53 mL, 3.8 mmol) and methanesulfonyl chloride (0.28 mL, 3.6 mmol) were added. The reaction was stirred at 0° C. for 15 minutes, then warmed to room temperature and stirred for 1.5 hours. The reaction was diluted with ethyl acetate, washed with water and brine, dried over sodium sulfate, filtered, and concentrated to give the title compound (725 mg, 100%) as a clear oil. $^1$H NMR (400 MHz, CDCl$_3$, δ): 7.48 (s, 1H), 4.47 (s, 2H), 1.86 (q, J=7.48 Hz, 2H), 1.52 (s, 6H), 0.69 (m, 3H).

Step 4:
3-bromo-4-(iodomethyl)-1-tert-pentyl-1H-pyrazole

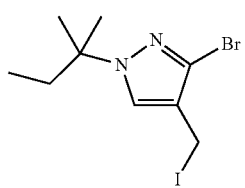

To a solution of 3-bromo-4-(chloromethyl)-1-tert-pentyl-1H-pyrazole (725 mg, 2.73 mmol) in acetone (25 mL) was added sodium iodide (4.09 g, 27.3 mmol). The reaction was heated at reflux for 2 hours, then cooled to room temperature and stirred overnight. The solvent was removed in vacuo and the residue was partitioned between ethyl acetate and water. The organic layer was washed with saturated aqueous sodium thiosulfate and brine. The organics were dried over sodium sulfate, filtered, and concentrated to yield the title compound (824 mg, 85%) as a brown oil. $^1$H NMR (400 MHz, CDCl$_3$, δ): 7.47 (s, 1H), 4.26 (s, 2H), 1.83 (q, J=7.41 Hz, 2H), 1.50 (s, 6H), 0.67 (t, J=7.51 Hz, 3H).

Step 5: 2'-tert-pentyl-4',6'-dihydrospiro[piperidine-4,5'-pyrazolo[3,4-c]pyridin]-7'(2'H)-one The title compound was prepared by a method analogous to that described for Intermediate 3 in Steps 4-8, using 3-bromo-4-(iodomethyl)-1-tert-pentyl-1H-pyrazole. +ESI (M+H) 277.3; $^1$H NMR (400 MHz, CD$_3$OD, δ): 7.67 (s, 1H), 3.22-3.37 (m, 4H), 2.93 (s, 2H), 1.92 (q, J=7.61 Hz, 2H), 1.88-2.05 (m, 4H), 1.57 (s, 6H), 0.67 (t, J=7.41 Hz, 3H).

Intermediate 6: 2'-cyclobutyl-4',6'-dihydrospiro[piperidine-4,5'-pyrazolo[3,4-c]pyridin]-7'(2'H)-one, shown below, was prepared as follows

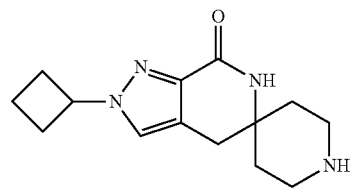 [SMILES: O=C1NC2(CCNCC2)Cc2cn(C3CCC3)nc21]

Step 1: ethyl 3-bromo-1-cyclobutyl-1H-pyrazole-4-carboxylate

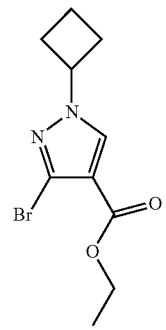

A mixture of ethyl 3-bromo-1H-pyrazole-4-carboxylate (1.00 g, 4.56 mmol), cyclobutyl bromide (0.65 mL, 6.9 mmol), and cesium carbonate (2.97 g, 9.13 mmol) in N,N-dimethylformamide (10 mL) was heated to 60° C. and stirred overnight. The reaction was cooled to room temperature and partitioned between 1:1 heptanes/ethyl acetate and water. The aqueous was extracted again with 1:1 heptanes/ethyl acetate. The combined organics were washed with brine, dried over sodium sulfate, filtered, and concentrated. Purification by flash column chromatography gave two product regioisomers as colorless oils.

ethyl 5-bromo-1-cyclobutyl-1H-pyrazole-4-carboxylate (230 mg, 18%): +ESI (M+H+1) 275.1; ¹H NMR (400 MHz, CDCl₃, δ): 7.98 (s, 1H), 4.98 (m, 1H), 4.30 (q, J=7.02 Hz, 2H), 2.61-2.74 (m, 2H), 2.43 (m, 2H), 1.84-1.95 (m, 2H), 1.34 (m, 3H).

ethyl 3-bromo-1-cyclobutyl-1H-pyrazole-4-carboxylate (570 mg, 46%): +ESI (M+H+1) 275.1; ¹H NMR (400 MHz, CDCl₃, δ): 7.87 (s, 1H), 4.69 (m, 1H), 4.29 (q, J=7.22 Hz, 2H), 2.41-2.61 (m, 4H), 1.78-1.98 (m, 2H), 1.34 (m, 3H).

Step 2:
(3-bromo-1-cyclobutyl-1H-pyrazol-4-yl)methanol

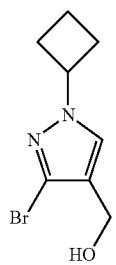

A solution of ethyl 3-bromo-1-cyclobutyl-1H-pyrazole-4-carboxylate (565 mg, 2.07 mmol) in tetrahydrofuran (10 mL) was cooled to −78° C. Diisobutylaluminum hydride (4.13 mL, 6.02 mmol, 1.5 M in toluene) was added slowly and the reaction was stirred at −78° C. for 1 hour. The reaction was then allowed to warm to room temperature and stir for an additional 2 hours. The reaction was diluted with ethyl acetate (20 mL) and saturated aqueous Rochelle's salt (20 mL). The mixture was stirred at room temperature overnight. The mixture was further diluted with ethyl acetate and was washed with water. The aqueous layer was extracted with ethyl acetate and the combined organics were dried over sodium sulfate, filtered, and concentrated to yield the title compound (478 mg, 100%) as a colorless oil. +APCI (M+H+1) 233.1; ¹H NMR (400 MHz, CDCl₃, δ): 7.40 (s, 1H), 4.62-4.71 (m, 1H), 4.51 (s, 2H), 2.39-2.59 (m, 4H), 1.74-1.92 (m, 3H).

Step 3: 2'-cyclobutyl-4',6'-dihydrospiro[piperidine-4,5'-pyrazolo[3,4-c]pyridin]-7'(2'H)-one The title compound was prepared by a method analogous to that described for Intermediate 5, Steps 3-5, using (3-bromo-1-cyclobutyl-1H-pyrazol-4-yl)methanol. +ESI (M+H) 261.3; ¹H NMR (400 MHz, CD₃OD, δ): 7.62 (s, 1H), 4.84-4.92 (m, 1H), 3.21-3.36 (m, 4H), 2.93 (s, 2H), 2.50-2.63 (m, 2H), 2.40-2.50 (m, 2H), 1.82-2.05 (m, 6H).

Intermediate 7: 2'-tert-butyl-4',6'-dihydro-8-azaspiro[bicyclo[3.2.1]octane-3,5'-pyrazolo[3,4-c]pyridin]-7'(2'H)-one hydrochloride, shown below, was prepared as follows

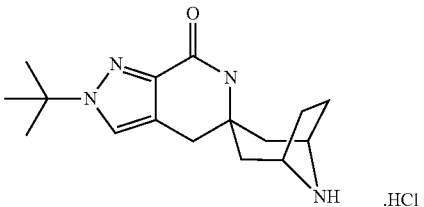 [SMILES: CC(C)(C)n1cc2c(n1)C(=O)NC1(C2)CC2CCC(C1)N2 ; ".HCl"]

Step 1: ethyl 3-iodo-1H-pyrazole-4-carboxylate

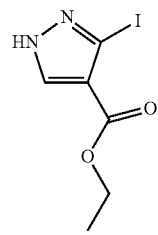

Ethyl 3-amino-1H-pyrazole-4-carboxylate (860.0 mg, 5.54 mmol) was dissolved in acetic acid (5 mL) and water (5 mL). Potassium iodide (921 mg, 5.54 mmol) was added and the mixture was stirred until all solids had dissolved. A solution of sodium nitrite (386 mg, 5.54 mmol) in water (2 mL) was then added dropwise. The reaction was stirred at room temperature for 2 minutes when stirring became hindered due to precipitate formation. Additional water (5 mL) was added and the reaction was allowed to stir overnight. The acetic acid was removed under reduced pressure. The brown residue was taken up in saturated aqueous sodium bicarbonate and was extracted with ethyl acetate (2×50 mL). The combined organics were washed with saturated aqueous sodium thiosulfate (50 mL), dried over sodium sulfate, filtered, and concentrated. Purification by flash column chromatography (10-80% ethyl acetate/heptanes) gave the title compound (863 mg, 59%) as a white solid. +APCI (M+H) 267.2; ¹H NMR (400 MHz, CDCl$_3$, δ): 12.63 (br. s., 1H), 8.13 (s, 1H), 4.34 (q, J=7.0 Hz, 2H), 1.38 (t, J=7.2 Hz, 3H).

Step 2: ethyl 1-tert-butyl-3-iodo-1H-pyrazole-4-carboxylate

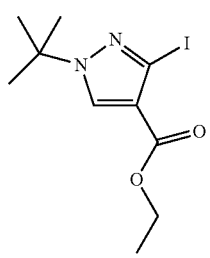

To a solution of ethyl 3-iodo-1H-pyrazole-4-carboxylate (1.10 g, 3.91 mmol) in tert-butanol (5 mL) was added sulfuric acid (0.40 mL, 4.18 mmol, 18 M). The reaction was heated to 100° C. and stirred for 3 hours. The reaction was cooled to room temperature and diluted with ethyl acetate (100 mL) and water (25 mL). The pH was adjusted to 8 with saturated aqueous sodium bicarbonate. The layers were separated and the organics were dried over sodium sulfate, filtered, and concentrated. Purification by flash column chromatography (7-60% ethyl acetate/heptanes) gave 2 regioisomeric products.

ethyl 1-tert-butyl-5-iodo-1H-pyrazole-4-carboxylate: $^1$H NMR (400 MHz, CDCl$_3$, δ): 7.91 (s, 1H), 4.32 (q, J=7.2 Hz, 2H), 1.83 (s, 9H), 1.37 (t, J=7.1 Hz, 3H).

ethyl 1-tert-butyl-3-iodo-1H-pyrazole-4-carboxylate (976 mg, 73%) as a clear oil: +APCI (M+H) 323.3; $^1$H NMR (400 MHz, CDCl$_3$, δ): 7.90 (s, 1H), 4.31 (q, J=7.0 Hz, 2H), 1.59 (s, 9H), 1.36 (t, J=7.1 Hz, 3H).

Step 3: 1-tert-butyl-3-iodo-4-(iodomethyl)-1H-pyrazole

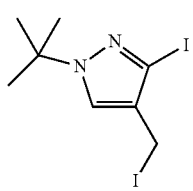

The title compound was prepared by a method analogous to that described for Intermediate 5, Steps 2-4, using ethyl 1-tert-butyl-3-iodo-1H-pyrazole-4-carboxylate. $^1$H NMR (400 MHz, CDCl$_3$, δ): 7.49 (s, 1H), 4.25 (s, 2H), 1.56 (s, 9H).

Step 4: (1R,5S)-8-tert-butyl 3-methyl 8-azabicyclo[3.2.1]octane-3,8-dicarboxylate

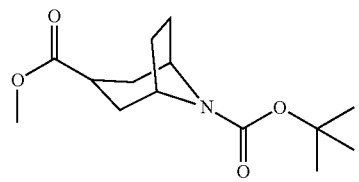 [SMILES: COC(=O)C1CC2CCC(C1)N2C(=O)OC(C)(C)C]

To a solution of (1R,5S)-8-(tert-butoxycarbonyl)-8-azabicyclo[3.2.1]octane-3-carboxylic acid (500 mg, 1.96 mmol) in N,N-dimethylformamide (5 mL) was added potassium carbonate (541 mg, 3.92 mmol) and methyl iodide (0.18 mL, 2.94 mmol). The reaction was stirred at room temperature for 18 hours. The reaction was diluted with ethyl acetate (50 mL) and heptanes (50 mL), and then washed with water (100 mL) and brine (50 mL). The organics were dried over sodium sulfate, filtered, and concentrated. Purification by flash column chromatography gave the title compound (486 mg, 92%) as a clear oil. $^1$H NMR (400 MHz, CDCl$_3$, δ): 4.17-4.29 (m, 2H), 3.65 (s, 3H), 2.75-2.86 (m, 1H), 1.93-2.01 (m, 2H), 1.79-1.92 (m, 2H), 1.67-1.76 (m, 2H), 1.58-1.66 (m, 2H), 1.45 (s, 9H).

Step 5: 2'-tert-butyl-4',6'-dihydro-8-azaspiro[bicyclo[3.2.1]octane-3,5'-pyrazolo[3,4-c]pyridin]-7'(2'H)-one hydrochloride The title compound was prepared by a method analogous to that described for Intermediate 3, Steps 4-8, using (1R,5S)-8-tert-butyl 3-methyl 8-azabicyclo[3.2.1]octane-3,8-dicarboxylate and 1-tert-butyl-3-iodo-4-(iodomethyl)-1H-pyrazole. +ESI (M+H) 289.2; $^1$H NMR (400 MHz, CD$_3$OD, δ): 7.69 (s, 1H), 4.03-4.10 (m, 2H), 2.74 (s, 2H), 2.39-2.46 (m, 2H), 2.10-2.25 (m, 6H), 1.59 (s, 9H).

Intermediate 8: 1H-pyrazolo[4,3-b]pyridine-6-carboxylic acid, shown below, was prepared as follows:

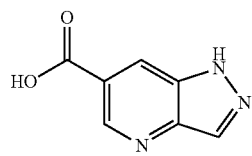 [SMILES: O=C(O)c1cnc2cn[nH]c2c1]

Step 1: diethyl 2-(5-bromo-3-nitropyridin-2-yl)malonate

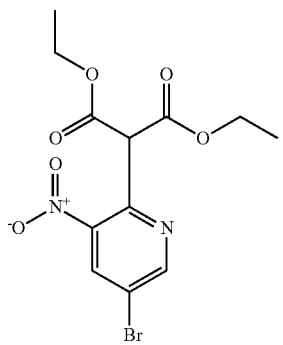

To a suspension of sodium hydride (5.08 g, 127 mmol) in N,N-dimethylformamide (75 mL) was added diethyl malonate (19.26 mL, 127 mmol) at 0° C. The solution was then stirred at ambient temperature for 30 minutes and a solution of 5-bromo-2-chloro-3-nitropyridine (30 g, 127 mmol) in N,N-dimethylformamide (75 mL) was added dropwise. The dark brown mixture was then stirred at 100° C. for 2 hours before being cooled to ambient temperature and quenched with a saturated solution of ammonium chloride (500 mL) at 0° C. The mixture was extracted with ethyl acetate (3×500 mL) and the combined organics were dried over magnesium sulfate and filtered. The solvent was removed in vacuo to give a dark brown oil which was purified by flash column chromatography (10% ethyl acetate/hexane) to afford diethyl 2-(5-bromo-3-nitropyridin-2-yl)malonate as a brown solid (31.8 g, 69%). $^1$HNMR (400 MHz, CDCl$_3$, δ): 8.86 (s, 1H), 8.61 (s, 1H), 5.44 (s, 1H), 4.29 (q, 4H), 1.27 (t, 6H).

Step 2: 5-bromo-2-methyl-3-nitropyridine

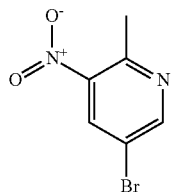

A mixture of the diethyl 2-(5-bromo-3-nitropyridin-2-yl) malonate (31.8 g, 88 mmol) in aqueous hydrochloric acid (6 M, 1.4 L) was stirred at reflux for 18 hours. The reaction mixture was cooled to ambient temperature and added very slowly to a saturated aqueous solution of aqueous sodium bicarbonate (4 L) at 0° C. The mixture was then extracted with dichloromethane (7 L), dried over magnesium sulfate and the solvent removed in vacuo to give 5-bromo-2-methyl-3-nitropyridine as an orange oil (13.8 g, 72%) which solidified upon standing. $^1$HNMR (300 MHz, CDCl$_3$, δ): 8.78 (s, 1H), 8.43 (s, 1H), 2.79 (s, 3H).

Step 3: 5-bromo-2-methylpyridin-3-amine

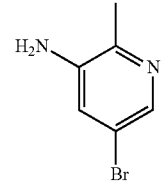

To a solution of 5-bromo-2-methyl-3-nitropyridine (13.8 g, 63.9 mmol) in industrial methylated spirit (330 mL) at 40° C. was added iron powder (20 g) (portionwise to avoid clumping) followed by concentrated aqueous hydrochloric acid (5 mL). The dark brown mixture was stirred vigorously at reflux for 2 hours and then cooled and filtered through Celite® (which was washed with 1 L of industrial methylated spirit). The solvent was then removed in vacuo and the residue taken up in ethyl acetate (200 mL) and washed with a saturated aqueous solution of sodium bicarbonate (200 mL), dried over magnesium sulfate and solvent removed in vacuo to give 5-bromo-2-methylpyridin-3-amine as an orange solid (10.7 g, 90%). $^1$HNMR (400 MHz, CDCl$_3$, δ): 7.91 (s, 1H), 7.00 (s, 1H), 3.75 (br.s., 2H), 2.25 (s, 3H).

Step 4: N-(5-bromo-2-methylpyridin-3-yl)acetamide

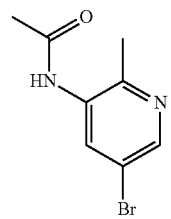

To a solution of 5-bromo-2-methylpyridin-3-amine (10.7 g, 57.5 mmol) in dichloromethane (575 mL) was added acetic anhydride (12 mL, 126.5 mmol) at 0° C. followed by triethylamine (22 mL, 158 mmol). The mixture was allowed to warm to ambient temperature and stirred for 18 hours at which point a further equivalent of acetic anhydride (6 mL, 63 mmol) was added. The mixture was stirred at ambient temperature for a further 72 hours. The reaction mixture was quenched with a saturated aqueous solution of sodium bicarbonate (500 mL) and the organic phase washed with saturated aqueous sodium chloride (500 mL), dried over magnesium sulfate and concentrated in vacuo to give a brown solid. This solid was triturated with 30% ethyl acetate in hexanes to yield N-(5-bromo-2-methylpyridin-3-yl)acetamide as an off-white solid (8.28 g, 63%). ¹HNMR (400 MHz, CD₃OD, δ): 8.31 (s, 1H), 8.18 (s, 1H), 2.43 (s, 3H), 2.18 (s, 3H).

Step 5: 6-bromo-1H-pyrazolo[4,3-b]pyridine

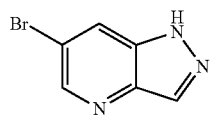

To a solution of N-(5-bromo-2-methylpyridin-3-yl)acetamide (8.28 g, 36 mmol) in chloroform (550 mL) at ambient temperature was added potassium acetate (4.32 g, 43.6 mmol), acetic acid (2.5 mL, 43.6 mmol) and followed by acetic anhydride (6.86 mL, 72.6 mmol). The mixture was stirred at ambient temperature for 15 minutes before being heated to 40° C. Isoamylnitrite was then added dropwise. The reaction was then stirred at 60° C. for 48 hours. The reaction mixture was poured slowly into a saturated solution of sodium bicarbonate (500 mL) at 0° C. The organic phase was retained and the aqueous phase extracted with dichloromethane (500 mL). The combined organics were then concentrated to a brown oil which was dissolved in methanol (500 mL). Aqueous sodium hydroxide (2 M, 500 mL) was added at 0° C. and the mixture stirred at ambient temperature for 1 hour before the methanol was removed in vacuo. The aqueous mixture was then extracted with ethyl acetate (3×500 mL). The combined organics were dried over magnesium sulfate, filtered, and the solvent removed in vacuo to give 6-bromo-1H-pyrazolo[4,3-b]pyridine as a light brown solid (5.5 g, 77%). ¹HNMR (400 MHz, CD₃OD, δ): 8.55 (s, 1H), 8.24 (s, 1H), 8.21 (s, 1H).

Step 6: methyl 1H-pyrazolo[4,3-b]pyridine-6-carboxylate

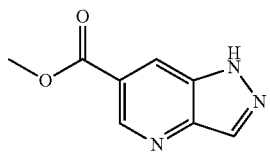

To a solution of 6-bromo-1H-pyrazolo[4,3-b]pyridine (5.5 g, 27.9 mmol) in methanol (125 mL) and acetonitrile (75 mL) was added triethylamine (22 mL, 156 mmol), 2,2'-bis(diphenylphosphino)-1,1'-binaphthyl (1.98 g, 3.07 mmol), and palladium dichloride (1.23 g, 6.98 mmol). The mixture was placed under 20 bar of carbon monoxide, heated to 100° C., and stirred vigorously for 18 hours. The reaction mixture was cooled to ambient temperature and filtered through Celite® before the solvent was removed in vacuo to yield a brown oil. This crude oil was then purified by flash column chromatography (50% ethyl acetate/hexanes) to give methyl 1H-pyrazolo[4,3-b]pyridine-6-carboxylate as a pale yellow solid (4.52 g, 92%). ¹HNMR (400 MHz, CDCl₃, δ): 10.56 (s, 1H), 9.23 (s, 1H), 8.35 (s, 1H), 8.40 (s, 1H), 4.01 (s, 3H).

Step 7: 1H-pyrazolo[4,3-b]pyridine-6-carboxylic acid

To a solution of methyl 1H-pyrazolo[4,3-b]pyridine-6-carboxylate (3.52 g, 20 mmol) in methanol (250 mL) and water (190 mL) at 0° C. was added aqueous sodium hydroxide (2M, 64 mL, 128 mmol), dropwise. The suspension was then allowed to warm to ambient temperature and stirred for 18 hours. The methanol was then removed in vacuo and the aqueous mixture extracted with ethyl acetate (250 mL). The aqueous layer was acidified (to pH 5-6) with 2 N aqueous hydrochloric acid (70 mL). The cream solid which had precipitated out was then filtered off and dried in a desiccator to yield the title compound (0.675 g, 21%). ¹HNMR (400 MHz, DMSO-d₆, δ): 8.97 (s, 1H), 8.45 (s, 1H), 8.39 (s, 1H).

Intermediate 9:
3-carbamoyl-1H-indazole-5-carboxylic acid, shown below, was prepared as follows

Step 1. methyl 3-cyano-1H-indazole-5-carboxylate

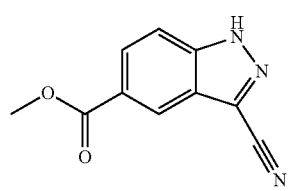

Methyl 3-iodo-1H-indazole-5-carboxylate (30.7 g, 102 mmol), zinc cyanide (20.3 g, 173 mmol), zinc dust (4.05 g, 61.9 mmol), [1,1'-bis(diphenylphosphino)ferrocene]-dichloropalladium(II), complex with dichloromethane (12 g, 15 mmol), and copper (I) iodide (19.7 g, 103 mmol) were combined in a 1 L round bottom flask. N,N-dimethylacetamide (500 mL) was added and the reaction mixture was purged with nitrogen for 10 minutes. The reaction was heated to 120° C. for 1 hour. The reaction was cooled to room temperature and was diluted with ethyl acetate (1 L), and allowed to stir for 20 minutes. The reaction mixture was filtered through a plug of Celite, rinsing with 500 mL ethyl acetate. The filtrate was added to a solution of saturated ammonium chloride and concentrated ammonium hydroxide (2 L) (prepared by adding ammonium hydroxide to a saturated aqueous solution of ammonium chloride until pH=8) and the biphasic solution was stirred vigorously for 1 hour. The resulting emulsion was filtered through a small pad of Celite. The layers were separated and the aqueous was extracted two additional times with ethyl acetate (1100 mL), each time filtering the resulting emulsion through Celite. The combined organic layers were washed with water (2×900 mL) and brine (900 mL), dried over sodium sulfate, filtered and concentrated. To the crude was added methanol (100 mL) and the mixture was stirred for 20 minutes. The resulting precipitate was filtered off and washed with methanol (10 mL). The filtrate was concentrated to give the title compound (13.2 g, 65%) as a solid. −ESI (M−H) 200.0; ¹H NMR (400 MHz, DMSO-d₆, δ): 8.43-8.45 (m, 1H), 8.05 (dd, J=8.8, 1.6 Hz, 1H), 7.85 (dd, J=8.9, 0.9 Hz, 1H), 3.88 (s, 3H).

Step 2. 3-carbamoyl-1H-indazole-5-carboxylic acid

A suspension of methyl 3-cyano-1H-indazole-5-carboxylate (50.0 g, 249 mmol) in methanol (1 L) was cooled to 10° C. A solution of urea hydrogen peroxide (241 g, 2.49 mol) in sodium hydroxide (1 L of 2.5 N) and water (100 mL) was added dropwise, maintaining an internal temperature below 25° C. When the addition was complete, the ice bath was removed and the reaction was allowed to stir at room temperature for 16 hours. A small amount of unreacted starting material was observed by HPLC. The reaction was cooled to 15° C. and additional urea hydrogen peroxide (50 g) was added portionwise. Vigorous bubbling was noted. The reaction was allowed to stir for another 2 hours. The crude reaction was filtered to remove the solids present and the filtrate was concentrated to remove the methanol. The remaining solution was cooled in an ice bath and 6 N hydrochloric acid (420 mL) was added dropwise to adjust the pH to 4. The solution was stirred for 20 minutes and the resulting tan solid was collected by filtration and dried to give 57.2 g of crude product. To the crude was added acetonitrile (700 mL) and dichloromethane (700 mL) and the mixture was stirred at room temperature for 1 hour. The solid was collected by filtration, washed with 1:1 acetonitrile:dichloromethane (400 mL) and dried to give the title compound (39.5 g, 77%) as a tan solid. +ESI (M+H) 206.1; ¹H NMR (400 MHz, DMSO-d₆, δ): 13.81 (s, 1H), 12.85 (br. s., 1H), 8.82 (d, J=0.8 Hz, 1H), 7.93 (dd, J=8.8, 1.6 Hz, 1H), 7.79-7.85 (m, 1H), 7.64 (d, J=8.6 Hz, 1H), 7.44 (s, 1H).

Intermediate 10: 3-cyano-1H-indazole-5-carboxylic acid, shown below, was prepared as follows

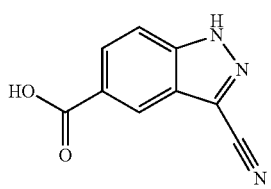 [SMILES: N#Cc1n[nH]c2ccc(C(=O)O)cc12]

Methyl 3-cyano-1H-indazole-5-carboxylate (500 mg, 2.5 mmol) was dissolved in methanol (12 mL) and 2 N aqueous lithium hydroxide (3.7 mL, 7 mmol) was added. The reaction was stirred at room temperature overnight. The reaction mixture was concentrated to remove the methanol and the residue was acidified to pH=4 with 1 N aqueous hydrochloric acid. The resulting yellow precipitate was collected by filtration, washed with water, and dried in a vacuum oven to provide the title compound (445 mg, 96%). −ESI (M−H) 186.4; ¹H NMR (400 MHz, DMSO-d₆, δ): 13.17 (br. s., 1H), 8.42 (s, 1H), 8.05 (dd, J=8.8, 1.6 Hz, 1H), 7.83 (d, 1H).

Intermediate 11: 3-cyano-1H-indazole-6-carboxylic acid, shown below, was prepared as follows

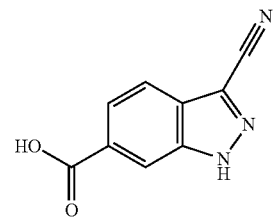 [SMILES: N#Cc1n[nH]c2cc(C(=O)O)ccc12]

Step 1: methyl 1H-indazole-6-carboxylate

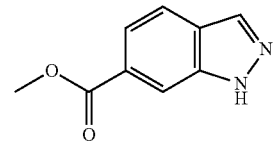

To a solution of 1H-indazole-6-carboxylic acid (3.00 g, 18.5 mmol) in N,N-dimethylformamide (46 mL) was added sodium carbonate (2.06 g, 19.4 mmol), followed by iodomethane (2.75 g, 1.21 mL, 19.4 mmol) dropwise. The mixture was stirred at room temperature overnight. The mixture was poured into half saturated sodium bicarbonate and extracted with ethyl acetate three times. The combined organic layers were washed with brine, dried over sodium sulfate, filtered and concentrated in vacuo to afford a brown oil. This residue was purified by flash column chromatography (12-100% ethyl acetate/heptanes) to afford methyl 1H-indazole-6-carboxylate as a yellow solid (2.95 g, 90%). ¹H NMR (400 MHz, CDCl₃, δ): 10.40 (br. s., 1H), 8.26 (s, 1H), 8.13 (s, 1H), 7.84 (d, J=8.4 Hz, 1H), 7.79 (d, J=8.4 Hz, 1H), 3.96 (s, 3H).

Step 2: methyl 3-iodo-1H-indazole-6-carboxylate

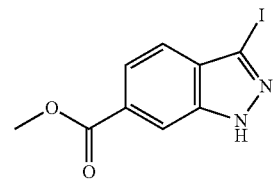

To a solution of methyl 1H-indazole-6-carboxylate (865 mg, 4.91 mmol) in N,N-dimethylformamide (12 mL) was added potassium hydroxide (840 mg, 3.05 mmol) followed by iodine (1.54 g, 5.9 mmol). The mixture was stirred at room temperature for 3 hours. Sodium bisulfate (30 mL of 5% aqueous) was added and the mixture was extracted with ethyl acetate twice. The combined organic layers were washed with brine, dried over sodium sulfate, filtered and concentrated in vacuo. The residue was purified via flash column chromatography (5-65% ethyl acetate/heptanes) to afford methyl 3-iodo-1H-indazole-6-carboxylate as a colorless solid (1.16 g, 78%). ¹H NMR (400 MHz, DMSO-d₆, δ): 13.84 (s, 1H), 8.13 (s, 1H), 7.72 (d, J=8.4 Hz, 1H), 7.54 (d, J=8.6 Hz, 1H), 3.87 (s, 3H).

Step 3: methyl 3-cyano-1H-indazole-6-carboxylate

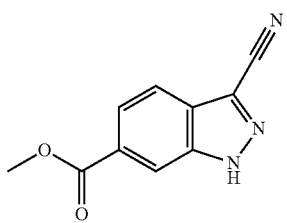

A mixture of methyl 3-iodo-1H-indazole-6-carboxylate (3.0 g, 9.9 mmol), zinc dust (400 mg, 6.11 mmol), zinc cyanide (2.0 g, 17.0 mmol), [1,1'-bis(diphenylphosphino)ferrocene]-dichloropalladium(II), complex with dichloromethane (1.15 g, 1.41 mmol), and copper (I) iodide (1.90 g, 9.97 mmol) in dimethylacetamide (55 mL) was purged with nitrogen for 15 minutes. The mixture was stirred at 120° C. for 15 hours. The reaction mixture was cooled, diluted with ethyl acetate (250 mL), and filtered through Celite, rinsing with ethyl acetate (100 mL). To the filtrate was added ~400 mL of a solution of saturated aqueous ammonium chloride and concentrated ammonium hydroxide (prepared by adding ammonium hydroxide to a saturated aqueous solution of ammonium chloride until pH=8). The mixture was stirred for 1 hour. The layers were then separated. The organic layer was washed with water and brine, dried over sodium sulfate, filtered and concentrated in vacuo. To the residue was added methanol (40 mL) and the mixture was stirred overnight. The mixture was filtered and the solid was dried in vacuo to give methyl 3-cyano-1H-indazole-6-carboxylate as a tan solid (1.47 g, 73%). ¹H NMR (400 MHz, DMSO-d₆, δ): 13.40 (br. s., 1H), 8.25 (s, 1H), 7.94 (d, J=8.6 Hz, 1H), 7.83 (d, J=8.4 Hz, 1H), 3.88 (s, 3H).

Step 4: 3-cyano-1H-indazole-6-carboxylic acid

To a solution of methyl 3-cyano-1H-indazole-6-carboxylate (1.47 g, 7.31 mmol) in methanol (36 mL) and tetrahydrofuran (20 mL) was added 2 N aqueous lithium hydroxide (16 mL, 32 mmol). The reaction was heated to 50° C. for 72 hours. The reaction was cooled to room temperature and concentrated. The residue was diluted with water and the pH was adjusted to 4 with 1 N aqueous hydrochloric acid. The resulting precipitate was filtered off, rinsed with water, and dried under vacuum to provide the title compound (500 mg, 37%) as a tan solid. +ESI (M+H) 188.2.

Intermediate 12:
1-methoxyisoquinoline-7-carboxylic acid, shown below, was prepared as follows

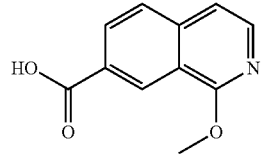

Step 1: 7-bromo-1-methoxyisoquinoline

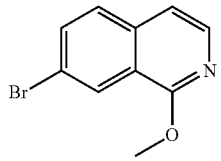

7-Bromo-1-chloroisoquinoline (570 mg, 2.4 mmol) was combined with methanol (10 mL) and sodium methoxide (25 wt % in methanol, 1.5 mL, 24 mmol) in a microwave vial. The vial was sealed and heated to 130° C. for 3 hours in a microwave. The reaction was concentrated. The crude residue was taken up in ethyl acetate and washed with water and saturated aqueous sodium bicarbonate. The aqueous layer was extracted two times with hot ethyl acetate. The combined organics were dried over sodium sulfate, filtered, and concentrated to give the title compound (520 mg, 93%). +ESI (M+H+1) 240.0; ¹H NMR (400 MHz, DMSO-d₆, δ): 8.25-8.28 (m, 1H), 8.04 (d, J=5.9 Hz, 1H), 7.86-7.89 (m, 2H), 7.40 (dd, J=6.0, 0.9 Hz, 1H), 4.03 (s, 3H).

Step 2: methyl 1-methoxyisoquinoline-7-carboxylate

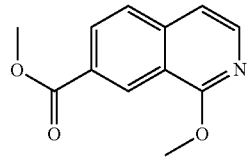 [SMILES: COC(=O)c1ccc2ccnc(OC)c2c1]

To a solution of 7-bromo-1-methoxyisoquinoline (520 mg, 2.2 mmol) in methanol (30 mL) was added sodium acetate (517 mg, 6.30 mmol) and [1,1'-bis(diphenylphosphino)ferrocene]-dichloropalladium(11), complex with dichloromethane (257 mg, 0.315 mmol). The mixture was evacuated and backfilled with nitrogen three times. The reaction vessel was then pressurized to 25 psi carbon monoxide. The reaction was heated to 70° C. and was agitated for 20 hours. The reaction was filtered, rinsing with methanol. The filtrate was concentrated. The resulting residue was taken up in dichloromethane and the remaining solids were filtered off. The filtrate was concentrated and purified by flash column chromatography (0-100% ethyl acetate/heptanes) to give the title compound (443 mg, 93%) as a white solid. +ESI (M+H) 218.1; $^1$H NMR (400 MHz, DMSO-d$_6$, δ): 8.77 (d, J=0.8 Hz, 1H), 8.20 (dd, J=8.6, 1.8 Hz, 1H), 8.13 (d, J=5.9 Hz, 1H), 8.00 (d, J=8.6 Hz, 1H), 7.46 (d, J=5.9 Hz, 1H), 4.08 (s, 3H), 3.90 (s, 3H).

Step 3: 1-methoxyisoquinoline-7-carboxylic acid

To a solution of methyl 1-methoxyisoquinoline-7-carboxylate (443 mg, 2.04 mmol) in methanol (10 mL) was added 2 N aqueous lithium hydroxide (20 mL). The reaction was stirred at room temperature for 24 hours. The reaction mixture was diluted with 1 N aqueous hydrochloric acid and ethyl acetate. The layers were separated and the aqueous was extracted two more times with ethyl acetate. The combined organics were washed with brine, dried over sodium sulfate, filtered, and concentrated to afford the title compound (414 mg, 100%) as a solid. +ESI (M+H) 204.1; $^1$H NMR (400 MHz, DMSO-d$_6$, δ): 13.24 (s, 1H), 8.76 (d, J=0.8 Hz, 1H), 8.18 (dd, J=8.6, 1.8 Hz, 1H), 8.11 (d, J=5.9 Hz, 1H), 7.97 (d, J=8.4 Hz, 1H), 7.45 (d, J=5.9 Hz, 1H), 4.07 (s, 3H).

Intermediate 13: 3-aminoisoquinoline-6-carboxylic acid, shown below, was prepared as follows:

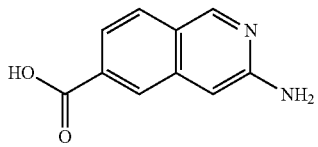 [SMILES: Nc1cc2cc(C(=O)O)ccc2cn1]

The title compound was prepared by a method analogous to that described for Intermediate 12, Steps 2-3, using 6-bromoisoquinolin-3-amine. +ESI (M+H) 189.0; $^1$H NMR (400 MHz, DMSO-d$_6$, δ): 13.15 (br. s., 1H), 8.94 (s, 1H), 8.20 (s, 1H), 7.91 (m, 1H), 7.62-7.59 (m, 1H), 6.78 (s, 1H), 6.14 (s, 2H).

Intermediate 14: 3-amino-1H-indazole-5-carboxylic acid, shown below, was prepared as follows

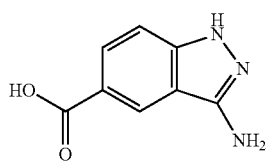 [SMILES: Nc1n[nH]c2ccc(C(=O)O)cc12]

To a solution of 3-cyano-4-fluorobenzoic acid (980.0 mg, 5.94 mmol) in ethanol (6 mL), was added hydrazine hydrate (0.89 mL, 17.8 mmol). The reaction was heated at reflux for 3 hours. The reaction was cooled to room temperature and ethanol was removed under reduced pressure. The resultant yellow oil was taken up in water (50 mL) and basified with 1 N aqueous sodium hydroxide (5 mL). The solution was washed once with ethyl acetate (25 mL). The aqueous phase was acidified to pH=3 with 6 N aqueous hydrochloric acid and was allowed to stir at room temperature for 1 hour. The resulting precipitate was collected by filtration and dried under vacuum to give the title compound (612 mg, 48%) as a pink solid. +ESI (M+H) 178.1; $^1$H NMR (400 MHz, DMSO-d$_6$, δ): 8.42-8.47 (m, 1H), 7.76 (dd, J=8.8, 1.6 Hz, 1H), 7.21 (d, J=8.8 Hz, 1H).

Intermediate 15: 3-amino-1H-indazole-6-carboxylic acid, shown below, was prepared as follows

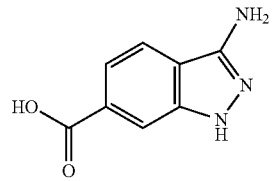 [SMILES: Nc1n[nH]c2cc(C(=O)O)ccc12]

To a solution of 4-cyano-3-fluorobenzoic acid (500 mg, 3.0 mmol) in n-butanol (9 mL) was added hydrazine monohydrate (0.5 mL, 10 mmol). The reaction was heated to 110° C. overnight. The reaction was cooled to room temperature and the precipitate was collected by filtration. The solid was then dissolved in 1 N aqueous sodium hydroxide (2 mL) and extracted with ethyl acetate (2×). The aqueous layer was acidified to pH=4 with 1 N aqueous hydrochloric acid. The resulting precipitate was collected by filtration and dried under vacuum to provide the title compound (140 mg, 26%) as a red solid. +ESI (M+H) 178.2; $^1$H NMR (400 MHz, CD$_3$OD, δ): 7.99-8.01 (m, 1H), 7.73 (dd, J=8.4, 0.8 Hz, 1H), 7.61 (dd, J=8.5, 1.3 Hz, 1H).

Intermediate 16: 2-methyl-3-oxo-2,3-dihydro-1H-indazole-5-carboxylic acid, shown below, was prepared as follows

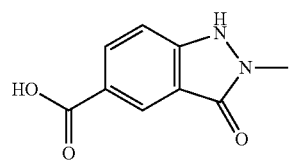

Step 1: methyl 3-hydroxy-1H-indazole-5-carboxylate

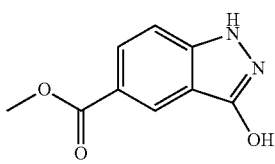

3-hydroxy-1H-indazole-5-carboxylic acid (1.5 g, 8.4 mmol) was suspended in methanol (17 mL). Concentrated hydrochloric acid (3.11 mL, 101 mmol) was added and the reaction was heated to 100° C. for 6 hours. The reaction was concentrated to provide the title compound (1.60 g, 99%). +ESI (M+H) 193.1; $^1$H NMR (400 MHz, DMSO-d$_6$, δ): 12.00

(br. s., 1H), 8.35 (s, 1H), 7.83 (dd, J=8.9, 1.7 Hz, 1H), 7.33 (dd, J=8.9, 0.7 Hz, 1H), 3.82 (s, 3H).

Step 2: 1-ethyl 5-methyl 3-hydroxy-1H-indazole-1,5-dicarboxylate

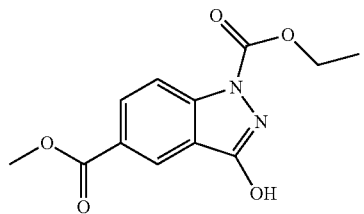 [SMILES: CCOC(=O)n1nc(O)c2cc(C(=O)OC)ccc21]

Methyl 3-hydroxy-1H-indazole-5-carboxylate (1.60 g, 8.33 mmol) was suspended in pyridine (10 mL). Ethyl chloroformate (0.90 mL, 9.3 mmol) was added slowly and the reaction was stirred at room temperature for 1 hour. Additional ethyl chloroformate (0.30 mL, 3.1 mmol) was added and the reaction was stirred for another 30 minutes. The reaction was poured into water (65 mL) and cooled in a refrigerator for 3 hours. The brown solid was collected by filtration, rinsed with water, and dried under vacuum to give the title compound (1.75 g, 80%). +ESI (M+H) 265.1; $^1$H NMR (400 MHz, CDCl$_3$, δ): 8.56 (s, 1H), 8.29 (d, J=7.8 Hz, 1H), 8.13 (br. s., 1H), 4.59 (q, J=7.0 Hz, 2H), 3.97 (s, 3H), 1.56 (t, J=7.0 Hz, 3H).

Step 3: 1-ethyl 5-methyl 2-methyl-3-oxo-2,3-dihydro-1H-indazole-1,5-dicarboxylate

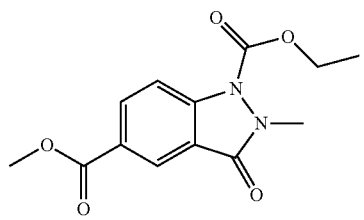 [SMILES: CCOC(=O)n1c2ccc(C(=O)OC)cc2c(=O)n1C]

1-Ethyl 5-methyl 3-hydroxy-1H-indazole-1,5-dicarboxylate (1.75 g, 6.62 mmol) was suspended in acetone (85 mL). Cesium carbonate (2.27 g, 6.95 mmol) and methyl iodide (1.3 mL, 20 mmol) were added and the reaction was stirred at reflux for 22 hours. The reaction was concentrated to dryness and the residue was partitioned between dichloromethane (60 mL) and water (100 mL). The layers were separated and the aqueous was extracted again with dichloromethane (60 mL). The combined organics were dried over magnesium sulfate, filtered, and concentrated. Purification by flash column chromatography (7-60% ethyl acetate/heptanes) gave two regioisomeric products.

1-ethyl 5-methyl 3-methoxy-1H-indazole-1,5-dicarboxylate (590 mg, 32%) as a white solid. $^1$H NMR (400 MHz, CDCl$_3$, δ): 8.41 (dd, J=1.6, 0.8 Hz, 1H), 8.22 (dd, J=9.2, 3.5 Hz, 1H), 8.14 (d, J=9.2 Hz, 1H), 4.57 (q, J=7.1 Hz, 2H), 4.20 (s, 3H), 3.95 (s, 3H), 1.51 (t, J=7.1 Hz, 3H).

1-ethyl 5-methyl 2-methyl-3-oxo-2,3-dihydro-1H-indazole-1,5-dicarboxylate (699 mg, 38%) as a yellow solid. +ESI (M+H) 279.1; $^1$H NMR (400 MHz, CDCl$_3$, δ): 8.56 (dd, J=1.8, 0.6 Hz, 1H), 8.30 (dd, J=8.8, 1.8 Hz, 1H), 7.93 (d, J=8.8 Hz, 1H), 4.50 (q, J=7.0 Hz, 2H), 3.94 (s, 3H), 3.67 (s, 3H), 1.48 (t, J=7.1 Hz, 3H).

Step 4: 2-methyl-3-oxo-2,3-dihydro-1H-indazole-5-carboxylic acid

1-Ethyl 5-methyl 2-methyl-3-oxo-2,3-dihydro-1H-indazole-1,5-dicarboxylate (300 mg, 1.08 mmol) was dissolved in ethanol (4 mL). Potassium hydroxide (485 mg, 8.62 mmol) was added and the reaction was stirred at room temperature for 1.5 hours. LCMS showed the reaction to be incomplete. An aqueous solution of potassium hydroxide (10 mL, 10 mmol, 1.0 M) was then added and the reaction was heated to 65° C. for 2 hours. The reaction was cooled to room temperature and concentrated. The resulting orange solid was dissolved in water and acidified with 1 N aqueous hydrochloric acid. The precipitate was collected by filtration and dried under vacuum to give the title compound (158 mg, 76%) as a white solid. +ESI (M+H) 193.1; $^1$H NMR (400 MHz, DMSO-d$_6$, δ): 12.75 (br. s., 1H), 11.06 (s, 1H), 8.15 (s, 1H), 7.99 (dd, J=8.7, 1.5 Hz, 1H), 7.28 (d, J=8.6 Hz, 1H), 3.37 (s, 3H).

Intermediate 17: 3-methoxy-1H-indazole-5-carboxylic acid, shown below, was prepared as follows

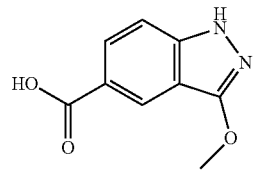

The title compound was prepared by a method analogous to that described for Intermediate 16, using 1-ethyl 5-methyl 3-methoxy-1H-indazole-1,5-dicarboxylate, the regioisomeric product formed in Step 3. +ESI (M+H) 193.1; $^1$H NMR (400 MHz, DMSO-d$_6$, δ): 12.65 (br. s., 1H), 12.26 (s, 1H), 8.18 (s, 1H), 7.86 (dd, J=8.9, 1.5 Hz, 1H), 7.38 (d, J=8.8 Hz, 1H), 3.99 (s, 3H).

Intermediate 18: 7-methoxy-1-(tetrahydro-2H-pyran-2-yl)-1H-indazole-5-carboxylic acid, shown below, was prepared as follows

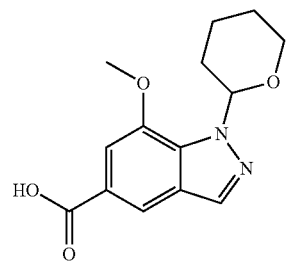 [SMILES: COc1cc(C(=O)O)cc2cnn(C3CCCCO3)c12]

Step 1: ethyl 7-methoxy-1-(tetrahydro-2H-pyran-2-yl)-1H-indazole-5-carboxylate

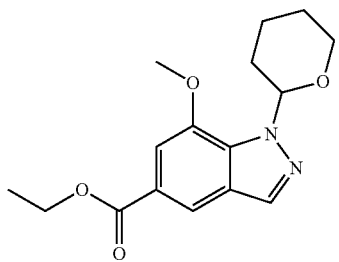 [SMILES: CCOC(=O)c1cc(OC)c2c(cnn2C2CCCCO2)c1]

To a mixture of ethyl 7-hydroxy-1-(tetrahydro-2H-pyran-2-yl)-1H-indazole-5-carboxylate (WO2009144554) (100 mg, 0.34 mmol) and potassium carbonate (95.1 mg, 0.68 mmol) in N,N-dimethylformamide (1 mL) was added methyl iodide (32 µL, 0.51 mmol). The reaction was stirred at room temperature overnight. The reaction was diluted with water and extracted with ethyl acetate (4×). The combined organic layers were washed with water and brine, dried over sodium sulfate, filtered, and concentrated to give the title compound (105 mg, 100%) as a yellow oil. +ESI (M+1-THP) 221.2; $^1$H NMR (400 MHz, CDCl$_3$, δ): 8.07-8.10 (m, 2H), 7.43 (d, J=0.98 Hz, 1H), 6.24 (dd, J=10.24, 2.44 Hz, 1H), 4.38 (q, J=7.15 Hz, 2H), 4.08 (dt, J=11.56, 2.02 Hz, 1H), 4.04 (s, 3H), 3.70-3.78 (m, 1H), 2.54-2.66 (m, 1H), 2.09-2.19 (m, 1H), 2.01-2.08 (m, 1H), 1.71-1.83 (m, 2H), 1.55-1.64 (m, 1H), 1.41 (t, J=7.12 Hz, 3H).

Step 2: 7-methoxy-1-(tetrahydro-2H-pyran-2-yl)-1H-indazole-5-carboxylic acid To a solution of ethyl 7-methoxy-1-(tetrahydro-2H-pyran-2-yl)-1H-indazole-5-carboxylate (102 mg, 0.33 mmol) in tetrahydrofuran (2 mL) was added 1 N aqueous lithium hydroxide (0.67 mL, 0.67 mmol). The reaction was stirred at room temperature overnight. LCMS showed the reaction to be incomplete. Additional lithium hydroxide (0.35 mL, 2 M, 0.7 mmol) was added and the reaction was heated to 40° C. for 1 hour. The reaction was then left stirring at room temperature for 70 hours. The tetrahydrofuran was removed in vacuo and the residue was acidified to pH=4 with 1 N aqueous hydrochloric acid. The solution was extracted with ethyl acetate (3×). The combined organics were washed with brine, dried over sodium sulfate, filtered, and concentrated to give the title compound (84 mg, 91%) as a solid. (M+1-THP) 193.2; $^1$H NMR (400 MHz, CDCl$_3$, δ): 8.18 (d, J=1.37 Hz, 1H), 8.12 (s, 1H), 7.46 (d, J=1.17 Hz, 1H), 6.26 (dd, J=10.15, 2.54 Hz, 1H), 4.07-4.12 (m, 1H), 4.06 (s, 3H), 3.65-3.81 (m, 1H), 2.54-2.72 (m, 1H), 2.10-2.22 (m, 1H), 2.01-2.10 (m, 1H), 1.71-1.85 (m, 2H), 1.57-1.67 (m, 1H).

Intermediate 19: 2-methoxyquinoline-7-carboxylic acid, shown below, was prepared as follows

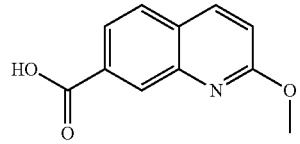

Step 1: 7-(ethoxycarbonyl)quinoline 1-oxide

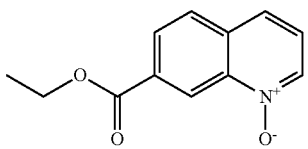 [SMILES: CCOC(=O)c1ccc2ccc[n+]([O-])c2c1]

To a solution of ethyl quinoline-7-carboxylate (1.02 g, 5.05 mmol) in dichloromethane (20 mL) was added peracetic acid (2.13 mL, 10.1 mmol, 32 wt % in acetic acid). The reaction was stirred at room temperature overnight. The reaction was partitioned between water and dichloromethane. The layers were separated and the aqueous was extracted with dichloromethane (4×). The combined organics were washed with water and brine, dried over sodium sulfate, filtered, and concentrated. The solid was concentrated from heptanes and ethyl acetate several times, then dried under vacuum to give the title compound (1.01 g, 92%) as a yellow solid. +ESI (M+H) 218.2; $^1$H NMR (400 MHz, CDCl$_3$, δ): 9.40 (s, 1H), 8.65 (d, J=6.05 Hz, 1H), 8.27 (dd, J=8.58, 1.56 Hz, 1H), 7.95 (d, J=8.39 Hz, 1H), 7.82 (d, J=8.58 Hz, 1H), 7.42 (dd, J=8.49, 6.15 Hz, 1H), 4.47 (q, J=7.02 Hz, 2H), 1.45 (t, J=7.1 Hz, 3H).

Step 2: ethyl 2-methoxyquinoline-7-carboxylate

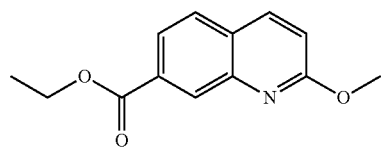 [SMILES: CCOC(=O)c1ccc2ccc(OC)nc2c1]

To a 0° C. solution of 7-(ethoxycarbonyl)quinoline 1-oxide (150 mg, 0.69 mmol) and toluene-4-sulphonyl chloride (171 mg, 0.89 mmol) in methanol (5 mL) was added triethylamine (0.19 mL, 1.4 mmol).

The reaction was stirred at room temperature overnight. LCMS showed the reaction was incomplete. Additional triethylamine (0.05 mL) was added and the reaction was stirred for another 4 hours. The reaction was concentrated and the residue partitioned between ethyl acetate and saturated aqueous sodium carbonate. The layers were separated and the aqueous was extracted two more times with ethyl acetate. The combined organics were washed with brine, dried over sodium sulfate, filtered, and concentrated. Purification by flash column chromatography (0~40% ethyl acetate/heptanes) gave the title compound (130 mg, 81%) as a pale yellow solid. +ESI (M+H) 232.2; ¹H NMR (400 MHz, CDCl₃, δ): 8.49-8.60 (m, 1H), 7.95-8.05 (m, 2H), 7.75 (d, J=8.19 Hz, 1H), 6.98 (d, J=8.78 Hz, 1H), 4.43 (q, J=7.22 Hz, 2H), 4.08 (s, 3H), 1.43 (t, J=7.12 Hz, 3H).

Step 3: 2-methoxyquinoline-7-carboxylic acid

To a solution of ethyl 2-methoxyquinoline-7-carboxylate (125 mg, 0.54 mmol) in tetrahydrofuran (1.5 mL) was added 2 N aqueous lithium hydroxide (0.81 mL, 1.6 mmol). The reaction was stirred at room temperature for 65 hours. The tetrahydrofuran was removed in vacuo and the residue was acidified to pH=4 with 1 N aqueous hydrochloric acid. The mixture was diluted with water and the resulting precipitate was collected by filtration and dried under vacuum to give the title compound (106 mg, 96%) as a white solid. +ESI (M+H) 204.2; ¹H NMR (400 MHz, CDCl₃, δ): 8.64 (d, J=1.37 Hz, 1H), 8.01-8.04 (m, 1H), 8.01 (s, 1H), 7.79 (d, J=8.58 Hz, 1H), 7.01 (d, J=8.78 Hz, 1H), 4.09 (s, 3H).

Intermediate 20:
2-(methylamino)quinoline-6-carboxylic acid, shown below, was prepared as follows

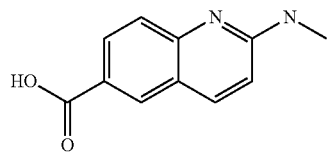

Step 1: ethyl quinoline-6-carboxylate

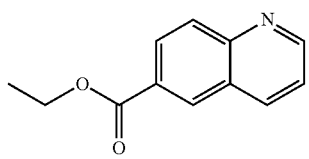

To a solution of quinoline-6-carboxylic acid (2.8 g, 16 mmol) in ethanol (100 mL) was added concentrated sulfuric acid (2 mL). The reaction was heated to reflux overnight. The solvent was evaporated to give a brown residue that was taken up in ethyl acetate (150 mL). The mixture was washed with water (2×30 mL), saturated aqueous sodium bicarbonate (2×30 mL), and brine (2×30 mL). The organic layer was dried over sodium sulphate, filtered, and concentrated to an oil.

Purification by flash column chromatography gave the title compound (2.0 g, 81%) as a brown solid.

Step 2: 6-(ethoxycarbonyl)quinoline 1-oxide

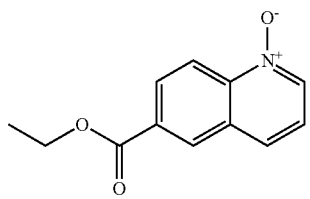 [SMILES: CCOC(=O)c1ccc2c(ccc[n+]2[O-])c1]

To ethyl quinoline-6-carboxylate (3.2 g, 16 mmol) in dichloromethane (120 mL) was added meta-chloroperoxybenzoic acid (4.9 g, 0.024 mol) portionwise. The reaction was stirred at room temperature for 4 hours. The reaction was diluted with dichloromethane and washed with saturated aqueous sodium carbonate (3×30 mL) and brine (2×40 mL). The organic layer was dried over sodium sulfate, filtered, and concentrated. Purification by flash column chromatography gave the title compound (2.45 g, 71%) as a brown solid. ¹H NMR (400 MHz, CDCl₃, δ): 8.81-8.79 (d, 1H), 8.62 (s, 2H), 8.35-8.33 (d, 1H), 7.87-7.85 (d, 1H), 7.39 (s, 1H), 4.49-4.44 (q, 2H), 1.47-1.43 (t, 3H).

Step 3: ethyl 2-(methylamino)quinoline-6-carboxylate

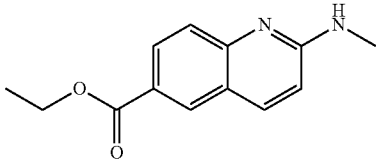 [SMILES: CCOC(=O)c1ccc2nc(NC)ccc2c1]

Trifluoromethanesulfonic anhydride (1.92 mL, 11.4 mmol) was added dropwise to a −70° C. solution of 6-(ethoxycarbonyl)quinoline 1-oxide (2.25 g, 10.4 mmol) in dichloromethane (150 mL). The mixture was stirred at −70° C. for 5 minutes. Then a solution of methylamine in tetrahydrofuran (31 mL, 62 mmol, 2 M) was added dropwise. The mixture was stirred at −70° C. for 5 minutes. The reaction was quenched with water (20 mL). The layers were separated and the aqueous was extracted with dichloromethane (3×30 mL). The combined organics were washed with brine, dried over sodium sulfate, filtered, and concentrated. Purification by flash column chromatography gave the title compound (850 mg, 35%) as a yellow solid. ¹H NMR (400 MHz, CDCl₃, δ): 8.33 (d, 1H), 8.16-8.13 (m, 1H), 7.90-7.87 (d, 1H), 7.70-7.67 (d, 1H), 6.68 (d, 1H), 5.30 (br. s., 1H), 4.43-4.38 (q, 2H), 3.13-3.12 (d, 3H), 1.44-1.40 (m, 3H).

Step 4: 2-(methylamino)quinoline-6-carboxylic acid

Aqueous sodium hydroxide (4 mL, 8 mmol, 2 N) was added to a solution of ethyl 2-(methylamino)quinoline-6-carboxylate (850 mg, 3.7 mmol) in ethanol (10 mL). The reaction was heated to 50° C. overnight. Ethanol was removed in vacuo and the residue was acidified to pH=5 with 1 N aqueous hydrochloric acid. The resulting precipitate was collected by filtration and dried under vacuum to give the title compound (710 mg, 96%) as a yellow solid. $^1$H NMR (400 MHz, DMSO-$d_6$, δ): 8.26 (d, 1H), 7.96-7.93 (m, 2H), 7.50 (d, 1H), 7.43 (d, 1H), 6.81 (d, 1H), 2.91 (d, 3H).

Intermediate 21:
7-(trifluoromethyl)-1H-indazole-5-carboxylic acid, shown below, was prepared as follows:

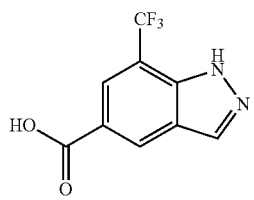 [SMILES: O=C(O)c1cc(C(F)(F)F)c2[nH]ncc2c1]

Step 1: 4-bromo-2-methyl-6-(trifluoromethyl)aniline

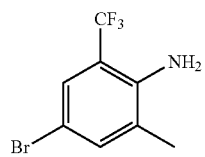

To a room temperature solution of 2-methyl-6-(trifluoromethyl)aniline (3.0 g, 17 mmol) in acetonitrile (85 mL) was added N-bromosuccinimide (3.0 g, 17 mmol) in small portions over 30 minutes. The reaction was allowed to stir for 1 hour. The reaction was poured into a water/brine mixture and was extracted with ethyl acetate (3×). The combined organics were dried over magnesium sulfate, filtered, and concentrated. Purification by flash column chromatography (0-40% ethyl acetate/heptanes) gave the title compound (4.13 g, 95%) as a brown oil. $^1$H NMR (400 MHz, CDCl$_3$, δ): 7.42 (d, J=2.34 Hz, 1H), 7.31 (s, 1H), 2.17 (s, 3H).

Step 2: 5-bromo-7-(trifluoromethyl)-1H-indazole

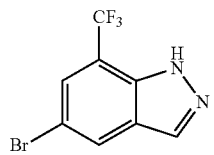 [SMILES: FC(F)(F)c1cc(Br)cc2cn[nH]c12]

To a solution of 4-bromo-2-methyl-6-(trifluoromethyl) aniline (3.3 g, 13 mmol) in toluene (65 mL) and glacial acetic acid (11.2 mL, 195 mmol) was added potassium acetate (10.2 g, 104 mmol) portionwise. After 15 minutes a large amount of precipitate had formed, hindering stirring of the reaction. The reaction was diluted with acetic acid (10 mL). Isoamyl nitrite (1.92 mL, 14.3 mmol) was then added dropwise and the reaction was stirred at room temperature for 3 hours. Additional isoamyl nitrite (0.5 mL, 3.7 mmol) was added and the reaction was left stirring for 15 hours. The reaction was diluted with water (100 mL) and stirred for 1.5 hours. The solution was partitioned between ethyl acetate and saturated aqueous sodium bicarbonate. The layers were separated and the organics were washed with brine, dried over magnesium sulfate, filtered, and concentrated. Purification by flash column chromatography (5-50% ethyl acetate/heptanes) gave the title compound (1.78 g, 52%) as a yellow powder. −ESI (M−H+1) 264.9; $^1$H NMR (400 MHz, CDCl$_3$, δ): 8.13 (s, 1H), 8.09-8.11 (m, 1H), 7.76 (dd, J=1.66, 0.88 Hz, 1H).

Step 3: methyl 7-(trifluoromethyl)-1H-indazole-5-carboxylate

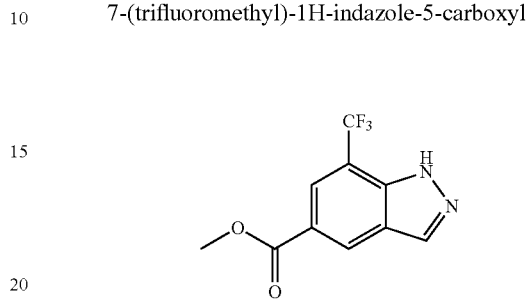

To a sealed tube was added [1,1'-bis(diphenylphosphino) ferrocene]-dichloropalladium(II), complex with dichloromethane (45.7 mg, 0.056 mmol), 5-bromo-7-(trifluoromethyl)-1H-indazole (100 mg, 0.38 mmol), triethylamine (105 μL, 0.752 mmol), and methanol (2 mL). The tube was capped and carbon monoxide was bubbled through for 5 minutes. The reaction was then heated to 70° C. for 5 hours. The reaction was cooled to room temperature and left stirring for 2 days. The reaction was concentrated and purified by flash column chromatography (0-50% ethyl acetate/heptanes) to give the title compound (64 mg, 69%) as a white powder. −ESI (M−H) 243.1; $^1$H NMR (400 MHz, CDCl$_3$, δ): 8.72 (s, 1H), 8.37 (s, 1H), 8.28 (s, 1H), 3.98 (s, 3H).

Step 4: 7-(trifluoromethyl)-1H-indazole-5-carboxylic acid

To a solution of methyl 7-(trifluoromethyl)-1H-indazole-5-carboxylate (62 mg, 0.25 mmol) in methanol (2 mL) and tetrahydrofuran (2 mL) was added 1 N aqueous lithium hydroxide (0.76 mL, 0.76 mmol). The reaction was heated to 60° C. for 17 hours. The reaction was concentrated and the residue was diluted with water and acidified to pH=3 with 1 N aqueous hydrochloric acid. The solution was extracted with dichloromethane (3×). The combined organics were washed with brine, dried over magnesium sulfate, filtered, and concentrated to give the title compound (17 mg, 29%) as an off-white powder. +ESI (M+H) 231.1.

Intermediate 22:
3-(methylamino)isoquinoline-6-carboxylic acid, shown below, was prepared as follows

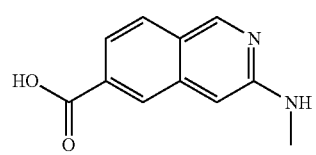

Step 1: 6-bromo-N-methylisoquinolin-3-amine

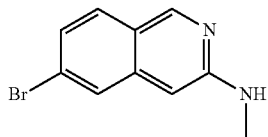

To a solution of 6-bromoisoquinolin-3-amine (50.0 mg, 2.6 mmol) in N,N-dimethylformamide (10 mL) was added N,N-dimethylformamide dimethylacetal (2 mL). The reaction vessel was sealed and heated in a Biotage Smith Synthesizer microwave to 110° C. for 20 minutes. Sodium triacetoxyborohydride (59 mg, 0.28 mmol) was then added to the reaction mixture. The vial was resealed and heated again to 110° C. on a Biotage Smith Synthesizer microwave for 10 minutes. The reaction was concentrated. The residue was dissolved in ethyl acetate (50 mL) and washed with brine (2×20 mL). The organics were dried over sodium sulfate, filtered, and concentrated. Purification by flash column chromatography gave the title compound (23 mg, 43%) as a white solid. $^1$H NMR (400 MHz, CDCl$_3$, δ): 8.76 (s, 1H), 7.74 (s, 1H), 7.61 (d, 1H), 7.28 (d, 1H), 6.40 (s, 1H), 5.09-5.07 (m, 1H), 2.97 (s, 3H).

Step 2: 3-(methylamino)isoquinoline-6-carboxylic acid

Methyl 3-(methylamino)isoquinoline-6-carboxylate was prepared by a method analogous to that described in Step 3 of Intermediate 21, using 6-bromo-N-methylisoquinolin-3-amine. To the crude material (580 mg, 2.7 mmol) was added water (5 mL), methanol (5 mL), and lithium hydroxide monohydrate (300 mg, 7 mmol). The mixture was stirred at room temperature overnight. The reaction was concentrated and the residue was acidified to pH=5 with 1 N aqueous hydrochloric acid. The resulting residue was dried under vacuum and purified by reversed-phase HPLC to give the title compound (512 mg, 89%) as a white solid. $^1$H NMR (400 MHz, CD$_3$OD, δ): 8.81 (s, 1H), 8.23 (s, 1H), 7.80 (d, 1H), 7.72 (d, 1H), 6.70 (s, 1H), 2.93 (s, 3H).

Intermediate 23:
2-(methylamino)quinoline-7-carboxylic acid, shown below, was prepared as follows

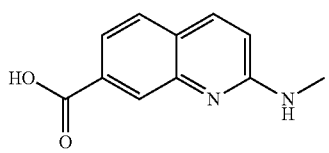

The title compound was prepared by a method analogous to that described in Steps 3-4 of Intermediate 20, using 7-(ethoxycarbonyl)quinoline 1-oxide. $^1$H NMR (400 MHz, DMSO-d$_6$, δ): 8.08 (s, 1H), 7.90 (d, 1H), 7.71-7.62 (m, 2H), 7.21 (s, 1H), 6.84 (d, 1H), 2.91 (d, 3H).

Intermediate 24: 5-methoxyquinoline-3-carboxylic acid, shown below, was prepared as follows

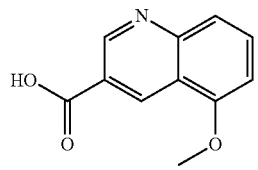

Methyl 5-methoxyquinoline-3-carboxylate (Organic and Biomolecular Chemistry, 7(12), 2612-2618; 2009) was saponified using aqueous lithium hydroxide. +ESI (M+H) 203.9; $^1$H NMR (400 MHz, DMSO-d$_6$, δ): 9.30 (d, 1H), 9.03 (d, 1H), 7.84-7.80 (m, 1H), 7.66 (d, 1H), 7.15 (d, 1H), 4.04 (s, 3H).

Intermediate 25:
2-(methylamino)-1H-benzo[d]imidazole-5-carboxylic acid, shown below, was prepared as follows

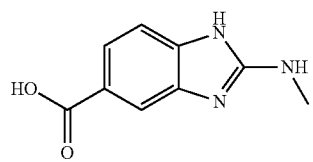

Step 1. methyl 2-(methylamino)-1H-benzo[d]imidazole-5-carboxylate

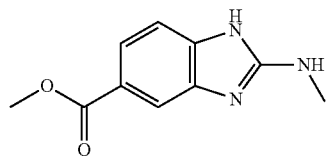

A mixture of 3,4-diaminobenzoic acid (15 g, 0.09 mol) and isothiocyanatomethane (6.6 g, 0.09 mol) was dissolved in tetrahydrofuran (90 mL). The reaction was heated at reflux for 3 hours and was then concentrated. The residue was poured into ice water. The resulting precipitate was filtered, washed with water, and dried under vacuum to give methyl 4-amino-3-(3-methylthioureido)benzoate (12.0 g, 56%).

To the solid (12 g, 0.05 mol) was added ethanol (200 mL), followed by methyl iodide (35.5 g, 0.25 mol). The reaction was heated to reflux and stirred overnight. The reaction was concentrated and the residue was basified with ammonium hydroxide. The solids were collected by filtration and washed with water. Purification by column chromatography (9-25% ethyl acetate/petroleum ether) gave the title compound (2.9 g, 28%) as a yellow solid. $^1$H NMR (400 MHz, CDCl$_3$, δ): 8.37 (s, 1H), 7.92-7.96 (m, 1H), 7.51 (d, J=8.4 Hz, 1H), 3.93 (s, 3H), 2.81 (s, 3H).

Step 2. 2-(methylamino)-1H-benzo[d]imidazole-5-carboxylic acid

3 N Aqueous hydrochloric acid (14 mL, 42 mmol) was added to methyl 2-(methylamino)-1H-benzo[d]imidazole-5-carboxylate (2.9 g, 14 mmol) and the reaction was stirred at reflux overnight. The reaction was concentrated to give the title compound (2.4 g, 90%) as a yellow solid. $^1$H NMR (400 MHz, CD$_3$OD, δ): 7.96-8.00 (m, 2H), 7.40 (d, J=8.4 Hz, 1H), 3.10 (s, 3H).

Intermediate 26:
2-amino-1H-benzo[d]imidazole-5-carboxylic acid, shown below, was prepared as follows

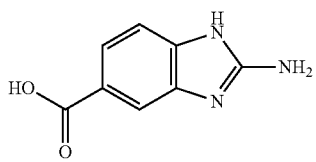 [SMILES: Nc1nc2cc(C(=O)O)ccc2[nH]1]

A solution of cyanogen bromide (5.0 mL, 5 M in acetonitrile, 25 mmol) was added to a mixture of methyl 3,4-diaminobenzoate (3.0 g, 18 mmol) in water (50 mL). The reaction was stirred at room temperature overnight. Aqueous ammonia (20 mL) and ethyl acetate (100 mL) were added to the reaction mixture and the layers were separated. The organics were dried over sodium sulfate, filtered, and concentrated. To the crude residue was added 2 N aqueous hydrochloric acid (18 mL, 36.0 mmol) and the mixture was heated at reflux overnight. The reaction was concentrated to give the title compound (2.90 g, 97%). $^1$H NMR (400 MHz, DMSO-d$_6$, δ): 8.75 (s, 2H), 7.84 (s, 1H), 7.77 (dd, J=1.2, 8.4 Hz, 1H), 7.38 (d, J=8.4 Hz, 1H).

Intermediate 27:
1-(4-methoxybenzylamino)isoquinoline-7-carboxylic acid, shown below, was prepared as follows

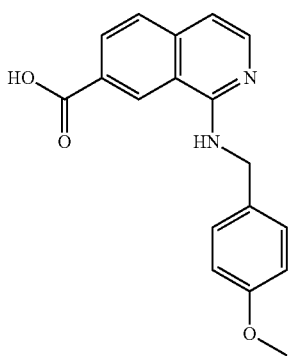 [SMILES: COc1ccc(CNc2nccc3ccc(C(=O)O)cc23)cc1]

Step 1: 1-oxo-1,2-dihydroisoquinoline-7-carboxylic acid

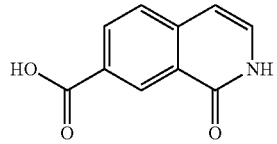 [SMILES: O=C(O)c1ccc2cc[nH]c(=O)c2c1]

To a suspension of 7-bromoisoquinolin-1 (2H)-one (70 g, 0.31 mol) in N,N-dimethylformamide (1 L) was added copper cyanide (56 g, 0.63 mol). The reaction was heated to 180° C. for 2 hours. The reaction was cooled to room temperature and was diluted with water (1 L). The solution was extracted with ethyl acetate (3×). The organics were dried over sodium sulfate, filtered, and concentrated to give crude 1-oxo-1,2-dihydroisoquinoline-7-carbonitrile (37 g). This crude material was taken up in ethanol (500 mL) and 1 N aqueous sodium hydroxide (400 mL) was added. The mixture was heated to reflux and stirred for 2 hours. The reaction was cooled to room temperature and the pH was adjusted to ~2 with 1 N aqueous hydrochloric acid. The solids were collected by filtration, rinsed with water, and dried under vacuum to give the title compound (35 g, 85%) as an off-white solid. $^1$H NMR (400 MHz, DMSO-d$_6$, δ): 13.15 (br. s., 1H), 11.49 (s, 1H), 8.75 (s, 1H), 8.17-8.14 (m, 1H), 7.75 (d, 1H), 7.34-7.29 (m, 1H), 6.62 (d, 1H).

Step 2: 1-chloroisoquinoline-7-carbonyl chloride

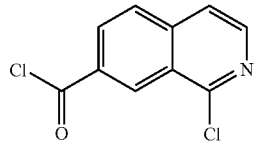 [SMILES: O=C(Cl)c1ccc2ccnc(Cl)c2c1]

Phosphorous oxychloride (74 mL, 793 mmol) was added to 1-oxo-1,2-dihydroisoquinoline-7-carboxylic acid (3.0 g, 20 mmol). The reaction was heated to 90° C. for 5 hours. The reaction was concentrated to dryness. The material was taken up in dichloromethane (250 mL) and saturated aqueous sodium bicarbonate (200 mL). The layers were separated and the aqueous was extracted again with dichloromethane (100 mL). The combined organics were dried over magnesium sulfate, filtered, and concentrated to give the title compound (3.0 g, 80%) as a yellow solid. +ESI (M+H) 227.1; $^1$H NMR (400 MHz, CDCl$_3$, δ): 9.18-9.22 (m, 1H), 8.44 (d, J=5.7 Hz, 1H), 8.32 (dd, J=8.8, 1.8 Hz, 1H), 7.95 (d, J=8.8 Hz, 1H), 7.68 (d, J=5.7 Hz, 1H).

Step 3: ethyl 1-chloroisoquinoline-7-carboxylate

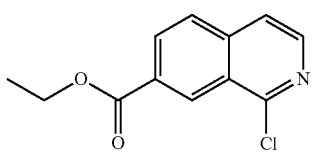 [SMILES: CCOC(=O)c1ccc2ccnc(Cl)c2c1]

1-Chloroisoquinoline-7-carbonyl chloride (3.02 g, 13.4 mmol) was dissolved in tetrahydrofuran (135 mL) and was cooled to 0° C. Ethanol (6.1 mL, 94 mmol) and triethylamine (2.05 mL, 14.7 mmol) were added. The reaction was allowed to warm to room temperature and stir for 2 hours. The reaction mixture was partitioned between ethyl acetate (500 mL) and saturated aqueous sodium bicarbonate (250 mL). The organic layer was dried over magnesium sulfate, filtered, and concentrated to give the title compound (3.0 g, 96%) as a yellow solid. +ESI (M+H) 236.1; $^1$H NMR (400 MHz, CDCl$_3$, δ): 9.06 (s, 1H), 8.30-8.39 (m, 2H), 7.89 (d, J=8.6 Hz, 1H), 7.63 (d, J=5.7 Hz, 1H), 4.48 (q, J=7.1 Hz, 2H), 1.46 (t, J=7.1 Hz, 3H).

Step 4: ethyl 1-(4-methoxybenzylamino)isoquinoline-7-carboxylate

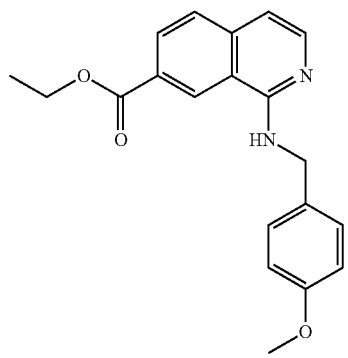 [SMILES: CCOC(=O)c1ccc2ccnc(NCc3ccc(OC)cc3)c2c1]

To a solution of ethyl 1-chloroisoquinoline-7-carboxylate (548 mg, 2.32 mmol) in N,N-dimethylformamide (9.3 mL) was added 4-methoxy-benzylamine (4.6 mL, 35 mmol) and potassium carbonate (5.14 g, 37.2 mmol). The reaction was heated to 70° C. and stirred overnight. The reaction was cooled to room temperature and was diluted with ethyl acetate and water. The layers were separated and the aqueous was extracted twice with ethyl acetate. The combined organics were washed with water and brine, dried over magnesium sulfate, filtered, and concentrated. Purification by flash column chromatography (0-35% ethyl acetate/heptanes) gave the title compound (430 mg, 55%) as a greenish oil. $^1$H NMR (400 MHz, CDCl$_3$, δ): 8.49 (s, 1H), 8.16 (dd, J=8.6, 1.6 Hz, 1H), 8.09 (d, J=5.9 Hz, 1H), 7.69 (d, J=8.6 Hz, 1H), 7.33-7.40 (m, 2H), 6.96 (d, J=5.9 Hz, 1H), 6.87-6.93 (m, 2H), 5.67 (br. s., 1H), 4.76 (d, J=5.1 Hz, 2H), 4.41 (q, J=7.2 Hz, 2H), 3.81 (s, 3H), 1.37-1.43 (m, 3H).

Step 5: 1-(4-methoxybenzylamino)isoquinoline-7-carboxylic acid

To a solution of ethyl 1-(4-methoxybenzylamino)isoquinoline-7-carboxylate (430 mg, 1.28 mmol) in methanol (8.5 mL) was added 6 N aqueous sodium hydroxide (1.1 mL, 6.4 mmol). The reaction was stirred at room temperature overnight. The reaction was concentrated. The residue was taken up in water and acidified with 1 N aqueous hydrochloric acid until a precipitate formed. The solid was collected by filtration and dried under vacuum to give the title compound (328 mg, 83%) as a yellow solid. $^1$H NMR (400 MHz, DMSO-d$_6$, δ): 8.92 (s, 1H), 8.30 (t, J=5.8 Hz, 1H), 8.06 (dd, J=8.4, 1.4Hz, 1H), 7.88 (d, J=5.7 Hz, 1H), 7.69 (d, J=8.6 Hz, 1H), 7.24-7.31 (m, 2H), 6.88 (d, J=5.7 Hz, 1H), 6.79-6.85 (m, 2H), 4.62 (d, J=5.9 Hz, 2H), 3.67 (s, 3H).

Intermediate 28: 3-methoxy-1H-indazole-6-carboxylic acid, shown below, was prepared as follows

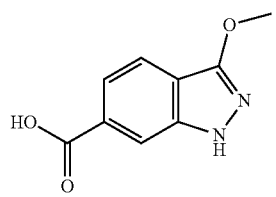

Step 1: methyl 3-hydroxy-1H-indazole-6-carboxylate

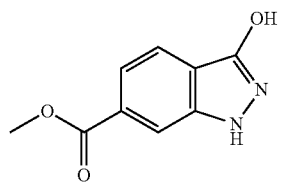

3-Oxo-2,3-dihydro-1H-indazole-6-carboxylic acid (1.5 g, 8.4 mmol) was suspended in methanol (17 mL). Concentrated hydrochloric acid (3.1 mL, 101 mmol) was added and the reaction was heated to reflux for 24 hours. The reaction was concentrated to give the title compound (1.6 g, 100%). +ESI (M+H) 193.1; $^1$H NMR (400 MHz, DMSO-d$_6$, δ): 11.98 (br. s., 1H), 7.89 (s, 1H), 7.72 (d, J=8.6 Hz, 1H), 7.50 (dd, J=8.5, 1.3 Hz, 1H), 3.85 (s, 3H).

Step 2: 1-ethyl 6-methyl 3-hydroxy-1H-indazole-1,6-dicarboxylate

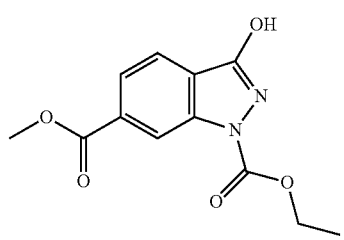 [SMILES: CCOC(=O)n1nc(O)c2ccc(C(=O)OC)cc21]

Methyl 3-hydroxy-1H-indazole-6-carboxylate (1.6 g, 8.3 mmol) was suspended in pyridine (10 mL). Ethyl chloroformate (1.0 mL, 10 mmol) was added slowly and the reaction was allowed to stir at room temperature for 2 hours. The reaction was poured into water (65 mL) and cooled in a refrigerator for 4 hours. The resulting brown precipitate was collected by filtration, rinsed with water, and dried under vacuum to give the title compound (1.35 g, 61%) as a beige solid. +ESI (M+H) 265.0; $^1$H NMR (400 MHz, CDCl$_3$, δ):

8.80 (d, J=6.0 Hz, 1H), 8.01 (dd, J=8.2, 1.2 Hz, 1H), 7.88 (d, J=8.6 Hz, 1H), 4.60 (q, J=7.0 Hz, 2H), 3.98 (s, 3H), 1.57 (t, J=7.1 Hz, 3H).

Step 3: 1-ethyl 6-methyl 3-methoxy-1H-indazole-1,6-dicarboxylate

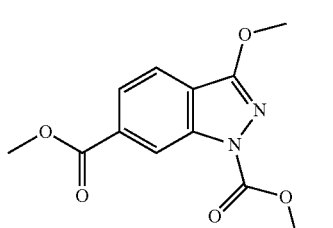

1-Ethyl 6-methyl 3-hydroxy-1H-indazole-1,6-dicarboxylate (1.35 g, 5.11 mmol) was suspended in acetone (65 mL). Cesium carbonate (1.75 g, 5.36 mmol) and methyl iodide (1.0 mL, 15 mmol) were added and the reaction was heated to reflux for 23 hours. The reaction was concentrated to dryness. The residue was taken up in dichloromethane (100 mL) and water (100 mL). The layers were separated and the aqueous was extracted again with dichloromethane. The combined organics were dried over magnesium sulfate, filtered, and concentrated. Purification by flash column chromatography gave two regioisomeric products.

1-ethyl 6-methyl 3-methoxy-1H-indazole-1,6-dicarboxylate (444 mg, 31%) as a white solid. $^1$H NMR (400 MHz, CDCl$_3$, δ): 8.78 (s, 1H), 7.96 (dd, J=8.2, 1.4 Hz, 1H), 7.70 (dd, J=8.2, 0.8 Hz, 1H), 4.57 (q, J=7.2 Hz, 2H), 4.19 (s, 3H), 3.96 (s, 3H), 1.51 (t, J=7.1 Hz, 3H).

1-ethyl 6-methyl 2-methyl-3-oxo-2,3-dihydro-1H-indazole-1,6-dicarboxylate (514 mg, 36%) as a yellow solid. $^1$H NMR (400 MHz, CDCl$_3$, δ): 8.56 (s, 1H), 8.00 (m, 1H), 7.92 (d, J=8.6 Hz, 1H), 4.49 (q, J=7.2 Hz, 2H), 3.97 (s, 3H), 3.69 (s, 3H), 1.49 (t, J=7.1 Hz, 3H).

Step 4: 3-methoxy-1H-indazole-6-carboxylic acid

1-Ethyl 6-methyl 3-methoxy-1H-indazole-1,6-dicarboxylate (444 mg, 1.60 mmol) was suspended in ethanol (5 mL). An aqueous solution of potassium hydroxide (16 mL, 16 mmol, 1 M) was added and the reaction was heated to 65° C. and stirred for 1.5 hours. The reaction was cooled to room temperature and concentrated. The residue was taken up in water and the solution was acidified with 1 N aqueous hydrochloric acid until a precipitate formed. The solid was collected by filtration, rinsed with water, and dried under vacuum to give the title compound (232 mg, 76%) as an orange solid. +ESI (M+H) 193.2; $^1$H NMR (400 MHz, DMSO-d$_6$, δ): 12.22 (s, 1H), 7.90-7.94 (m, 1H), 7.64 (d, J=8.4 Hz, 1H), 7.53 (dd, J=8.4, 1.4 Hz, 1H), 3.99 (s, 3H).

Intermediate 29:
3-(trifluoromethyl)-1H-indazole-5-carboxylic acid, shown below, was prepared as follows

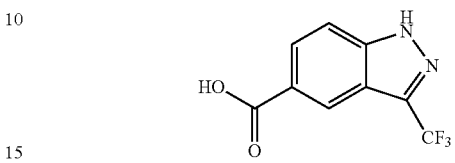

The title compound was prepared by a method analogous to that described in Steps 3-4 of Intermediate 21, using 5-bromo-3-(trifluoromethyl)-1H-indazole. +ESI (M+H) 231.1.

Intermediate 30:
1-(4-methoxybenzylamino)isoquinoline-6-carboxylic acid, shown below, was prepared as follows

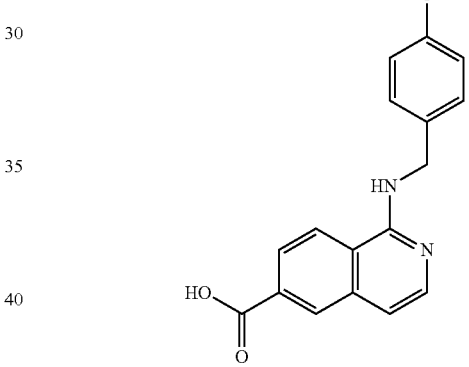

Step 1: 1-oxo-1,2-dihydroisoquinoline-6-carboxylic acid

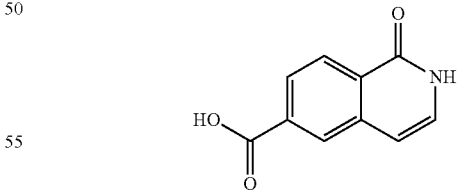

A mixture of 6-bromoisoquinolin-1(2H)-one (30 g, 0.134 mol), triethylamine (17.6 g, 0.174 mol), palladium(II) chloride (0.24 g, 1.34 mmol) and 2,2'-bis(diphenylphosphino)-1,1'-binaphthyl (0.84 g, 1.34 mmol) in methanol (300 mL) was pressurized with 2 MPa of carbon monoxide. The reaction was heated to 100° C. and stirred for 12 hours. The reaction mixture was filtered through Celite and concentrated. The residue was washed with water and the solid was dried under vacuum to give crude methyl 1-oxo-1,2-dihydroisoquinoline- 6-carboxylate (23.8 g, 95.2%) as a yellow solid. The solid was diluted with tetrahydrofuran (200 mL) and water (200 mL). To this mixture was added lithium hydroxide (16.8 g, 0.4 mol) and the reaction was stirred at room temperature for 4 hours. The reaction mixture was washed with ethyl acetate (3×) and these washings were discarded. The aqueous layer was acidified with 4 N aqueous hydrochloric acid to pH=5. The resulting precipitate was collected by filtration and dried under vacuum to give the title compound (11.3 g, 49%) as a yellow solid. $^1$H NMR (400 MHz, DMSO-$d_6$, δ): 11.48 (s, 1H), 8.24 (d, 2H), 7.93 (d, 1H), 7.22 (d, 1H), 6.68 (d, 1H).

Step 2:
1-(4-methoxybenzylamino)isoquinoline-6-carboxylic acid

The title compound was prepared by a method analogous to that described in Steps 2-5 of Intermediate 27, using 1-oxo-1,2-dihydroisoquinoline-6-carboxylic acid. +ESI (M+H) 309.2; $^1$H NMR (400 MHz, CD$_3$OD, δ): 8.37 (d, J=1.56 Hz, 1H), 8.34 (d, J=8.78 Hz, 1H), 8.12 (dd, J=8.68, 1.66 Hz, 1H), 7.67 (d, J=6.44 Hz, 1H), 7.29-7.36 (m, 2H), 7.15 (d, J=6.24 Hz, 1H), 6.86-6.93 (m, 2H), 4.73 (s, 2H), 3.76 (s, 3H).

Intermediate 31:
1-(methylamino)isoquinoline-7-carboxylic acid, shown below, was prepared as follows:

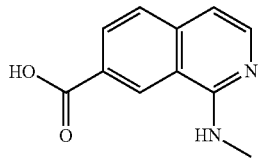

Step 1: ethyl 1-(methylamino)isoquinoline-7-carboxylate

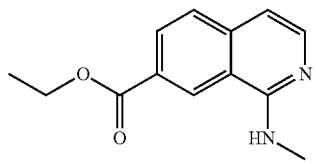 [SMILES: CCOC(=O)c1ccc2ccnc(NC)c2c1]

A solution of methylamine in tetrahydrofuran (30 mL, 60 mmol, 2 M) was added to ethyl 1-chloroisoquinoline-7-carboxylate (formed in Step 3 of Intermediate 27) (705 mg, 2.99 mmol) in a sealed tube. The reaction was heated to 60° C. and stirred overnight. LCMS indicated the reaction was not complete. Additional methylamine (10 mL, 20 mmol, 2 M in THF) was added and the reaction was heated to 60° C. for another 18 hours. The reaction was cooled to room temperature and concentrated. The residue was partitioned between water and dichloromethane. The organic layer was dried over magnesium sulphate, filtered, and concentrated. Purification by flash column chromatography (25-65% ethyl acetate/heptanes) gave the title compound (584 mg, 85%) as a yellow oil that solidified upon standing. +ESI (M+H) 231.1; $^1$H NMR (400 MHz, DMSO-$d_6$, δ): 8.83-8.94 (m, 1H), 8.07 (dd, J=8.58, 1.56 Hz, 1H), 7.99 (d, J=5.85 Hz, 1H), 7.89 (d, J=4.49 Hz, 1H), 7.77 (d, J=8.58 Hz, 1H), 6.92 (d, J=5.07 Hz, 1H), 4.38 (q, J=7.02 Hz, 2H), 2.97 (d, J=4.49 Hz, 3H), 1.38 (t, J=7.12 Hz, 3H).

Step 2: 1-(methylamino)isoquinoline-7-carboxylic acid

The title compound was prepared by a method analogous to that described in Step 3 of Intermediate 19, using ethyl 1-(methylamino)isoquinoline-7-carboxylate. +ESI (M+H) 203.1; $^1$H NMR (400 MHz, DMSO-$d_6$, δ): 13.03 (br. s., 1H), 8.87 (s, 1H), 8.06 (dd, J=8.51, 1.47 Hz, 1H), 7.97 (d, J=5.67 Hz, 1H), 7.85 (d, J=4.50 Hz, 1H), 7.75 (d, J=8.41 Hz, 1H), 6.91 (d, J=5.87 Hz, 1H), 2.95 (d, J=4.50 Hz, 3H).

Intermediate 32:
3-(trifluoromethyl)-1H-indazole-6-carboxylic acid, shown below, was prepared as follows

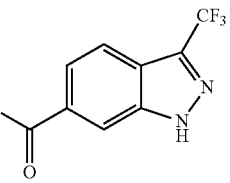

Step 1:
1-(4-bromo-2-fluorophenyl)-2,2,2-trifluoroethanol

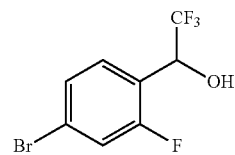

To a 0° C. solution of 4-bromo-2-fluorobenzaldehyde (1.00 g, 4.93 mmol) in tetrahydrofuran (50 mL) was added trimethylsilyl trifluoromethane (0.77 mL, 4.9 mmol) dropwise over 5 minutes. The reaction was stirred at 0° C. for 10 minutes. Then tetrabutylammonium fluoride (0.49 mL, 0.49 mmol, 1 M in tetrahydrofuran) was slowly added and the reaction was allowed to gradually warm to room temperature and stir for 3 days. The reaction was concentrated and the residue was taken up in dichloromethane. The solution was washed once with 1 N aqueous hydrochloric acid and once with brine. The organics were dried over magnesium sulfate, filtered, and concentrated. Purification by column chromatography (0-50% ethyl acetate/heptanes) gave the title compound (1.0 g, 75%) as a clear oil. $^1$H NMR (400 MHz, CDCl$_3$, δ): 7.48 (d, J=7.61 Hz, 1H), 7.39 (d, J=1.76 Hz, 1H), 7.29 (dd, J=9.56, 1.95 Hz, 1H), 5.33-5.40 (m, 1H), 2.70 (d, J=5.46 Hz, 1H).

Step 2: 1-(4-bromo-2-fluorophenyl)-2,2,2-trifluoroethanone

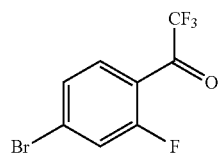 [SMILES: O=C(c1ccc(Br)cc1F)C(F)(F)F]

To a solution of 1-(4-bromo-2-fluorophenyl)-2,2,2-trifluoroethanol (1.09 g, 3.99 mmol) in ethyl acetate (30 mL) was added 2-iodoxybenzoic acid (2.28 g, 7.97 mmol). The reaction was heated to reflux overnight. The reaction was cooled to room temperature and diluted with heptanes (30 mL). The mixture was filtered through Celite and the filtrate was concentrated to give the title compound (1.03 g, 95%) as a pale yellow oil. $^1$H NMR (400 MHz, CDCl$_3$, δ): 7.44 (dd, J=10.15, 1.56 Hz, 1H), 7.48 (m, 1H), 7.76 (m, 1H).

Step 3: 6-bromo-3-(trifluoromethyl)-1H-indazole

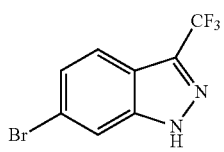

Hydrazine hydrate (3.5 mL, 45 mmol) was added to a solution of 1-(4-bromo-2-fluorophenyl)-2,2,2-trifluoroethanone (1.00 g, 3.69 mmol) in 1-butanol (15 mL). The reaction was heated to reflux for 5 hours, then cooled to room temperature and left stirring overnight. The reaction was diluted with water (50 mL) and extracted with ethyl acetate (3×). The combined organics were washed with brine, dried over magnesium sulfate, filtered, and concentrated. Purification by flash column chromatography (0-50% ethyl acetate/heptanes) gave the title compound (310 mg, 32%) as an off-white solid. $^1$H NMR (400 MHz, CDCl$_3$, δ): 7.42 (dd, J=8.58, 1.56 Hz, 1H), 7.72 (d, J=8.58 Hz, 1H), 7.75 (dd, J=1.56, 0.78 Hz, 1H).

Step 4: 3-(trifluoromethyl)-1H-indazole-6-carboxylic acid

The title compound was prepared by a method analogous to that described in Steps 3-4 of Intermediate 21, using 6-bromo-3-(trifluoromethyl)-1H-indazole. −ESI (M−H) 229.1.

Intermediate 33: 2-methyl-3-oxo-2,3-dihydro-1H-indazole-6-carboxylic acid, shown below, was prepared as follows

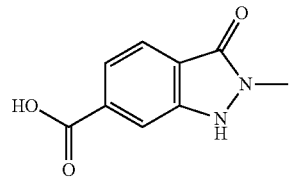

To a suspension of 1-ethyl 6-methyl 2-methyl-3-oxo-2,3-dihydro-1H-indazole-1,6-dicarboxylate (formed in Step 3 of Intermediate 28) (514 mg, 1.85 mmol) in ethanol (6 mL) was added 1 N aqueous potassium hydroxide (18.5 mL, 18.5 mmol). The reaction was heated to 65° C. for 1.5 hours. The reaction was cooled to room temperature and concentrated to dryness. The residue was taken up in water and acidified with 1 N aqueous hydrochloric acid until a precipitate formed. The solid was collected by filtration and dried under vacuum to give the title compound (196 mg, 55%) as a brown solid. $^1$H NMR (400 MHz, DMSO-d$_6$, δ): 13.12 (br. s., 1H), 10.61 (br. s., 1H), 7.76 (s, 1H), 7.70 (d, J=8.2 Hz, 1H), 7.60 (dd, J=8.2, 1.2 Hz, 1H), 3.38 (s, 3H).

Intermediate 34: 3-chloro-1H-pyrrolo[3,2-b]pyridine-6-carboxylic acid, shown below, was prepared as follows

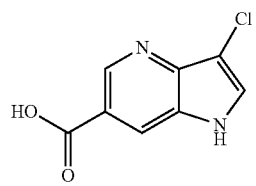 [SMILES: O=C(O)c1cnc2c(Cl)c[nH]c2c1]

Step 1: methyl 3-chloro-1H-pyrrolo[3,2-b]pyridine-6-carboxylate

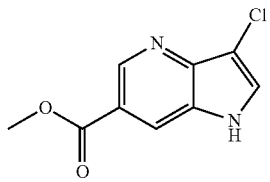

To a 0° C. solution of methyl 1H-pyrrolo[3,2-b]pyridine-6-carboxylate (1.00 g, 5.68 mmol) in N,N-dimethylformamide (15 mL) was added N-chlorosuccinimide (895 mg, 5.96 mmol). The reaction was allowed to gradually warm to room temperature and stir overnight. The reaction was diluted with water (125 mL) and stirred for 20 minutes. The resulting solid was collected by filtration, washed with water, and dried under vacuum to give the title compound (1.11 g, 93%) as an orange powder. +ESI (M+H) 211.0; $^1$H NMR (400 MHz, DMSO-$d_6$, δ): 11.99 (br. s., 1H), 8.92 (d, J=2.0 Hz, 1H), 8.31 (d, J=1.8 Hz, 1H), 8.08 (d, J=3.1 Hz, 1H), 3.88 (s, 3H).

Step 2: 3-chloro-1H-pyrrolo[3,2-b]pyridine-6-carboxylic acid

Methyl 3-chloro-1H-pyrrolo[3,2-b]pyridine-6-carboxylate (1.10 g, 5.22 mmol) was suspended in 1,4-dioxane (25 mL) and 6 N aqueous hydrochloric acid (8.7 mL) was added. The reaction was allowed to stir at room temperature overnight. The reaction was then concentrated to give the title compound (1.2 g, 100%). +ESI (M+H) 197.1; $^1$H NMR (400 MHz, DMSO-$d_6$, δ): 12.50 (br. s., 1H), 8.92 (d, J=1.6 Hz, 1H), 8.46 (br. s., 1H), 8.19 (br. s., 1H).

Intermediate 35: 3-(methylamino)-1H-indazole-6-carboxylic acid, shown below, was prepared as follows

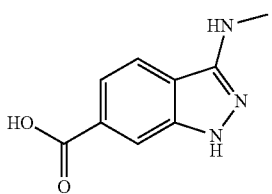

Step 1: 4-bromo-2-fluoro-N-methylbenzothioamide

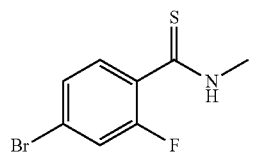

A mixture of 4-bromo-2-fluoro-N-methylbenzamide (500 mg, 2 mmol) and Lawesson reagent (872 mg, 2.16 mmol) in toluene (10 mL) was heated to 100° C. and stirred for 4 hours. The reaction was cooled to room temperature, diluted with toluene, and filtered. The filtrate was concentrated and purification of the residue by flash column chromatography (0-20% ethyl acetate/heptanes) gave the title compound (520 mg, 97%) as a yellow solid. +ESI (M+H+1) 250.1; $^1$H NMR (400 MHz, CDCl$_3$, δ): 8.09 (t, J=8.58 Hz, 1H), 8.03 (br. s., 1H), 7.35 (dd, J=8.19, 2.15 Hz, 1H), 7.27 (dd, J=11.41, 1.85 Hz, 1H), 3.36 (dd, J=4.88, 0.78 Hz, 3H).

Step 2: 6-bromo-N-methyl-1H-indazol-3-amine

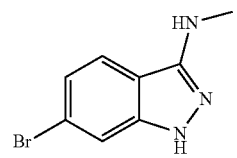

Anhydrous hydrazine (0.25 mL, 8.1 mmol) was added to a solution of 4-bromo-2-fluoro-N-methylbenzothioamide (200 mg, 0.8 mmol) in dimethylsulfoxide (2.5 mL). The reaction was heated to 100° C. and stirred for 2 hours. The reaction was cooled to room temperature and diluted with ethyl acetate and water. The layers were separated and the aqueous was extracted with ethyl acetate (3×). The combined organics were washed with saturated aqueous sodium carbonate and brine, dried over sodium sulfate, filtered, and concentrated. Purification by flash column chromatography (20-100% ethyl acetate/heptanes) gave the title compound (98 mg, 54%) as a white solid. +ESI (M+H+1) 228.0; $^1$H NMR (400 MHz, CD$_3$OD, δ): 7.52 (d, J=8.58 Hz, 1H), 7.43 (s, 1H), 7.04 (d, J=8.39 Hz, 1H), 2.94 (s, 3H).

Step 3: methyl 3-(methylamino)-1H-indazole-6-carboxylate

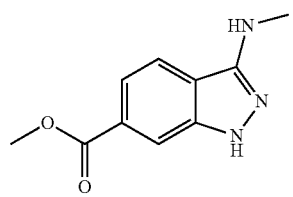

The title compound was prepared by a method analogous to that described in Step 2 of Intermediate 12, using 6-bromo-N-methyl-1H-indazol-3-amine. +ESI (M+H) 206.2; $^1$H NMR (400 MHz, CD$_3$OD, δ): 7.95 (t, J=1.17 Hz, 1H), 7.67 (dd, J=8.39, 0.78 Hz, 1H), 7.55 (dd, J=8.49, 1.27 Hz, 1H), 3.90 (s, 3H), 2.96 (s, 3H).

Step 4: 3-(methylamino)-1H-indazole-6-carboxylic acid

To a solution of methyl 3-(methylamino)-1H-indazole-6-carboxylate (30.0 mg, 0.15 mmol) in 1,4-dioxane (0.2 mL) was added 3 N aqueous hydrochloric acid (0.2 mL, 0.6 mmol). The mixture was heated to 100° C. for 2 hours. The reaction was concentrated and dried under vacuum to give the title compound (33 mg, 99%) as a tan solid. +ESI (M+H)

192.1; ¹H NMR (400 MHz, CD₃OD, δ): 8.09 (s, 1H), 7.98 (dd, J=8.58, 0.78 Hz, 1H), 7.85 (dd, J=8.58, 1.37 Hz, 1H), 3.12 (s, 3H).

Intermediate 36:
3-methoxyisoquinoline-7-carboxylic acid, shown below, was prepared as follows:

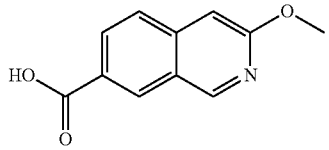

Step 1: 7-bromo-3-methoxyisoquinoline

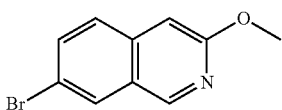

A mixture of 7-bromo-3-chloroisoquinoline (100 mg, 0.4 mmol) and sodium methoxide (113 mg, 2.1 mmol) in diglyme (1 mL) was heated to 150° C. for 1 hour. The reaction was cooled to room temperature and diluted with toluene and water. The layers were separated and the aqueous layer was extracted with toluene (3×). The combined organics were washed with water and brine, dried over sodium sulfate, filtered, and concentrated to an oil. The oil was dried under vacuum overnight to give the title compound (83 mg, 85%) as a yellow solid. +ESI (M+H+1) 240.1; ¹H NMR (400 MHz, CDCl₃, δ): 8.87 (s, 1H), 8.01-8.05 (m, 1H), 7.58-7.64 (m, 1H), 7.53-7.58 (m, 1H), 6.97 (s, 1H), 4.02 (s, 3H).

Step 2: 3-methoxyisoquinoline-7-carboxylic acid

The title compound was prepared by a method analogous to that described in Steps 3-4 of Intermediate 21, using 7-bromo-3-methoxyisoquinoline. +ESI (M+H) 204.2; ¹H NMR (400 MHz, CD₃OD, δ): 9.08 (s, 1H), 8.71 (s, 1H), 8.14 (dd, J=8.78, 1.56 Hz, 1H), 7.83 (d, J=8.78 Hz, 1H), 7.17 (s, 1H), 4.02 (s, 3H).

Intermediate 37:
1-(methylamino)isoquinoline-6-carboxylic acid, shown below, was prepared as follows

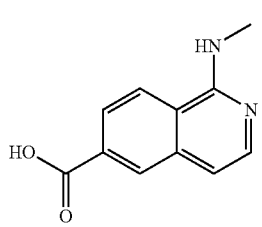

Step 1: ethyl 1-chloroisoquinoline-6-carboxylate

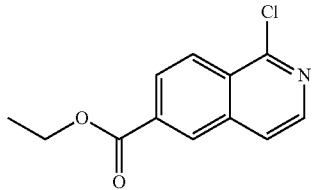 [SMILES: CCOC(=O)c1ccc2c(Cl)nccc2c1]

The title compound was prepared by a method analogous to that described in Steps 1-3 of Intermediate 27, using 6-bromoisoquinolin-1 (2H)-one. ¹H NMR (400 MHz, CDCl₃, δ): 8.56 (d, J=1.6 Hz, 1H), 8.38 (d, J=8.8 Hz, 1H), 8.34 (d, J=5.7 Hz, 1H), 8.25 (dd, J=8.8, 1.6 Hz, 1H), 7.70 (d, J=6.0 Hz, 1H), 4.47 (q, J=7.0 Hz, 2H), 1.45 (t, J=7.1 Hz, 3H).

Step 2: ethyl 1-(methylamino)isoquinoline-6-carboxylate

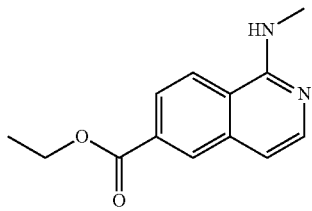 [SMILES: CCOC(=O)c1ccc2c(NC)nccc2c1]

The title compound was prepared by a method analogous to that described in Step 1 of Intermediate 31, using ethyl 1-chloroisoquinoline-6-carboxylate. +ESI (M+H) 231.1; ¹H NMR (400 MHz, CDCl₃, δ): 8.39 (s, 1H), 8.06-8.14 (m, 2H), 8.00 (d, J=5.9 Hz, 1H), 7.02 (d, J=6.0 Hz, 1H), 4.44 (q, J=7.3 Hz, 2H), 3.25 (d, J=4.7 Hz, 3H), 1.43 (t, J=7.1 Hz, 3H).

Step 3: 1-(methylamino)isoquinoline-6-carboxylic acid

To a suspension of ethyl 1-(methylamino)isoquinoline-6-carboxylate (150 mg, 0.65 mmol) in ethanol (2.5 mL) was added 1 N aqueous potassium hydroxide (6.5 mL, 6.5 mmol). The reaction was heated to 65° C. for 1.5 hours. The reaction was cooled to room temperature and concentrated to dryness. The solid was dissolved in water and the solution was acidified with 1 N HCl. The mixture was concentrated. The solid was dissolved in water (50 mL) and extracted twice with 2-butanol (50 mL). The combined organics were washed with brine (20 mL), dried over magnesium sulfate, filtered, and concentrated to give the title compound (95 mg, 72%) as a white solid. +ESI (M+H) 203.2; ¹H NMR (400 MHz, DMSO-d₆, δ): 13.07 (br.s., 1H), 10.25 (d, J=4.9 Hz, 1H), 8.74 (d, J=8.8 Hz, 1H), 8.51 (s, 1H), 8.15 (dd, J=8.6, 1.8 Hz, 1H), 7.67 (d, J=6.8 Hz, 1H), 7.35 (d, J=7.0 Hz, 1H), 3.15 (d, J=4.7 Hz, 3H).

Intermediate 38:
1-methoxyisoquinoline-6-carboxylic acid

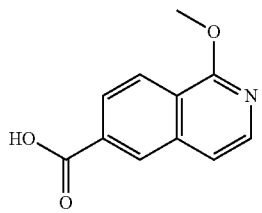

A solution of sodium methoxide was prepared by slowly adding sodium metal (870 mg, 37 mmol) to methanol (25 mL) with stirring. After all of the sodium metal had reacted, this solution was added to ethyl 1-chloroisoquinoline-6-carboxylate (440 mg, 1.9 mmol). The resulting suspension was heated to reflux and stirred for 3 days. The reaction mixture was cooled to room temperature and concentrated. The residue was partitioned between water and ethyl acetate. The layers were separated and the aqueous layer was acidified with 1 N aqueous hydrochloric acid until a precipitate formed. The solid was collected by filtration and dried under vacuum to give the title compound (294 mg, 78%) as a white solid. $^1$H NMR (400 MHz, DMSO-d$_6$, δ): 8.50 (d, J=1.2 Hz, 1H), 8.23 (d, J=8.8 Hz, 1H), 8.02-8.10 (m, 2H), 7.54 (d, J=6.0 Hz, 1H), 4.05 (s, 3H).

Intermediate 39:
3-(methylamino)-1H-indazole-5-carboxylic acid, shown below, was prepared as follows:

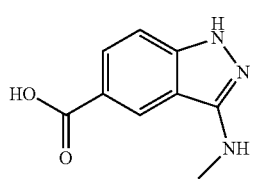

Step 1: 5-bromo-2-fluoro-N-methylbenzamide

To a mixture of 5-bromo-2-fluorobenzoic acid (200 mg, 0.91 mmol) in dichloromethane (5 mL) was added oxalyl chloride (0.16 mL, 1.8 mmol), followed by 1 drop of N,N-dimethylformamide. The reaction was stirred at room temperature for 1.5 hours. The reaction was concentrated and the resulting residue was dissolved in dichloromethane (3 mL) and cooled to 0° C. Methylamine (2.3 mL, 5 mmol, 2 M in tetrahydrofuran) was added and the reaction was allowed to stir at 0° C. for 30 minutes. The reaction was quenched with water and the mixture was concentrated. The residue was diluted with water and the resulting solids were filtered, rinsed with water, and dried under vacuum to give the title compound (196.6 mg, 93%) as a white solid. +ESI (M+H+1) 234.1; $^1$H NMR (400 MHz, CDCl$_3$, δ); 8.22 (dd, J=6.83, 2.73 Hz, 1H), 7.55 (ddd, J=8.68, 4.49, 2.63 Hz, 1H), 7.00 (dd, J=11.32, 8.58 Hz, 1H), 6.67 (br. s., 1H), 3.02 (dd, J=4.88, 1.17 Hz, 3H).

Step 2: 5-bromo-2-fluoro-N-methylbenzothioamide

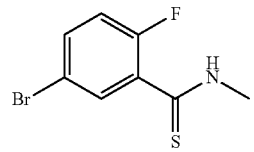

A mixture of 5-bromo-2-fluoro-N-methylbenzamide (500 mg, 2 mmol) and Lawesson's reagent (872 mg, 2.16 mmol) in toluene (10 mL) was heated to 100° C. and stirred for 3.5 hours. The reaction was cooled to room temperature, diluted with toluene, and filtered. The filtrate was concentrated and purified by flash column chromatography (0-20% ethyl acetate/heptanes) to give the title compound (494 mg, 92%) as a yellow oil that solidified upon standing. +ESI (M+H+1) 250.1; $^1$H NMR (400 MHz, CDCl$_3$, δ): 8.20 (dd, J=6.93, 2.63 Hz, 1H), 8.06 (br.s., 1H), 7.47 (ddd, J=8.73, 4.44, 2.63 Hz, 1H), 6.95 (dd, J=11.12, 8.78 Hz, 1H), 3.32 (dd, J=4.88, 0.78 Hz, 3H).

Step 3: 5-bromo-N-methyl-1H-indazol-3-amine

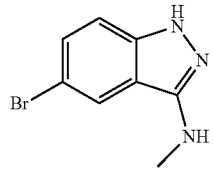

A mixture of 5-bromo-2-fluoro-N-methylbenzothioamide (480 mg, 1.9 mmol) and anhydrous hydrazine (0.61 mL, 19 mmol) in dimethylsulfoxide (6 mL) was heated to 80° C. and stirred for 1 hour. The temperature was increased to 100° C. and the reaction was stirred for 40 minutes. The temperature was increased further to 130° C. and the reaction was stirred for another 45 minutes. The reaction was cooled to room temperature and diluted with ethyl acetate and brine. The layers were separated and the aqueous was extracted with ethyl acetate (4×). The combined organics were washed with water and brine, dried over sodium sulfate, filtered, and concentrated. Purification by flash column chromatography (20-70% ethyl acetate/heptanes) gave the title compound (103 mg, 23%) as a white solid. +ESI (M+H+1) 228.0; $^1$H NMR (400 MHz, CD₃OD, δ): 7.78 (dd, J=1.85, 0.68 Hz, 1H), 7.29-7.40 (m, 1H), 7.17 (dd, J=8.88, 0.68 Hz, 1H), 2.94 (s, 3H).

Step 4: methyl 3-(methylamino)-1H-indazole-5-carboxylate

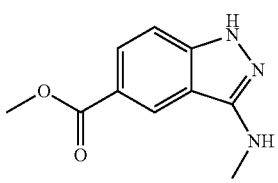

The title compound was prepared by a method analogous to that described in Step 3 of Intermediate 21, using 5-bromo-N-methyl-1H-indazol-3-amine. +ESI (M+H) 206.2; ¹H NMR (400 MHz, CD₃OD, δ): 8.44 (dd, J=1.56, 0.78 Hz, 1H), 7.92 (dd, J=8.78, 1.56 Hz, 1H), 7.26 (dd, J=8.78, 0.78 Hz, 1H), 3.88 (s, 3H), 2.96 (s, 3H).

Step 5: 3-(methylamino)-1H-indazole-5-carboxylic acid

Methyl 3-(methylamino)-1H-indazole-5-carboxylate (60.0 mg, 0.29 mmol) was dissolved in 1,4-dioxane (0.5 mL). 3N Aqueous hydrochloric acid (0.3 mL, 0.9 mmol) was added and the reaction was heated to 100° C. for 11.5 hours. The heat was removed and the reaction was left stirring at room temperature overnight. The reaction was concentrated to give the title compound (63 mg, 95%) as a tan solid. +ESI (M+H) 192.1; ¹H NMR (400 MHz, CD₃OD, δ): 8.61 (d, J=0.78 Hz, 1H), 8.19 (dd, J=8.80, 1.57 Hz, 1H), 7.38 (d, J=8.80 Hz, 1H), 3.02 (s, 3H).

Intermediate 40: 3-aminoisoquinoline-7-carboxylic acid, shown below, was prepared as follows

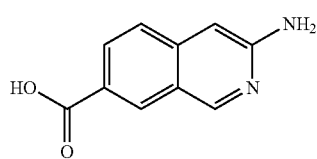 [SMILES: Nc1cc2ccc(C(=O)O)cc2cn1]

The title compound was prepared by a method analogous to that described in Steps 3-4 of Intermediate 21, using 7-bromoisoquinolin-3-amine. +ESI (M+H) 189.2; ¹H NMR (400 MHz, CD₃OD, δ): 8.87 (s, 1H), 8.52 (d, J=0.78 Hz, 1H), 7.98 (dd, J=8.78, 1.76 Hz, 1H), 7.54 (d, J=8.78 Hz, 1H), 6.77 (s, 1H).

Intermediate 41: 3-(methylamino)isoquinoline-7-carboxylic acid, shown below, was prepared as follows

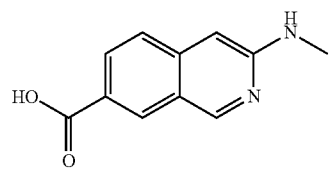

Step 1: 7-bromo-N-methylisoquinolin-3-amine

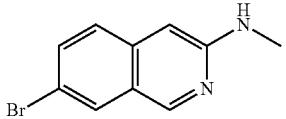

A mixture of 7-bromo-3-chloroisoquinoline (100 mg, 0.4 mmol), methylamine hydrochloride (139 mg, 2.06 mmol), and potassium carbonate (456 mg, 3.30 mmol) in 1-methoxy-2-(2-methoxyethoxy)ethane (1 mL) was heated to 150° C. and stirred for 60 hours. Additional methylamine hydrochloride (100 mg, 1.5 mmol) and potassium carbonate (200 mg, 1.4 mmol) were added and heating was continued for another 40 hours. The reaction was cooled to room temperature and diluted with water. The mixture was stirred for 30 minutes. The resulting solid was filtered off, rinsed with water and dried under vacuum. Purification by flash column chromatography (10-30% ethyl acetate/heptanes) gave the title compound (82 mg) as a pale yellow solid. −APCI (M−H+1) 237.8; ¹H NMR (400 MHz, CDCl₃, δ): 8.70 (s, 1H), 7.84 (d, J=1.95 Hz, 1H), 7.48 (dd, J=8.97, 2.15 Hz, 1H), 7.38 (d, J=8.97 Hz, 1H), 6.39 (s, 1H), 2.92 (s, 3H).

Step 2: 3-(methylamino)isoquinoline-7-carboxylic acid

The title compound was prepared by a method analogous to that described in Steps 3-4 of Intermediate 21, using 7-bromo-N-methylisoquinolin-3-amine. +ESI (M+H) 203.1;

$^1$H NMR (400 MHz, CD$_3$OD, δ): 8.87 (s, 1H), 8.51 (s, 1H), 7.98 (dd, J=8.88, 1.66 Hz, 1H), 7.58 (d, J=8.78 Hz, 1H), 6.60 (s, 1H), 2.93 (s, 3H).

Intermediate 42: 3-chloro-1H-pyrrolo[2,3-b]pyridine-5-carboxylic acid, shown below, was prepared as follows

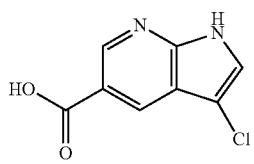 [SMILES: O=C(O)c1cnc2[nH]cc(Cl)c2c1]

A suspension of 1H-pyrrolo[2,3-b]pyridine-5-carboxylic acid (250 mg, 1.5 mmol) in N,N-dimethylformamide (5 mL) was warmed to 40° C. N-chlorosuccinimide (243 mg, 1.62 mmol) was added and the mixture was stirred at 55° C. for 5 hours. The reaction was cooled to room temperature and left stirring for 2 days. The mixture was diluted with water (20 mL) and stirred overnight. The resulting solid was collected by filtration and dried to give the title compound (161 mg, 55%). +ESI (M+H) 197.1; $^1$H NMR (400 MHz, DMSO-d$_6$, δ): 13.08 (br. s., 1H), 12.39 (br. s., 1H), 8.86 (d, J=1.8 Hz, 1H), 8.40 (d, J=1.2 Hz, 1H), 7.84 (d, J=2.5 Hz, 1H).

Intermediate 43: 6-bromo-3-methoxyisoquinoline, shown below, was prepared as follows

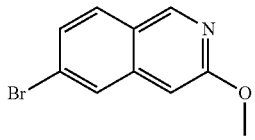

A mixture of 6-bromoisoquinolin-3-ol (606 mg, 2.70 mmol), silver carbonate (1.5 g, 5.3 mmol), and N,N-dimethylformamide (12 mL) was stirred at room temperature for 16 minutes. Methyl iodide (186 μL, 2.97 mmol) was added and the reaction was left stirring for 18 hours. The reaction was diluted with methanol and filtered through Celite. The filtrate was concentrated and purified by flash column chromatography to give the title compound (90 mg, 14%). +ESI (M+H+1) 240.0; $^1$H NMR (400 MHz, CDCl$_3$, δ): 8.91 (s, 1H), 7.86 (d, J=1.8 Hz, 1H), 7.73 (d, J=8.8 Hz, 1H), 7.43 (dd, J=8.8, 1.8 Hz, 1H), 6.90 (s, 1H), 4.02 (s, 3H).

Intermediate 44: 2-chloroquinoline-7-carboxylic acid, shown below, was prepared as follows

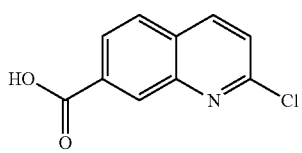 [SMILES: O=C(O)c1ccc2ccc(Cl)nc2c1]

Step 1: ethyl 2-chloroquinoline-7-carboxylate

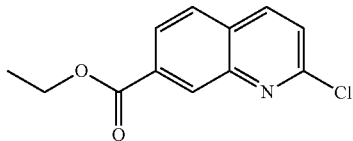 [SMILES: CCOC(=O)c1ccc2ccc(Cl)nc2c1]

Phosphorus oxychloride (1.94 mL, 20.7 mmol) was added to a solution of 7-(ethoxycarbonyl)quinoline 1-oxide (450 mg, 2.07 mmol) in dichloromethane (15 mL). The reaction was heated to 50° C. for 3 hours. The reaction was then cooled to room temperature and was slowly poured into 200 mL of water, with stirring. The mixture was allowed to stir for 1 hour and was then neutralized with 1 N aqueous potassium hydroxide. The mixture was extracted with dichloromethane (3×). The extracts were washed with brine, dried over magnesium sulfate, filtered, and concentrated. Purification by column chromatography (0-20% ethyl acetate/heptanes) gave the title compound (254 mg, 52%) as a white solid. $^1$H NMR (400 MHz, CDCl$_3$, δ): 8.70-8.79 (m, 1H), 8.13-8.18 (m, 2H), 7.87 (d, J=8.39 Hz, 1H), 7.47 (d, J=8.58 Hz, 1H), 4.44 (q, J=7.02 Hz, 2H), 1.43 (t, J=7.12 Hz, 3H).

Step 2: 2-chloroquinoline-7-carboxylic acid

To a solution of ethyl 2-chloroquinoline-7-carboxylate (800 mg, 3.4 mmol) in tetrahydrofuran (10 mL) was added 1 N aqueous lithium hydroxide (7 mL, 7 mmol). The reaction was stirred at room temperature overnight. The reaction was concentrated and the residue was diluted with water and acidified with 1 N aqueous hydrochloric acid. The resulting precipitate was collected by filtration and dried under vacuum to give the title compound (648 mg, 92%) as a white powder. +ESI (M+H) 208.1; $^1$H NMR (400 MHz, DMSO-d$_6$, δ): 13.43 (s, 1H), 8.53 (d, J=8.7 Hz, 1H), 8.44-8.45 (m, 1H), 8.14 (d, J=8.4 Hz, 1H), 8.07-8.11 (m, 1H), 7.70 (d, J=8.5 Hz, 1H).

Intermediate 44: 2-((2,2,2-trifluoroethyl)amino)quinoline-7-carboxylic acid, shown below, was prepared as follows

Step 1: methyl quinoline-7-carboxylate

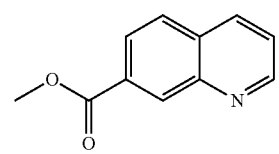

The title compound was prepared by a method analogous to that described in Step 3 of Intermediate 21 using 7-bromoquinoline as the starting material.

Step 2: 7-(methoxycarbonyl)quinoline 1-oxide, shown below, was prepared as follows:

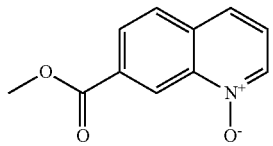

To a solution of methyl quinoline-7-carboxylate (17.8 g, 94.87 mmol) in dichloromethane (315 mL) was added peracetic acid (39.9 mL, 190 mmol, 32% in acetic acid). The reaction was stirred at room temperature overnight. Peracetic acid (10 mL, 48 mmol, 32% in acetic acid) was added and the mixture was stirred for 5 h. The reaction mixture was diluted with a saturated solution of aqueous sodium bicarbonate. The aqueous phase was extracted into dichloromethane (2×1 L). The extracts were combined, dried over magnesium sulfate, filtered and concentrated under reduced pressure. Purification by flash chromatography (2-15% methanol in dichloromethane) gave the title compound (17.4 g, 90%) as a yellow solid. $^1$H NMR (400 MHz, CHLOROFORM-d, δ): 9.41 (1H, s), 8.56 (1H, dd, J=6.0, 0.8 Hz), 8.24 (1H, dd, J=8.5, 1.7 Hz), 7.93 (1H, d, J=8.6 Hz), 7.75 (1H, d, J=8.6 Hz), 7.39 (1H, dd, J=8.6, 6.0 Hz), 4.01 (3H, s)

Step 3: methyl 2-((2,2,2-trifluoroethyl)amino)quinoline-7-carboxylate, shown below, was prepared as follows

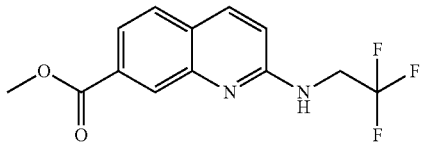 [SMILES: COC(=O)c1ccc2ccc(NCC(F)(F)F)nc2c1]

To a solution of 7-(methoxycarbonyl)quinoline 1-oxide (200 mg, 0.984 mmol) and 2,2,2-trifluoroethylamine (292 mg, 0.295 mmol) at 0° C. was added 4-methylbenzenesulphonic anhydride (964 mg, 2.95 mmol) portionwise over a period of 45 minutes. The reaction was allowed to warm up to room temperature and stirred overnight. The reaction was diluted with dichloromethane and washed with a saturated solution of ammonium chloride. The aqueous layer was extracted into dichloromethane (1×). The organics were combined and washed with brine, dried over magnesium sulfate, filtered and concentrated under reduced pressure. Purification by flash chromatography gave the title compound (172 mg, 62%). +ESI (M+H) 285.1

Step 4: 2-((2,2,2-trifluoroethyl)amino)quinoline-7-carboxylic acid

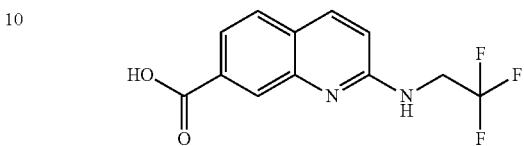

To a solution of methyl 2-((2,2,2-trifluoroethyl)amino)quinoline-7-carboxylate (172 mg, 0.605 mmol) in tetrahydrofuran (5 mL) was added aqueous lithium hydroxide (1.82 mL, 1.82 mmol, 1M solution) at room temperature. The reaction was stirred for 2.5 days. The solvent was removed under reduced pressure and the residue was acidified with 1N aqueous hydrochloric acid. The resulting precipitate was filtered and dried to give the title compound (65 mg, 40%) +ESI (M+H) 271.1, $^1$H NMR (400 MHz, DMSO-d6, δ): 4.31-4.41 (m, 2H) 7.01 (d, J=8.87 Hz, 1H) 7.69-7.80 (m, 2H) 8.06 (d, J=8.66 Hz, 1H) 8. 14 (s, 1H) 13.03 (bs, 1H)

Intermediate 45: 2-((2,2-difluoropropyl)amino)quinoline-7-carboxylic acid, shown below, was prepared as follows

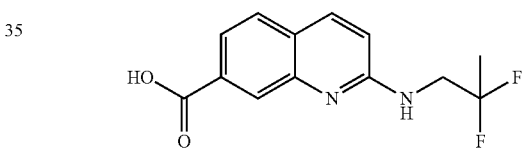

The title compound was prepared by a method analogous to that described for Intermediate 44, using 2,2-difluoroethylamine instead of 2,2,2-trifluoroethylamine. +ESI (M+H) 267.2; $^1$H NMR (400 MHz, DMSO-d6, δ): 1.63 (t, J=19.02 Hz, 3H) 3.89-3.99 (m, 2H) 6.97 (d, J=8.97 Hz, 1H) 7.54 (t, 1H) 7.62-7.68 (m, 1H) 7.71 (d, J=8.19 Hz, 1H) 7.96 (d, J=9.10 Hz, 1H) 8.06-8.09 (m, 1H) 12.95 (bs, 1H).

Intermediate 46: 7-chloro-1H-benzo[d][1,2,3]triazole-5-carboxylic acid, shown below, was prepared as follows

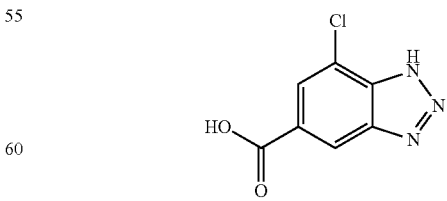

To a solution of 3,4-diamino-5-chlorobenzoic acid (125 mg, 0.67 mmol) in concentrated sulfuric acid (0.45 mL) was added water (2 mL) at 0° C. The reaction mixture was stirred at 0° C. for 1 h. The mixture was left stirring overnight. The reaction was diluted with water and the resulting precipitate was filtered to give the title compound (124 mg, 94%) as a brown solid. +APCI (M+H) 198.0; $^1$H NMR (400 MHz, METHANOL-$d_4$, δ): 8.53 (d, J=1.2 Hz, 1H), 8.10 (d, J=1.0 Hz, 1H)

Example 1

1'-isopropyl-1-(2-methyl-1H-benzo[d]imidazole-5-carbonyl)-4',6'-dihydrospiro[piperidine-4,5'-pyrazolo[3,4-c]pyridin]-7'(1'H)-one

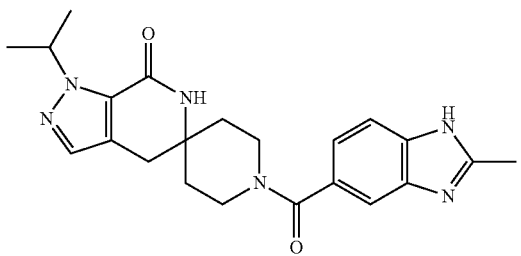 [SMILES: Cc1nc2cc(C(=O)N3CCC4(CC3)Cc3cnn(C(C)C)c3C(=O)N4)ccc2[nH]1]

To a solution of 2-methyl-1H-benzo[d]imidazole-5-carboxylic acid (42 mg, 0.13 mmol) in dichloromethane (2 mL) was added 1'-isopropyl-4',6'-dihydrospiro[piperidine-4,5'-pyrazolo[3,4-c]pyridin]-7'(1'H)-one hydrochloride salt (42 mg, 0.13 mmol), triethylamine (0.01 mL, 0.07 mmol), and (1H-7-azabenzotriazol-1-yl)-1,1,3,3-tetramethyl uronium hexafluorophosphate (54.8 mg, 0.144 mmol). The reaction mixture was stirred at room temperature overnight. The mixture was concentrated in vacuo, and the resultant solids were dissolved in ethyl acetate, washed with saturated sodium bicarbonate and dried over sodium sulfate, filtered, and concentrated in vacuo. The residue was dissolved in dimethyl sulfoxide (1 mL) and purified by reversed-phase HPLC (column: Waters XBridge C18 19×100, 5 µm; mobile phase A: 0.03% NH$_4$OH in water (v/v); mobile phase B: 0.03% NH$_4$OH in acetonitrile (v/v); gradient: 90% A/10% B linear to 0% A/100% B in 8.5 min, hold at 0% A/100% B for 10.0 min; flow: 25 mL/min. +ESI (M+H) 407.2; HPLC retention time 1.74 minutes (Method A)

Example 2

1-(3,7-dimethyl-1H-indazole-5-carbonyl)-1'-isopropyl-4',6'-dihydrospiro[piperidine-4,5'-pyrazolo[3,4-c]pyridin]-7'(1'H)-one

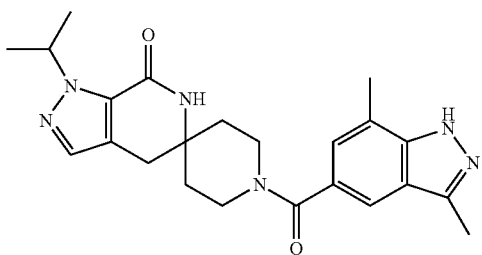 [SMILES: Cc1n[nH]c2c(C)cc(C(=O)N3CCC4(CC3)Cc3cnn(C(C)C)c3C(=O)N4)cc12]

To a solution of 1'-isopropyl-4',6'-dihydrospiro[piperidine-4,5'-pyrazolo[3,4-c]pyridin]-7 (1'H)-one hydrochloride salt (Intermediate 2, 430 mg, 1.3 mmol) and 3,7-dimethyl-1H-indazole-5-carboxylic acid (306 mg, 1.6 mmol) in dimethylformamide (2 mL) was added triethylamine (0.75 mL, 5.4 mmol), 4-dimethylaminopyridine (33 mg, 0.37 mmol), and 1-propanephosphonic acid cyclic anhydride (0.52 mL, 1.74 mmol, 50% solution in ethyl acetate), and the reaction mixture was stirred overnight at room temperature. The reaction mixture was concentrated in vacuo, taken up in ethyl acetate and washed with saturated aqueous sodium bicarbonate. The organic layer was dried over sodium sulfate, filtered, and concentrated to a solid. The solid was purified via flash column chromatography (0-15% methanol/dichloromethane) to afford a glassy solid. The glassy solid was stirred in ethyl acetate for 16 hours and the resulting solid collected by vacuum filtration to afford the desired product as a white solid (138 mg). +ESI (M+H) 421.0; $^1$H NMR (400 MHz, CD$_3$OD, δ): 7.65 (s, 1H) 7.42 (s, 1H) 7.21 (s, 1H) 5.50 (m, 1H) 3.95 (br. s., 1H) 3.50-3.62 (br. s., 3H) 2.97 (s, 2H) 2.56 (m, 6H) 1.83 (br. s., 4H) 1.44 (d, 6H).

Example 3

1'-isopropyl-1-(2-methyl-2H-indazole-5-carbonyl)-4',6'-dihydrospiro[piperidine-4,5'-pyrazolo[3,4-c]pyridin]-7'(1'H)-one

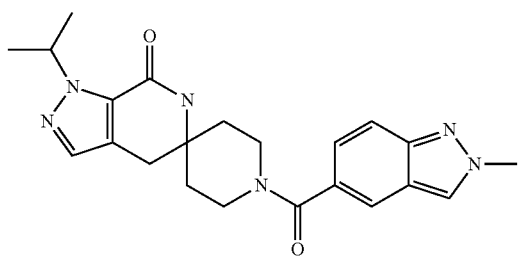 [SMILES: CC(C)n1ncc2c1C(=O)NC1(CCN(C(=O)c3ccc4nn(C)cc4c3)CC1)C2]

To a solution of 2-methyl-2H-indazole-5-carboxyllic acid (28 mg, 0.16 mmol) in dry dimethylformamide was added 1-ethyl-3-(3-dimethylaminopropyl) carbodiimide (37 mg, 0.19 mmol) and 1-hydroxybenzotriazole (26 mg, 0.19 mmol) N,N-diisopropylethylamine (84 µL, 0.48 mmol). The reaction mixture was stirred at room temperature for 10 minutes and then 1'-isopropyl-4',6'-dihydrospiro[piperidine-4,5'-pyrazolo[3,4-c]pyridin]-7'(1'H)-one hydrochloride was added (Intermediate 2, 30 mg, 0.12 mmol) and the reaction was stirred for 16 hours. The mixture was poured into chilled water and the resulting precipitate was collected by vacuum filtration. The obtained solid was triturated from diethyl ether to afford 1'-isopropyl-1-(2-methyl-2H-indazole-5-carbonyl)-4',6'-dihydrospiro[piperidine-4,5'-pyrazolo[3,4-c]pyridin]-7' (1'H)-one (25 mg). +ESI (M+H) 407.3; $^1$H NMR (400 MHz, DMSO-$d_6$, δ): 8.41 (s, 1H), 7.85 (s, 1H), 7.75 (s, 1H), 7.63 (d, 1H), 7.40 (s, 1H), 7.20 (s, 1H), 5.40 (m, 1H), 4.18 (s, 3H), 3.60 (br. s., 4H), 2.85 (s, 2H), 1.70 (br. s., 4H), 1.35 (d, 6H).

The compounds listed in Table 1 below were prepared using procedures analogous to those described above for the synthesis of the compounds of Examples 1-3 using the appropriate starting materials which are available commercially, prepared using preparations well-known to those skilled in the art, or prepared in a manner analogous to routes described above for other intermediates. The compounds listed below were isolated initially as the free base and may be converted to a pharmaceutically acceptable salt for testing.

TABLE 1

| Ex. | R₁ | R₂ | Analytical Data |
|---|---|---|---|
| 4 | iPr[a] | 7-methyl-1H-indazol-5-yl carbonyl (attached via C=O) | +ESI (M + H) 407.3; HPLC retention time 2.16 minutes (Method A) |
| 5 | iPr | 1H-indazol-5-yl carbonyl | +ESI (M + H) 393.3; HPLC retention time 2.07 minutes (Method A) |
| 6 | tBu[b] | 1H-indazol-5-yl carbonyl | +ESI (M + H) 407.1; $^1$H NMR (500 MHz, DMSO-$d_6$, δ): 13.23 (s, 1 H), 8.14 (s, 1 H), 7.83 (d, 2 H), 7.59 (s, 1 H), 7.36 (d, J = 8.5 Hz, 1 H), 7.33 (s, 1 H), 3.50 (br. s., 4 H), 2.85 (s, 2 H), 1.64 (m, 13 H). |
| 7 | tBu | 7-methyl-1H-indazol-5-yl carbonyl | +ESI (M + H) 421.2; 1H NMR (500 MHz, DMSO-$d_6$, δ): 13.31 (br. s., 1 H), 8.12 (s, 1 H), 7.83 (s, 1 H), 7.62 (s, 1 H), 7.33 (s, 1 H), 7.14 (s, 1 H), 3.64 (m, 4 H), 2.85 (s, 2 H), 2.53 (s, 3 H), 1.64 (m, 13 H). |
| 8 | tBu | 3,7-dimethyl-1H-indazol-5-yl carbonyl | +ESI (M + H) 435.3; $^1$H NMR (400 MHz, CDCl$_3$, δ): 10.34 (m, 1 H), 7.57 (s, 1 H), 7.23 (s, 1 H), 7.15 (s, 1 H), 6.59 (m, 1 H), 3.59 (m, 4 H), 2.83 (s, 2 H), 2.55 (br. s., 3 H), 2.49 (s, 3 H), 1.86 (br. s., 4 H), 1.70 (s, 9 H). |
| 9 | iPr | 1H-pyrrolo[2,3-b]pyridin-5-yl carbonyl | +ESI (M + H) 393.1; $^1$H NMR (300 MHz, DMSO-$d_6$, δ): 11.85 (s, 1 H), 8.25 (s, 1 H), 8.00 (s, 1 H), 7.85 (s, 1 H), 7.55 (m, 1 H), 7.40 (s, 1 H), 6.50 (m, 1 H), 5.40 (m, 1 H), 3.60 (m, 4 H), 2.85 (s, 2 H), 1.75 (br. s, 4 H), 1.35 (d, 6 H). |
| 10 | iPr | 1H-pyrrolo[3,2-b]pyridin-6-yl carbonyl | +ESI (M + H) 393.2; $^1$H NMR (400 MHz, DMSO-$d_6$, δ): 11.55 (s, 1 H), 8.35 (s, 1 H), 7.90 (s, 1 H), 7.85 (m, 2 H), 7.40 (s, 1 H), 6.60 (s, 1 H), 5.40 (m, 1 H), 3.60 (m, 4 H), 2.85 (s, 2 H), 1.75 (m, 4 H), 1.35 (d, 6 H). |

TABLE 1-continued

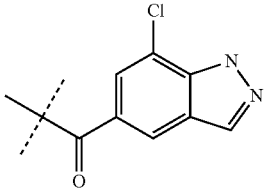

| Ex. | R₁ | R₂ | Analytical Data |
|---|---|---|---|
| 11 | iPr | 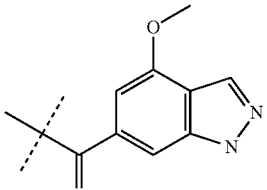 | +ESI (M + H) 427.2; ¹H NMR (400 MHz, DMSO-d₆, δ): 13.78 (s, 1 H), 8.26 (s, 1 H), 7.90 (s, 1 H), 7.80 (s, 1 H), 7.45 (s, 1 H), 7.41 (s, 1 H), 5.40 (m, 1 H), 3.60 (m, 4 H), 2.85 (s, 2 H), 1.75 (br. s., 4 H), 1.38 (d, 6 H). |
| 12 | iPr | 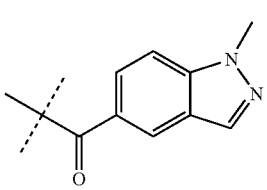 | +ESI (M + H) 423.2; HPLC retention time 2.19 minutes (Method A) |
| 13 | iPr | 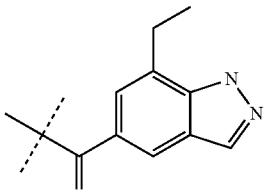 | +ESI (M + H) 407.3; ¹H NMR (300 MHz, DMSO-d₆, δ): 8.15 (s, 1 H), 7.88 (s, 1 H), 7.80 (s, 1 H), 7.70 (d, 1 H), 7.40 (m, 2 H), 5.45 (m, 1 H), 4.06 (s, 3 H), 2.85 (s, 2 H), 1.70 (br. s., 4 H), 1.35 (d, 6 H). |
| 14 | iPr | 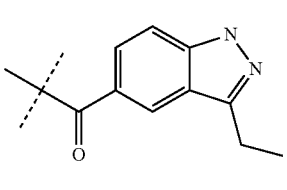 | +ESI (M + H) 421.2; ¹H NMR (300 MHz, DMSO-d₆, δ): 13.35 (s, 1 H), 8.15 (s, 1 H), 7.86 (s, 1 H), 7.62 (s, 1 H), 7.41 (s, 1 H), 7.15 (s, 1 H), 5.40 (m, 1 H), 3.60 (m, 4 H), 2.95 (m, 4 H), 1.70 (br. s., 4 H), 1.30 (m, 9 H). |
| 15 | iPr | 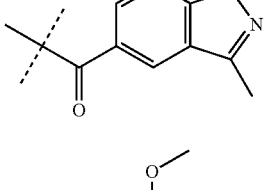 | +ESI (M + H) 421.4; ¹H NMR (400 MHz DMSO-d₆, δ): 12.78 (s, 1 H), 7.85 (s, 1 H), 7.78 (s, 1 H), 7.50 (d, 1 H), 7.40 (s, 1 H), 7.36 (d, 1 H), 5.40 (m, 1 H), 3.60 (m, 4 H), 2.94 (q, 2 H), 2.85 (s, 2 H), 2.70 (br. s., 4 H), 1.35 (m, 9 H). |
| 16 | iPr | 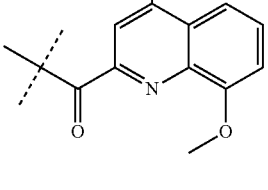 | +ESI (M + 30H) 407.3; HPLC retention time 2.15 minutes (Method A) |
| 17 | iPr |  | +ESI (M + H) 464.3; ¹H NMR (300 MHz DMSO-d₆, δ): 7.92 (s, 1 H), 7.68 (m, 1 H), 7.50 (t, 1 H), 7.41 (s, 1 H), 7.24 (s, 1 H), 5.42 (m, 1 H), 4.10 (s, 3 H), 3.92 (s, 1 H), 3.90-3.38 (m, 4 H), 2.86 (s, 2 H), 1.85-1.52 (m, 4 H), 1.38 (m, 6 H). |

TABLE 1-continued

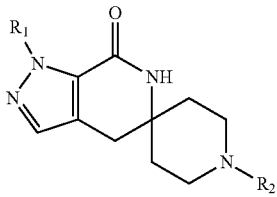

| Ex. | R₁ | R₂ | Analytical Data |
|---|---|---|---|
| 18 | iPr | 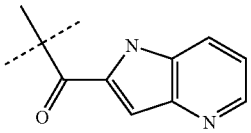 | +ESI (M + H) 393.2; ¹H NMR (300 MHz, DMSO-d₆, δ): 11.81 (s, 1 H), 8.38 (m, 1 H), 7.95 (s, 1 H), 7.76 (d, 1 H), 7.41 (s, 1 H), 7.19 (m, 1 H), 6.85 (s, 1 H), 5.42 (m, 1 H), 4.02-3.58 (m, 4 H), 2.90 (s, 1 H), 1.86-1.46 (m, 4 H), 1.39 (d, 6 H). |
| 19 | iPr | 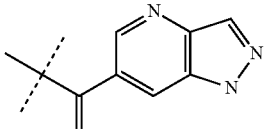 | +ESI (M + H) 394.0; ¹H NMR (300 MHz, DMSO-d₆, δ): 13.56 (s, 1 H), 8.56 (s, 1 H), 8.38 (s, 1 H), 8.08 (s, 1 H), 7.94 (s, 1 H), 7.42 (s, 1 H), 5.42 (m, 1 H), 3.94-3.41 (m, 4 H), 2.86 (s, 1 H), 1.87-1.60 (m, 4 H), 1.35 (m, 6 H). |
| 20 | iPr | 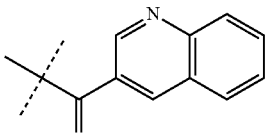 | +ESI (M + H) 404.3; HPLC retention time 2.10 minutes (Method A) |
| 21 | iPr | 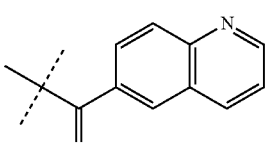 | +ESI (M + H) 404.3; HPLC retention time 1.79 minutes (Method A) |
| 22 | iPr | 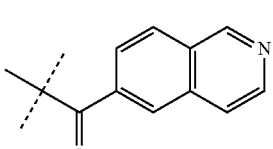 | +ESI (M + H) 404.3; HPLC retention time 1.75 minutes (Method A) |
| 23 | iPr | 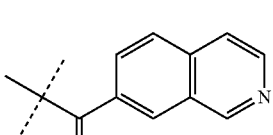 | +ESI (M + H) 404.3; HPLC retention time 1.76 minutes (Method A) |
| 24 | iPr | 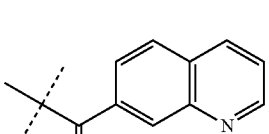 | +ESI (M + H) 404.3; HPLC retention time 1.84 minutes (Method A) |
| 25 | iPr | 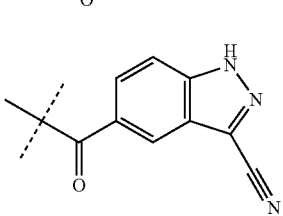 | +ESI (M + H) 418.3; ¹H NMR (400 MHz, DMSO-d₆, δ): 12.81 (s, 1 H), 7.85 (s, 2 H), 7.80 (dd, J = 8.7, 0.9 Hz, 1 H), 7.51 (dd, J = 8.7, 1.5 Hz, 1 H), 7.38 (s, 1 H), 5.39 (s, 1 H), 3.32 - 3.87 (m, 4 H), 2.83 (s, 2 H), 1.69 (m, 4 H), 1.33 (d, J = 6.4 Hz, 6 H). |

TABLE 1-continued

| Ex. | R₁ | R₂ | Analytical Data |
|---|---|---|---|
| 26 | iPr | 6-methoxyquinolin-3-yl carbonyl | +ESI (M + H) 434.4; ¹H NMR (400 MHz, DMSO-d₆, δ): 8.68 (d, J = 2.1 Hz, 1 H), 8.26 (d, J = 1.4 Hz, 1 H), 7.87-7.96 (m, 2 H), 7.40-7.47 (m, 2 H), 7.38 (s, 1 H), 5.33-5.46 (m, 1 H), 3.88 (s, 3 H), 3.74-3.86 (m, 1 H), 3.60-3.74 (m, 1 H), 3.44-3.58 (m, 1 H), 3.31-3.44 (m, 1 H), 2.83 (s, 2 H), 1.59-1.82 (m, 4 H), 1.28-1.39 (m, 6 H). |
| 27 | iPr | 3-carbamoyl-1H-indazol-5-yl carbonyl | +ESI (M + H) 436.3; ¹H NMR (400 MHz, DMSO-d₆, δ): 13.66 (br. s., 1 H), 8.16 (s, 1 H), 7.86 (s, 1 H), 7.75 (br. s., 1 H), 7.62 (d, J = 8.6 Hz, 1 H), 7.34-7.39 (m, 3 H), 5.33-5.43 (m, 1 H), 3.36-3.93 (m, 4 H), 2.83 (s, 2 H), 1.51-1.78 (m, 4 H), 1.33 (d, J = 6.7 Hz, 6 H). |
| 28 | iPr | 2-methoxyquinolin-7-yl carbonyl | +ESI (M + H) 434.0; HPLC retention time 2.57 minutes (Method A) |
| 29 | iPr | 2-(methylamino)quinolin-7-yl carbonyl | +ESI (M + H) 433.0; HPLC retention time 1.75 minutes (Method A) |
| 30 | iPr | 1-methoxyisoquinolin-7-yl carbonyl | +ESI (M + H) 434.2; HPLC retention time 2.48 minutes (Method A) |
| 31 | iPr | 3-chloro-1H-pyrazolo[3,4-b]pyridin-5-yl carbonyl | +ESI (M + H) 427.2; HPLC retention time 2.35 minutes (Method A) |
| 32 | iPr | 3-chloro-1H-pyrrolo[3,2-b]pyridin-6-yl carbonyl | +ESI (M + H) 427.2; HPLC retention time 1.89 minutes (Method A) |
| 33 | iPr | 2-(methylamino)-1H-benzimidazol-5-yl carbonyl | +ESI (M + H) 422.2; HPLC retention time 1.66 minutes (Method B) |

TABLE 1-continued

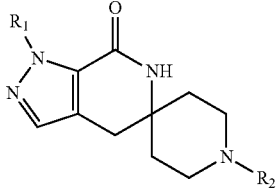

| Ex. | R₁ | R₂ | Analytical Data |
|---|---|---|---|
| 34 | iPr | 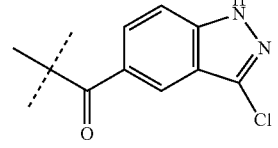 | +ESI (M + H) 427.2; HPLC retention time 2.32 minutes (Method A) |
| 35 | iPr | 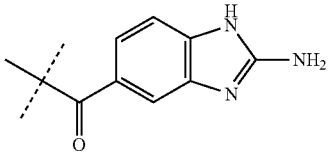 | +ESI (M + H) 408.2; HPLC retention time 1.61 minutes (Method B) |
| 36 | iPr | 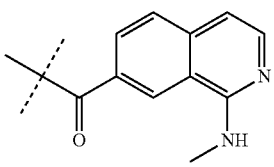 | +ESI (M + H) 433.2; HPLC retention time 1.89 minutes (Method A) |
| 37 | iPr | 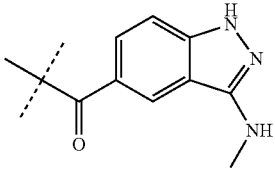 | +ESI (M + H) 422.2; HPLC retention time 1.86 minutes (Method A) |
| 38 | iPr | 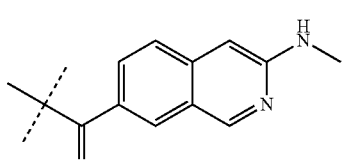 | +ESI (M + H) 433.1; HPLC retention time 1.92 minutes (Method A) |

[a] = the term "iPr" is used to designate an isopropyl group
[b] = the term "tBu" is used to designate a t-butyl group The compounds listed in Table 2 below were prepared using procedures analogous to those described above for the synthesis of the compounds of Examples 1-3 using the appropriate starting materials which are available commercially, prepared using preparations well-known to those skilled in the art, or prepared in a manner analogous to routes described above for other intermediates. The compounds listed below were isolated initially as the free base and may be converted to a pharmaceutically acceptable salt for testing.

TABLE 2

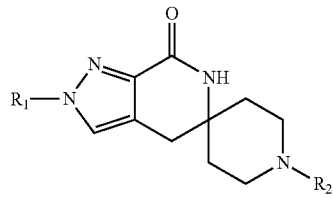

| Ex. | R$_1$ | R$_2$ | Analytical Data |
|---|---|---|---|
| 39 | iPr[a] | (5-indazolyl carbonyl) | +APCI (M + H) 393.2; $^1$H NMR (400 MHz, CD$_3$OD, δ): 8.12 (s, 1 H), 7.89 (s, 1 H), 7.59 (m, 2 H), 7.44 (dd, J = 8.7, 1.3 Hz, 1 H), 4.55 (m, 1 H), 3.76 (m, 4 H), 2.94 (s, 2 H), 1.82 (br. s., 4 H), 1.48 (d, J = 6.6 Hz, 6 H). |
| 40 | iPr | (2-methylbenzimidazol-5-yl carbonyl) | +APCI (M + H) 407.2; $^1$H NMR (400 MHz, CD$_3$OD, δ): 8.05 (br. s., 1 H), 7.54 (m, 2 H), 7.26 (dd, J = 8.4, 1.4 Hz, 1 H), 6.67 (d, J = 6.2 Hz, 1 H), 4.55 (m, 1 H), 3.77 (m, 4 H), 2.94 (s, 2 H), 2.57 (s, 3 H), 1.81 (m, 4 H), 1.48 (d, J = 6.6 Hz, 6 H). |
| 41 | tBu[b] | (5-indazolyl carbonyl) | +APCI (M + H) 407.2; $^1$H NMR (400 MHz, CDCl$_3$, δ): 8.11 (br. s., 1 H), 7.84 (s, 1 H), 7.52 (d, 1 H), 7.44 (dd, 1 H), 7.38 (s, 1 H), 6.22 (s, 1 H), 3.51-3.62 (m, 2 H), 2.84 (s, 2 H), 1.73-1.93 (m, 4 H), 1.60 (s, 9 H). |
| 42 | iPr | (7-methylindazol-5-yl carbonyl) | +APCI (M + H) 407.3; $^1$H NMR (400 MHz, CDCl$_3$, δ): 11.67 (br. s., 1 H), 8.06 (s, 1 H), 7.62 (s, 1 H), 7.24 (d, J = 11.3 Hz, 1 H), 7.18 (d, J = 11.3 Hz, 2 H), 6.35 (m, 1 H), 4.53 (m, 1 H), 3.60 (t, J = 10.4 Hz, 2 H), 2.81 (s, 2 H), 2.54 (s, 3 H), 1.73 (m, 6 H), 1.49 (d, J = 6.6 Hz, 6 H). |
| 43 | iPr | (3,7-dimethylindazol-5-yl carbonyl) | +APCI (M + H) 421.3; $^1$H NMR (400 MHz, CDCl$_3$, δ): 10.81 (br. s., 1 H), 7.59 (s, 1 H), 7.27 (s, 1 H), 7.18 (s, 1 H), 6.77 (s, 1 H), 4.55 (spt, J = 6.7 Hz, 1 H), 3.62 (t, J = 10.1 Hz, 2 H), 2.84 (s, 2 H), 2.58 (s, 3 H), 2.53 (s, 3 H), 1.71-1.94 (m, 4 H), 1.50 (d, 6 H). |
| 44 | tBu | (7-methylindazol-5-yl carbonyl) | +APCI (M + H) 421.0; $^1$H NMR (400 MHz, CDCl$_3$, δ): 11.17 (br. s., 1 H), 8.11 (s, 1 H), 7.67 (s, 1 H), 7.40 (s, 1 H), 7.24 (s, 1 H), 6.66 (s, 1 H), 3.57 (m, 2 H), 3.67-4.20 (m, 2 H), 2.86 (s, 2 H), 2.59 (s, 3 H), 1.83 (m, 4 H), 1.63 (s, 9 H). |
| 45 | tBu | (3,7-dimethylindazol-5-yl carbonyl) | +APCI (M + H) 435.1; $^1$H NMR (400 MHz, CDCl$_3$, δ): 10.93 (br. s., 1 H), 7.62 (s, 1 H), 7.40 (s, 1 H), 7.21 (s, 1 H), 6.74 (br. s., 1 H), 3.76-4.12 (m, 2 H), 3.64 (t, J = 10.2 Hz, 2 H), 2.86 (s, 2 H), 2.60 (s, 3 H), 2.55 (s, 3 H), 1.69-1.87 (m, 4 H), 1.63 (s, 9 H). |

TABLE 2-continued

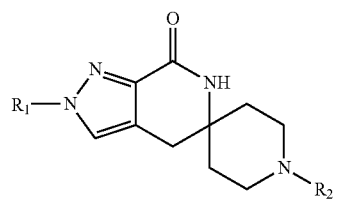

| Ex. | R₁ | R₂ | Analytical Data |
|---|---|---|---|
| 46 | tBu | 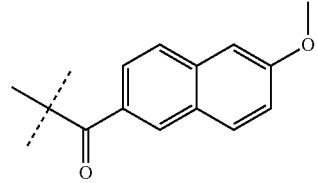 | +ESI (M + H) 447.2; HPLC retention time 2.73 minutes (Method A) |
| 47 | t-amyl | 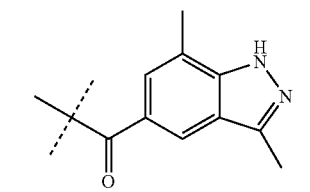 | +ESI (M + H) 449.2; HPLC retention time 2.35 minutes (Method A) |
| 48 | tBu | 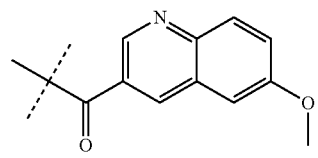 | +APCI (M + H) 448.6; $^1$H NMR (400 MHz, CDCl₃, δ): 8.74 (d, J = 2.1 Hz, 1 H), 8.10 (d, J = 1.6 Hz, 1 H), 7.96 (d, J = 9.4 Hz, 1 H), 7.37 (dd, J = 9.3, 2.8 Hz, 1 H), 7.24 (d, J = 6.4 Hz, 1 H), 7.05 (d, J = 2.7 Hz, 1 H), 3.93-4.16 (m, 1 H), 3.89 (s, 3 H), 3.45-3.78 (m, 3 H), 2.82 (s, 2 H), 1.60-2.04 (m, 4 H), 1.57 (s, 9 H). |
| 49 | tBu | 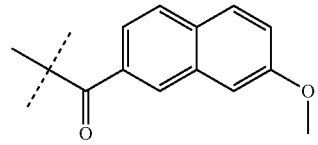 | +ESI (M+30H) 447.0; HPLC retention time 2.72 minutes (Method A) |
| 50 | tBu | 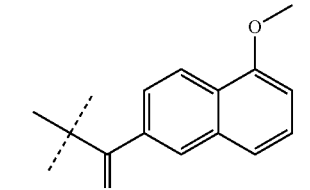 | +ESI (M + H) 447.0; HPLC retention time 2.76 minutes (Method A) |
| 51 | tBu | 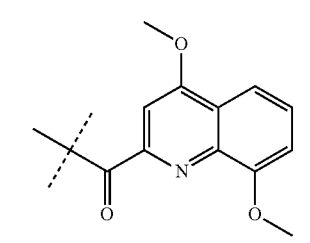 | +ESI (M + H) 478.0; HPLC retention time 2.24 minutes (Method A) |
| 52 | tBu | 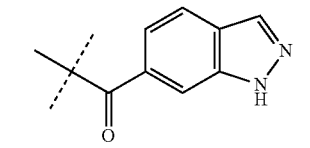 | +ESI (M + H) 407.0; HPLC retention time 2.09 minutes (Method A) |

TABLE 2-continued

| Ex. | R₁ | R₂ | Analytical Data |
|---|---|---|---|
| 53 | tBu | 6-acyl-3-cyano-1H-indazole | +ESI (M + H) 432.2; HPLC retention time 2.35 minutes (Method A) |
| 54 | tBu | 5-acyl-1H-indazole-3-carboxamide | +ESI (M + H) 450.2; HPLC retention time 1.95 minutes (Method A) |
| 55 | tBu | 7-acyl-1-methoxyisoquinoline | +ESI (M + H) 448.4; ¹H NMR (400 MHz, CDCl₃, δ): 8.27-8.30 (m, 1 H), 8.04 (d, J = 5.9 Hz, 1 H), 7.74-7.79 (m, 1 H), 7.66-7.70 (m, 1 H), 7.37 (s, 1 H), 7.20-7.24 (m, 1 H), 6.07 (s, 1 H), 4.13 (s, 3 H), 3.56 (br. s., 4 H), 2.85 (s, 2 H), 1.62-2.01 (m, 4 H), 1.60 (s, 9 H). |
| 56 | tBu | 2-acyl-4-methoxy-7-methyl-1H-indole | +ESI (M + H) 450.2; HPLC retention time 2.79 minutes (Method A) |
| 57 | cyclobutyl | 5-acyl-3,7-dimethyl-1H-indazole | +ESI (M + H) 433.1; HPLC retention time 2.14 minutes (Method A) |
| 58 | tBu | 6-acyl-2-aminoquinoline | +ESI (M + H) 433.2; HPLC retention time 1.79 minutes (Method A) |
| 59 | tBu | 6-acyl-3-aminoisoquinoline | +ESI (M + H) 433.2; HPLC retention time 1.83 minutes (Method B) |

TABLE 2-continued

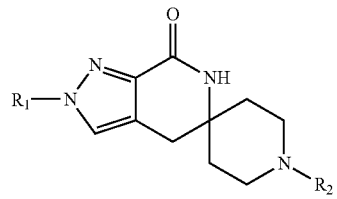

| Ex. | R₁ | R₂ | Analytical Data |
|---|---|---|---|
| 60 | tBu | 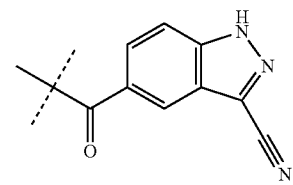 | +ESI (M + H) 432.2; HPLC retention time 2.27 minutes (Method A) |
| 61 | tBu | 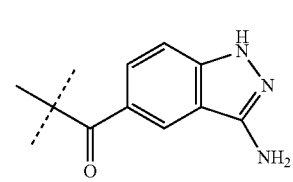 | +ESI (M + H) 422.2; HPLC retention time 1.67 minutes (Method B) |
| 62 | tBu | 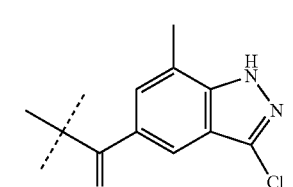 | +ESI (M + H) 455.2; HPLC retention time 2.39 minutes (Method A) |
| 63 | tBu | 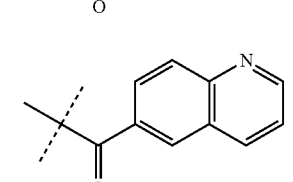 | +ESI (M + H) 418.2; HPLC retention time 1.9 minutes (Method B) |
| 64 | tBu | 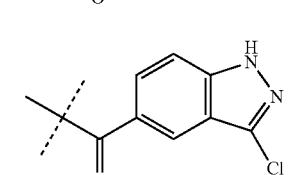 | +ESI (M + H) 441.1; HPLC retention time 2.31 minutes (Method A) |
| 65 | tBu | 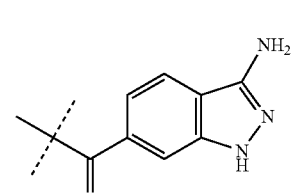 | +ESI (M + H) 422.3; $^1$H NMR (400 MHz, CD$_3$OD, δ): 7.78 (d, J = 8.19 Hz, 1 H), 7.65 (s, 1 H), 7.34 (s, 1 H), 7.01 (dd, J = 8.29, 1.27 Hz, 1 H), 3.87-4.00 (m, 1 H), 3.70-3.82 (m, 1 H), 3.51-3.65 (m, 1 H), 3.40-3.49 (m, 1 H), 2.93 (s, 2 H), 1.82-1.93 (m, 2 H), 1.70-1.79 (m, 2 H), 1.58 (s, 9 H). |
| 66 | tBu | 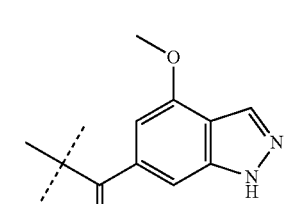 | +ESI (M + H) 437.2; HPLC retention time 2.21 minutes (Method A) |

TABLE 2-continued

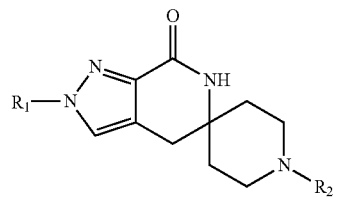

| Ex. | R₁ | R₂ | Analytical Data |
|---|---|---|---|
| 67 | tBu | 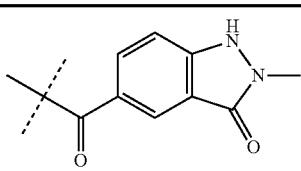 | +ESI (M + H) 437.2; HPLC retention time 1.86 minutes (Method A) |
| 68 | tBu | 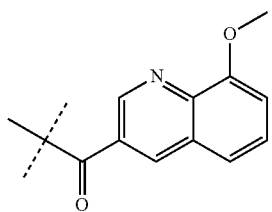 | +ESI (M + H) 448.2; HPLC retention time 2.08 minutes (Method A) |
| 69 | tBu | 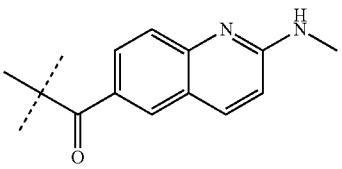 | +ESI (M + H) 447.2; HPLC retention time 1.86 minutes (Method A) |
| 70 | tBu | 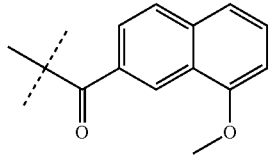 | +ESI (M + H) 447.2; HPLC retention time 2.79 minutes (Method A) |
| 71 | tBu | 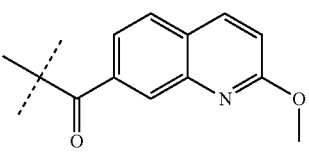 | +ESI (M + H) 448.2; HPLC retention time 2.55 minutes (Method A) |
| 72 | tBu | 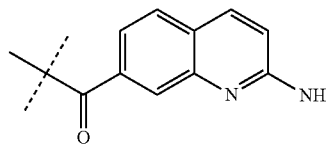 | +ESI (M + H) 433.1; ¹H NMR (400 MHz, DMSO-d₆, δ): 7.88 (m, 1 H), 7.72 (br. s., 1 H), 7.62-7.68 (m, 2 H), 7.34 (s, 1 H), 7.07 (m, 1 H), 6.76 (d, J = 8.97 Hz, 1 H), 6.53 (br. s., 2 H), 3.30-3.84 (m, 4 H), 2.74-2.83 (m, 2 H), 1.55-1.72 (m, 4 H), 1.49 (s, 9 H). |
| 73 | tBu | 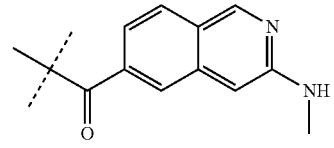 | +ESI (M+30H) 447.3; HPLC retention time 1.86 minutes (Method A) |
| 74 | tBu | 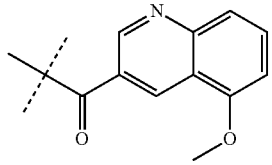 | +ESI (M + H) 448.3; HPLC retention time 2.15 minutes (Method A) |

TABLE 2-continued

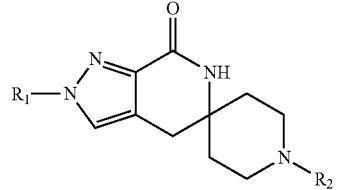

| Ex. | R₁ | R₂ | Analytical Data |
|---|---|---|---|
| 75 | tBu | 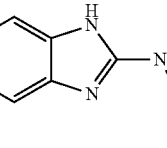 | +ESI (M + H) 436.2; HPLC retention time 1.81 minutes (Method A) |
| 76 | tBu | 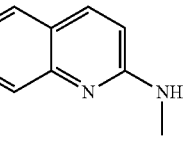 | +ESI (M + H) 447.3; ¹H NMR (400 MHz, DMSO-d₆, δ): 7.82 (d, J = 9.0 Hz, 1 H), 7.72 (s, 1 H), 7.60-7.67 (m, 2 H), 7.39-7.43 (m, 1 H), 7.03-7.14 (m, 2 H), 6.75 (d, J = 9.0 Hz, 1 H), 3.31-3.86 (m, 4 H), 2.87 (d, J = 4.7 Hz, 3 H), 2.79 (s, 2 H), 1.55-1.74 (m, 4 H), 1.49 (s, 9 H). |
| 77 | tBu | 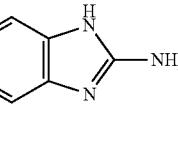 | +ESI (M + H) 422.2; HPLC retention time 1.78 minutes (Method A) |
| 78 | tBu | 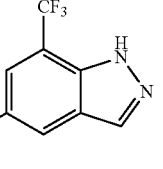 | +ESI (M + H) 475.2; HPLC retention time 2.34 minutes (Method A) |
| 79 | tBu | 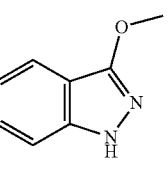 | +ESI (M + H) 437.0; HPLC retention time 2.27 minutes (Method A) |
| 80 | tBu |  | +ESI (M + H) 475.2; HPLC retention time 2.49 minutes (Method A) |
| 81 | tBu | 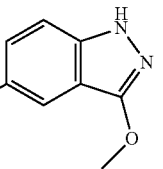 | +ESI (M + H) 437.2; HPLC retention time 2.20 minutes (Method A) |

TABLE 2-continued

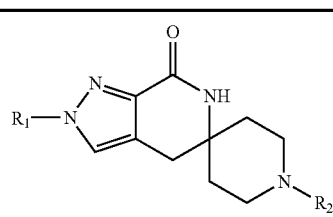

| Ex. | R₁ | R₂ | Analytical Data |
|---|---|---|---|
| 82 | tBu | 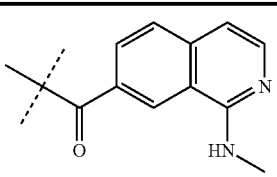 | +ESI (M + H) 447.4; ¹H NMR (400 MHz, DMSO-d₆, δ): 8.23 (s, 1 H), 7.92 (d, J = 5.87 Hz, 1 H), 7.69-7.78 (m, 3 H), 7.57 (dd, J = 8.31, 1.47 Hz, 2 H), 6.89 (d, J = 5.87 Hz, 1 H), 3.33-3.85 (m, 4 H), 2.95 (d, J = 4.30 Hz, 3 H), 2.82 (s, 2 H), 1.55-1.79 (m, 4 H), 1.52 (s, 9 H). |
| 83 | tBu | 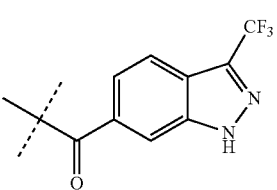 | +ESI (M + H) 475.2; HPLC retention time 2.62 minutes (Method A) |
| 84 | tBu | 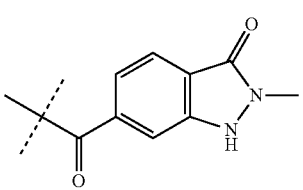 | +ESI (M + H) 437.2; HPLC retention time 2.27 minutes (Method A) |
| 85 | tBu | 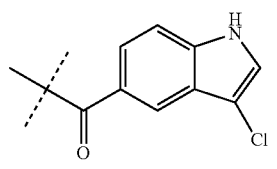 | +ESI (M + H) 440.1; HPLC retention time 2.53 minutes (Method A) |
| 86 | tBu | 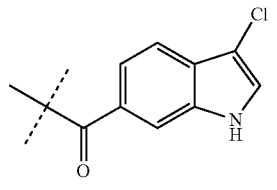 | +ESI (M + H) 440.1; HPLC retention time 2.66 minutes (Method A) |
| 87 | tBu | 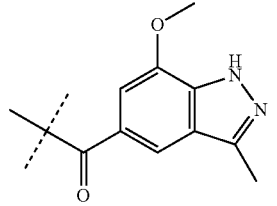 | +ESI (M + H) 451.1; HPLC retention time 2.2 minutes (Method A) |
| 88 | tBu | 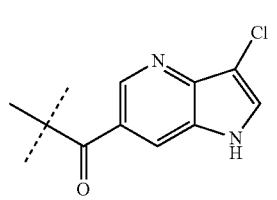 | +ESI (M + H) 441.1; HPLC retention time 1.9 minutes (Method A) |

TABLE 2-continued

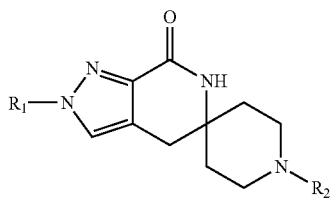

| Ex. | R₁ | R₂ | Analytical Data |
|---|---|---|---|
| 89 | tBu | [6-(methylamino)-1H-indazol-3-yl via carbonyl] | +ESI (M + H) 436.2; HPLC retention time 1.66 minutes (Method B) |
| 90 | tBu | [3-methoxyisoquinolin-7-yl via carbonyl] | +ESI (M + H) 448.3; HPLC retention time 2.35 minutes (Method A) |
| 91 | tBu | [1-(methylamino)isoquinolin-6-yl via carbonyl] | +ESI (M + H) 447.2; HPLC retention time 1.86 minutes (Method A) |
| 92 | tBu | [1-methoxyisoquinolin-6-yl via carbonyl] | +ESI (M + H) 448.0; HPLC retention time 2.46 minutes (Method A) |
| 93 | tBu | [3-(methylamino)-1H-indazol-5-yl via carbonyl] | +ESI (M + H) 436.1; HPLC retention time 1.90 minutes (Method A) |
| 94 | tBu | [3-aminoisoquinolin-7-yl via carbonyl] | +ESI (M + H) 433.1; HPLC retention time 1.73 minutes (Method A) |
| 95 | tBu | [3-(methylamino)isoquinolin-7-yl via carbonyl] | +ESI (M + H) 447.2; HPLC retention time 1.93 minutes (Method A) |

TABLE 2-continued

| Ex. | $R_1$ | $R_2$ | Analytical Data |
|---|---|---|---|
| 96 | tBu | (5-carbonyl-3-chloro-7-azaindole) | +ESI (M + H) 441.1; HPLC retention time 2.21 minutes (Method A) |
| 97 | tBu | (benzotriazole-5-carbonyl) | +ESI (M + H) 402.8; HPLC retention time 1.91 minutes (Method A) |
| 98 | tBu | (4-chloro-benzotriazole-6-carbonyl) | |

$^a$= the term "iPr" is used to designate an isopropyl group
$^b$= the term "tBu" is used to designate a t-butyl group

Example 99

2'-tert-butyl-1-(7-methoxy-1H-indazole-5-carbonyl)-4',6'-dihydrospiro[piperidine-4,5'-pyrazolo[3,4-c]pyridin]-7'(2'H)-one

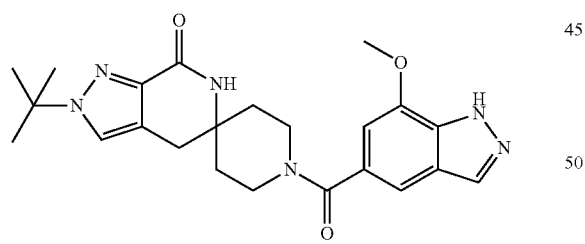

To a mixture of 2'-tert-butyl-4',6'-dihydrospiro[piperidine-4,5'-pyrazolo[3,4-c]pyridin]-7'(2'H)-one hydrochloride salt (Intermediate 4, 25 mg, 0.075 mmol) and 7-methoxy-1-(tetrahydro-2H-pyran-2-yl)-1H-indazole-5-carboxylic acid (Intermediate 18, 25 mg, 0.090 mmol) in N,N-dimethylformamide (0.4 mL) was added triethylamine (0.05 mL, 0.37 mmol). The mixture was stirred for 5 minutes. Then 1-propanephosphonic acid cyclic anhydride (0.09 mL, 0.1 mmol, 50% solution in ethyl acetate) was added and the reaction was stirred at room temperature overnight. The reaction was diluted with water and extracted with ethyl acetate (3x). The combined organic layers were washed with brine, dried over sodium sulfate, filtered, and concentrated to a yellow gum. To this crude material was added hydrochloric acid (0.19 mL, 0.75 mmol, 4 M in dioxane). The mixture was stirred at room temperature overnight. The reaction was concentrated. Purification by reversed-phase HPLC gave the title compound (3.4 mg, 10%). +ESI (M+H) 437.3; HPLC retention time 2.12 minutes (Method A).

Example 100

1-(1-aminoisoquinoline-7-carbonyl)-2'-tert-butyl-4',6'-dihydrospiro[piperidine-4,5'-pyrazolo[3,4-c]pyridin]-7'(2'H)-one

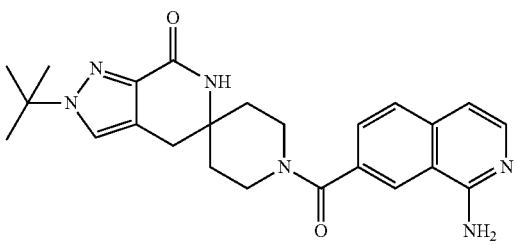 [SMILES: CC(C)(C)n1cc2c(n1)C(=O)NC1(CCN(C(=O)c3ccc4ccnc(N)c4c3)CC1)C2]

Step 1: 2'-tert-butyl-1-(1-(4-methoxybenzylamino) isoquinoline-7-carbonyl)-4',6'-dihydrospiro[piperidine-4,5'-pyrazolo[3,4-c]pyridin]-7'(2'H)-one

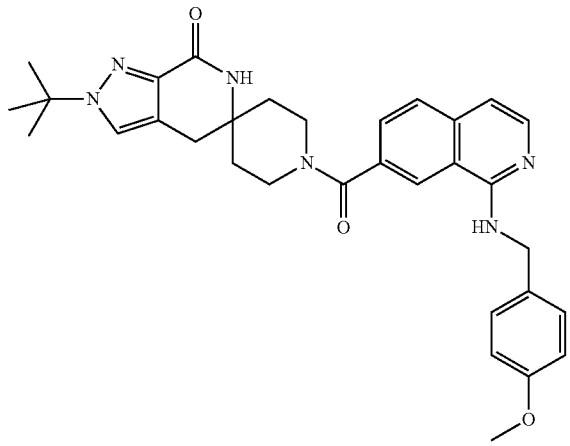 [SMILES: COc1ccc(CNc2nccc3ccc(C(=O)N4CCC5(CC4)Cc4cn(C(C)(C)C)nc4C(=O)N5)cc23)cc1]

The title compound was prepared by a method analogous to that described in Example 3, using 2'-tert-butyl-4',6'-dihydrospiro[piperidine-4,5'-pyrazolo[3,4-c]pyridin]-7'(2'H)-one hydrochloride salt (Intermediate 4) and 1-(4-methoxybenzylamino)isoquinoline-7-carboxylic acid (Intermediate 27). +ESI (M+H) 553.5.

Step 2: 1-(1-aminoisoquinoline-7-carbonyl)-2'-tert-butyl-4',6'-dihydrospiro[piperidine-4,5'-pyrazolo[3,4-c]pyridin]-7'(2'H)-one To a solution of 2'-tert-butyl-1-(1-(4-methoxybenzylamino)isoquinoline-7-carbonyl)-4',6'-dihydrospiro[piperidine-4,5'-pyrazolo[3,4-c]pyridin]-7'(2'H)-one (28 mg, 0.051 mmol) in trifluoroacetic acid (0.51 mL) was added anisol (8.3 µL, 0.076 mmol). The reaction was heated to 65° C. and stirred for 19 hours. The reaction was concentrated. Purification by reversed-phase HPLC gave the title compound (7.1 mg, 32%). +ESI (M+H) 433.2; HPLC retention time 1.79 minutes (Method A).

Example 101

1-(1-aminoisoquinoline-6-carbonyl)-2'-tert-butyl-4',6'-dihydrospiro[piperidine-4,5'-pyrazolo[3,4-c]pyridin]-7'(2'H)-one

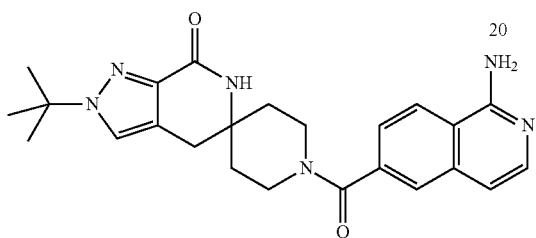 [SMILES: CC(C)(C)n1cc2c(n1)C(=O)NC1(CCN(C(=O)c3ccc4c(N)nccc4c3)CC1)C2]

The title compound was prepared by a method analogous to that described for Example 100, using 1-(4-methoxybenzylamino)isoquinoline-6-carboxylic acid (Intermediate 30) in Step 1. +ESI (M+H) 433.2; HPLC retention time 1.82 minutes (Method A).

Example 102

2'-tert-butyl-1-(3-methoxyisoquinoline-6-carbonyl)-4',6'-dihydrospiro[piperidine-4,5'-pyrazolo[3,4-c]pyridin]-7'(2'H)-one

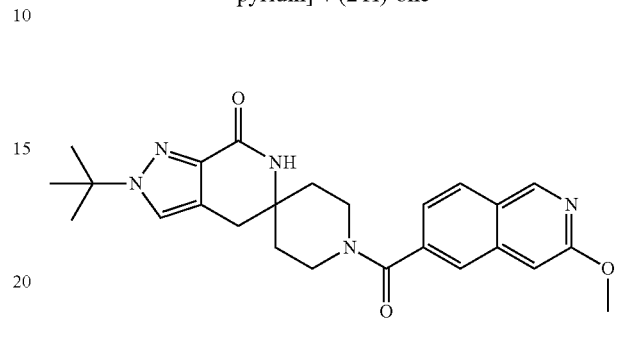

To a solution of 6-bromo-3-methoxyisoquinoline (Intermediate 43, 89.9 mg, 0.378 mmol) in 1,4-dioxane (6 mL) was added 2'-tert-butyl-4',6'-dihydrospiro[piperidine-4,5'-pyrazolo[3,4-c]pyridin]-7'(2'H)-one hydrochloride salt (Intermediate 4, 244 mg, 0.727 mmol) and sodium acetate (130 mg, 1.5 mmol). Nitrogen gas was bubbled through the mixture for 15 minutes. Then added [1,1'-bis(diphenylphosphino)ferrocene]-dichloropalladium(II), complex with dichloromethane (102 mg, 0.125 mmol), capped the reaction vessel and bubbled through carbon monoxide gas for 5 minutes. The reaction was then heated to 80° C. for 18 hours. The reaction was cooled to room temperature and diluted with ethyl acetate. The mixture was filtered through Celite and the filtrate was concentrated. Purification by reversed-phase HPLC gave the title compound. +ESI (M+H) 448.1; HPLC retention time 2.26 minutes (Method A).

Example 103

2'-tert-butyl-1-(1-(dimethylamino)isoquinoline-7-carbonyl)-4',6'-dihydrospiro[piperidine-4,5'-pyrazolo[3,4-c]pyridin]-7'(2'H)-one Step 1: 2'-tert-butyl-1-(1-chloroisoquinoline-7-carbonyl)-4',6'-dihydrospiro[piperidine-4,5'-pyrazolo[3,4-c]pyridin]-7'(2'H)-one

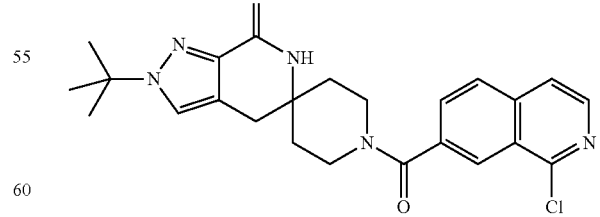

The title compound was prepared by a method analogous to that described for Example 2, using 2'-tert-butyl-4',6'-dihydrospiro[piperidine-4,5'-pyrazolo[3,4-c]pyridin]-7'(2'H)-one hydrochloride salt (Intermediate 4) and 1-chloroisoquinoline-7-carboxylic acid, and omitting 4-dimethylaminopyridine. +ESI (M+H) 452.3; ¹H NMR (400 MHz, CDCl₃, δ): 8.37 (s, 1H), 8.32 (d, J=5.7 Hz, 1H), 7.89 (d, J=8.4 Hz, 1H), 7.75-7.79 (m, 1H), 7.62 (d, J=5.7 Hz, 1H), 7.39 (s, 1H), 6.42 (s, 1H), 3.43-3.73 (m, 4H), 2.87 (s, 2H), 1.64-2.01 (m, 4H), 1.61 (s, 9H).

Step 2: 2'-tert-butyl-1-(1-(dimethylamino)isoquinoline-7-carbonyl)-4',6'-dihydrospiro[piperidine-4,5'-pyrazolo[3,4-c]pyridin]-7'(2'H)-one A solution of dimethylamine in methanol (1.75 mL, 3.50 mmol, 2 M) was added to 2'-tert-butyl-1-(1-chloroisoquinoline-7-carbonyl)-4',6'-dihydrospiro[piperidine-4,5'-pyrazolo[3,4-c]pyridin]-7'(2'H)-one (158 mg, 0.350 mmol). The reaction vessel was sealed and the mixture was heated to 60° C. and stirred for 65 hours. The reaction was cooled to room temperature and concentrated. Purification by flash column chromatography (1-15% methanol/dichloromethane) gave the title compound (99 mg, 61%) as a white solid. +APCI (M+H) 461.4; ¹H NMR (400 MHz, CDCl₃, δ): 8.16-8.20 (m, 1H), 8.12 (d, J=5.9 Hz, 1H), 7.75 (d, J=8.2 Hz, 1H), 7.58-7.64 (m, 1H), 7.37 (s, 1H), 7.14 (d, J=5.9 Hz, 1H), 6.00 (br. s., 1H), 3.40-3.71 (m, 4H), 3.10-3.28 (m, 6H), 2.85 (s, 2H), 1.64-1.99 (m, 4H), 1.60 (s, 9H).

Example 104

2'-tert-butyl-1-(2-chloroquinoline-7-carbonyl)-4',6'-dihydrospiro[piperidine-4,5'-pyrazolo[3,4-c]pyridin]-7'(2'H)-one

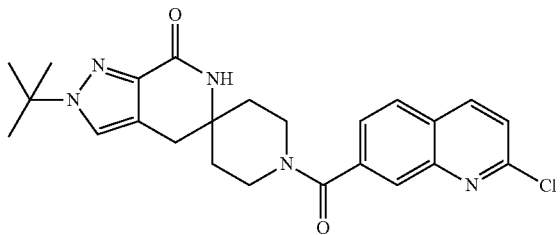 [SMILES: CC(C)(C)n1cc2c(n1)C(=O)NC1(CCN(C(=O)c3ccc4ccc(Cl)nc4c3)CC1)C2]

The title compound was prepared by a method analogous to that described for Example 3 using 2'-tert-butyl-4',6'-dihydrospiro[piperidine-4,5'-pyrazolo[3,4-c]pyridin]-7'(2'H)-one hydrochloride salt (Intermediate 4) and 2-chloroquinoline-7-carboxylic acid (Intermediate 44). +ESI (M+H) 452.3; ¹H NMR (400 MHz, CDCl₃, δ): 8.12 (d, J=8.2 Hz, 1H), 7.98 (br. s., 1H), 7.88 (dd, J=8.4 Hz, 1H), 7.61 (dd, J=8.4, 1.6 Hz, 1H), 7.44 (d, J=8.6 Hz, 1H), 7.39 (s, 1H), 5.91 (br. s., 1H), 4.06-4.22 (m, 1H), 3.38-3.64 (m, 3H), 2.85 (br. s., 2H), 1.67-1.97 (m, 4H), 1.61 (s, 9H).

Example 105

2'-tert-butyl-1-(2-(dimethylamino)quinoline-7-carbonyl)-4',6'-dihydrospiro[piperidine-4,5'-pyrazolo[3,4-c]pyridin]-7'(2'H)-one

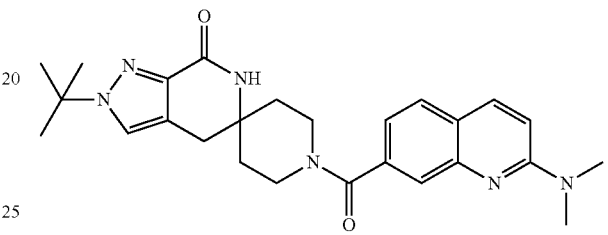

A solution of dimethylamine in tetrahydrofuran (2.2 mL, 4.4 mmmol, 2.0 M) was added to 2'-tert-butyl-1-(2-chloroquinoline-7-carbonyl)-4',6'-dihydrospiro[piperidine-4,5'-pyrazolo[3,4-c]pyridin]-7'(2'H)-one (100 mg, 0.2 mmol). The reaction vessel was sealed and the mixture was heated to 70° C. for 15 hours. The reaction was cooled to room temperature and concentrated. Purification by reversed-phase HPLC gave the title compound (25 mg, 25%). +ESI (M+H) 461.2; HPLC retention time 1.96 minutes (Method A).

The compounds listed in Table 3 below were prepared using a procedure analogous to that described above for the synthesis of the Example 105 using the appropriate starting materials which are available commercially, prepared using preparations well-known to those skilled in the art, or prepared in a manner analogous to routes described above for other intermediates. The compounds listed below were isolated initially as the free base and may be converted to a pharmaceutically acceptable salt for testing.

TABLE 3

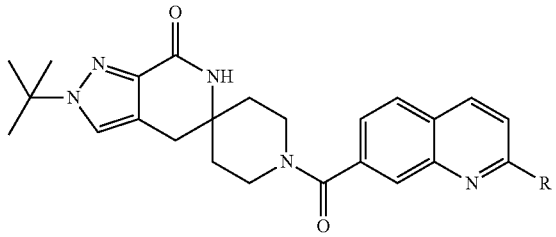

| Ex. | R | Analytical Data |
|---|---|---|
| 106 | ![cyclopropylamino] | +ESI (M + H) 473.1; HPLC retention time 2.21 minutes (Method B). |

TABLE 3-continued

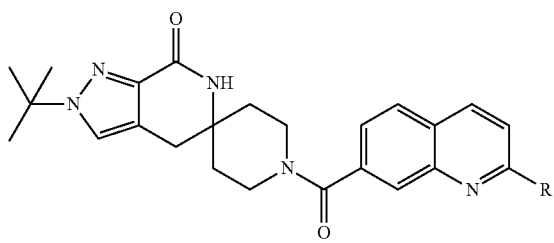

| Ex. | R | Analytical Data |
|---|---|---|
| 107 | (isopropylamino) | +ESI (M + H) 475.2; HPLC retention time 1.82 minutes (Method A) |
| 108 | (N-methyl-N-ethylamino) | +ESI (M + H) 475.4; $^1$H NMR (400 MHz, CDCl$_3$, δ): 7.82 (d, J = 8.76 Hz, 1 H), 7.56-7.66 (m, 2 H), 7.37 (s, 1 H), 7.13-7.18 (m, 1 H), 6.89 (d, J = 9.15 Hz, 1 H), 5.79 (s, 1 H), 4.02-4.15 (m, 1 H), 3.68 (m, 2 H), 3.41-3.62 (m, 3 H), 3.17-3.22 (m, 3 H), 2.84 (s, 2 H), 1.66-1.93 (m, 4 H), 1.61 (s, 9 H), 1.21 (m, 3 H). |
| 109 | (cyclobutylamino) | +APCI (M + H) 487.6; $^1$H NMR (400 MHz, CDCl$_3$, δ): 7.80 (d, J = 8.91 Hz, 1 H), 7.58-7.61 (m, 2 H), 7.37 (s, 1 H), 7.19 (dd, J = 9.76, 1.53 Hz, 1 H), 6.64 (d, J = 8.95 Hz, 1 H), 5.81 (s, 1 H), 4.98-5.04 (m, 1 H), 4.39-4.49 (m, 1 H), 4.02-4.16 (m, 1 H), 3.40-3.64 (m, 3 H), 2.83 (s, 2 H), 2.43-2.52 (m, 2 H), 1.72-1.96 (m, 8 H), 1.61 (s, 9 H). |
| 110 | (n-propylamino) | +APCI (M + H) 475.6; $^1$H NMR (400 MHz, CDCl$_3$, δ): 7.79 (d, J = 8.81 Hz, 1 H), 7.61-7.62 (m, 1 H), 7.59 (d, J = 8.21 Hz, 1 H), 7.37 (s, 1 H), 7.19 (dd, J = 8.17, 1.57 Hz, 1 H), 6.65 (d, J = 8.81 Hz, 1 H), 5.79 (s, 1 H), 4.69-4.73 (m, 1 H), 4.00-4.15 (m, 1 H), 3.41-3.63 (m, 5 H), 2.83 (s, 2 H), 1.64-1.92 (m, 6 H), 1.61 (s, 9 H), 1.02 (t, J = 7.41 Hz, 3 H). |
| 111 | (2-methoxyethylamino) | +APCI (M + H) 491.6; $^1$H NMR (400 MHz, CDCl$_3$, δ): 7.77 (d, J = 8.91 Hz, 1 H), 7.63-7.64 (m, 1 H), 7.59 (d, J = 8.13 Hz, 1 H), 7.37 (s, 1 H), 7.19 (dd, J = 8.20, 1.56 Hz, 1 H), 6.65 (d, J = 8.78 Hz, 1 H), 5.79 (s, 1 H), 5.05-5.10 (m, 1 H), 4.03-4.13 (m, 1 H), 3.70-3.73 (m, 2 H), 3.63 (t, 2 H), 3.43-3.61 (m, 3 H), 3.40 (s, 3 H), 2.84 (s, 2 H), 1.66-1.93 (m, 4 H), 1.61 (s, 9 H). |
| 112 | (ethylamino) | +APCI (M + H) 461.5; $^1$H NMR (400 MHz, CDCl$_3$, δ): 7.79 (d, J = 8.82 Hz, 1 H), 7.62-7.63 (m, 1 H), 7.59 (d, J = 8.21 Hz, 1 H), 7.37 (s, 1 H), 7.19 (dd, J = 8.19, 1.57 Hz, 1 H), 6.64 (d, J = 8.81 Hz, 1 H), 5.78 (s, 1 H), 4.67-4.71 (m, 1 H), 4.00-4.15 (m, 1 H), 3.44-3.59 (m, 5 H), 2.84 (s, 2 H), 1.64-1.94 (m, 4 H), 1.61 (s, 9 H), 1.29 (t, J = 7.22 Hz, 3 H). |
| 113 | (oxetan-3-ylamino) | +ESI (M + H) 489.3; HPLC retention time 1.8 minutes (Method A) |

The compounds listed in Table 4 below were prepared using procedures analogous to those described above for the synthesis of the compounds of Examples 1-3 using the appropriate starting materials which are available commercially, prepared using preparations well-known to those skilled in the art, or prepared in a manner analogous to routes described above for other intermediates. The compounds listed below were isolated initially as the free base and may be converted to a pharmaceutically acceptable salt for testing.

TABLE 4

| Ex. | R$_1$ | R$_2$ | Analytical Data |
|---|---|---|---|
| 114 | tBu[a] | (2,7-dimethyl-2H-indazol-5-yl)carbonyl | +ESI (M + H) 461.2; $^1$H NMR (400 MHz, CDCl$_3$, δ): 7.68 (s, 1 H), 7.34 (s, 1 H), 7.25 (s, 1 H), 6.23 (s, 1 H), 4.85 (br. s., 1 H), 4.26 (br. s., 1 H), 2.64-2.78 (m, 2 H), 2.61 (s, 3 H), 2.56 (s, 3 H), 1.74-2.36 (m, 8 H), 1.59 (s, 9 H). |

[a] = the term "tBu" is used to designate a t-butyl group

The compounds listed in Table 5 below were prepared using a procedure analogous to that described above for the synthesis of the Example 103 using the appropriate starting materials which are available commercially, prepared using preparations well-known to those skilled in the art, or prepared in a manner analogous to routes described above for other intermediates. The compounds listed below were isolated initially as the free base and may be converted to a pharmaceutically acceptable salt for testing.

TABLE 5

| Ex. | R | Analytical Data |
|---|---|---|
| 115 | cyclopropylamino | +ESI (M + H) 473.3; HPLC retention time 2.01 minutes (Method A). |
| 116 | isopropylamino | +ESI (M + H) 475.3; HPLC retention time 2.06 minutes (Method A) |

TABLE 5-continued

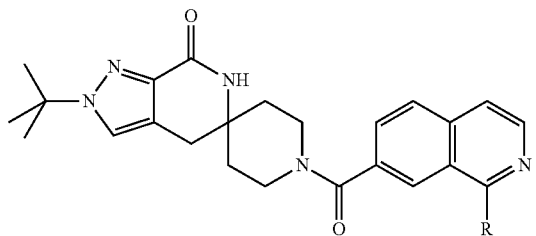

| Ex. | R | Analytical Data |
|---|---|---|
| 117 | | +ESI (M + H) 475.3; HPLC retention time 1.99 minutes (Method A) |
| 118 | | +ESI (M + H) 487.3; HPLC retention time 2.12 minutes (Method A) |
| 119 | | +ESI (M + H) 475.3; HPLC retention time 2.08 minutes (Method A) |
| 120 | | +ESI (M + H) 491.3; HPLC retention time 1.99 minutes (Method A) |
| 121 | | +ESI (M + H) 461.2; HPLC retention time 1.98 minutes (Method A) |
| 122 | | +ESI (M + H) 489.3; HPLC retention time 1.85 minutes (Method A) |

Example 123

2'-(tert-butyl)-1-(1-(tert-butylamino)isoquinoline-7-carbonyl)-4',6'-dihydrospiro[piperidine-4,5'-pyrazolo[3,4-c]pyridin]-7'(2'H)-one

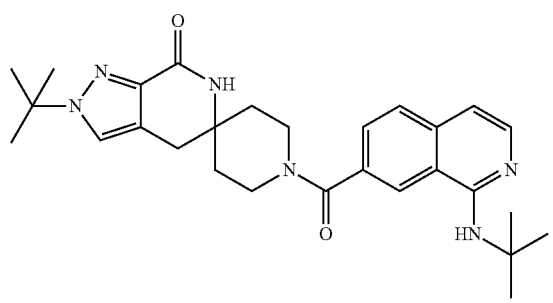 [SMILES: CC(C)(C)Nc1nccc2ccc(C(=O)N3CCC4(CC3)Cc3cn(C(C)(C)C)nc3C(=O)N4)cc12]

Step 1: 1-chloroisoquinoline-7-carboxylic acid

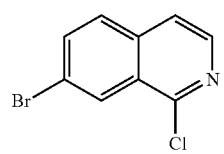

To a suspension of 7-bromo-1-chloroisoquinoline (2.000 g, 8.247 mmoles) in THF (12 mL) and diethyl ether (12 mL) cooled down to −78° C. was added n-BuLi (3.96 mL, 9.9 mmol, 2.5M in hexanes). Stirred for five minutes and then bubbled carbon dioxide while venting with a needle for approximately one minute. The reaction mixture was warmed up to 0° C. and 15 mL of a 1N aqueous sodium hydroxide were added. The mixture was diluted with diethyl ether stirred for 18 h. The organic and aqueous layers were separated and the organics were washed with 1N aqueous sodium hydroxide and water. The aqueous fractions were combined and acidified to pH 4 with 1N aqueous hydrochloric acid. The resulting solids were collected by filtration and dried to give the title compound (1.252 g, 73%). +ESI (M+H) 208.1 $^1$H NMR (400

MHz, DMSO-d$_6$) d ppm 13.58 (br. s., 1H) 8.86 (m, 1H) 8.43 (d, J=5.67 Hz, 1H) 8.33 (dd, J=8.61, 1.57 Hz, 1H) 8.19 (d, J=8.41 Hz, 1H) 8.01 (dd, 1H)

Step 2: 2'-(tert-butyl)-1-(1-(tert-butylamino)iso-quinoline-7-carbonyl)-4',6'-dihydrospiro[piperidine-4,5'-pyrazolo[3,4-c]pyridin]-7'(2'H)-one To a suspension of 1-chloroisoquinoline-7-carboxylic acid (100 mg, 0.482 mmol), RuPhos (6.5 mg, 0.014 mmol), BrettPhos (11.2 mg, 0.014 mmol) and sodium tert-butoxide (70.2 mg, 0.723 mmol) in dioxane (0.5 mL) was added t-butylamine (0.254 mL, 2.41 mmol). The vessel was sealed and mixture was heated to 110° C. and stirred overnight. The reaction was cooled down to room temperature and lithium bistrimethylsilylamide (0.136 mL, 0.723 mmol) was added. The reaction mixture was heated to 110° C. and left stirring overnight. The reaction mixture was cooled down to room temperature and filtered through celite and rinsed with methanol. The filtrate was concentrated under reduced pressure and 1N aqueous sodium hydroxide (1 mL) was added. Partitioned between ethyl acetate and a mixture of water and 1N aqueous sodium hydroxide. The layers were separated and the aqueous layer was acidified to pH 4. The aqueous layer was extracted into ethyl acetate. The extracts were dried over magnesium sulfate, filtered and concentrated under reduced pressure to obtain 1-(tert-butylamino)isoquinoline-7-carboxylic acid.

To a suspension of 1-(tert-butylamino)isoquinoline-7-carboxylic acid (24.7 mg, 0.101 mmol) and 2'-tert-butyl-4',6'-dihydrospiro[piperidine-4,5'-pyrazolo[3,4-c]pyridine]-7'(2'H)-one hydrochloride salt (33.9 mg, 0.101 mmol) in N,N-dimethylformamide (1 mL) was added triethylamine (0.07 mL, 0.50 mmol). The reaction mixture was stirred at room temperature for 10 minutes. Then 1-propanephosphonic acid cyclic anhydride (0.07 mL, 0.12 mmol, 50% solution in ethyl acetate) was added and the reaction mixture was stirred at room temperature overnight. N,N-dimethylformamide was removed under reduced pressure and the residue was purified by reversed-phase HPLC to give 2'-(tert-butyl)-1-(1-(tert-butylamino)isoquinoline-7-carbonyl)-4',6'-dihydrospiro[piperidine-4,5'-pyrazolo[3,4-c]pyridin]-7'(2'H)-one (6.1 mg, 24%). +ESI (m+H) 489.3; HPLC retention time 2.94 minutes (Method B).

The compounds listed in Table 6 below were prepared using procedures analogous to those described above for the synthesis of the compounds of Examples 1-3 using the appropriate starting materials which are available commercially, prepared using preparations well-known to those skilled in the art, or prepared in a manner analogous to routes described above for other intermediates. The compounds listed below were isolated initially as the free base and may be converted to a pharmaceutically acceptable salt for testing.

TABLE 6

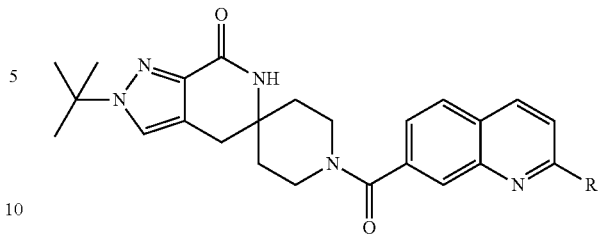

| Ex. | R | Analytical Data |
|---|---|---|
| 124 | ![structure with NH, CF2, F] | +ESI (M + H) 515.3; HPLC retention time 2.08 minutes (Method A) |
| 125 | ![structure with NH, CF, F] | +ESI (M + H) 511.3; HPLC retention time 2.10 minutes (Method A) |

PHARMACOLOGICAL DATA

Biological Protocols

The utility of the compounds of present invention, in the treatment of diseases (such as are detailed herein) in animals, particularly mammals (e.g., humans) may be demonstrated by the activity thereof in conventional assays known to one of ordinary skill in the art, including the in vitro and in vivo assays described below. Such assays also provide a means whereby the activities of the compound of the present invention can be compared with the activities of other known compounds.

Direct Inhibition of the Activities of ACC1 and ACC2

The ACC inhibitory activity of the compound of the present invention was demonstrated by methods based on standard procedures. For example direct inhibition of ACC activity, for the compound of Formula (I) was determined using preparations of recombinant human ACC1 (rhACC1) and recombinant human ACC2 (rhACC2). Representative sequences of the recombinant human ACC1 and ACC2 that can be used in the assay are provided in FIG. 1 (SEQ ID NO. 1) and FIG. 2 (SEQ. ID NO. 2), respectively.

[1] Preparation of rhACC1. Two liters of SF9 cells, infected with recombinant baculovirus containing full length human ACC1 cDNA, were suspended in ice-cold lysis buffer (25 mM Tris, pH 7.5; 150 mM NaCl; 10% glycerol; 5 mM imidazole (EMD Bioscience; Gibbstown, N.J.); 2 mM TCEP (BioVectra; Charlottetown, Canada); Benzonase nuclease (10000 U/100 g cell paste; Novagen; Madison, Wis.); EDTA-free protease inhibitor cocktail (1 tab/50 mL; Roche Diagnostics; Mannheim, Germany). Cells were lysed by 3 cycles of freeze-thaw and centrifuged at 40,000×g for 40 minutes (4° C.). Supernatant was directly loaded onto a HisTrap FF crude column (GE Healthcare; Piscataway, N.J.) and eluted with an imidazole gradient up to 0.5 M over 20 column volumes (CV). ACC1-containing fractions were pooled and diluted 1:5 with 25 mM Tris, pH 7.5, 2 mM TCEP, 10% glycerol and direct loaded onto a CaptoQ (GE Healthcare) column and eluted with an NaCl gradient up to 1 M over 20 CV's. Phosphate groups were removed from purified ACC1 by incubation with lambda phosphatase (100 U/10 μM target protein; New England Biolabs; Beverly, Mass.) for 14 hours at 4° C.; okadaic acid was added (1 μM final concentration; Roche Diagnostics) to inhibit the phosphatase. Purified ACC1 was exchanged into 25 mM Tris, pH 7.5, 2 mM TCEP, 10% glycerol, 0.5 M NaCl by 6 hour dialysis at 4° C. Aliquots were prepared and frozen at −80° C.

[2] Measurement of rhACC1 inhibition. hACC1 was assayed in a Costar #3676 (Costar, Cambridge, Mass.) 384-well plate using the Transcreener ADP detection FP assay kit (Bellbrook Labs, Madison, Wis.) using the manufacturer's recommended conditions for a 50 μM ATP reaction. The final conditions for the assay were 50 mM HEPES, pH 7.2, 10 mM $MgCl_2$, 7.5 mM tripotassium citrate, 2 mM DTT, 0.1 mg/mL BSA, 30 μM acetyl-CoA, 50 μM ATP, and 10 mM $KHCO_3$ Typically, a 10 μl reaction was run for 120 min at 25° C., and 10 μl of Transcreener stop and detect buffer was added and the combination incubated at room temp for an additional 1 hour. The data was acquired on a Envision Fluorescence reader (PerkinElmer) using a 620 excitation Cy5 FP general dual mirror, 620 excitation Cy5 FP filter, 688 emission (S) and a 688 (P) emission filter.

[3] Preparation of rhACC2. Human ACC2 inhibition was measured using purified recombinant human ACC2 (hrACC2). Briefly, a full length Cytomax clone of ACC2 was purchased from Cambridge Bioscience Limited and was sequenced and subcloned into PCDNA5 FRT TO-TOPO (Invitrogen, Carlsbad, Calif.). The ACC2 was expressed in CHO cells by tetracycline induction and harvested in 5 liters of DMEM/F12 with glutamine, biotin, hygromycin and blasticidin with 1 μg/mL tetracycline (Invitrogen, Carlsbad, Calif.). The conditioned medium containing ACC2 was then applied to a Softlink Soft Release Avidin column (Promega, Madison, Wis.) and eluted with 5 mM biotin. 4 mgs of ACC2 were eluted at a concentration of 0.05 mg/mL (determined by A280) with an estimated purity of 95% (determined by A280). The purified ACC2 was dialyzed in 50 mM Tris, 200 mM NaCl, 4 mM DTT, 2 mM EDTA, and 5% glycerol. The pooled protein was frozen and stored at −80° C., with no loss of activity upon thawing. For measurement of ACC2 activity and assessment of ACC2 inhibition, test compounds were dissolved in DMSO and added to the rhACC2 enzyme as a 5× stock with a final DMSO concentration of 1%.

[4] Measurement of human ACC2 inhibition. hACC2 was assayed in a Costar #3676 (Costar, Cambridge, Mass.) 384-well plate using the Transcreener ADP detection FP assay kit (Bellbrook Labs, Madison, Wis.) using the manufacturer's recommended conditions for a 50 uM ATP reaction. The final conditions for the assay were 50 mM HEPES, pH 7.2, 5 mM $MgCl_2$, 5 mM tripotassium citrate, 2 mM DTT, 0.1 mg/mL BSA, 30 μM acetyl-CoA, 50 μM ATP, and 8 mM $KHCO_3$ Typically, a 10 μl reaction was run for 50 min at 25° C., and 10 μl of Transcreener stop and detect buffer was added and the combination incubated at room temp for an additional 1 hour. The data was acquired on an Envision Fluorescence reader (PerkinElmer) using a 620 excitation Cy5 FP general dual mirror, 620 excitation Cy5 FP filter, 688 emission (S) and a 688 (P) emission filter.

The results using the recombinant hACC1 and recombinant hACC2 Transcreener assays described above are summarized in the table below for the Compounds of Formula (I) exemplified in the Examples above.

| Example | hACC1 IC50 (nM) | n | hACC2 IC50 (nM) | n |
| --- | --- | --- | --- | --- |
| 1 | 417 | 3 | 312 | 3 |
| 2 | 24.2 | 8 | 19 | 8 |
| 3 | 3920 | 3 | 2280 | 3 |
| 4 | 43 | 6 | 38 | 6 |
| 5 | 227 | 4 | 174 | 4 |
| 6 | 269 | 3 | 305 | 3 |
| 7 | 62 | 3 | 47 | 3 |
| 8 | 27 | 3 | 18 | 3 |
| 9 | 648 | 3 | 560 | 3 |
| 10 | 403 | 3 | 498 | 3 |
| 11 | 88 | 3 | 72 | 3 |
| 12 | 35 | 3 | 37 | 3 |
| 13 | 2040 | 3 | 1550 | 3 |
| 14 | 131 | 3 | 91 | 3 |
| 15 | 251 | 3 | 143 | 3 |
| 16 | 118 | 3 | 90 | 3 |
| 17 | 72 | 3 | 31 | 3 |
| 18 | 657 | 3 | 719 | 3 |
| 19 | 1480 | 4 | 2010 | 4 |
| 20 | 336 | 3 | 299 | 3 |
| 21 | 619 | 3 | 341 | 3 |
| 22 | 1250 | 3 | 843 | 3 |
| 23 | 621 | 3 | 520 | 3 |
| 24 | 688 | 3 | 320 | 3 |
| 25 | 259 | 3 | 137 | 3 |
| 26 | 121 | 3 | 60 | 3 |
| 27 | 296 | 3 | 132 | 3 |
| 28 | 158 | 4 | 56 | 4 |
| 29 | 33 | 3 | 9.2 | 3 |
| 30 | 98 | 3 | 30 | 3 |
| 31 | 179 | 3 | 96 | 3 |
| 32 | 154 | 3 | 56 | 3 |
| 33 | 523 | 3 | 108 | 3 |
| 34 | 116 | 3 | 50 | 3 |
| 35 | 487 | 3 | 91 | 3 |
| 36 | 67 | 3 | 28 | 3 |
| 37 | 302 | 3 | 127 | 3 |
| 38 | 364 | 3 | 107 | 3 |
| 39 | 329 | 4 | 97 | 4 |
| 40 | 656 | 4 | 177 | 4 |
| 41 | 164 | 3 | 67 | 3 |
| 42 | 68 | 3 | 29 | 3 |
| 43 | 29 | 4 | 11 | 4 |
| 44 | 26 | 3 | 10 | 3 |
| 45 | 6.6 | 7 | 2.1 | 7 |
| 46 | 36 | 3 | 5.3 | 3 |
| 47 | 21 | 7 | 2.7 | 7 |
| 48 | 30 | 3 | 9.2 | 3 |
| 49 | 8.5 | 3 | 3.8 | 3 |
| 50 | 30 | 3 | 7.5 | 3 |
| 51 | 15 | 3 | 4.4 | 3 |
| 52 | 88 | 3 | 17 | 3 |
| 53 | 47 | 3 | 13 | 3 |
| 54 | 21 | 3 | 5.1 | 3 |
| 55 | 14 | 4 | 2.6 | 4 |
| 56 | 7.4 | 3 | 1.9 | 3 |
| 57 | 50 | 3 | 13 | 3 |
| 58 | 149 | 3 | 12 | 3 |
| 59 | 123 | 3 | 14 | 3 |
| 60 | 43 | 3 | 14 | 3 |
| 61 | 94 | 3 | 13 | 3 |
| 62 | 8.4 | 3 | 2.1 | 3 |
| 63 | 160 | 3 | 28 | 3 |
| 64 | 23 | 4 | 4.0 | 4 |
| 65 | 256 | 3 | 56 | 3 |
| 66 | 17 | 3 | 2.4 | 3 |
| 67 | 1340 | 3 | 311 | 3 |
| 68 | 221 | 3 | 68 | 3 |
| 69 | 185 | 3 | 28 | 3 |
| 70 | 5.8 | 3 | 2.4 | 3 |
| 71 | 20 | 4 | 5.2 | 4 |
| 72 | 28 | 4 | 5.9 | 4 |
| 73 | 48 | 4 | 5.5 | 4 |
| 74 | 18 | 3 | 3.2 | 3 |
| 75 | 79 | 3 | 11 | 3 |
| 76 | 5.6 | 5 | 1.7 | 5 |
| 77 | 80 | 3 | 8.4 | 3 |
| 78 | 155 | 3 | 34 | 3 |

| Example | hACC1 IC50 (nM) | n | hACC2 IC50 (nM) | n |
|---|---|---|---|---|
| 79 | 216 | 3 | 18 | 3 |
| 80 | 78 | 3 | 21 | 3 |
| 81 | 46 | 3 | 5.3 | 3 |
| 82 | 21 | 3 | 6.4 | 3 |
| 83 | 163 | 3 | 19 | 3 |
| 84 | 194 | 3 | 33 | 3 |
| 85 | 27 | 3 | 5.9 | 3 |
| 86 | 18 | 3 | 4.1 | 3 |
| 87 | 17 | 3 | 2.1 | 3 |
| 88 | 19 | 4 | 4.2 | 4 |
| 89 | 343 | 3 | 44 | 3 |
| 90 | 209 | 3 | 31 | 3 |
| 91 | 240 | 3 | 51 | 3 |
| 92 | 244 | 3 | 55 | 3 |
| 93 | 65 | 3 | 8.6 | 3 |
| 94 | 130 | 3 | 23 | 3 |
| 95 | 105 | 3 | 9.2 | 3 |
| 96 | 62 | 3 | 7.1 | 3 |
| 97 | 219 | 3 | 45 | 3 |
| 98 | | | | |
| 99 | 23 | 1 | 5.6 | 1 |
| 100 | 62 | 3 | 21 | 3 |
| 101 | 160 | 3 | 26 | 3 |
| 102 | 78 | 3 | 12 | 3 |
| 103 | 73 | 4 | 8.9 | 4 |
| 104 | 89 | 3 | 16 | 3 |
| 105 | 7.4 | 3 | 1.5 | 3 |
| 106 | 7.5 | 3 | 2.6 | 3 |
| 107 | 6.1 | 3 | 2.2 | 3 |
| 108 | 15 | 3 | 2.4 | 3 |
| 109 | 3.4 | 3 | 1.0 | 3 |
| 110 | 5.6 | 3 | 1.1 | 3 |
| 111 | 27 | 3 | 3.3 | 3 |
| 112 | 8.9 | 3 | 1.8 | 3 |
| 113 | 507 | 3 | 44 | 3 |
| 114 | 4820 | 3 | 612 | 3 |
| 115 | 29 | 4 | 2.9 | 4 |
| 116 | 20 | 4 | 4.7 | 4 |
| 117 | 332 | 4 | 54 | 4 |
| 118 | 17 | 4 | 2.7 | 4 |
| 119 | 24 | 4 | 2.5 | 4 |
| 120 | 47 | 4 | 6.1 | 4 |
| 121 | 17 | 4 | 2.7 | 4 |
| 122 | 494 | 4 | 77 | 4 |
| 123 | 78 | 1 | 6.3 | 1 |
| 124 | 6.5 | 3 | 1.72 | 3 |
| 125 | 9.0 | 3 | 1.7 | 3 |

"n" is used to designate the number of assay runs

Sequence Listing 1 provides a sequence of recombinant human ACC1 (SEQ. ID NO. 1) that can be employed in the Transcreener in vitro assay.

Sequence Listing 2 provides a sequence of recombinant human ACC2 (SEQ. ID NO. 2) that can be employed in the Transcreener in vitro assay.

Acute In Vivo Assessment of ACC Inhibition in Experimental Animals

The ACC inhibitory activity of the compounds of the present invention can be confirmed in vivo by evaluation of their ability to reduce malonyl-CoA levels in liver and muscle tissue from treated animals.

Measurement of malonyl-CoA production inhibition in experimental animals can be determined using the following methodology.

In this method, male Sprague-Dawley Rats, maintained on standard chow and water ad libitum (225-275 g), were randomized prior to the study. Animals were either fed, or fasted for 18 hours prior to the beginning of the experiment. Two hours into the light cycle the animals were orally dosed with a volume of 5 mL/kg, (0.5% methyl cellulose; vehicle) or with the appropriate compound (prepared in vehicle). Fed vehicle controls were included to determine baseline tissue malonyl-CoA levels while fasted animals were included to determine the effect fasting had on malonyl-CoA levels. One hour after compound administration the animals were asphyxiated with $CO_2$ and the tissues were removed. Specifically, blood was collected by cardiac puncture and placed into BD Microtainer tubes containing EDTA (BD Biosciences, N.J.), mixed, and placed on ice. Plasma was used to determine drug exposure. Liver and quadriceps were removed, immediately freeze-clamped, wrapped in foil and stored in liquid nitrogen.

Tissues were pulverized under liquid $N_2$ to ensure uniformity in sampling. Malonyl-CoA was extracted from the tissue (150-200 mg) with 5 volumes 10% tricarboxylic acid in Lysing Matrix A (MP Biomedicals, PN 6910) in a FastPrep FP120 (Thermo Scientific, speed=5.5; for 45 seconds). The supernatant containing malonyl-CoA was removed from the cell debris after centrifugation at 15000×g for 30 minutes (Eppendorf Centrifuge 5402). Samples were stably frozen at −80C until analysis was completed.

Analysis of malonyl CoA levels in liver and muscle tissue can be evaluated using the following methodology.

The method utilized the following materials: Malonyl-CoA tetralithium salt and malonyl-$^{13}C_3$—CoA trilithium salt which were purchased from Isotec (Miamisburg, Ohio, USA), sodium perchlorate (Sigma, cat no. 410241), trichloroacetic acid (ACROS, cat no. 42145), phosphoric acid (J. T. Baker, cat no. 0260-01), ammonium formate (Fluka, cat no. 17843), methanol (HPLC grade, J. T. Baker, cat no. 9093-33), and water (HPLC grade, J. T. Baker, 4218-03) were used to make the necessary mobile phases. Strata-X on-line solid phase extraction columns, 25 µm, 20 mm×2.0 mm I.D (cat no. 00M-S033-B0-CB) were obtained from Phenomenex (Torrance, Calif., USA). SunFire C18 reversed-phase columns, 3.5 µm, 100 mm×3.0 mm I.D. (cat no. 186002543) were purchased from Waters Corporation (Milford, Mass., USA).

This method may be performed utilizing the following equipment. Two-dimensional chromatography using an Agilent 1100 binary pump, an Agilent 1100 quaternary pump and two Valco Cheminert 6-port two position valves. Samples were introduced via a LEAP HTC PAL auto sampler with Peltier cooled stack maintained at 10° C. and a 20 µL sampling loop. The needle wash solutions for the autosampler were 10% trichloroacetic acid in water (w/v) for Wash 1 and 90:10 methanol:water for Wash 2. The analytical column (Sunfire) was maintained at 35° C. using a MicroTech Scientific Micro-LC Column Oven. The eluent was analyzed on an ABI Sciex API3000 triple quadrupole mass spectrometer with Turbo Ion Spray.

Two-dimensional chromatography was performed in parallel using distinct gradient elution conditions for on-line solid phase extraction and reversed-phase chromatography. The general design of the method was such that the first dimension was utilized for sample clean-up and capture of the analyte of interest followed by a brief coupling of both dimensions for elution from the first dimension onto the second dimension. The dimensions were subsequently uncoupled allowing for gradient elution of the analyte from the second dimension for quantification while simultaneously preparing the first dimension for the next sample in the sequence. When both dimensions were briefly coupled together, the flow of the mobile phase in the first dimension was reversed for analyte elution on to the second dimension, allowing for optimal peak width, peak shape, and elution time.

The first dimension of the HPLC system utilized the Phenomenex strata-X on-line solid phase extraction column and the mobile phase consisted of 100 mM sodium perchlorate/0.1% (v/v) phosphoric acid for solvent A and methanol for solvent B.

The second dimension of the HPLC system utilized the Waters SunFire C18 reversed-phase column and the mobile phase consisted of 100 mM ammonium formate for solvent A and methanol for solvent B. The initial condition of the gradient was maintained for 2 minutes and during this time the analyte was transferred to the analytical column. It was important that the initial condition was at a sufficient strength to elute the analyte from the on-line SPE column while retaining it on the analytical. Afterwards, the gradient rose linearly to 74.5% A in 4.5 minutes before a wash and re-equilibration step.

Mass spectrometry when coupled with HPLC can be a highly selective and sensitive method for quantitatively measuring analytes in complex matrices but is still subject to interferences and suppression. By coupling a two dimensional HPLC to the mass spectrometer, these interferences were significantly reduced. Additionally, by utilizing the Multiple Reaction Monitoring (MRM) feature of the triple quadrupole mass spectrometer, the signal-to-noise ratio was significantly improved.

For this assay, the mass spectrometer was operated in positive ion mode with a TurbolonSpray voltage of 2250V. The nebulizing gas was heated to 450° C. The Declustering Potential (DP), Focusing Potential (FP), and Collision Energy (CE) were set to 60, 340, and 42 V, respectively. Quadrupole 1 (Q1) resolution was set to unit resolution with Quadrupole 3 (Q3) set to low. The CAD gas was set to 8. The MRM transitions monitored were for malonyl CoA: 854.1→347.0 m/z (L. Gao et al. (2007) *J. Chromatogr. B* 853,303-313); and for malonyl-$^{13}C_3$—CoA: 857.1→350.0 m/z with dwell times of 200 ms. The eluent was diverted to the mass spectrometer near the expected elution time for the analyte, otherwise it was diverted to waste to help preserve the source and improve robustness of the instrumentation. The resulting chromatograms were integrated using Analyst software (Applied Biosystems). Tissue concentrations for malonyl CoA were calculated from a standard curve prepared in a 10% solution of trichloroacetic acid in water.

Samples comprising the standard curve for the quantification of malonyl-CoA in tissue extracts were prepared in 10% (w/v) trichloroacetic acid (TCA) and ranged from 0.01 to 1 µmol/µL. Malonyl-$^{13}C_3$—CoA (final concentration of 0.4 µmol/µL) was added to each standard curve component and sample as an internal standard.

Six intra-assay quality controls were prepared; three from a pooled extract prepared from fasted animals and three from a pool made from fed animals. These were run as independent samples spiked with 0, 0.1 or 0.3 µmol/µL $^{12}$C-malonyl-CoA as well as malonyl-$^{13}C_3$—CoA (0.4 µmol/µL). Each intra-assay quality control contained 85% of aqueous tissue extract with the remaining portion contributed by internal standard (0.4 µmol/µL) and $^{12}$C-malonyl-CoA. Inter assay controls were included in each run; they consist of one fasted and one fed pooled sample of quadriceps and/or one fasted and one fed pooled sample of liver. All such controls are spiked with malonyl-$^{13}C_3$—CoA (0.4 µmol/µL).

All publications, including but not limited to issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A compound of structure

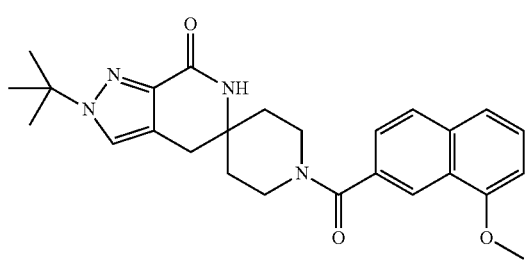 [SMILES: COc1cccc2ccc(C(=O)N3CCC4(CC3)Cc3cn(C(C)(C)C)nc3C(=O)N4)cc12]

or a pharmaceutically acceptable salt thereof.

2. A compound of structure

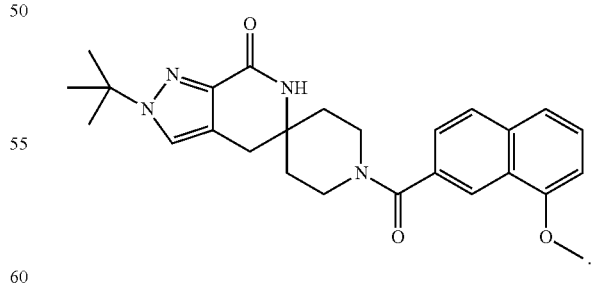

3. A pharmaceutical composition comprising a therapeutically effective amount of a compound of claim 1 or a pharmaceutically acceptable salt thereof and a pharmaceutically acceptable excipient, diluent, or carrier.

* * * * *